US011229636B2

(12) United States Patent
Ujjinamatada et al.

(10) Patent No.: US 11,229,636 B2
(45) Date of Patent: Jan. 25, 2022

(54) SUBSTITUTED TETRAHYDROQUINOLINONE COMPOUNDS AS ROR GAMMA MODULATORS

(71) Applicant: Aurigene Discovery Technologies Limited, Bangalore (IN)

(72) Inventors: Ravi Kotrabasaiah Ujjinamatada, Bangalore (IN); Chetan Pandit, Bangalore (IN)

(73) Assignee: AURIGENE DISCOVERY TECHNOLOGIES LIMITED, Bangalore (IN)

( * ) Notice: Subject to any disclaimer, the term of this patent is extended or adjusted under 35 U.S.C. 154(b) by 35 days.

(21) Appl. No.: 16/709,692

(22) Filed: Dec. 10, 2019

(65) Prior Publication Data

US 2020/0113892 A1 Apr. 16, 2020
US 2021/0113551 A9 Apr. 22, 2021

Related U.S. Application Data

(63) Continuation of application No. 15/574,243, filed as application No. PCT/IB2016/052773 on May 13, 2016, now abandoned.

(30) Foreign Application Priority Data

May 15, 2015 (IN) .......................... 2448/CHE/2015

(51) Int. Cl.
| | | |
|---|---|---|
| *A61K 31/4709* | (2006.01) | |
| *A61K 31/506* | (2006.01) | |
| *A61K 31/501* | (2006.01) | |
| *A61K 31/4985* | (2006.01) | |
| *C07D 405/04* | (2006.01) | |
| *C07D 487/04* | (2006.01) | |
| *C07D 239/26* | (2006.01) | |
| *C07D 409/04* | (2006.01) | |
| *C07D 401/04* | (2006.01) | |
| *C07D 401/14* | (2006.01) | |
| *C07D 403/04* | (2006.01) | |

(52) U.S. Cl.
CPC ...... *A61K 31/4709* (2013.01); *A61K 31/4985* (2013.01); *A61K 31/501* (2013.01); *A61K 31/506* (2013.01); *C07D 239/26* (2013.01); *C07D 401/04* (2013.01); *C07D 401/14* (2013.01); *C07D 403/04* (2013.01); *C07D 405/04* (2013.01); *C07D 409/04* (2013.01); *C07D 487/04* (2013.01)

(58) Field of Classification Search
CPC .. A61P 31/501; A61P 31/4985; C07D 405/04; C07D 487/04; C07D 239/26; C07D 409/04; C07D 401/04; C07D 401/14; C07D 403/04

USPC ......................................................... 514/313
See application file for complete search history.

(56) References Cited

U.S. PATENT DOCUMENTS

| | | |
|---|---|---|
| 9,481,674 B1 | 11/2016 | Claremon et al. |
| 9,663,515 B2 | 5/2017 | Claremon et al. |
| 9,845,308 B2 | 12/2017 | Claremon et al. |
| 9,855,229 B2 | 1/2018 | Khairatkar-Joshi et al. |
| 2016/0122318 A1 | 5/2016 | Claremon et al. |
| 2016/0122345 A1 | 5/2016 | Claremon et al. |
| 2016/0346234 A1 | 12/2016 | Khairatkar-joshi et al. |
| 2018/0200247 A1 | 7/2018 | Ujjinamatada et al. |

FOREIGN PATENT DOCUMENTS

| | | |
|---|---|---|
| EP | 3294713 A1 | 3/2018 |
| JP | 2007-533752 A | 11/2007 |
| JP | 2017-505318 A | 2/2017 |
| WO | WO 02/46173 A1 | 6/2002 |
| WO | WO 2005/082856 A2 | 9/2005 |
| WO | WO 2005/103022 A1 | 11/2005 |
| WO | WO 2012/027965 A1 | 3/2012 |
| WO | WO 2012/028100 A1 | 3/2012 |
| WO | WO 2012/100732 A1 | 8/2012 |
| WO | WO 2012/100734 A1 | 8/2012 |
| WO | WO 2013/029338 A1 | 3/2013 |
| WO | WO 2013/166013 A1 | 11/2013 |
| WO | WO 2013/169588 A1 | 11/2013 |
| WO | WO 2013/171729 A2 | 11/2013 |

(Continued)

OTHER PUBLICATIONS

"Extended European Search Report dated Sep. 26, 2018 in Europe Patent Application No. 16795974.1, filed on May 13, 2016", 9 pages.

(Continued)

*Primary Examiner* — Tracy Vivlemore
*Assistant Examiner* — Ebenezer O Sackey
(74) *Attorney, Agent, or Firm* — Duane Morris LLP; Thomas J. Kowalski; Deborah L. Lu

(57) ABSTRACT

The present invention provides substituted tetrahydroquinolinone and related compounds of formula (I), which are therapeutically useful as modulators of Retinoic acid receptor-related orphan receptors (RORs), more particularly as RORγ modulators. These compounds are useful in the treatment and prevention of diseases and/or disorder, in particular their use in diseases and/or disorder mediated by RORγ receptor. The present invention also provides preparation of the compounds and pharmaceutical formulations comprising at least one of the substituted tetrahydroquinolinone or related compounds of formula (I), together with a pharmaceutically acceptable carrier, diluent or excipient therefor.

41 Claims, No Drawings

(56) References Cited

FOREIGN PATENT DOCUMENTS

| | | |
|---|---|---|
| WO | WO 2014/125426 A1 | 8/2014 |
| WO | WO 2014/179564 A1 | 11/2014 |
| WO | WO 2015/017335 A1 | 2/2015 |
| WO | WO 2015/035032 A1 | 3/2015 |
| WO | WO 2015/082533 A1 | 6/2015 |
| WO | WO 2015/083130 A1 | 6/2015 |
| WO | WO 2015/101928 A1 | 7/2015 |
| WO | WO 2015/116904 A1 | 8/2015 |
| WO | WO 2015/145371 A1 | 10/2015 |
| WO | WO 2015/159233 A1 | 10/2015 |
| WO | WO 2015/160654 A1 | 10/2015 |
| WO | WO 2016/061160 A1 | 4/2016 |
| WO | WO 2016/185342 A1 | 11/2016 |
| WO | WO 2017/010399 A1 | 1/2017 |
| WO | WO 2017/024018 A1 | 2/2017 |
| WO | WO 2017/087608 A1 | 5/2017 |
| WO | WO 2017/132432 A1 | 8/2017 |

OTHER PUBLICATIONS

"International Preliminary Report on Patentability dated Nov. 30, 2017 in International Patent Application No. PCT/IB2016/052773, filed on May 13, 2016", 8 pages.

"International Search Report and Written Opinion dated Sep. 5, 2016 in International Patent Application No. PCT/IB2016/052773, filed on May 13, 2016", 10 pages.

"Office Action dated Sep. 11, 2019 in U.S. Appl. No. 15/574,243, filed Nov. 15, 2017 and published as US 2018-200247 A1 on Jul. 19, 2018", 6 pages.

"Office Action dated Jan. 11, 2019 in U.S. Appl. No. 15/574,243, filed Nov. 15, 2017 and published as US 2018200247 A1 on Jul. 19, 2018", 12 pages.

"Search Report dated Jan. 14, 2020 in Japanese Patent Application No. 2017-559113, filed on May 13, 2016", 61 pages. (Including partial English translation from Japanese produced by machine translation provided on the Japanese Patent Office website).

Annunziato, et al., "Type 17 T Helper Cells-Origins, Features and Possible Roles in Rheumatic Disease", Nature Reviews Rheumatology, 2009, 5:325-331.

Buonocore, et al., "Innate Lymphoid Cells Drive lnterleukin-23-Dependent Innate Intestinal Pathology", Nature, Apr. 29, 2010, 464(7293):1371-1375.

Chang, et al., "The Therapeutic Potential of RORγ Modulators in the Treatment of Human Disease", Journal of Experimental Pharmacology, 2012, 4:141-148.

Eberl, et al., "An Essential Function for the Nuclear Receptor RORγt in the Generation of Fetal Lymphoid Tissue Inducer Cells", Nature Immunology, Dec. 21, 2003, 5(1):64-73.

Figueroa-Vega, et al., "Increased Circulating Pro-Inflammatory Cytokines and Th17 Lymphocytes in Hashimoto's Thyroiditis", The Journal of Clinical Endocrinology and Metabolism, Dec. 2009, 95(2):953-962.

He, et al., "RORγt, a Novel Isoform of an Orphan Receptor, Negatively Regulates Fas Ligand Expression and IL-2 Production in T Cells", Immunity, Dec. 1998, 9(6):797-806.

Hueber, et al., "Cutting Edge: Mast Cells Express IL-17A in Rheumatoid Arthritis Synovium", Journal of Immunology, 2010, 184(7):3336-3340.

Ivanov, et al., "The Orphan Nuclear Receptor RORγt Directs the Differentiation Program of Proinflammatory IL-17+ T Helper Cells", Cell, Sep. 22, 2006, 126(6):1121-1133.

Jetten, Anton M., "Retinoid-Related Orphan Receptors (RORs): Critical Roles in Development, Immunity, Circadian Rhythm, and Cellular Metabolism", Nuclear Receptor Signaling, 2009, 7:1-32.

Jetten, et al., "Retinoid-related Orphan Receptors (RORs): Roles in Cellular Differentiation and Development", Advances in Developmental Biology, 2006, 16:313-355.

Jetten, et al., "The ROR Nuclear Orphan Receptor Subfamily: Critical Regulators of Multiple Biological Processes", Progress in Nucleic Acid Research and Molecular Biology, 2001, 69:205-247.

Jia, et al., "The T Helper Type 17/Regulatory T Cell Imbalance in Patients with Acute Kawasaki Disease", Clinical and Experimental Immunology, 2010, 162(1):131-137.

Kastelein, et al., "Discovery and Biology of IL-23 and IL-27: Related but Functionally Distinct Regulators of Inflammation", Annual Review of Immunology, 2007, 25:221-242.

Korn, et al., "IL-17 and Th17 Cells", Annual Review of Immunology, 2009, 27:485-517.

Leung, et al., "The Cytokine Milieu in the Interplay of Pathogenic Th1/Th17 Cells and Regulatory T Cells in Autoimmune Disease", Cellular & Molecular Immunology, 2010, 7(3):182-189.

Louten, et al., "Development and Function of TH17 Cells in Health and Disease", The Journal of Allergy and Clinical Immunology, May 2009, 123(5):1004-1011.

Manel, et al., "The Differentiation of Human TH-17 Cells Requires Transforming Growth Factor-β and Induction of the Nuclear Receptor RORγT", Nature Immunology, Jun. 2008, 9(6):641-649.

Marelli, et al., "Tumor Targeting via Integrin Ligands", Frontiers in Oncology, Aug. 2013, 3(222):1-12.

Miossec, et al., "Interleukin-17 and Type 17 Helper T Cells", The New England Journal of Medicine, Aug. 27, 2009, 361:888-898.

Steinman, Lawrence, "A Rush to Judgment on Th17", Journal of Experimental Medicine, 2008, 205(7):1517-1522.

Sutton, et al., "Interleukin-1 and IL-23 Induce Innate IL-17 Production from γδ T Cells, Amplifying Th17 Responses and Autoimmunity", Immunity, Aug. 21, 2009, 31(2):331-341.

Wang, et al., "Mathematical Modeling in Cancer Drug Discovery", Drug Discovery Today, 2013, 19(2):145-150.

Zou, et al., "TH17 Cells in Tumour Immunity and Immunotherapy", Nature Reviews Immunology, Apr. 2010, 10(4):248-256.

SUBSTITUTED TETRAHYDROQUINOLINONE COMPOUNDS AS ROR GAMMA MODULATORS

This patent application is a continuation of U.S. patent application Ser. No. 15/574,243, filed on Nov. 15, 2017, entitled "Substituted Tetrahydroquinolinone Compounds as ROR Gamma Modulators," naming Ravi K. Ujjinamatada and Chetan Pandit as inventors; which is a national stage of international patent application number PCT/IB2016/052773, filed on May 13, 2016, entitled "Substituted Tetrahydroquinolinone Compounds as ROR Gamma Modulators," naming Ravi K. Ujjinamatada and Chetan Pandit as inventors; which claims the benefit of Indian provisional patent application no. 2448/CHE/2015, filed on May 15, 2015, entitled "Substituted Tetrahydroquinolinone Compounds as ROR Gamma Modulators,"; the specifications of which are hereby incorporated by reference in their entirety.

FIELD OF THE INVENTION

This invention relates to compounds useful for the treatment of diseases and/or disorder associated with Retinoic acid receptor-related orphan receptors (RORs), and more particularly compounds that modulate the function of RORγ. The invention also provides pharmaceutically acceptable compositions comprising compounds of the present invention and methods of using said compositions in the treatment of diseases and/or disorder associated with RORγ.

BACKGROUND OF THE INVENTION

Retinoid-related orphan receptors (RORs) are transcription factors which belong to the steroid hormone nuclear receptor super family (Jetten & Joo, Adv. Dev. Biol. 16:313-355, 2006). Several nuclear receptors are still characterized as orphan receptors because the identification of ligands for these receptors is still elusive or controversial. The ROR family consists of three members, ROR alpha (RORα), ROR beta (RORβ) and ROR gamma (RORγ), each encoded by a separate gene (RORA, RORB and RORC, respectively). RORs contain four principal domains shared by the majority of nuclear receptors: an N-terminal A/B domain, a DNA-binding domain, a hinge domain, and a ligand binding domain. Each ROR gene generates several isoforms which differ only in their N-terminal A/B domain. Two isoforms of RORγ have been identified: RORγ1 and RORγt (also known as RORγ2). RORγ is a term used to describe both RORγ1 and/or RORγt.

Upon activation by antigen-presenting cells naive T helper cells undergo clonal expansion and will ultimately differentiate in cytokine secreting effector T cells, such as Th1 and Th2 subtypes. A third and distinct effector subset has been identified, which plays a key role in providing immunity to bacteria and fungi at mucosal surfaces (Kastelein, et al., Ann. Rev. Immunol. 25: 221-242, 2007). This effector T helper cell subset can be distinguished based on its ability to produce large quantities of IL-17A/F, IL-21 and IL-22, and is named Th17 (Miossec, et al., New Eng. J. Med. 361: 888-898, 2009).

RORγ1 is expressed in a variety of tissues including thymus, muscle, kidney and liver, while RORγt is exclusively expressed in the cells of the immune system. RORγt is highly expressed in Th17 cells (He, et al., Immunity 9: 797-806, 1998). Studies have shown that Th17 cells are one of the important drivers of the inflammatory process in tissue-specific autoimmunity (Steinman, J. Exp. Med. 205: 1517-1522, 2008; Leung, et al., Cell. Mol. Immunol. 7: 182-189, 2010). There is evidence that Th17 cells are activated during the disease process and are responsible for recruiting other inflammatory cells types, especially neutrophils, to mediate pathology in the target tissues (Korn, et al., Ann. Rev. Immunol. 27:485-517, 2009). In addition, Th17 cells or their products have been shown to be associated with the pathology of a variety of human inflammatory and autoimmune disorders including multiple sclerosis, rheumatoid arthritis, psoriasis, Crohn's disease and asthma (Jetten, Nucl. Recept. Signal. 7: e003, 2009; Manel, et al., Nat. Immunol. 9:641-649, 2008).

RORγt was shown to play a crucial role in non-Th17 lymphoid cells. In these studies, RORγt was critically important in innate lymphoid cells expressing Thy1, SCA-1 and IL-23R proteins. Genetic disruption of RORγ in a mouse colitis model dependent on these innate lymphoid cells, prevented colitis development (Buonocore, et al., Nature 464: 1371-1375, 2010). In addition, RORγt was shown to play a crucial role in other non-Th17 cells, such as mast cells (Hueber, et al., J Immunol. 184: 3336-3340, 2010). Finally, RORγt expression and secretion of Th17-type of cytokines was reported for Lymphoid Tissue Inducer cells, NK T-cells, NK cells (Eberl, et al., Nat. Immunol. 5: 64-73, 2004) and gamma-delta T-cells (Sutton, et al., Nat. Immunol. 31: 331-341, 2009; Louten, et al., J Allergy Clin. Immunol. 123: 1004-1011, 2009), suggesting an important function for RORγt in these subtypes of cells.

Based on the role of IL-17 producing cells (either Th17 or non-Th17 cells) RORγt has been identified as a key mediator in the pathogenesis of several diseases (Louten, et al., J Allergy Clin. Immunol. 123: 1004-1011, 2009; Annunziato et al., Nat. Rev. Rheumatol. 5: 325-331, 2009). This was confirmed using several disease models representative of autoimmune diseases. Genetic ablation of the RORγ gene in mice prevented the development of experimental autoimmune diseases, such as experimental autoimmune encephalomyelitis (EAE) and colitis (Ivanov, et al., Cell 126: 1121-33, 2006; Buonocore, et al., Nature 464: 1371-1375, 2010).

Being a critical mediator in Th17-cells and other non-Th17 cells, inhibition of RORγt is expected to have a beneficial effect on autoimmune diseases, such as, but not limited to rheumatoid arthritis, psoriasis, multiple sclerosis, inflammatory bowel disease, Crohn's disease and asthma (Annunziato, et al., Nat. Rev. Immunol. 5: 325-331, 2009; Louten, et al., J Allergy Clin. Immunol. 123: 1004-1011, 2009). RORγt deficient mice show very little Th17 cells. In addition, RORγt deficiency resulted in amelioration of EAE. Inhibition of RORγt may also be beneficial in other diseases, which are characterized by increased levels of Th17 cells and/or elevated levels of Th17 hallmark cytokines such as IL-17, IL-22 and IL-23. Examples of such diseases are Kawasaki Disease (Jia, et al., Clin. Exp. Immunol. 162: 131-137, 2010) and Hashimoto's thyroiditis (Figueroa-Vega, et al., J Clin. Endocrinol. Metab. 95: 953-62, 2010).

RORγ inverse agonist SR2211 is a cell-permeable piperazine containing biphenyl compound that binds directly to retinoic acid receptor related orphan receptor γ (RORγ) and acts as a highly selective, inverse agonist. It is reported to block the transcriptional activity of RORγ and suppress the synthesis of IL-17 in EL-4 murine lymphoma cell line. SR2211 exhibits only a minimal effect on ROR alpha and LXR alpha activity, indicating that the functional effect is due to selective inhibition of RORγ alone.

The nature and relevance of Th17 cells in mouse models of cancer and human disease are known (Zou et al., *Nature*

Reviews Immunology 10, 248-256 (April 2010)). Evidences suggest that the effector T cell subset is also involved in tumor immunology, thus giving a way to a new target for cancer therapy.

Thus in view of the role RORγ plays in the pathogenesis of diseases, there is a need of compounds that modulate RORγ activity, which can be used in the treatment of diseases mediated by RORγ. Disclosed herein are substituted tetrahydroquinolinone and related compounds that are useful as modulators of ROR-gamma activity.

SUMMARY OF THE INVENTION

Provided herein are substituted tetrahydroquinolinone and related compounds and pharmaceutical compositions thereof, which are useful as RORγ modulators.

In one aspect, the present invention provides compounds of formula (I):

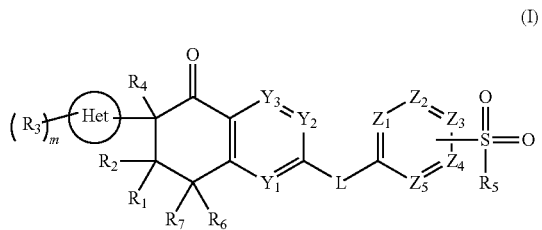

(I)

or a pharmaceutically acceptable salt or a stereoisomer thereof;
wherein,
ring Het is heterocyclyl;
each $Y_1$, $Y_2$ and $Y_3$ are independently $CR_a$ or N, wherein 0-2 of $Y_1$, $Y_2$ and $Y_3$ are N;
each $Z_1$, $Z_2$, $Z_3$, $Z_4$ and $Z_5$ are independently $CR_a$ or N, wherein 0-3 of $Z_1$, $Z_2$, $Z_3$, $Z_4$ and $Z_5$ are N;
L is *—$NR_b$—C(O)—$(CR_bR_c)_n$—, *—C(O)—$NR_b$—$(CR_bR_c)_n$—, *—$NR_b$—$S(O)_2$—$(CR_bR_c)_n$— or *—$S(O)_2$—$NR_b$—$(CR_bR_c)_n$—; wherein the group marked with * is connected to the ring containing $Y_1$, $Y_2$ and $Y_3$;
each $R_1$, $R_2$, $R_6$ and $R_7$ are independently hydrogen, halo, alkyl, hydroxy, hydroxyalkyl, cyano, alkoxy, haloalkyl, haloalkoxy, alkenyl, alkynyl, cycloalkyl, aryl, heteroaryl, —$COR_d$ or —$COOR_d$;
$R_3$ at each occurrence is independently hydroxy, halo, alkyl, alkylamino, alkoxy, haloalkyl, haloalkoxy or cycloalkyl; alternatively, two $R_3$ on the same carbon together form an oxo (=O) group;
$R_4$ is hydrogen, alkyl or alkoxy;
$R_5$ is alkyl, —$(CH_2)_nNR_bR_c$, hydroxyalkyl, cycloalkyl, aryl or heterocyclyl;
$R_a$ is hydrogen, alkyl, alkoxy, halo, cycloalkyl or aryl;
$R_b$ and $R_c$ are each independently hydrogen, alkyl or alkoxyalkyl;
alternatively, $R_b$ and $R_c$ on the same atom together form a ring;
$R_d$ is hydrogen, alkyl, alkoxy or cycloalkyl;
m is 0 to 3; and
n is 0 to 3.

In a further aspect, the present invention relates to pharmaceutical compositions comprising a compound of formula (I), or a pharmaceutically acceptable salt or a stereoisomer thereof and processes for preparing such compositions.

In yet another aspect, the present invention relates to the preparation of the compounds of formula (I).

In yet another aspect of the present invention, it provides substituted tetrahydroquinolinone and related compounds of formula (I), which are used for the treatment and prevention of diseases or disorder, in particular their use in diseases or disorder mediated by steroid hormone nuclear receptors—particularly RORs, more particularly RORγ.

DETAILED DESCRIPTION OF THE INVENTION

The present invention provides substituted tetrahydroquinolinone and related compounds which are useful for treatment of disease(s) or disorder(s) associated with Retinoic acid receptor-related orphan receptors (RORs), and more particularly compounds that modulate the function of RORγ.

Each embodiment is provided by way of explanation of the invention, and not by way of limitation of the invention. In fact, it will be apparent to those skilled in the art that various modifications and variations can be made to the compounds, compositions, and methods described herein without departing from the scope or spirit of the invention. For instance, features illustrated or described as part of one embodiment can be applied to another embodiment to yield a still further embodiment. Thus it is intended that the present invention include such modifications and variations and their equivalents. Other objects, features, and aspects of the present invention are disclosed in, or are obvious from, the following detailed description. It is to be understood by one of ordinary skill in the art that the present discussion is a description of exemplary embodiments only, and is not to be construed as limiting the broader aspects of the present invention.

In certain embodiments, the present invention relates to compounds of formula (I):

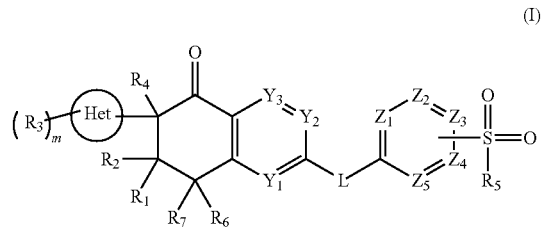

(I)

or a pharmaceutically acceptable salt or a stereoisomer thereof;
wherein,
ring Het is heterocyclyl;
each $Y_1$, $Y_2$ and $Y_3$ are independently $CR_a$ or N, wherein 0-2 of $Y_1$, $Y_2$ and $Y_3$ are N;
each $Z_1$, $Z_2$, $Z_3$, $Z_4$ and $Z_5$ are independently $CR_a$ or N, wherein 0-3 of $Z_1$, $Z_2$, $Z_3$, $Z_4$ and $Z_5$ are N;
L is *—$NR_b$—C(O)—$(CR_bR_c)_n$—, *—C(O)—$NR_b$—$(CR_bR_c)_n$—, *—$NR_b$—$S(O)_2$—$(CR_bR_c)_n$— or *—$S(O)_2$—$NR_b$—$(CR_bR_c)_n$—; wherein the group marked with * is connected to the ring containing $Y_1$, $Y_2$ and $Y_3$;
each $R_1$, $R_2$, $R_6$ and $R_7$ are independently hydrogen, halo, alkyl, hydroxy, hydroxyalkyl, cyano, alkoxy, haloalkyl, haloalkoxy, alkenyl, alkynyl, cycloalkyl, aryl, heteroaryl, —$COR_d$ or —$COOR_d$;
$R_3$ at each occurrence is independently hydroxy, halo, alkyl, alkylamino, alkoxy, haloalkyl, haloalkoxy or cycloalkyl; alternatively, two $R_3$ on the same carbon together form an oxo (=O) group;

$R_4$ is hydrogen, alkyl or alkoxy;

$R_5$ is alkyl, $-(CH_2)_n NR_b R_c$, hydroxyalkyl, cycloalkyl, aryl or heterocyclyl;

$R_a$ is hydrogen, alkyl, alkoxy, halo, cycloalkyl or aryl;

$R_b$ and $R_c$ are each independently hydrogen, alkyl or alkoxyalkyl;

alternatively, $R_b$ and $R_c$ on the same atom together form a ring;

$R_d$ is hydrogen, alkyl, alkoxy or cycloalkyl;

m is 0 to 3; and n is 0 to 3.

In certain embodiments, the present invention relates to compounds of formula (I) or a pharmaceutically acceptable salt or a stereoisomer thereof, wherein, ring Het is heterocyclyl;

$Y_1$, $Y_2$ and $Y_3$ are each independently $CR_a$ or N, wherein 0-2 of $Y_1$, $Y_2$ and $Y_3$ are N;

$Z_1$, $Z_2$, $Z_3$, $Z_4$ and $Z_5$ are each independently $CR_a$ or N, wherein 0-3 of $Z_1$, $Z_2$, $Z_3$, $Z_4$ and $Z_5$ are N;

L is *—$NR_b$—C(O)—$(CR_b R_c)_n$—; or *—C(O)—$NR_b$—$(CR_b R_c)_n$—; wherein the group marked with * is connected to the ring containing $Y_1$, $Y_2$ and $Y_3$;

$R_1$, $R_2$, $R_6$ and $R_7$ are each independently hydrogen, halo or alkyl;

$R_3$ at each occurrence is independently hydroxy, halo, alkyl, alkylamino, alkoxy, haloalkyl, haloalkoxy or cycloalkyl; alternatively, two $R_3$ on the same carbon together form an oxo (=O) group;

$R_4$ is hydrogen, alkyl or alkoxy;

$R_5$ is alkyl, $-(CH_2)_n NR_b R_c$ or hydroxyalkyl;

$R_a$ is hydrogen, alkyl, alkoxy, halo, cycloalkyl or aryl;

$R_b$ and $R_c$ are each independently hydrogen or alkyl;

alternatively, $R_b$ and $R_c$ on the same atom together form a ring;

m is 0 to 3; and n is 0 to 3.

In certain embodiments, the present invention relates to compounds of formula (IA):

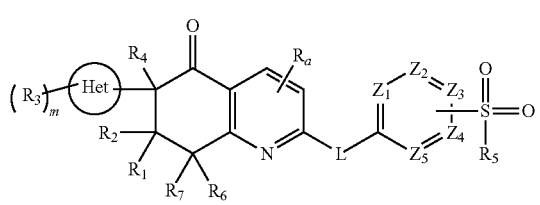

(IA)

or a pharmaceutically acceptable salt or a stereoisomer thereof;

wherein, ring Het, $R_1$, $R_2$, $R_3$, $R_4$, $R_5$, $R_6$, $R_7$, $R_a$, L, $Z_1$, $Z_2$, $Z_3$, $Z_4$, $Z_5$ and m are same as defined in formula (I).

In certain embodiments, the present invention relates to compounds of formula (IB):

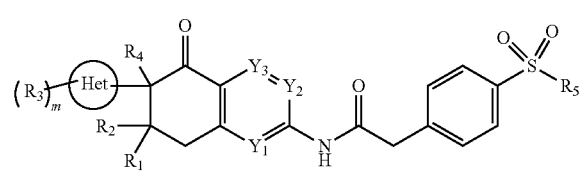

(IB)

or a pharmaceutically acceptable salt or a stereoisomer thereof, wherein, ring Het, $R_1$, $R_2$, $R_3$, $R_4$, $R_5$, $Y_1$, $Y_2$, $Y_3$ and m are same as defined in formula (I).

In certain embodiments, the present invention relates to compounds of formula (IC):

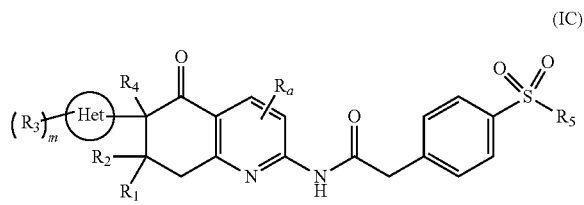

(IC)

or a pharmaceutically acceptable salt or a stereoisomer thereof;

wherein, ring Het, $R_1$, $R_2$, $R_3$, $R_4$, $R_5$, $R_a$ and m are same as defined in formula (I).

In certain embodiments, the present invention relates to compounds of formula (ID):

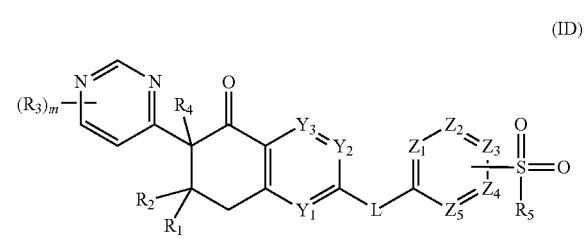

(ID)

or a pharmaceutically acceptable salt or a stereoisomer thereof;

wherein,

L, $R_1$, $R_2$, $R_3$, $R_4$, $R_5$, $Y_1$, $Y_2$, $Y_3$, $Z_1$, $Z_2$, $Z_3$, $Z_4$, $Z_5$ and m are same as defined in formula (I).

In certain embodiments, the present invention relates to compounds of formula (IE):

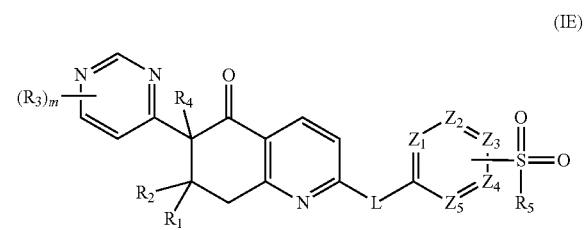

(IE)

or a pharmaceutically acceptable salt or a stereoisomer thereof;

wherein,

L, $R_1$, $R_2$, $R_3$, $R_4$, $R_5$, $Z_1$, $Z_2$, $Z_3$, $Z_4$, $Z_5$ and m are same as defined in formula (I).

In certain embodiments, the present invention relates to compounds of formula (IF):

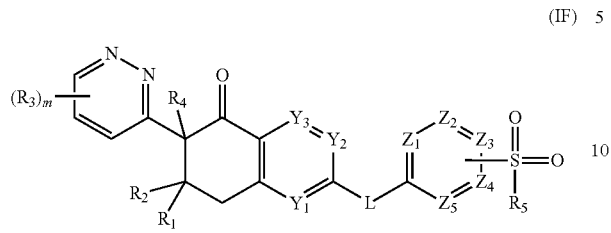

(IF)

or a pharmaceutically acceptable salt or a stereoisomer thereof;

wherein,

L, $R_1$, $R_2$, $R_3$, $R_4$, $R_5$, $Y_1$, $Y_2$, $Y_3$, $Z_1$, $Z_2$, $Z_3$, $Z_4$, $Z_5$ and m are same as defined in formula (I).

In certain embodiments, the present invention relates to compounds of formula (IG):

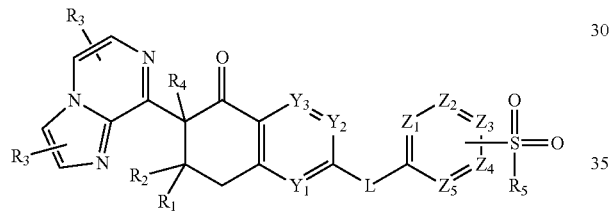

(IG)

or a pharmaceutically acceptable salt or a stereoisomer thereof;

wherein,

L, $R_1$, $R_2$, $R_3$, $R_4$, $R_5$, $Y_1$, $Y_2$, $Y_3$, $Z_1$, $Z_2$, $Z_3$, $Z_4$ and $Z_5$ are same as defined in formula (I).

In accordance with any of the foregoing embodiments, in certain embodiments, ring Het is monocyclic or bicyclic heterocyclic ring.

In yet further embodiments, the ring Het is pyridyl, pyridazinyl, pyridazinone, pyrimidinyl, pyrazinyl, pyrazolyl, imidazopyrazinyl, imidazopyridyl, pyrrolopyrazinyl, thienyl, benzodioxolyl, benzimidazolyl, imidazolyl, imidazopyridazinyl or tetrahydroisoquinolinonyl.

In yet further embodiments, the ring Het is pyrazinyl, pyridazinone, pyrazolyl, imidazopyridyl, pyrrolopyrazinyl, thienyl, benzodioxolyl, benzimidazolyl, imidazolyl or tetrahydroisoquinolinonyl.

In yet further embodiments, the ring Het is pyridyl.

In yet further embodiments, the ring Het is pyridazinyl.

In yet further embodiments, the ring Het is pyrimidinyl.

In yet further embodiments, the ring Het is imidazopyrazinyl.

In yet further embodiments, the ring Het comprises its N-Oxides thereof.

In certain embodiments, 0-2 of $Y_1$, $Y_2$ and $Y_3$ are N.

In yet further embodiments,

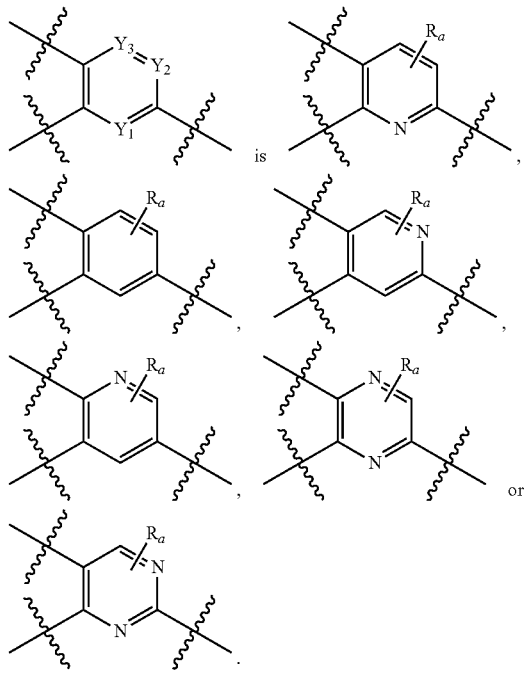

is

In certain embodiments, each $Z_1$, $Z_2$, $Z_3$, $Z_4$ and $Z_5$ are CH.

In yet further embodiments,

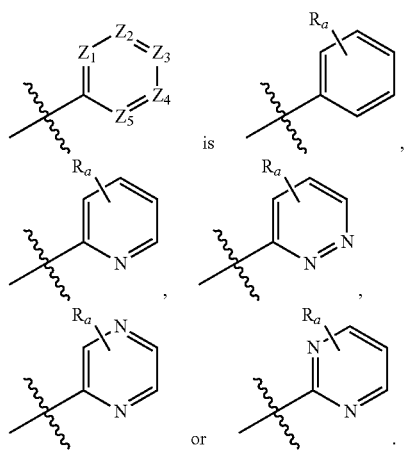

is

In yet further embodiments, L is *—NHCOCH$_2$— or *—CONHCH$_2$— wherein the group marked with * is connected to the ring containing $Y_1$, $Y_2$ and $Y_3$.

In certain embodiments of formula (I), (IA), (IB), (IC), (ID), (IE), (IF) or (IG), $R_1$ and $R_2$ are independently hydrogen.

In certain embodiments of formula (I), (IA), (IB), (IC), (ID), (IE), (IF) or (IG), $R_1$ and $R_2$ are independently alkyl, in another embodiment the alkyl is $C_1$-$C_6$ alkyl (e.g. methyl, ethyl or isopropyl).

In certain embodiments of formula (I), (IA), (IB), (IC), (ID), (IE), (IF) or (IG), $R_1$ is hydrogen and $R_2$ is alkyl, in another embodiment the alkyl is $C_1$-$C_6$ alkyl (e.g. methyl).

In certain embodiments of formula (I), (IA), (IB), (IC), (ID), (IE), (IF) or (IG), $R_3$ is alkoxy, in another embodiment the alkoxy is methoxy or isopropyloxy.

In certain embodiments of formula (I), (IA), (IB), (IC), (ID), (IE), (IF) or (IG), $R_3$ is haloalkyl, in another embodiment the haloalkyl is —$CF_3$.

In certain embodiments of formula (I), (IA), (IB), (IC), (ID), (IE), (IF) or (IG), $R_3$ is hydroxy.

In certain embodiments of formula (I), (IA), (IB), (IC), (ID), (IE), (IF) or (IG), $R_3$ is alkyl, in another embodiment the alkyl is $C_1$-$C_6$ alkyl (e.g. methyl, ethyl or isopropyl).

In certain embodiments of formula (I), (IA), (IB), (IC), (ID), (IE), (IF) or (IG), $R_3$ is halo, in another embodiment the halo is —F or —Cl.

In certain embodiments of formula (I), (IA), (IB), (IC), (ID), (IE), (IF) or (IG), two $R_3$ on the same carbon together form an oxo (=O) group.

In certain embodiments of formula (I), (IA), (IB), (IC), (ID), (IE), (IF) or (IG), $R_3$ is haloalkyloxy, in another embodiment the haloalkyloxy is —$OCF_3$.

In certain embodiments of formula (I), (IA), (IB), (IC), (ID), (IE), (IF) or (IG), $R_3$ is cycloalkyl, in another embodiment the cycloalkyl is cyclopropyl.

In certain embodiments of formula (I), (IA), (IB), (IC), (ID), (IE), (IF) or (IG), $R_4$ is alkyl, in another embodiment the alkyl is $C_1$-$C_6$ alkyl (e.g. —$CH_3$ or —$C_2H_5$).

In certain embodiments of formula (I), (IA), (IB), (IC), (ID), (IE), (IF) or (IG), $R_4$ is hydrogen.

In certain embodiments of formula (I), (IA), (IB), (IC), (ID), (IE), (IF) or (IG), $R_5$ is alkyl, in another embodiment the alkyl is $C_1$-$C_6$ alkyl (e.g. —$CH_3$ or —$C_2H_5$).

In certain embodiments of formula (I), (IA), (IB), (IC), (ID), (IE), (IF) or (IG), $R_a$ is hydrogen.

In certain embodiments of formula (I), (IA), (IB), (IC), (ID), (IE), (IF) or (IG), $R_a$ is alkyl, in another embodiment the alkyl is $C_1$-$C_6$ alkyl (e.g. methyl or ethyl).

In certain embodiments of formula (I), (IA), (IB), (IC), (ID), (IE), (IF) or (IG), $R_a$ is halo, in another embodiment the halo is fluoro.

In certain embodiments of formula (I), (IA), (IB), (IC), (ID), (IE), (IF) or (IG), $R_6$ and $R_7$ are independently hydrogen.

In certain embodiments of formula (I), (IA), (IB), (IC), (ID), (IE), (IF) or (IG), m is 1 or 2.

In certain embodiments, the present invention provides a compound selected from the group consisting of:

| Compound No. | IUPAC Name |
| --- | --- |
| 1 | N-(4,6-dimethyl-5-oxo-6-(pyridin-2-yl)-5,6,7,8-tetrahydroquinolin-2-yl)-2-(4-(ethylsulfonyl)phenyl)acetamide; |
| 2 | 2-(4-(ethylsulfonyl)phenyl)-N-(6-(6-methoxypyridin-3-yl)-6-methyl-5-oxo-5,6,7,8-tetrahydroquinolin-2-yl)acetamide; |
| 3 | 2-(4-(ethylsulfonyl)phenyl)-N-(6-methyl-5-oxo-6-(6-(trifluoromethyl)pyridin-3-yl)-5,6,7,8-tetrahydroquinolin-2-yl)acetamide; |
| 4 | 2-(4-(ethylsulfonyl)phenyl)-N-(6-(5-methoxypyridin-2-yl)-7,7-dimethyl-5-oxo-5,6,7,8-tetrahydroquinolin-2-yl)acetamide; |
| 5 | 2-(4-(ethylsulfonyl)phenyl)-N-(6-(4-methoxypyridin-2-yl)-6-methyl-5-oxo-5,6,7,8-tetrahydroquinolin-2-yl)acetamide; |
| 6 | 2-(4-(ethylsulfonyl)phenyl)-N-(6-(imidazo[1,2-a]pyrazin-8-yl)-6-methyl-5-oxo-5,6,7,8-tetrahydroquinolin-2-yl)acetamide; |
| 7 | N-(6-(2,6-dimethylpyrimidin-4-yl)-6-methyl-5-oxo-5,6,7,8-tetrahydroquinolin-2-yl)-2-(4-(ethylsulfonyl)phenyl)acetamide; |
| 8 | N-(6-methyl-5-oxo-6-(5-(trifluoromethyl)pyridin-2-yl)-5,6,7,8-tetrahydroquinolin-2-yl)-2-(4-(methylsulfonyl)phenyl)acetamide; |
| 9 | 2-(4-(ethylsulfonyl)phenyl)-N-(6-methyl-6-(2-methylimidazo[1,2-a]pyrazin-8-yl)-5-oxo-5,6,7,8-tetrahydroquinolin-2-yl)acetamide; |
| 10 | N-(6-(5-chloropyridin-2-yl)-6-methyl-5-oxo-5,6,7,8-tetrahydroquinolin-2-yl)-2-(4-(methylsulfonyl)phenyl)acetamide; |
| 11 | 2-(4-(ethylsulfonyl)phenyl)-N-(6-(imidazo[1,2-a]pyrazin-8-yl)-3,6-dimethyl-5-oxo-5,6,7,8-tetrahydroquinolin-2-yl)acetamide; |
| 12 | 2-(4-(ethylsulfonyl)phenyl)-N-(6-(6-methoxypyridazin-3-yl)-6-methyl-5-oxo-5,6,7,8-tetrahydroquinolin-2-yl)acetamide; |
| 13 | N-(6-(imidazo[1,2-a]pyridin-8-yl)-6-methyl-5-oxo-5,6,7,8-tetrahydroquinolin-2-yl)-2-(4-(methylsulfonyl)phenyl)acetamide; |
| 14 | N-(6-ethyl-6-(imidazo[1,2-a]pyrazin-8-yl)-5-oxo-5,6,7,8-tetrahydroquinolin-2-yl)-2-(4-(ethylsulfonyl)phenyl)acetamide; |
| 15 | 2-(4-(ethylsulfonyl)phenyl)-N-(6-methyl-5-oxo-6-(pyrrolo[1,2-a]pyrazin-1-yl)-5,6,7,8-tetrahydroquinolin-2-yl)acetamide; |
| 16 | 2-(4-(ethylsulfonyl)phenyl)-N-(6-methyl-6-(6-methylimidazo[1,2-a]pyrazin-8-yl)-5-oxo-5,6,7,8-tetrahydroquinolin-2-yl)acetamide; |
| 17 | 2-(4-(ethylsulfonyl)phenyl)-N-(6-(6-methoxypyridin-3-yl)-4,6-dimethyl-5-oxo-5,6,7,8-tetrahydroquinolin-2-yl)acetamide; |
| 18 | N-(4,6-dimethyl-5-oxo-6-(pyridin-3-yl)-5,6,7,8-tetrahydroquinolin-2-yl)-2-(4-(ethylsulfonyl)phenyl)acetamide; |
| 19 | 2-(4-(ethylsulfonyl)phenyl)-N-(6-(6-methoxypyridin-2-yl)-4,6-dimethyl-5-oxo-5,6,7,8-tetrahydroquinolin-2-yl)acetamide; |
| 20 | 2-(4-(ethylsulfonyl)phenyl)-N-(6-(5-methoxypyridin-2-yl)-4,6-dimethyl-5-oxo-5,6,7,8-tetrahydroquinolin-2-yl)acetamide; |
| 21 | 2-(4-(ethylsulfonyl)phenyl)-N-(6-(4-methoxypyrimidin-2-yl)-4,6-dimethyl-5-oxo-5,6,7,8-tetrahydroquinolin-2-yl)acetamide; |
| 22 | 2-(4-(ethylsulfonyl)phenyl)-N-(6-(4-methoxypyridin-2-yl)-4,6-dimethyl-5-oxo-5,6,7,8-tetrahydroquinolin-2-yl)acetamide; |
| 23 | 2-(4-(ethylsulfonyl)phenyl)-N-(6-(3-fluoropyridin-2-yl)-4,6-dimethyl-5-oxo-5,6,7,8-tetrahydroquinolin-2-yl)acetamide; |
| 24 | N-(6-(5-chloro-3-methoxypyridin-2-yl)-4,6-dimethyl-5-oxo-5,6,7,8-tetrahydroquinolin-2-yl)-2-(4-(ethylsulfonyl)phenyl)acetamide; |
| 25 | 2-(4-(ethylsulfonyl)phenyl)-N-(6-(2-methoxypyrimidin-5-yl)-4,6-dimethyl-5-oxo-5,6,7,8-tetrahydroquinolin-2-yl)acetamide; |

-continued

| Compound No. | IUPAC Name |
|---|---|
| 26 | 2-(4-(ethylsulfonyl)phenyl)-N-(6-(imidazo[1,2-a]pyrazin-8-yl)-4,6-dimethyl-5-oxo-5,6,7,8-tetrahydroquinolin-2-yl)acetamide; |
| 27 | 2-(4-(ethylsulfonyl)phenyl)-N-(6-(5-methoxypyrazin-2-yl)-4,6-dimethyl-5-oxo-5,6,7,8-tetrahydroquinolin-2-yl)acetamide; |
| 28 | N-(6-(2,6-dimethylpyrimidin-4-yl)-4,6-dimethyl-5-oxo-5,6,7,8-tetrahydroquinolin-2-yl)-2-(4-(ethylsulfonyl)phenyl)acetamide; |
| 29 | N-(6-(4,6-dimethylpyrimidin-2-yl)-4,6-dimethyl-5-oxo-5,6,7,8-tetrahydroquinolin-2-yl)-2-(4-(ethylsulfonyl)phenyl)acetamide; |
| 30 | 2-(4-(ethylsulfonyl)phenyl)-N-(6-(2-methoxypyrimidin-4-yl)-4,6-dimethyl-5-oxo-5,6,7,8-tetrahydroquinolin-2-yl)acetamide; |
| 31 | 2-(4-(ethylsulfonyl)phenyl)-N-(6-(6-methoxypyridazin-3-yl)-4,6-dimethyl-5-oxo-5,6,7,8-tetrahydroquinolin-2-yl)acetamide; |
| 32 | N-(4,6-dimethyl-5-oxo-6-(5-(trifluoromethyl)pyridin-2-yl)-5,6,7,8-tetrahydroquinolin-2-yl)-2-(4-(methylsulfonyl)phenyl)acetamide; |
| 33 | N-(6-(imidazo[1,2-a]pyrazin-8-yl)-4,6-dimethyl-5-oxo-5,6,7,8-tetrahydroquinolin-2-yl)-2-(4-(methylsulfonyl)phenyl)acetamide; |
| 34 | N-(4,6-dimethyl-6-(6-methylpyridazin-3-yl)-5-oxo-5,6,7,8-tetrahydroquinolin-2-yl)-2-(4-(ethylsulfonyl)phenyl)acetamide; |
| 35 | N-(6-(6-methoxypyridazin-3-yl)-4,6-dimethyl-5-oxo-5,6,7,8-tetrahydroquinolin-2-yl)-2-(4-(methylsulfonyl)phenyl)acetamide; |
| 36 | 2-(4-(ethylsulfonyl)phenyl)-N-(6-(4-hydroxypyrimidin-2-yl)-4,6-dimethyl-5-oxo-5,6,7,8-tetrahydroquinolin-2-yl)acetamide; |
| 37 | 2-(4-(ethylsulfonyl)phenyl)-N-(6-(2-hydroxypyridin-4-yl)-4,6-dimethyl-5-oxo-5,6,7,8-tetrahydroquinolin-2-yl)acetamide; |
| 38 | N-(6-(5-chloro-3-hydroxypyridin-2-yl)-4,6-dimethyl-5-oxo-5,6,7,8-tetrahydroquinolin-2-yl)-2-(4-(ethylsulfonyl)phenyl)acetamide; |
| 39 | 2-(4-(ethylsulfonyl)phenyl)-N-(6-(6-hydroxypyridin-2-yl)-4,6-dimethyl-5-oxo-5,6,7,8-tetrahydroquinolin-2-yl)acetamide; |
| 40 | 2-(4-(ethylsulfonyl)phenyl)-N-(6-(6-hydroxypyridin-3-yl)-6-methyl-5-oxo-5,6,7,8-tetrahydroquinolin-2-yl)acetamide; |
| 41 | N-(6-(6-ethylpyridazin-3-yl)-6-methyl-5-oxo-5,6,7,8-tetrahydroquinolin-2-yl)-2-(4-(ethylsulfonyl)phenyl)acetamide; |
| 42 | N-(6-(benzo[d][1,3]dioxol-5-yl)-4,6-dimethyl-5-oxo-5,6,7,8-tetrahydroquinolin-2-yl)-2-(4-(ethylsulfonyl)phenyl)acetamide; |
| 43 | N-(4,6-dimethyl-6-(1-methyl-1H-benzo[d]imidazol-5-yl)-5-oxo-5,6,7,8-tetrahydroquinolin-2-yl)-2-(4-(ethylsulfonyl)phenyl)acetamide; |
| 44 | N-(4,6-dimethyl-6-(2-methyl-1-oxo-1,2,3,4-tetrahydroisoquinolin-7-yl)-5-oxo-5,6,7,8-tetrahydroquinolin-2-yl)-2-(4-(ethylsulfonyl)phenyl)acetamide; |
| 45 | 2-(4-(ethylsulfonyl)phenyl)-N-(6-methyl-6-(5-methylthiophen-2-yl)-5-oxo-5,6,7,8-tetrahydroquinolin-2-yl)acetamide; |
| 46 | N-(6-(3,5-dimethyl-1H-pyrazol-1-yl)-6-methyl-5-oxo-5,6,7,8-tetrahydroquinolin-2-yl)-2-(4-(ethylsulfonyl)phenyl)acetamide; |
| 47 | 2-(4-(ethylsulfonyl)phenyl)-N-(6-methyl-5-oxo-6-(1H-pyrazol-1-yl)-5,6,7,8-tetrahydroquinolin-2-yl)acetamide; |
| 48 | 2-(4-(ethylsulfonyl)phenyl)-N-(6-(imidazo[1,2-a]pyrazin-8-yl)-6,8-dimethyl-5-oxo-5,6,7,8-tetrahydroquinolin-2-yl)acetamide; |
| 49 | 2-(4-(ethylsulfonyl)phenyl)-N-(6-methyl-6-(3-methylimidazo[1,2-a]pyrazin-8-yl)-5-oxo-5,6,7,8-tetrahydroquinolin-2-yl)acetamide; |
| 50 | 2-(4-(ethylsulfonyl)phenyl)-N-(6-(2-isopropylpyrimidin-4-yl)-6-methyl-5-oxo-5,6,7,8-tetrahydroquinolin-2-yl)acetamide; |
| 51 | N-(6-(2,6-dimethylimidazo[1,2-a]pyrazin-8-yl)-6-methyl-5-oxo-5,6,7,8-tetrahydroquinolin-2-yl)-2-(4-(ethylsulfonyl)phenyl)acetamide; |
| 52 | N-(4,6-dimethyl-6-(2-methylimidazo[1,2-a]pyrazin-8-yl)-5-oxo-5,6,7,8-tetrahydroquinolin-2-yl)-2-(4-(ethylsulfonyl)phenyl)acetamide; |
| 53 | N-(4,6-dimethyl-5-oxo-6-(6-(trifluoromethyl)pyridazin-3-yl)-5,6,7,8-tetrahydroquinolin-2-yl)-2-(4-(ethylsulfonyl)phenyl)acetamide; |
| 54 | 2-(4-(ethylsulfonyl)phenyl)-N-(6-(imidazo[1,2-a]pyrazin-8-yl)-7-methyl-5-oxo-5,6,7,8-tetrahydroquinolin-2-yl)acetamide; |
| 55 | 2-(4-(ethylsulfonyl)phenyl)-N-(6-methyl-5-oxo-6-(6-(trifluoromethyl)pyridazin-3-yl)-5,6,7,8-tetrahydroquinolin-2-yl)acetamide; |
| 56 | 2-(4-(ethylsulfonyl)phenyl)-N-(6-(5-methoxypyrimidin-2-yl)-6-methyl-5-oxo-5,6,7,8-tetrahydroquinolin-2-yl)acetamide; |
| 57 | 2-(4-(ethylsulfonyl)phenyl)-N-(6-(6-isopropoxypyridazin-3-yl)-6-methyl-5-oxo-5,6,7,8-tetrahydroquinolin-2-yl)acetamide; |
| 58 | 2-(4-(ethylsulfonyl)-2-fluorophenyl)-N-(6-methyl-6-(2-methylimidazo[1,2-a]pyrazin-8-yl)-5-oxo-5,6,7,8-tetrahydroquinolin-2-yl)acetamide; |
| 59 | N-(6-methyl-6-(2-methylimidazo[1,2-a]pyrazin-8-yl)-5-oxo-5,6,7,8-tetrahydroquinolin-2-yl)-2-(4-(methylsulfonyl)phenyl)acetamide; |
| 60 | 2-(4-(ethylsulfonyl)phenyl)-N-(6-(5-isopropylpyrazin-2-yl)-6-methyl-5-oxo-5,6,7,8-tetrahydroquinolin-2-yl)acetamide; |
| 61 | 2-(4-(ethylsulfonyl)phenyl)-N-(6-(5-methoxypyrimidin-2-yl)-4,6-dimethyl-5-oxo-5,6,7,8-tetrahydroquinolin-2-yl)acetamide; |
| 62 | 2-(4-(ethylsulfonyl)phenyl)-N-(6-(6-isopropylpyridazin-3-yl)-6-methyl-5-oxo-5,6,7,8-tetrahydroquinolin-2-yl)acetamide; |
| 63 | N-(6-(6-ethylpyridazin-3-yl)-4,6-dimethyl-5-oxo-5,6,7,8-tetrahydroquinolin-2-yl)-2-(4-(ethylsulfonyl)phenyl)acetamide; |

-continued

| Compound No. | IUPAC Name |
|---|---|
| 64 | 2-(4-(ethylsulfonyl)phenyl)-N-(6-(2-methoxy-6-methylpyrimidin-4-yl)-6-methyl-5-oxo-5,6,7,8-tetrahydroquinolin-2-yl)acetamide; |
| 65 | 2-(4-(ethylsulfonyl)phenyl)-N-(6-(6-methoxy-2-methylpyrimidin-4-yl)-6-methyl-5-oxo-5,6,7,8-tetrahydroquinolin-2-yl)acetamide; |
| 66 | 2-(4-(ethylsulfonyl)phenyl)-N-(6-(3-fluoro-2-methylimidazo[1,2-a]pyrazin-8-yl)-6-methyl-5-oxo-5,6,7,8-tetrahydroquinolin-2-yl)acetamide; |
| 67 | 2-(4-(ethylsulfonyl)phenyl)-N-(6-methyl-6-(2-methyl-6-(trifluoromethyl)-pyrimidin-4-yl)-5-oxo-5,6,7,8-tetrahydroquinolin-2-yl)acetamide; |
| 68 | 2-(4-(ethylsulfonyl)phenyl)-N-(6-methyl-6-(5-methylimidazo[1,2-a]pyrazin-8-yl)-5-oxo-5,6,7,8-tetrahydroquinolin-2-yl)acetamide; |
| 69 | N-(6-(2,6-dimethylpyrimidin-4-yl)-7,7-dimethyl-5-oxo-5,6,7,8-tetrahydroquinolin-2-yl)-2-(4-(ethylsulfonyl)phenyl)acetamide; |
| 70 | N-(4,6-dimethyl-6-(1-methyl-6-oxo-1,6-dihydropyridazin-3-yl)-5-oxo-5,6,7,8-tetrahydroquinolin-2-yl)-2-(4-(ethylsulfonyl)phenyl)acetamide; |
| 71 | N-(6-(3-cyclopropylimidazo[1,2-a]pyrazin-8-yl)-6-methyl-5-oxo-5,6,7,8-tetrahydroquinolin-2-yl)-2-(4-(ethylsulfonyl)phenyl)acetamide; |
| 72 | 2-(4-(ethylsulfonyl)phenyl)-N-(6-methyl-5-oxo-6-(2-(trifluoromethyl)-imidazo[1,2-a]pyrazin-8-yl)-5,6,7,8-tetrahydroquinolin-2-yl)acetamide; |
| 73 | 2-(4-(ethylsulfonyl)phenyl)-N-(6-(5-methoxypyridazin-3-yl)-4,6-dimethyl-5-oxo-5,6,7,8-tetrahydroquinolin-2-yl)acetamide; |
| 74 | 2-(4-(ethylsulfonyl)phenyl)-N-(6-methyl-5-oxo-6-(3-(trifluoromethyl)-imidazo[1,2-a]pyrazin-8-yl)-5,6,7,8-tetrahydroquinolin-2-yl)acetamide; |
| 75 | N-(4,6-dimethyl-6-(2-methylimidazo[1,2-b]pyridazin-6-yl)-5-oxo-5,6,7,8-tetrahydroquinolin-2-yl)-2-(4-(ethylsulfonyl)phenyl)acetamide; |
| 76 | N-(6-(5-cyclopropyl-6-methoxypyridazin-3-yl)-4,6-dimethyl-5-oxo-5,6,7,8-tetrahydroquinolin-2-yl)-2-(4-(ethylsulfonyl)phenyl)acetamide; |
| 77 | 2-(4-(ethylsulfonyl)phenyl)-N-(6-(imidazo[1,2-b]pyridazin-6-yl)-4,6-dimethyl-5-oxo-5,6,7,8-tetrahydroquinolin-2-yl)acetamide; |
| 78 | 2-(4-(ethylsulfonyl)phenyl)-N-(6-methyl-6-(6-methyl-2-(trifluoromethyl)-pyrimidin-4-yl)-5-oxo-5,6,7,8-tetrahydroquinolin-2-yl)acetamide; |
| 79 | N-(6-(2,6-dimethylpyrimidin-4-yl)-6-methyl-5-oxo-5,6,7,8-tetrahydroquinolin-2-yl)-2-(5-(ethylsulfonyl)pyridin-2-yl)acetamide; |
| 80 | 2-(5-(ethylsulfonyl)pyridin-2-yl)-N-(6-(6-methoxypyridazin-3-yl)-4,6-dimethyl-5-oxo-5,6,7,8-tetrahydroquinolin-2-yl)acetamide; |
| 81 | N-(6-(2,6-dimethylpyrimidin-4-yl)-6,7-dimethyl-5-oxo-5,6,7,8-tetrahydroquinolin-2-yl)-2-(4-(ethylsulfonyl)phenyl)acetamide; |
| 82 | N-(6-(2,6-dimethylpyrimidin-4-yl)-7-methyl-5-oxo-5,6,7,8-tetrahydroquinolin-2-yl)-2-(4-(ethylsulfonyl)phenyl)acetamide; |
| 83 | N-(7-(2,6-dimethylpyrimidin-4-yl)-7-methyl-8-oxo-5,6,7,8-tetrahydroisoquinolin-3-yl)-2-(4-(ethylsulfonyl)phenyl)acetamide; |
| 84 | 2-(4-(ethylsulfonyl)phenyl)-N-(6-(2-hydroxypyridin-3-yl)-4,6-dimethyl-5-oxo-5,6,7,8-tetrahydroquinolin-2-yl)acetamide; |
| 85 | 2-(4-(ethylsulfonyl)phenyl)-N-(6-(3-hydroxypyridin-2-yl)-4,6-dimethyl-5-oxo-5,6,7,8-tetrahydroquinolin-2-yl)acetamide; |
| 86 | 2-(4-(ethylsulfonyl)phenyl)-N-(6-(2-hydroxy-4-methylpyridin-3-yl)-4,6-dimethyl-5-oxo-5,6,7,8-tetrahydroquinolin-2-yl)acetamide; |
| 87 | 2-(4-(ethylsulfonyl)phenyl)-N-(6-(3-hydroxypyridin-2-yl)-7,7-dimethyl-5-oxo-5,6,7,8-tetrahydroquinolin-2-yl)acetamide; |
| 88 | 2-(4-(ethylsulfonyl)phenyl)-N-(6-(5-hydroxypyridin-2-yl)-4,6-dimethyl-5-oxo-5,6,7,8-tetrahydroquinolin-2-yl)acetamide; |
| 89 | N-(6-(3-hydroxypyridin-2-yl)-4,6-dimethyl-5-oxo-5,6,7,8-tetrahydroquinolin-2-yl)-2-(4-(methylsulfonyl)phenyl)acetamide; |
| 90 | 2-(4-(ethylsulfonyl)phenyl)-N-(6-(5-hydroxypyridin-2-yl)-7,7-dimethyl-5-oxo-5,6,7,8-tetrahydroquinolin-2-yl)acetamide; |
| 91 | 2-(4-(ethylsulfonyl)phenyl)-N-(6-(3-hydroxypyridin-2-yl)-7-methyl-5-oxo-5,6,7,8-tetrahydroquinolin-2-yl)acetamide; |
| 92 | N-(6-(5-chloroimidazo[1,2-a]pyrazin-8-yl)-6-methyl-5-oxo-5,6,7,8-tetrahydroquinolin-2-yl)-2-(4-(ethylsulfonyl)phenyl)acetamide; |
| 93 | N-(6-(6-chloropyridazin-3-yl)-6-methyl-5-oxo-5,6,7,8-tetrahydroquinolin-2-yl)-2-(4-(ethylsulfonyl)phenyl)acetamide; |
| 94 | 3-(2-(2-(4-(ethylsulfonyl)phenyl)acetamido)-4,6-dimethyl-5-oxo-5,6,7,8-tetrahydroquinolin-6-yl)-6-methoxypyridazine 1-oxide; |
| 95 | 2-(4-(ethylsulfonyl)phenyl)-N-(6-(6-methoxy-4-methylpyridazin-3-yl)-4,6-dimethyl-5-oxo-5,6,7,8-tetrahydroquinolin-2-yl)acetamide; |
| 96 | 2-(4-(ethylsulfonyl)phenyl)-N-(6-(6-methoxy-5-methylpyridazin-3-yl)-4,6-dimethyl-5-oxo-5,6,7,8-tetrahydroquinolin-2-yl)acetamide; |
| 97 | 2-(4-(ethylsulfonyl)phenyl)-N-(6-(3-fluoroimidazo[1,2-a]pyrazin-8-yl)-6-methyl-5-oxo-5,6,7,8-tetrahydroquinolin-2-yl)acetamide; |
| 98 | N-(6-(6-(dimethylamino)pyridazin-3-yl)-4,6-dimethyl-5-oxo-5,6,7,8-tetrahydroquinolin-2-yl)-2-(4-(ethylsulfonyl)phenyl)acetamide; |
| 99 | 6-(2,6-dimethylpyrimidin-4-yl)-N-(4-(ethylsulfonyl)benzyl)-6-methyl-5-oxo-5,6,7,8-tetrahydroquinoline-2-carboxamide; |
| 100 | N-(6-(2,6-dimethylpyrimidin-4-yl)-6-methyl-5-oxo-5,6,7,8-tetrahydronaphthalen-2-yl)-2-(4-(ethylsulfonyl)phenyl)acetamide; |
| 101 | 2-(4-(ethylsulfonyl)phenyl)-N-(6-(3-hydroxypyridin-2-yl)-4,6-dimethyl-5-oxo-5,6,7,8-tetrahydroquinolin-2-yl)acetamide; (Isomer-1 of Compound-84); |

| Compound No. | IUPAC Name |
|---|---|
| 102 | 2-(4-(ethylsulfonyl)phenyl)-N-(6-(3-hydroxypyridin-2-yl)-4,6-dimethyl-5-oxo-5,6,7,8-tetrahydroquinolin-2-yl)acetamide; (Isomer-2 of Compound-84); |
| 103 | N-(6-(2,6-dimethylpyrimidin-4-yl)-6-methyl-5-oxo-5,6,7,8-tetrahydroquinolin-2-yl)-2-(4-(ethylsulfonyl)phenyl)acetamide; (Isomer-1 of Compound-7); |
| 104 | N-(6-(2,6-dimethylpyrimidin-4-yl)-6-methyl-5-oxo-5,6,7,8-tetrahydroquinolin-2-yl)-2-(4-(ethylsulfonyl)phenyl)acetamide; (Isomer-2 of Compound-7); |
| 105 | 2-(4-(ethylsulfonyl)phenyl)-N-(6-methyl-6-(2-methylimidazo[1,2-a]pyrazin-8-yl)-5-oxo-5,6,7,8-tetrahydroquinolin-2-yl)acetamide; (Isomer-1 of Compound-9); |
| 106 | 2-(4-(ethylsulfonyl)phenyl)-N-(6-methyl-6-(2-methylimidazo[1,2-a]pyrazin-8-yl)-5-oxo-5,6,7,8-tetrahydroquinolin-2-yl)acetamide; (Isomer-2 of Compound-9); |
| 107 | N-(6-(2,6-dimethylpyrimidin-4-yl)-4,6-dimethyl-5-oxo-5,6,7,8-tetrahydroquinolin-2-yl)-2-(4-(ethylsulfonyl)phenyl)acetamide; (Isomer-1 of Compound-28); |
| 108 | N-(6-(2,6-dimethylpyrimidin-4-yl)-4,6-dimethyl-5-oxo-5,6,7,8-tetrahydroquinolin-2-yl)-2-(4-(ethylsulfonyl)phenyl)acetamide; (Isomer-2 of Compound-28); |
| 109 | 2-(4-(ethylsulfonyl)phenyl)-N-(6-(6-methoxypyridazin-3-yl)-4,6-dimethyl-5-oxo-5,6,7,8-tetrahydroquinolin-2-yl)acetamide; (Isomer-1 of Compound-31); |
| 110 | 2-(4-(ethylsulfonyl)phenyl)-N-(6-(6-methoxypyridazin-3-yl)-4,6-dimethyl-5-oxo-5,6,7,8-tetrahydroquinolin-2-yl)acetamide; (Isomer-2 of Compound-31); |
| 111 | 2-(4-(ethylsulfonyl)phenyl)-N-(6-(5-methoxypyrimidin-2-yl)-6-methyl-5-oxo-5,6,7,8-tetrahydroquinolin-2-yl)acetamide; (Isomer-1 of Compound-56); |
| 112 | 2-(4-(ethylsulfonyl)phenyl)-N-(6-(5-methoxypyrimidin-2-yl)-6-methyl-5-oxo-5,6,7,8-tetrahydroquinolin-2-yl)acetamide; (Isomer-2 of Compound-56); |
| 113 | 2-(4-(ethylsulfonyl)phenyl)-N-(6-methyl-6-(3-methylimidazo[1,2-a]pyrazin-8-yl)-5-oxo-5,6,7,8-tetrahydroquinolin-2-yl)acetamide; (Isomer-1 of Compound-49); |
| 114 | 2-(4-(ethylsulfonyl)phenyl)-N-(6-methyl-6-(3-methylimidazo[1,2-a]pyrazin-8-yl)-5-oxo-5,6,7,8-tetrahydroquinolin-2-yl)acetamide; (Isomer-2 of Compound-49); |
| 115 | 2-(4-(ethylsulfonyl)phenyl)-N-(6-(6-methoxy-2-methylpyrimidin-4-yl)-6-methyl-5-oxo-5,6,7,8-tetrahydroquinolin-2-yl)acetamide; (Isomer-1 of Compound-65); |
| 116 | 2-(4-(ethylsulfonyl)phenyl)-N-(6-(6-methoxy-2-methylpyrimidin-4-yl)-6-methyl-5-oxo-5,6,7,8-tetrahydroquinolin-2-yl)acetamide; (Isomer-2 of Compound-65); |
| 117 | 2-(4-(ethylsulfonyl)phenyl)-N-(6-methyl-6-(6-methylimidazo[1,2-a]pyrazin-8-yl)-5-oxo-5,6,7,8-tetrahydroquinolin-2-yl)acetamide; (Isomer-1 of Compound-16); |
| 118 | 2-(4-(ethylsulfonyl)phenyl)-N-(6-methyl-6-(6-methylimidazo[1,2-a]pyrazin-8-yl)-5-oxo-5,6,7,8-tetrahydroquinolin-2-yl)acetamide; (Isomer-2 of Compound-16); |
| 119 | 2-(4-(ethylsulfonyl)phenyl)-N-(6-(2-methoxy-6-methylpyrimidin-4-yl)-6-methyl-5-oxo-5,6,7,8-tetrahydroquinolin-2-yl)acetamide; (Isomer-1 of Compound-64); |
| 120 | 2-(4-(ethylsulfonyl)phenyl)-N-(6-(2-methoxy-6-methylpyrimidin-4-yl)-6-methyl-5-oxo-5,6,7,8-tetrahydroquinolin-2-yl)acetamide; (Isomer-2 of Compound-64); |
| 121 | 2-(4-(ethylsulfonyl)phenyl)-N-(6-methyl-5-oxo-6-(3-(trifluoromethyl)imidazo[1,2-a]pyrazin-8-yl)-5,6,7,8-tetrahydroquinolin-2-yl)acetamide; (Isomer-1 of Compound-74); |
| 122 | 2-(4-(ethylsulfonyl)phenyl)-N-(6-methyl-5-oxo-6-(3-(trifluoromethyl)imidazo[1,2-a]pyrazin-8-yl)-5,6,7,8-tetrahydroquinolin-2-yl)acetamide; (Isomer-2 of Compound-74); |
| 123 | N-(6-(2,6-dimethylpyrimidin-4-yl)-6-methyl-5-oxo-5,6,7,8-tetrahydroquinolin-2-yl)-2-(5-(ethylsulfonyl)pyridin-2-yl)acetamide; (Isomer-1 of Compound-79); |
| 124 | N-(6-(2,6-dimethylpyrimidin-4-yl)-6-methyl-5-oxo-5,6,7,8-tetrahydroquinolin-2-yl)-2-(5-(ethylsulfonyl)pyridin-2-yl)acetamide; (Isomer-2 of Compound-79); |
| 125 | 6-(2,6-dimethylpyrimidin-4-yl)-N-(4-(ethylsulfonyl)benzyl)-6-methyl-5-oxo-5,6,7,8-tetrahydroquinoline-2-carboxamide; (Isomer-1 of Compound-99); |
| 126 | 6-(2,6-dimethylpyrimidin-4-yl)-N-(4-(ethylsulfonyl)benzyl)-6-methyl-5-oxo-5,6,7,8-tetrahydroquinoline-2-carboxamide; (Isomer-2 of Compound-99); |
| 127 | N-(7-(2,6-dimethylpyrimidin-4-yl)-7-methyl-8-oxo-5,6,7,8-tetrahydroisoquinolin-3-yl)-2-(4-(ethylsulfonyl)phenyl)acetamide; (Isomer-1 of Compound-83); |
| 128 | N-(7-(2,6-dimethylpyrimidin-4-yl)-7-methyl-8-oxo-5,6,7,8-tetrahydroisoquinolin-3-yl)-2-(4-(ethylsulfonyl)phenyl)acetamide; (Isomer-2 of Compound-83); |
| 129 | 2-(4-(ethylsulfonyl)phenyl)-N-(6-(3-fluoro-2-methylimidazo[1,2-a]pyrazin-8-yl)-6-methyl-5-oxo-5,6,7,8-tetrahydroquinolin-2-yl)acetamide; |
| 130 | 2-(4-(ethylsulfonyl)phenyl)-N-(6-(3-fluoro-2-methylimidazo[1,2-a]pyrazin-8-yl)-6-methyl-5-oxo-5,6,7,8-tetrahydroquinolin-2-yl)acetamide; |
| 131 | N-(6-(6-ethyl-2-methylpyrimidin-4-yl)-6-methyl-5-oxo-5,6,7,8-tetrahydroquinolin-2-yl)-2-(4-(ethylsulfonyl)phenyl)acetamide; |
| 132 | N-(6-(2-ethyl-6-methylpyrimidin-4-yl)-6-methyl-5-oxo-5,6,7,8-tetrahydroquinolin-2-yl)-2-(4-(ethylsulfonyl)phenyl)acetamide; |
| 133 | N-(6-(2,6-diethylpyrimidin-4-yl)-6-methyl-5-oxo-5,6,7,8-tetrahydroquinolin-2-yl)-2-(4-(ethylsulfonyl)phenyl)acetamide; |
| 134 | 7-(2,6-dimethylpyrimidin-4-yl)-N-(4-(ethylsulfonyl)benzyl)-7-methyl-8-oxo-5,6,7,8-tetrahydroisoquinoline-3-carboxamide; |
| 135 | 2-(4-(ethylsulfonyl)phenyl)-N-(6-(2-methoxy-6-methylpyrimidin-4-yl)-4,6-dimethyl-5-oxo-5,6,7,8-tetrahydroquinolin-2-yl)acetamide; |
| 136 | N-(7-(2,6-dimethylpyrimidin-4-yl)-7-methyl-8-oxo-5,6,7,8-tetrahydroquinolin-3-yl)-2-(4-(ethylsulfonyl)phenyl)acetamide; |
| 137 | N-(6-(2,6-dimethylpyrimidin-4-yl)-6-methyl-5-oxo-5,6,7,8-tetrahydroquinazolin-2-yl)-2-(4-(ethylsulfonyl)phenyl)acetamide; |
| 138 | N-(6-(2,6-dimethylpyrimidin-4-yl)-6-methyl-5-oxo-5,6,7,8-tetrahydroquinoxalin-2-yl)-2-(4-(ethylsulfonyl)phenyl)acetamide; |

-continued

| Compound No. | IUPAC Name |
|---|---|
| 139 | 2-(4-(ethylsulfonyl)phenyl)-N-(6-methyl-6-(2-methyl-6-(trifluoromethoxy)-pyrimidin-4-yl)-5-oxo-5,6,7,8-tetrahydroquinolin-2-yl)acetamide; |
| 140 | 6-(2,6-dimethylpyrimidin-4-yl)-N-(4-(ethylsulfonyl)benzyl)-7-isopropyl-5-oxo-5,6,7,8-tetrahydroquinoline-2-carboxamide; |
| 141 | 6-(2,6-dimethylpyrimidin-4-yl)-N-(4-(ethylsulfonyl)benzyl)-8-isopropyl-5-oxo-5,6,7,8-tetrahydroquinoline-2-carboxamide; and |
| 142 | 6-(2,6-dimethylpyrimidin-4-yl)-N-(4-(ethylsulfonyl)benzyl)-7-isopropyl-6-methyl-5-oxo-5,6,7,8-tetrahydroquinoline-2-carboxamide; | or a pharmaceutically acceptable salt or a stereoisomer thereof.

In certain embodiments, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^{2}H$ ("D"), $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically labeled compounds of the present inventions can generally be prepared by following procedures analogous to those disclosed in the schemes and/or in the examples herein below, by substituting an isotopically labeled reagent for a non-isotopically labeled reagent.

The present invention also provides a pharmaceutical composition that includes at least one compound described herein and at least one pharmaceutically acceptable excipient (such as a pharmaceutically acceptable carrier or diluent). Preferably, the pharmaceutical composition comprises a therapeutically effective amount of at least one compound described herein. The compounds described in the present invention may be associated with a pharmaceutically acceptable excipient (such as a carrier or a diluent) or be diluted by a carrier, or enclosed within a carrier which can be in the form of a capsule, sachet, paper or other container.

The compounds and pharmaceutical compositions of the present invention are useful for modulating the activity of RORγ, which is believed to be related to a variety of disease states.

The present invention further provides a method of modulating the function of RORγ in a subject in need thereof by administering to the subject one or more compounds described herein in the amount effective to cause inhibition of such receptor.

The compounds of the invention are typically administered in the form of a pharmaceutical composition. Such compositions can be prepared using procedures well known in the pharmaceutical art and comprise at least one compound of the invention. The pharmaceutical composition of the present invention comprises one or more compounds described herein and one or more pharmaceutically acceptable excipients. Typically, the pharmaceutically acceptable excipients are approved by regulatory authorities or are generally regarded as safe for human or animal use. The pharmaceutically acceptable excipients include, but are not limited to, carriers, diluents, glidants and lubricants, preservatives, buffering agents, chelating agents, polymers, gelling agents, viscosifying agents, solvents and the like.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters and polyoxyethylene.

The pharmaceutical composition may also include one or more pharmaceutically acceptable auxiliary agents, wetting agents, suspending agents, preserving agents, buffers, sweetening agents, flavouring agents, colorants or any combination of the foregoing.

The pharmaceutical compositions may be in conventional forms, for example, tablets, capsules, solutions, suspensions, injectables or products for topical application. Further, the pharmaceutical composition of the present invention may be formulated so as to provide desired release profile.

Administration of the compounds of the invention, in pure form or in an appropriate pharmaceutical composition, can be carried out using any of the accepted routes of administration of pharmaceutical compositions. The route of administration may be any route which effectively transports the active compound of the patent application to the appropriate or desired site of action. Suitable routes of administration include, but are not limited to, oral, nasal, buccal, dermal, intradermal, transdermal, parenteral, rectal, subcutaneous, intravenous, intraurethral, intramuscular or topical.

Solid oral formulations include, but are not limited to, tablets, capsules (soft or hard gelatin), dragees (containing the active ingredient in powder or pellet form), troches and lozenges.

Liquid formulations include, but are not limited to, syrups, emulsions, and sterile injectable liquids, such as suspensions or solutions.

Topical dosage forms of the compounds include ointments, pastes, creams, lotions, powders, solutions, eye or ear drops, impregnated dressings, and may contain appropriate conventional additives such as preservatives, solvents to assist drug penetration.

The pharmaceutical compositions of the present patent application may be prepared by conventional techniques known in literature.

Suitable doses of the compounds for use in treating the diseases or disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. Mode of administration, dosage forms, and suitable pharmaceutical excipients can also be well used and adjusted by those skilled in the art. All changes and modifications are envisioned within the scope of the present patent application.

Compounds of the present invention are particularly useful because they may modulate the activity of Retinoid-related orphan receptor gamma (RORγ), i.e., they prevent, inhibit, or suppress the action of RORγ, and/or may elicit RORγ modulating effect. Compounds of the invention are thus useful in the treatment of those conditions in which inhibition of a ROR gamma activity is required.

In certain embodiments, the present invention provides a method of treating a RORγ mediated disorder or disease in a subject comprising administering to a subject in need thereof a compound of the present invention.

In certain embodiments, the present invention provides a method comprising conjointly administering to the subject a second therapeutic agent.

In certain embodiments, the present invention provides a method of reducing amount of IL-17 and other effector cytokines of Th17 cells in a subject, comprising administering to the subject a compound of the present invention.

It is contemplated that compounds disclosed in the present invention, provide therapeutic benefits to subjects suffering from immune or inflammatory disorder or disease. Accordingly, one embodiment of the invention provides a method of treating a disorder or disease selected from the group consisting of immune or inflammatory disorder or disease. The method comprises administering a therapeutically effective amount of a compound of the present invention, to a subject in need thereof to ameliorate a symptom of a RORγ mediated disorder or disease.

In certain embodiments, the disorder or disease is an immune disorder or disease.

In certain embodiments, the disorder or disease is an inflammatory disorder or disease.

In certain embodiments, the disorder or disease is an autoimmune disorder or disease.

In certain embodiments, the disorder or disease is rheumatoid arthritis, psoriasis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, asthma, epidermal hyperplasia, scleroderma or ulcerative colitis.

In certain embodiments, the disorder or disease is cartilage inflammation, bone degradation, arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, dermatomyositis, psoriatic arthritis, vasculitis, myolitis, polymyolitis, dermatomyolitis, osteoarthritis, polyarteritis nodossa, Wegener's granulomatosis, arteritis, polymyalgia rheumatica, sarcoidosis, sclerosis, primary biliary sclerosis, sclerosing cholangitis, dermatitis, atopic dermatitis, atherosclerosis, Still's disease, chronic obstructive pulmonary disease, Guillain-Barre disease, Type I diabetes mellitus, Graves' disease, Addison's disease, Raynaud's phenomenon, autoimmune hepatitis, psoriatic epidermal hyperplasia, plaque psoriasis, guttate psoriasis, inverse psoriasis, pustular psoriasis, erythrodermic psoriasis, or an immune disorder or disease associated with or arising from activity of pathogenic lymphocytes.

In certain embodiments, the psoriasis is plaque psoriasis, guttate psoriasis, inverse psoriasis, pustular psoriasis or erythrodermic psoriasis.

In certain embodiments, the disorder or disease is rheumatoid arthritis.

In certain embodiments, the subject is a mammal, e.g., a human.

In certain embodiments, the present invention provides compounds for use as a medicament.

In certain embodiments, the invention provides the use of the compounds of the present invention in the manufacture of a medicament.

In certain embodiments, the invention provides the use of the compounds of the present invention in the manufacture of a medicament for the treatment of an immune disorder or an inflammatory disorder or disease.

In certain embodiments, the present invention provides compounds for use as a medicament.

In certain embodiments, the medicament is for treating a disease or disorder mediated by RORγ.

In certain embodiments, the present invention provides compounds for use as a medicament for the treatment of an immune or an inflammatory disorder or disease.

Further, it is contemplated that the compounds of the present invention can inhibit the activity of RORγ. Accordingly, another embodiment of the invention provides a method of inhibiting the activity of RORγ. The method comprises exposing a RORγ to an effective amount of a compound of the present invention to inhibit said RORγ.

Also, it is contemplated that the compounds of the present invention can reduce the amount of interleukin-17 (IL-17) and other effector cytokines of Th17 cells, in a subject. IL-17 is a cytokine that affects numerous biological functions, including inducing and mediating pro-inflammatory responses. Accordingly, another aspect of the invention provides a method of reducing the amount of IL-17 and other effector cytokines of Th17 cells, in a subject. The method comprises administering to a subject an effective amount of a compound of the present invention to reduce the amount of IL-17 and other effector cytokines of Th17 cells, in the subject.

In certain embodiments, administering the compound reduces the amount of IL-17 and other effector cytokines produced by Th17 cells, in the subject. A change in the amount of IL-17 and other effector cytokines produced by, for example, Th17 cells can be measured using procedures described in the literature, such as an ELISA assay or intracellular staining assay.

Further, it is contemplated that compound of the present invention may inhibit the synthesis of IL-17 and other effector cytokines of Th17 cells, in a subject.

Accordingly, another aspect of the invention provides a method of inhibiting the synthesis of IL-17 and other effector cytokines of Th17 cells, in a subject. The method comprises administering to a subject an effective amount of a compound of the present invention to inhibit the synthesis of IL-17 and other effector cytokines of Th17 cells, in the subject.

In certain embodiments, the subject is a human.

The method(s) of treatment of the present patent application comprise administering a safe and effective amount of a compound according to formula (I) or a pharmaceutically acceptable salt thereof to a patient (particularly a human) in need thereof.

Compounds of the invention are indicated both in the therapeutic and/or prophylactic treatment of the above-mentioned conditions. For the above-mentioned therapeutic uses the dosage administered will, of course, vary with the compound employed, the mode of administration, the treatment desired and the disorder or disease indicated.

Definitions and Abbreviations

Unless defined otherwise, all technical and scientific terms used herein have the same meaning and the meaning of such terms is independent at each occurrence thereof and is as commonly understood by one of skill in art to which the subject matter herein belongs. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, the term 'compound(s)' comprises the compounds disclosed in the present invention. Preferably, the term 'compound(s)' comprises the compounds of formula (I), or a pharmaceutically acceptable salt or a stereoisomer thereof.

As used herein, the term "optionally substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic and aliphatic. It is understood that the substituent may be further substituted.

As used herein, the term "alkyl" refers to a hydrocarbon chain radical that includes solely carbon and hydrogen atoms in the backbone, containing no unsaturation, and which is attached to the rest of the molecule by a single bond. The alkane radical may be straight or branched. For example, the term "$C_1$-$C_6$ alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neo-pentyl, 3,3-dimethylpropyl, hexyl, 2-methylpentyl, and the like).

As used herein, the term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Examples of alkenyl groups are, but not limited to, ethenyl, 1-propenyl, 2-propenyl, isopropenyl, 1-butenyl, 2-butenyl, 3-butenyl and isobutenyl. The substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl or heteroaryl groups is contemplated.

As used herein, the term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Examples of alkynyl groups are, but not limited to, ethynyl, propyn-1-yl or propyn-2-yl. The substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl or heteroaryl groups is contemplated.

As used herein, the term "alkoxy" refers the radical —O-alkyl, wherein the alkyl is as defined above. Representative examples of alkoxy include, but are not limited to, methoxy, ethoxy, propoxy, 2-propoxy, butoxy, tert-butoxy, pentyloxy, hexyloxy and heptyloxy. The alkyl portion of the alkoxy may be optionally substituted.

As used herein, the term "alkoxyalkyl" refers the radical -alkyl-O-alkyl, wherein the alkyl group is further substituted by alkoxy. Representative examples of alkoxyalkyl include, but are not limited to, methoxymethyl, methoxyethyl, ethoxymethyl, isopropoxymethyl and ethoxy ethyl.

As used herein, the term "aryl" alone or in combination with other term(s) means a carbocyclic aromatic system containing one or more rings wherein such rings may be fused. The term "fused" means that the second ring is attached or formed by having two adjacent atoms in common with the first ring. The term "fused" is equivalent to the term "condensed". Unless otherwise specified, an aryl group typically has from 6 to about 14 carbon atoms but the invention is not limited in that respect. The term ($C_6$-$C_{12}$) aryl refers to an aryl group having six to twelve carbon atoms. Examples of aryl groups include but are not limited to phenyl, naphthyl, indanyl, and the like. Unless otherwise specified, all aryl groups described herein may be optionally substituted.

As used herein, the term "cycloalkyl" refers to $C_3$-$C_{10}$ saturated cyclic hydrocarbon ring. A cycloalkyl may be a single ring, which typically contains from 3 to 7 carbon ring atoms. Examples of single-ring cycloalkyls include cyclopropyl, cyclobutyl, cyclopentyl, cyclohexyl, cycloheptyl and the like. A cycloalkyl may alternatively be polycyclic or contain more than one ring. Examples of polycyclic cycloalkyls include bridged, fused, and spirocyclic carbocyclyls.

As used herein, the term "halo" or "halogen" alone or in combination with other term(s) means fluorine, chlorine, bromine or iodine.

As used herein, the term "haloalkyl" means alkyl substituted with one or more halogen atoms, wherein the alkyl groups are as defined above. The term "halo" is used herein interchangeably with the term "halogen" means F, Cl, Br or I. Examples of "haloalkyl" include but are not limited to fluoromethyl, difluoromethyl, trifluoromethyl, 2,2,2-trifluoroethyl and the like.

As used herein, the term "haloalkoxy" refers the radical —O-haloalkyl, wherein the haloalkyl is as defined above. Representative examples of haloalkoxy include, but are not limited to, fluoromethoxy, trifluoromethoxy and 2-fluoroethoxy.

As used herein, the term "aminoalkyl" refers to an alkyl group substituted with an amino group.

"Hydroxy" or "hydroxyl" refers to —OH group.

As used herein, the term "hydroxyalkyl" refers to an alkyl as defined above, having one or more of the available hydrogen of the alkyl replaced by a hydroxyl group. For example, a hydroxyalkyl includes, but are not limited to, —CH$_2$CH$_2$OH, —CH$_2$CH$_2$CH$_2$OH and —C(OH)(CH$_3$)(CH$_3$).

As used herein, the term "heterocyclyl" includes definitions of "heterocycloalkyl" and "heteroaryl". The heterocyclyl may be attached to the main structure at any heteroatom or carbon atom that results in the creation of a stable structure. Unless set forth or recited to the contrary, all heterocyclyl groups described or claimed herein may be substituted or unsubstituted.

The term "heterocycloalkyl" refers to a non-aromatic, saturated or partially saturated, monocyclic or polycyclic ring system of 3 to 15 members having at least one heteroatom or heterogroup selected from O, N, S, S(O), S(O)$_2$, NH or C(O) with the remaining ring atoms being independently selected from the group consisting of carbon, oxygen, nitrogen and sulfur. Examples of "Heterocycloalkyl" include, but are not limited to azetidinyl, oxetanyl, imidazolidinyl, benzodioxolyl, tetrahydroisoquinolinonyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, azepanyl, 2-aza-bicyclo[2.2.2]octanyl, azocinyl, chromanyl, xanthenyl and N-oxides thereof. A heterocycloalkyl group can be optionally substituted with one or more suitable groups by one or more aforesaid groups.

The term "heteroaryl" refers to an aromatic heterocyclic ring system containing 5 to 20 ring atoms, suitably 5 to 10 ring atoms, which may be a single ring (monocyclic) or multiple rings (bicyclic, tricyclic or polycyclic) fused together or linked covalently. The rings may contain from 1 to 5 heteroatoms selected from N, O and S, wherein the N or S atom is optionally oxidized, or the N atom is optionally quarternized. Any suitable ring position of the heteroaryl moiety may be covalently linked to the defined chemical structure. Examples of heteroaryl include, but are not limited to oxazolyl, isoxazolyl, imidazolyl, furyl, indolyl, isoindolyl, pyrrolyl, triazolyl, triazinyl, tetrazoyl, thienyl, oxadiazolyl, thiazolyl, isothiazolyl, pyridyl, pyrimidinyl, pyrazinyl, pyridazinyl, pyridazinone, imidazopyrazinyl, imidazopyridyl, pyrrolopyrazinyl, tetrahydroisoquinolinonyl, pyrazolyl, benzofuranyl, benzothiazolyl, benzoxazolyl, benzimidazolyl, benzothienyl, benzopyranyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl and phthalazinyl. Unless set forth or recited to the contrary, all heteroaryl groups described or claimed herein may be substituted or unsubstituted.

The term "pharmaceutically acceptable salt" includes salts prepared from pharmaceutically acceptable bases or acids including inorganic or organic bases and inorganic or organic acids. Examples of such salts include, but are not limited to, acetate, benzenesulfonate, benzoate, bicarbonate, bisulfate, bitartrate, borate, bromide, camsylate, carbonate, chloride, citrate, clavulanate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate, diphosphate, polygalacturonate, salicylate, stearate, sulfate, subacetate, succinate, tannate, tartrate, teoclate, tosylate, triethiodide and valerate. Examples of salts derived from inorganic bases include, but are not limited to, aluminum, ammonium, calcium, copper, ferric, ferrous, lithium, magnesium, potassium, sodium, and zinc.

As used herein, the term "pharmaceutically acceptable carrier" refers to any of the standard pharmaceutical carriers, such as a phosphate buffered saline solution, water, emulsions {e.g., such as an oil/water or water/oil emulsions), and various types of wetting agents. The compositions also can include stabilizers and preservatives. For examples of carriers, stabilizers and adjuvants known in literature.

The term "stereoisomers" refers to any enantiomers, diastereoisomers, or geometrical isomers of the compounds of formula (I), wherever they are chiral or when they bear one or more double bond. When the compounds of the formula (I) and related formulae are chiral, they can exist in racemic or in optically active form. Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

The term "SEA Syndrome" refers to Seronegative Enthesopathy and Arthropathy Syndrome.

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

As used herein, the term "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

As used herein, the term "comprise" or "comprising" is generally used in the sense of include, that is to say permitting the presence of one or more features or components.

As used herein, the term "composition" is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

As used herein, the term "including" as well as other forms, such as "include", "includes" and "included" is not limiting.

The abbreviations used in the entire specification may be summarized herein below with their particular meaning. Xantphos—4,5-Bis(diphenylphosphino)-9,9-dimethylxanthene; $K_2CO_3$—potassium carbonate; HATU—1-[Bis(dimethylamino)methylene]-1H-1,2,3-triazolo[4,5-b]pyridinium 3-oxid hexafluorophosphate; DIPEA—N,N-Diisopropylethylamine; °C.—Degree Celsius; $M^+$—Molecular ion; m—Multiplet; mL—Milliliter; h—Hour(s); δ—Delta; Pd/C—Palladium on activated Carbon; MS—Mass Spectroscopy; DMF—N,N-dimethyl formamide; RM—Reaction mixture; RT—Room temperature; RB/RBF—Round Bottom Flask THF—Tetrahydrofuran; Conc—Concentrated; LC-MS—Liquid Chromatography-Mass Spectroscopy; $^1$H or H—proton; NMR—Nuclear Magnetic Resonance; MHz—Megahertz (frequency); $CDCl_3$—Deuterated Chloroform; $CD_3OD$—Deuterated Methanol; Hz—Hertz; s—Singlet; br s—Broad singlet; d—Doublet; dd—doublet of doublets; td—triplet of doublets; ddd—doublet of doublet of doublets; dt—doublet of triplets; q—Quartet; t—Triplet; J—Coupling constant; DMSO-$d^6$—Deuterated Dimethylsulfoxide; %—Percentage; $H_2$—Hydrogen; M—Molarity; N—Normality; g—Gram; min—Minutes; mol—Moles; wt—Weight.

Methods for preparing compounds described herein are illustrated in the following examples. The schemes are given for the purpose of illustrating the invention, and are not intended to limit the scope or spirit of the invention. Starting materials shown in the schemes can be obtained from commercial sources or prepared based on procedures described in the literature. Furthermore, where specific acids, bases, reagents, coupling agents, solvents, etc. are mentioned, it is understood that other suitable acids, bases, reagents, coupling agents etc. may be used and are included within the scope of the present invention. Modifications to reaction conditions, for example, temperature, duration of the reaction or combinations thereof, are envisioned as part of the present invention. All possible stereoisomers are envisioned within the scope of this invention.

The intermediates required for the synthesis are commercially available or alternatively, these intermediates can be prepared using known literature methods. The invention is described in greater detail by way of specific examples.

Unless otherwise stated, work-up includes distribution of the reaction mixture between the organic and aqueous phase indicated within parentheses, separation of layers and drying the organic layer over sodium sulphate, filtration and evaporation of the solvent. Purification, unless otherwise mentioned, includes purification by silica gel chromatographic techniques, generally using ethyl acetate/hexane mixture of a suitable polarity as the mobile phase. Use of a different eluent system is indicated within parentheses.

It is contemplated that some of the intermediates disclosed in the present invention are used for the next step without any characterization data.

The MS data provided in the examples described below were obtained as follows:

Mass spectrum: Shimadzu LCMS 2020; Agilent 1100; LCMSD VL and Agilent 1100; API 2000

The NMR data provided in the examples described below were obtained as follows:

$^1$H NMR: Varian 300 and 400 MHz.

INTERMEDIATES

Intermediate-1: Synthesis of 2-(4-(ethylsulfonyl)phenyl)acetamide

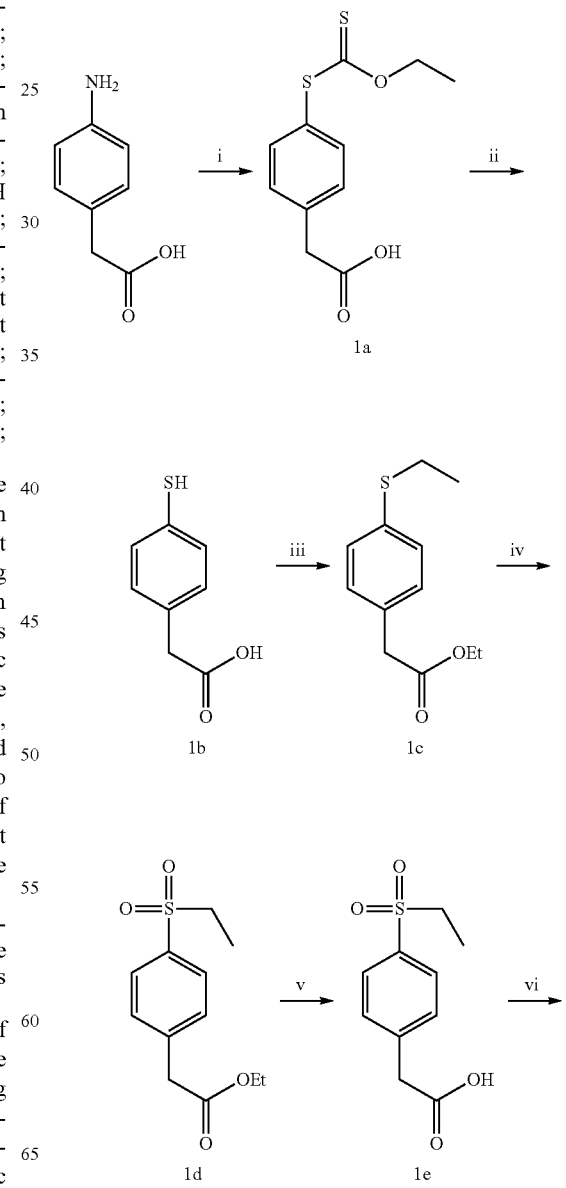

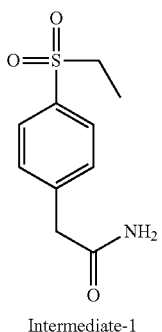

Intermediate-1

Step-i: 2-(4-((ethoxycarbonothioyl)thio)phenyl)acetic acid

To a 250 mL round bottom flask, was added 4-aminophenylacetic acid (8.5 g, 52.0 mmol), water (28 mL) and conc. hydrochloric acid (11.5 mL) and then cooled to 0° C. To the same flask, aqueous sodium nitrite (3.9 g, 56.2 mmol in 28 mL of water) was added drop wise and reaction mass was stirred at 0° C. for 45 minutes. The resulting cold diazonium salt solution was added drop wise to a mixture of potassium ethylxanthate (10.4 g, 648 mmol), water (16.8 mL) and 2 M sodium carbonate (42 mL). The reaction mixture was maintained at 45° C. for 2 h. The reaction mixture was cooled to 0° C., acidified to pH 1.0 with conc. hydrochloric acid and extracted with diethyl ether. The combined organic layer was washed with water followed by brine. The organic layer was dried over anhydrous sodium sulfate, filtered and evaporated under reduced pressure to get crude titled compound (19 g). The crude product was used for the next step immediately without any further purification.

Step-ii: 2-(4-mercaptophenyl)acetic acid

To a 250 mL round bottom flask, was added 2-(4-((ethoxycarbonothioyl)thio)phenyl)acetic acid (19 g, 74.1 mmol) and ethanol (72 mL). To the same flask, was added a solution of potassium hydroxide (15 g, 267.0 mmol) in water (72 mL) and then refluxed for 20 h. The major portion of ethanol was evaporated under reduced pressure to get a residue. The residue was acidified to pH 2.0 with conc. hydrochloric acid at 0° C. The aqueous layer was extracted with diethyl ether. The organic layer was washed with water followed brine. The organic layer was dried over anhydrous sodium sulfate, filtered and evaporated under reduced pressure to get crude product (7 g). The crude product was used for next step without any further purification. LC-MS: 166.9 [M−H]$^+$.

Step-iii: ethyl 2-(4-(ethylthio)phenyl)acetate

To a 100 mL round bottom flask, was added 2-(4-mercaptophenyl)acetic acid (7 g, 41.6 mmol), potassium carbonate (23 g, 166.4 mmol) and N,N-dimethylformamide (50 mL). To the same flask, was added ethyl bromide (13.6 g, 124.8 mmol) and stirred at room temperature for 2.5 h. The reaction mixture was partitioned between ethyl acetate and water. The organic phase was separated and washed with brine, dried over anhydrous sodium sulfate and evaporated under reduced pressure to obtain crude product. The crude product was purified by column chromatography using 10% ethyl acetate in hexane as eluent to get titled compound (6 g, 65%). $^1$H NMR (400 MHz, CDCl$_3$): δ 7.30 (d, J=8.0 Hz, 2H), 7.22 (d, J=8.0 Hz, 2H), 4.18 (q, J'=7.2 Hz, J''=14.4 Hz, 2H), 3.57 (s, 2H), 2.96 (q, J'=7.6 Hz, J''=14.8 Hz, 2H), 1.33 (t, J=7.6 Hz, 3H), 1.25 (t, J=7.6 Hz, 3H).

Step-iv: ethyl 2-(4-(ethylsulfonyl)phenyl) acetate

To a 250 mL round bottom flask, was added ethyl 2-(4-(ethylthio)phenyl)acetate (5.5 g, 24.5 mmol) and dichloromethane (82.5 mL). The reaction mixture was cooled to 0° C. To the same flask, was added m-chloroperbenzoic acid (12.6 g, 73.0 mmol) at 0° C. The reaction mixture was stirred at room temperature for 12 h. The resulting suspension was filtered through a pad of celite. The filtrate was washed with water followed by saturated sodium bicarbonate solution and brine. The organic layer was dried over anhydrous sodium sulfate, filtered and evaporated under reduced pressure to get crude product. The crude product was purified by column chromatography using 60-120 mesh silica gel and 50% ethyl acetate in hexane as eluents to get titled compound (5.1 g, 82%). $^1$H NMR (400 MHz, DMSO-d$^6$): δ 7.84 (d, J=8.4 Hz, 2H), 7.56 (d, J=8.8 Hz, 2H), 4.10 (q, J'=7.2 Hz, J''=14.4 Hz, 2H), 3.83 (s, 2H), 3.31 (q, J'=7.2 Hz, J''=14.8 Hz, 2H), 1.07-1.21 (m, 6H); LC-MS: 257.2 [M+H]$^+$.

Step-v: 2-(4-(ethylsulfonyl)phenyl)acetic acid

To a 50 mL round bottom flask, was added ethyl 2-(4-(ethylsulfonyl)phenyl)acetate (2.5 g, 9.8 mmol) and ethanol (18 mL). To the same flask, was added a solution of sodium hydroxide in water (1.42 g, 35.5 mmol in 18 mL of water) and then stirred at room temperature for 12 h. The volatiles were evaporated under reduced pressure to obtain the residue. The residue was acidified to pH 5.0 with 1.0 N hydrochloric acid and was extracted with ethyl acetate. The organic layer was separated and washed with brine, dried over sodium sulfate and evaporated under reduced pressure to get titled compound (2.4 g, 91%). $^1$H NMR (400 MHz, DMSO-d$^6$): δ 12.5 (brs, 1H), 7.84 (d, J=8.4 Hz, 2H), 7.56 (d, J=8.4 Hz, 2H), 3.74 (s, 2H), 3.13 (q, J'=7.2 Hz, J''=14.8 Hz, 2H), 1.20 (t, J=7.6 Hz, 3H).

Step-vi: 2-(4-(ethylsulfonyl)phenyl)acetamide

To a 50 mL round bottom flask, was added 2-(4-(ethylsulfonyl)phenyl)acetic acid (0.5 g, 2.3 mmol) and thionyl chloride (5 mL). The reaction mixture was stirred at room temperature for 6 h. The volatiles were evaporated under reduced pressure to get the solid. The solid was dissolved in dichloromethane (10 mL) and treated with aqueous ammonia (5 mL) at room temperature for 12 h. The volatiles were evaporated to get the crude residue. The crude residue was extracted with 10% methanol in chloroform. The combined organic phase was washed with water, dried over anhydrous sodium sulfate and evaporated under reduced pressure to get the titled compound (0.36 g, 72%). $^1$H NMR (300 MHz, DMSO-d$^6$): δ 7.80-7.83 (m, 2H), 7.58 (br s, 1H), 7.54-7.51 (m, 2H), 7.00 (br s, 1H), 3.52 (s, 2H), 3.33 (q, J'=9.6 Hz, J''=16.8 Hz, 2H), 1.21 (t, J=7.5 Hz, 3H). LC-MS: 228.1 [M+H]$^+$.

The below intermediates were prepared according to the protocol described in the synthesis of Intermediate-1 with appropriate variations in reactants, quantities of reagents, solvents and reaction conditions.

| Intermediate No. | Structure | Characterization Data |
|---|---|---|
| 2 | H₂N, O=S(=O)(CH₃)-C₆H₄-CH₂-C(=O)NH₂ | LC-MS: 214.2 [M + H]⁺. |
| 3 | Et-S(=O)₂-C₆H₃(F)-CH₂-C(=O)NH₂ | LC-MS: 245.9 [M + H]⁺. |

Intermediate-4: Synthesis of 2-iodo-3-((4-methoxybenzyl)oxy)pyridine

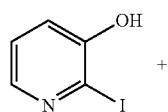

+

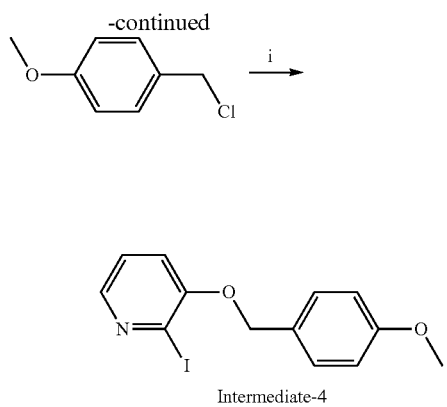

Intermediate-4

To a mixture of 2-iodopyridin-3-ol (1.5 g, 6.7 mmol) and 1-(chloromethyl)-4-methoxybenzene (1.27 g, 8.1 mmol) in DMF (10 mL) was added potassium carbonate (1.87 g, 13.5 mmol) and heated to 80° C. for 2 h. Reaction mixture was cooled to RT, diluted with water, extracted into ethyl acetate, organic portion washed with water, brine solution, dried over sodium sulphate and concentrated to get the titled compound (2.2 g, 95%). ¹H NMR (300 MHz, DMSO-d⁶): δ 7.98-7.99 (m, 1H), 7.36-7.40 (m, 2H), 7.12-7.16 (m, 2H), 6.89-7.03 (m, 3H), 5.1 (s, 2H), 3.81-3.80 (s, 3H). LC-MS: 342.2 [M+H]⁺.

The below intermediates were prepared according to the protocol described in the synthesis of Intermediate-4 with appropriate variations in reactants, quantities of reagents, solvents and reaction conditions.

| Intermediate No. | Structure | Characterization Data |
|---|---|---|
| 5 | 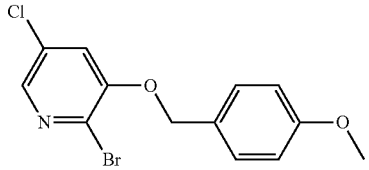 [SMILES: COc1ccc(COc2cc(Cl)cnc2Br)cc1] | ¹H NMR (300 MHz, DMSO-d⁶): δ 8.07 (d, J = 2.1 Hz, 1H), 7.83 (d, J = 2.1 Hz, 1H), 7.39-7.42 (m, 2H), 6.96-6.99 (m, 2H), 5.2 (s, 2H), 3.81-3.76 (s, 3H). |
| 6 | 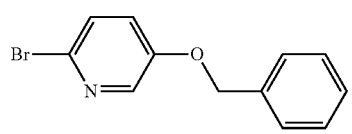 [SMILES: Brc1ccc(OCc2ccccc2)cn1] | LC-MS: 264.2 [M + H]⁺ |

Intermediate-7: Synthesis of 3-iodo-2-((4-methoxybenzyl)oxy)pyridine

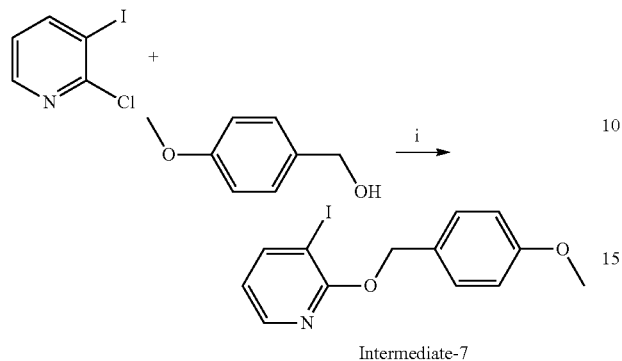

Intermediate-7

To a mixture of 2-chloro-3-iodopyridine (1 g, 4.1 mmol) and (4-methoxyphenyl)methanol (0.57 g, 4.1 mmol) in THF (10 mL), was added potassium tert-butoxide (0.7 g, 6.2 mmol) and then heated to 100° C. in a sealed tube for 2 h. The reaction mixture was cooled to room temperature, diluted with ethyl acetate and washed with water. The organic layer was separated, dried over sodium sulfate, filtered and concentrated to get titled compound (1.75 g). This was used as such in the next step without further purification. LC-MS: 342.1 [M+H]$^+$.

Intermediate-8: Synthesis of 3-bromo-2-((4-methoxybenzyl)oxy)-6-methylpyridine

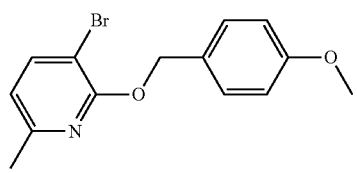 [SMILES: COc1ccc(COc2nc(C)ccc2Br)cc1]

This intermediate was prepared using the similar protocol described in the synthesis of Intermediate-7.

Intermediate-9: Synthesis of 8-chloroimidazo[1,2-a]pyrazine

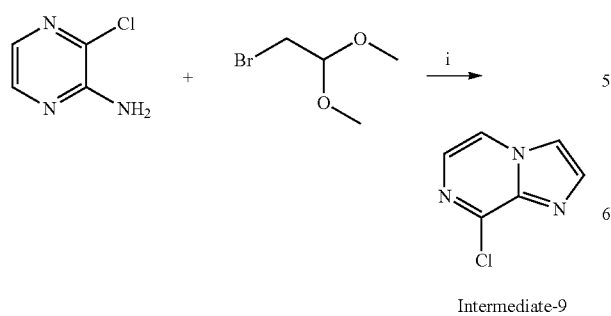

Intermediate-9

2-bromo-1,1-dimethoxyethane (3.7 g, 19.3 mmol) was added to a mixture of 48% hydrobromic acid and water (0.5 mL+5 mL) and refluxed for an hour. The reaction mixture was cooled to room temperature and extracted with ethyl acetate. The organic layer was separated, dried over sodium sulphate, filtered and concentrated to get residue. This residue was dissolved in 1,2-dimethoxyethane, and added into a mixture of 3-chloropyrazin-2-amine (1 g, 7.7 mmol) and 48% Aq. HBr (0.15 mL) and refluxed for 3 h. The reaction mixture was cooled and the dark solid formed was filtered, washed with water and dried to get the titled compound. LC-MS: 154.2 [M+H]$^+$.

Intermediate-10: Synthesis of 8-chloro-2-methylimidazo[1,2-a]pyrazine

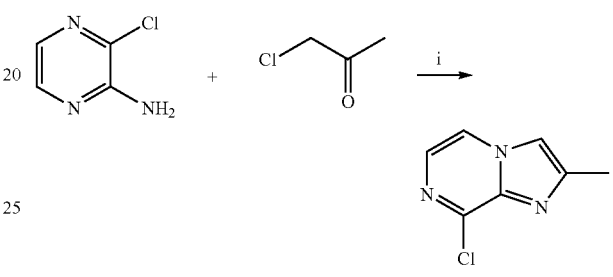

Intermediate-10

A mixture of 3-chloropyrazin-2-amine (2 g, 15.4 mmol) and 1-chloropropan-2-one (4 mL) was heated to 90° C. for 16 h in a sealed tube. The reaction mixture was then cooled to room temperature and the solid formed was filtered, washed with ether and dried to get the titled compound (1.4 g, 53%). LC-MS: 168.3 [M+H]$^+$.

Intermediate-11: Synthesis of 8-bromo-6-methylimidazo[1,2-a]pyrazine

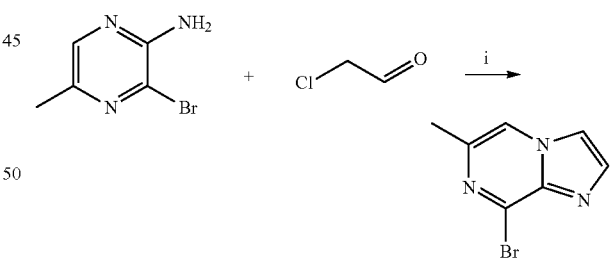

Intermediate-11

A mixture of 3-bromo-5-methylpyrazin-2-amine (1 g, 5.3 mmol) in chloroacetaldehyde (5 mL) was heated to 100° C. for 1 h. The reaction mixture was cooled to room temperature, diluted with ethyl acetate and washed with water. The organic layer was dried over sodium sulphate, filtered and concentrated to get residue. The residue was purified by flash chromatography using 20% ethyl acetate in hexanes to get pure titled compound (0.6 g, 53%). $^1$H NMR (300 MHz, DMSO-d$^6$): δ 8.40 (d, J=0.9 Hz, 1H), 8.02 (d, J=0.6 Hz, 1H), 7.79 (d, J=0.9 Hz, 1H), 2.37 (s, 3H).

Intermediate-12: Synthesis of 8-bromoimidazo[1,2-a]pyridine

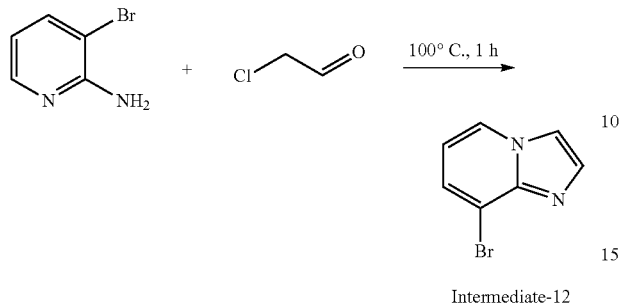

Intermediate-12

8-bromoimidazo[1,2-a]pyridine was prepared by procedure similar to the one described in the synthesis of Intermediate-10 with appropriate variations in reactants, quantities of reagents, solvents and reaction conditions. LC-MS: 197.2 [M]+.

Intermediate-13: Synthesis of 1-bromopyrrolo[1,2-a]pyrazine

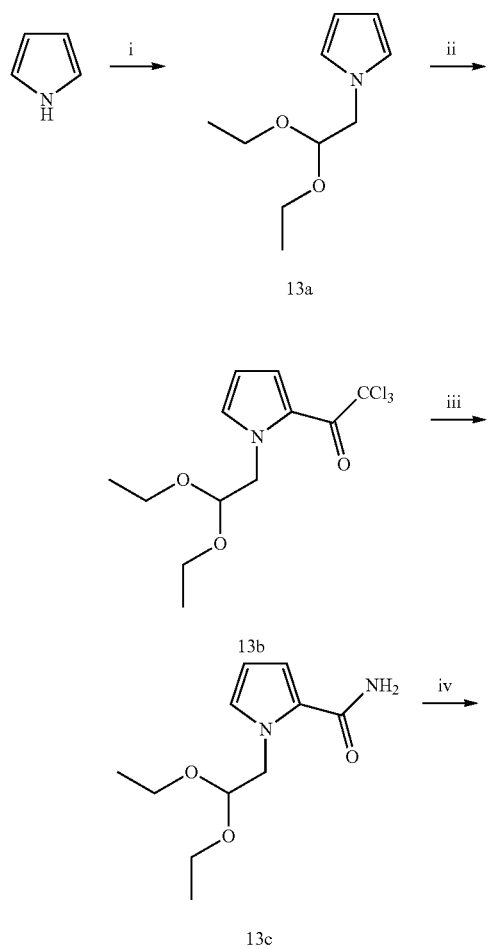

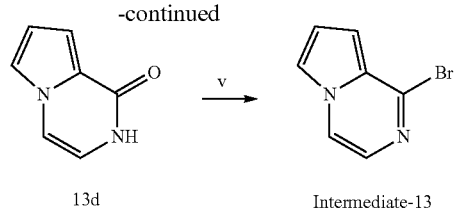

Step-i: Synthesis of 1-(2,2-diethoxyethyl)-1H-pyrrole

To a solution of 1H-pyrrole (20 g, 298 mmol) in DMF (200 mL) was added 60% sodium hydride (10.7 g, 447 mmol) at 0° C. then warmed to room temperature and stirred for 10-15 minutes at the same temperature and then cooled back to 0° C. To this mixture, 2-bromo-1,1-diethoxyethane (58.5 g, 298 mmol) was added dropwise. The reaction mixture was warmed gradually to room temperature and then heated to 70° C. for 6 h. The reaction was quenched with ice-water, extracted with ethyl acetate. The organic portion was dried over anhydrous sodium sulphate, filtered and concentrated to get residue which on purification by column chromatography using 10% ethyl acetate in hexane as eluent yielded the titled compound (25 g, 45.8%). LC-MS: 184.0 [M+H]+.

Step-ii: Synthesis of 2,2,2-trichloro-1-(1-(2,2-diethoxyethyl)-1H-pyrrol-2-yl)ethan-1-one To a stirred mixture of 1-(2,2-diethoxyethyl)-1H-pyrrole (25 g, 136.6 mmol) and 2,6-lutidine (16 g, 150 mmol) in chloroform (250 mL) was added trichloroacetyl chloride (27 g, 150 mmol) over a duration of 6 h. The reaction mixture was then stirred at room temperature for 12 h. The volatiles were evaporated under reduced pressure to get crude compound which on purification by column chromatography using 10% ethyl acetate in hexane as eluent yielded the titled compound (25 g, 56%). $^1$H NMR (300 MHz, CDCl$_3$): δ 7.54-7.56 (m, 1H), 7.09-7.10 (m, 1H), 6.22-6.25 (m, 1H), 4.63-4.66 (m, 3H), 4.39-4.40 (m, 2H), 3.60-3.70 (m, 2H), 3.41-3.49 (m, 2H), 1.12-1.16 (t, J=6.9 Hz, 6H).

Step-iii: Synthesis of 1-(2,2-diethoxyethyl)-1H-pyrrole-2-carboxamide 2,2,2-trichloro-1-(1-(2,2-diethoxyethyl)-1H-pyrrol-2-yl)ethan-1-one (25 g, 76 mmol) was slowly added to a mixture of ammonium hydroxide (125 mL) and ethyl acetate (270 mL) at 0° C. The reaction mixture was then stirred at room temperature for 16 h. The reaction mixture was extracted into ethyl acetate. The organic layer was dried over sodium sulphate, filtered and concentrated to get residue which on purification by column chromatography using 30% ethyl acetate in hexane yielded the titled compound (8 g, 46.2%). $^1$H NMR (300 MHz, DMSO-d$^6$): δ 7.47 (br s, 1H), 6.84-6.86 (m, 1H), 6.78-6.80 (m, 1H), 5.96-5.98 (m, 1H), 4.59-4.63 (m, 3H), 4.30-4.32 (m, 2H), 3.52-3.60 (m, 2H), 3.29-3.21-3.29 (m, 2H), 0.9-1.02 (m, 6H).

Step-iv: Synthesis of pyrrolo[1,2-a]pyrazin-1(2H)-one

A mixture of 1-(2,2-diethoxyethyl)-1H-pyrrole-2-carboxamide (3 g, 13.2 mmol) in acetic acid (30 mL) was heated to reflux for 6 h. The reaction mixture was cooled to room temperature and the volatiles were evaporated to get residue. Diethyl ether was added to this to get solid. The solid was filtered and washed with ether to get pure titled compound (1.7 g, 96.5%). LC-MS: 135.4 [M+H]⁺.

Step-v: Synthesis of 1-bromopyrrolo[1,2-a]pyrazine

To a mixture of pyrrolo[1,2-a]pyrazin-1(2H)-one (2.5 g, 18.6 mmol) in acetonitrile (25 mL) was added POBr₃ (10.5 g, 37 mmol) and heated to 80° C. for 3 h. The reaction mixture was slowly poured onto ice cold water, neutralized with aqueous ammonium hydroxide and extracted into ethyl acetate. The organic layer was dried over anhydrous sodium sulphate, filtered and concentrated to get residue, which on purification by column chromatography using 30% ethyl acetate in hexane as eluent yielded the titled compound (1.8 g, 50%). LC-MS: 198.9 [M+2H]⁺.

Intermediate-14: Synthesis of 3-chloro-6-vinylpyridazine

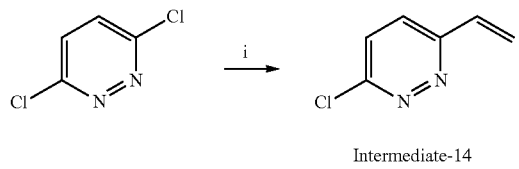

Intermediate-14

A stirred mixture of 3,6-dichloropyridazine (5 g, 33.5 mmol), vinyl boronic acid pinacol ester (5.1 g, 40.3 mmol) and potassium carbonate (13.8 g, 100.5 mmol) in a mixture of 1,4-dioxane (50 mL) and water (20 mL) was degassed with nitrogen gas for 15 min. Pd(dppf)Cl₂ (245.1 mg, 0.4 mmol) was then added and the mixture heated to 80° C. for 3 h. The reaction mixture was cooled to room temperature and separated aqueous layer. The organic portion was dried over Na₂SO₄, filtered and concentrated to get residue. The residue was purified by flash chromatography (SiO₂) using 40% ethyl acetate in hexanes to yield the titled compound. LC-MS: 140.9 [M+H]⁺.

Intermediate-15: Synthesis of 2-(5-(ethylsulfonyl)pyridin-2-yl)acetamide

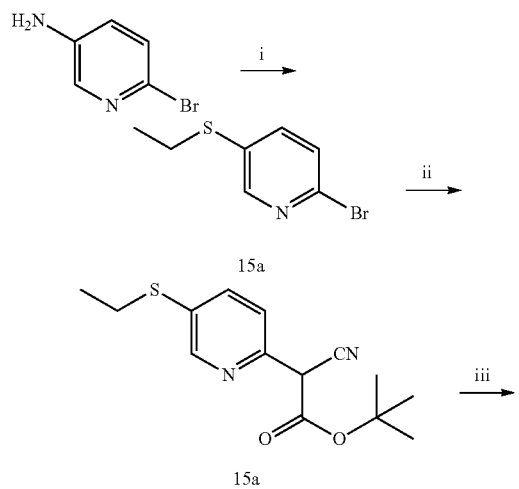

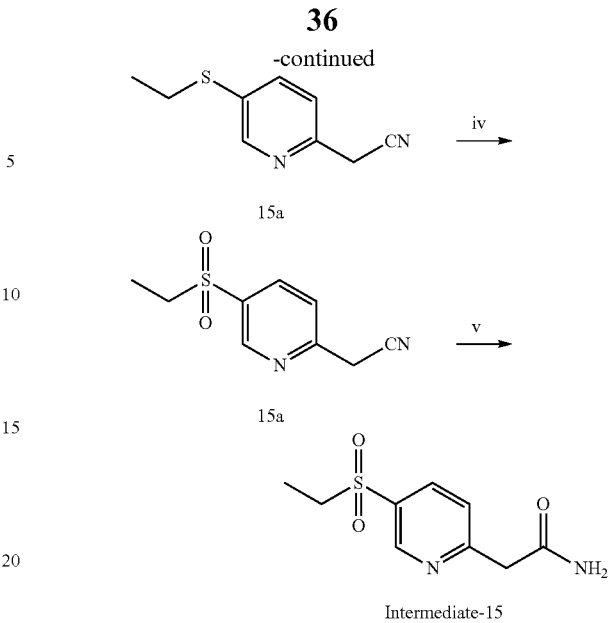

Intermediate-15

Step-i: Synthesis of 2-bromo-5-(ethylthio)pyridine

To a solution of 3-Amino-6-bromopyridine (5.5 g, 31.8 mmol) and diethyl disulfide (5.83 g, 47.7 mmol) in EDC (50 mL) at 60° C. was dropwise added 90% tert-butyl nitrite (5.5 g, 47.7 mmol) and the stirring was continued at 60° C. for 1 h. The reaction mixture was washed with water, brine, dried over anhydrous sodium sulfate and evaporated under reduced pressure to get the crude product. The crude product was purified by column chromatography (60-120 mesh silica gel and 0-12% EtOAc in hexane) to obtain 2-bromo-5-(ethylthio)pyridine (3.5 g, 51%). ¹H NMR (300 MHz, CDCl₃): δ 8.30 (d, J=2.7 Hz, 1H), 7.47-7.51 (m, 1H), 7.38-7.41 (m, 1H), 2.91-2.98 (m, 2H), 1.34 (t, J=7.2 Hz, 3H); LC-MS: 220.0 [M+2H]⁺.

Step-ii: Synthesis of tert-butyl 2-cyano-2-(5-(ethylthio)pyridin-2-yl)acetate

To the degassed mixture of 2-bromo-5-(ethylthio)pyridine (7.0 g, 25.1 mmol), tert-butyl 2-cyanoacetate (6.49 g, 50.2 mmol) and cesium carbonate (24.53 g, 75.3 mmol) in dioxane (100 mL) in a sealed tube, was added copper iodide (0.96 g, 5.02 mmol) and pyridine-2-carboxylic acid (1.24 g, 10.04 mmol). The sealed tube was screw capped. The contents of the sealed tube were stirred at 110° C. for 6 h. The reaction mixture was cooled to room temperature and filtered through a pad of celite. The filtrate was evaporated to dryness under reduced pressure and subjected to column chromatography (60-120 mesh silica gel, 10-30% ethyl acetate) in hexane to obtain tert-butyl 2-cyano-2-(5-(ethylthio)pyridin-2-yl)acetate (5 g, 71%). ¹H NMR (300 MHz, CDCl₃): δ 14.02 (br s, 1H), 7.60-7.63 (m, 1H), 7.53-7.57 (m, 1H), 7.23-7.24 (m, 1H), 2.76-2.83 (m, 2H), 1.53 (s, 9H), 1.28 (t, J=7.2 Hz, 3H); LC-MS: 222.9 [M−56+H]⁺.

Step-iii: Synthesis of 2-(5-(ethylthio)pyridin-2-yl)acetonitrile

To a solution of tert-butyl 2-cyano-2-(5-(ethylthio)pyridin-2-yl)acetate (5 g, 17.9 mmol) in DCM (25 mL) was added trifluoroacetic acid (25 mL). The reaction mixture was stirred at room temperature for 6 h. The volatiles were evaporated under reduced pressure to get the residue. The residue was partitioned between water and DCM. The organic layer was washed with brine, dried over anhydrous sodium sulfate and evaporated under reduced pressure to get the crude product. The crude product was purified by column chromatography (60-120 mesh silica gel and 20-50% EtOAc in hexane) to obtain 2-(5-(ethylthio)pyridin-2-yl)acetonitrile (1.4 g, 44%). $^1$H NMR (300 MHz, CDCl$_3$): δ 8.51 (d, J=2.4 Hz, 1H), 7.65-7.68 (m, 1H), 7.36 (d, J=7.8 Hz, 1H), 3.91 (s, 2H), 2.93-3.00 (m, 2H), 1.35 (t, J=7.2 Hz, 3H); LC-MS: 178.8 [M+H]$^+$.

Step-iv: Synthesis of 2-(5-(ethylsulfonyl)pyridin-2-yl)acetonitrile

To a solution of 2-(5-(ethylthio)pyridin-2-yl)acetonitrile (1.3 g, 7.3 mmol) in DCM (50 mL) at 0° C., was slowly added m-chloroperbenzoic acid (~77%, 3.6 g, 16.1 mmol). The reaction mixture was allowed to warm to room temperature and stirred at room temperature for 12 h. The reaction mixture was filtered through a pad of celite. The filtrate was washed with water, saturated aqueous sodium bicarbonate and brine. Then, the organic layer was dried over anhydrous sodium sulfate and evaporated under reduced pressure to get the crude product. The crude product was purified by column chromatography (60-120 mesh silica gel and 10-30% EtOAc in hexane) to obtain 2-(5-(ethylsulfonyl)pyridin-2-yl)acetonitrile (1.14 g, 75%). $^1$H NMR (300 MHz, CDCl$_3$): δ 9.08 (d, J=2.4 Hz, 1H), 8.4-8.27 (m, 1H), 7.70 (d, J=8.1 Hz, 1H), 4.08 (s, 2H), 3.15-3.26 (m, 2H), 1.36 (t, J=7.2 Hz, 3H); LC-MS: 211.0 [M+H]$^+$.

Step-v: Synthesis of 2-(5-(ethyl sulfonyl)pyridin-2-yl)acetamide

A mixture of 2-(5-(ethylsulfonyl)pyridin-2-yl)acetonitrile (1.05 g, 5.0 mmol) and 90% aqueous sulfuric acid (5.0 mL) was stirred at 70° C. for 1.5 h. The reaction mixture was cooled to room temperature, neutralized with saturated aqueous sodium bicarbonate and extracted with 10% methanol in chloroform. The organic layer was dried over anhydrous sodium sulfate and evaporated under reduced pressure to get 2-(5-(ethyl sulfonyl)pyridin-2-yl)acetamide (0.7 g, 61%). $^1$H NMR (400 MHz, DMSO-d$_6$): δ 8.92 (d, J=2.4 Hz, 1H), 8.20-8.24 (m, 1H), 7.61-7.64 (m, 2H), 7.10 (br s, 1H), 3.74 (s, 2H), 3.35-3.42 (m, 2H), 1.55 (t, J=7.2 Hz, 3H); LC-MS: 229.0 [M+H]$^+$.

Intermediate-16 (Mixture): Synthesis of 6-bromo-3-methoxy-4-methylpyridazine and 3-bromo-6-methoxy-4-methylpyridazine

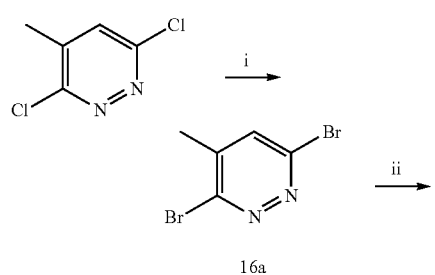

16a

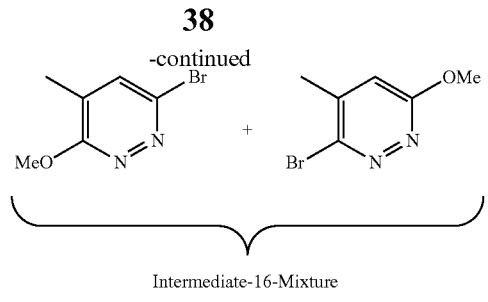

Intermediate-16-Mixture

Step-i: Synthesis of 3,6-dibromo-4-methylpyridazine

A suspension of 3,6-dichloro-4-methylpyridazine (10 g, 61.3 mmol) in 30-33% HBr in acetic acid (200 mL) was stirred at room temperature for 24 h. The precipitate was collected by filtration. The precipitate was suspended in DCM and neutralized with saturated aqueous sodium bicarbonate. The organic layer was separated, washed with brine, dried over anhydrous sodium sulfate and evaporated under reduced pressure to get 3,6-dibromo-4-methylpyridazine (6.8 g, 44%). $^1$H NMR (300 MHz, CDCl$_3$): δ 7.50 (d, J=1.2 Hz, 1H), 2.41 (d, J=0.6 Hz, 3H); LC-MS: 253.1 [M+3H]$^+$.

Step-ii: Synthesis of 6-bromo-3-methoxy-4-methylpyridazine and 3-bromo-6-methoxy-4-methylpyridazine To 3,6-dibromo-4-methylpyridazine (4.7 g, 18.7 mmol) in THF (25 mL) and methanol (25 mL) was added sodium methoxide (2.35 g, 37.4 mmol) and stirred at 25° C. for 2 h. The volatiles were evaporated under reduced pressure to get the residue. The residue was partitioned between ethyl acetate and water. The organic layer was separated, washed with brine, dried over anhydrous sodium sulfate and evaporated under reduced pressure to get the mixture of 6-bromo-3-methoxy-4-methylpyridazine and 3-bromo-6-methoxy-4-methylpyridazine (3.5 g, 89%). $^1$H NMR (300 MHz, CDCl$_3$): δ 7.31 (d, J=0.9 Hz, 1H), 6.80 (d, J=0.6 Hz, 1H), 4.10 (s, 3H), 4.07 (s, 3H), 2.34 (d, J=1.2 Hz, 3H), 2.20 (d, J=0.9 Hz, 1H); LC-MS: 205.1 [M+3H]$^+$.

Intermediate-17: Synthesis of 4-bromo-2-isopropylpyrimidine

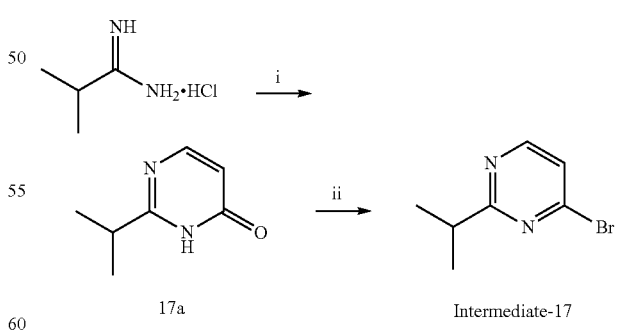

17a    Intermediate-17

Step-i: Synthesis of 2-isopropylpyrimidin-4(3H)-one

The mixture of methyl 3-methoxyacrylate (4.0 g, 34.4 mmol), isobutyrimidamide hydrochloride (12.64 g, 103.2 mmol) and potassium carbonate (15.2 g, 110.1 mmol) in ethanol (50 mL) was stirred at 85° C. for 10 h. The reaction mixture was filtered through a pad of celite. The filtrate was evaporated under reduced pressure to get 2-isopropylpyrimidin-4(3H)-one (4.0 g, 84%). $^1$H NMR (400 MHz, DMSO-$d_6$): δ 12.37 (br s, 1H), 7.84 (d, J=6.6 Hz, 1H), 6.14 (d, J=6.6 Hz, 1H), 2.71-2.83 (m, 1H), 0.97 (d, J=6.9 Hz, 6H)); LC-MS: 138.9 [M+H]$^+$.

Step-ii: Synthesis of 4-bromo-2-isopropylpyrimidine

To the suspension of 2-isopropylpyrimidin-4(3H)-one (2.0 g, 14.5 mmol) in acetonitrile (30 mL) was added phosphorus oxybromide (6.24 g, 21.75 mmol). The reaction mixture was stirred at 90° C. for 1 h. The obtained clear solution was evaporated under reduced pressure to get the residue. The residue was partitioned between water and ethyl acetate. The organic layer was washed with brine, dried over anhydrous sodium sulfate and evaporated under reduced pressure to get the crude product. The crude product was purified by column chromatography (60-120 mesh silica gel, 10-30% EtOAc in hexane) to obtain 4-bromo-2-isopropylpyrimidine (1.85 g, 59%). $^1$H NMR (300 MHz, CDCl$_3$): δ 8.34 (d, J=5.4 Hz, 1H), 7.34 (d, J=5.1 Hz, 1H), 3.15-3.24 (m, 1H), 1.35 (d, J=6.6 Hz, 6H); LC-MS: 203.2 [M+2H]$^+$.

Intermediate-18: Synthesis of 8-chloro-3-fluoro-2-methylimidazo[1,2-a]pyrazine

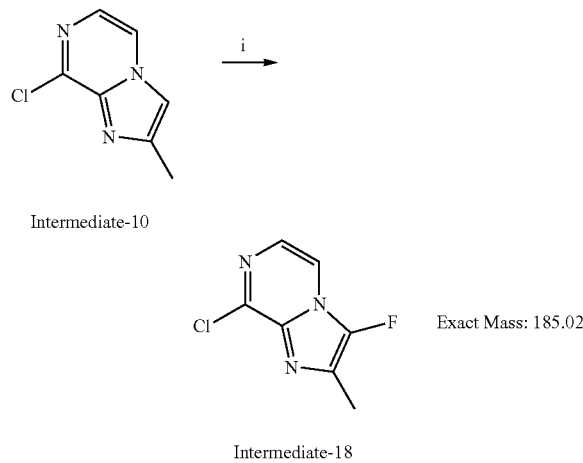

To a solution of 8-chloro-2-methylimidazo[1,2-a]pyrazine (2.5 g, 14.9 mmol) in acetonitrile (25 mL) at 0° C., was added a solution of Selectfluor (5.3 g, 14.9 mmol) in THF:Water (1:1, 25 mL) for 20 min. The reaction mixture was allowed to warm to room temperature and stirred at room temperature for 72 h. The reaction mixture was concentrated under reduced pressure to get the residue. The residue was partitioned between ethyl acetate and water. The organic layer was washed with brine, dried over anhydrous sodium sulfate and evaporated under reduced pressure to get the crude product. The crude product was purified by column chromatography (60-120 mesh silica gel and 0-30% ethyl acetate in hexane) to get 8-chloro-3-fluoro-2-methylimidazo[1,2-a]pyrazine (0.8 g, 27%). $^1$H NMR (300 MHz, CDCl$_3$): δ 7.82 (d, J=4.5 Hz, 1H), 7.70 (d, J=4.5 Hz, 1H), 2.51 (s, 3H); LC-MS: 186.2[M+H]$^+$

Intermediate-19: Synthesis of 8-chloro-3-methylimidazo[1,2-a]pyrazine

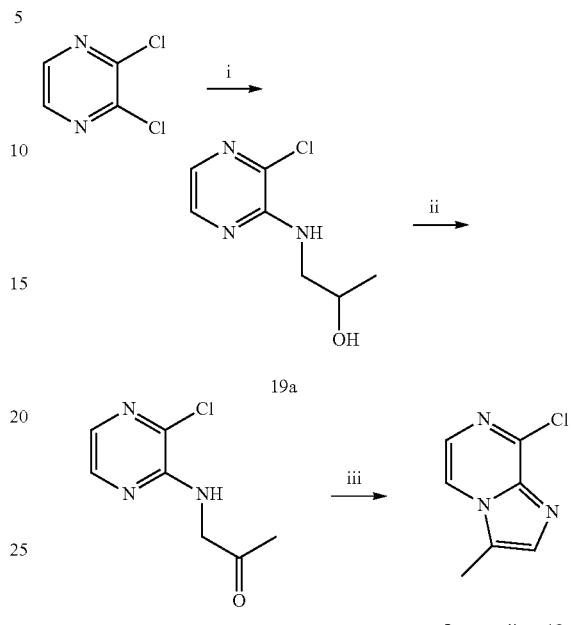

Step i: Synthesis of 1-((3-chloropyrazin-2-yl)amino)propan-2-ol

A mixture of 2,3-dichloropyrazine (29 g, 194 mmol) and 2-hydroxy-1-propanamine (29 g, 400 mmol) in dioxane (100 mL) was refluxed for 7 h under nitrogen atmosphere and the solvent was evaporated under vacuum. The residue was partitioned between chloroform and water, then the chloroform layer was washed with water, dried over sodium sulphate, filtered and concentrated under vacuum to afford 1-((3-chloropyrazin-2-yl)amino)propan-2-ol as an oil and subjected to column chromatography (230-400 mesh silica gel, 10-30% hexane in ethyl acetate to obtain 1-((3-chloropyrazin-2-yl)amino)propan-2-ol (29 g, 80.5%). LC-MS: 188.3 [M+H]$^+$.

Step ii: Synthesis of 1-((3-chloropyrazin-2-yl)amino)propan-2-one

A solution of oxalyl chloride (23.3 g, 140 mmol) in DCM (100 ml) was cooled to −78° C. under nitrogen atmosphere. To the reaction mixture, was added DMSO (28.5 g, 366 mmol) at −78° C. and stirred for 10 min. A solution of 1-((3-chloropyrazin-2-yl)amino)propan-2-ol (26.4 g, 140 mmol) in DCM (150 ml) was added to the reaction mixture at −78° C., stirred for 45 min, added TEA (71.0 g, 700 mmol) and then stirred at room temperature for 3 h. The mixture was treated with 300 g ice and extracted with DCM. The DCM extract was washed with water, dried over sodium sulfate, filtered and concentrated under reduced pressure to give 1-((3-chloropyrazin-2-yl)amino)propan-2-one (22 g, 84%). 1HNMR (300 MHz, CDCl$_3$): δ 7.93 (d, J=2.7 Hz, 1H), 7.64 (d, J=3.0 Hz, 1H), 6.00 (bars, 1H), 4.34 (t, J=4.8 Hz, 2H) 2.29 (s, 3H), LC-MS: 186.2 [M+H]$^+$.

Step iii: Synthesis of
8-chloro-3-methylimidazo[1,2-a]pyrazine

A mixture of 1-((3-chloropyrazin-2-yl)amino)propan-2-one (1 g, 59 mmol), TFA (22.5 ml) and triflic anhydride (35 ml) was stirred at rt for 2 h. The volatiles were evaporated under reduced pressure to obtain a residue. The residue was extracted with DCM and the DCM extract was washed with water, dried over sodium sulfate, filtered and concentrated under vacuum to obtain 8-chloro-3-methylimidazo[1,2-a]pyrazine (7.9 g, 80%). $^1$HNMR (400 MHz, DMSO-$d_6$): δ 8.46 (d, J=4.8 Hz, 1H), 7.76 (d, J=4.4 Hz, 1H), 7.68 (s, 1H), 2.23 (s, 3H), LC-MS: 168.2 [M+H]$^+$.

Intermediate-20: Synthesis of 8-chloro-3-(trifluoromethyl)imidazo[1,2-a]pyrazine

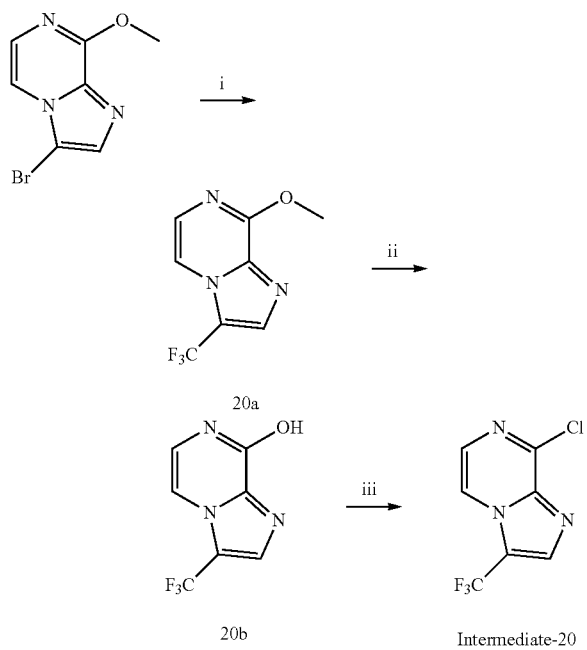

20a

20b

Intermediate-20

Step-i: Synthesis of 8-methoxy-3-(trifluoromethyl)imidazo[1,2-a]pyrazine

To a well stirred solution of silver(I)fluoride (3.4 g, 26.5 mmol) in DMF (20 ml), was added trifluoromethyltrimethylsilane and stirred at room temperature for 0.5 h. To the reaction mixture, was added copper (2.4 g, 39.0 mmol) and stirred at room temperature for 4 h. Then added 3-bromo-8-methoxyimidazo[1,2-a]pyrazine (5.5 g, 24.1 mmol) and stirred at 90° C. for 5 h. The reaction mixture was cooled and partitioned between ethyl acetate and water. The organic layer was washed with water, brine, dried over anhydrous sodium sulfate and concentrated under reduced pressure to get the crude product. The crude product was purified by column chromatography (60-120 mesh silica gel and 10-20% EtOAc in hexane) to obtain 8-methoxy-3-(trifluoromethyl)imidazo[1,2-a]pyrazine (1.5 g, 29%). LC-MS: 218.3 [M+H]$^+$.

Step-ii: Synthesis of 3-(trifluoromethyl)imidazo[1,2-a]pyrazin-8-ol 8-methoxy-3-(trifluoromethyl)imidazo[1,2-a]pyrazine (1.5 g, 7.0 mmol) was dissolved in 48% HBr in water (10 mL) and stirred at 60° C. for 2 h. The volatiles were evaporated under reduced pressure to get the residue. The residue was neutralized with 10% sodium bicarbonate solution and extracted with ethyl acetate. The organic layer was washed with water, brine, dried over anhydrous sodium sulfate and concentrated under reduced pressure to get 3-(trifluoromethyl)imidazo[1,2-a]pyrazin-8-ol (0.85 g, 57%). LC-MS: 204.2 [M+H]$^+$.

Step-iii: Synthesis of 8-chloro-3-(trifluoromethyl)imidazo[1,2-a]pyrazine

The mixture of 3-(trifluoromethyl)imidazo[1,2-a]pyrazin-8-ol (0.8 g, 3.9 mmol) and phosphorous oxychloride (10 mL) and N,N-dimethylaniline (0.1 mL) was stirred at 130° C. for 2 h. The volatiles were evaporated under reduced pressure to get the residue. The residue was neutralized with 10% sodium bicarbonate solution and extracted ethyl acetate. The organic layer was washed with water, brine, dried over anhydrous sodium sulphate and evaporated under reduced pressure to get 8-chloro-3-(trifluoromethyl)imidazo[1,2-a]pyrazine (0.54 g, 63%). $^1$H NMR (300 MHz, DMSO-$d_6$): δ 8.70 (d, J=4.5 Hz, 1H), 8.47 (s, 1H), 7.98 (d, J=4.8 Hz, 1H); LC-MS: 222.2 [M+2H]$^+$.

Intermediate-21: Synthesis of 4-bromo-6-methyl-2-(trifluoromethyl)pyrimidine

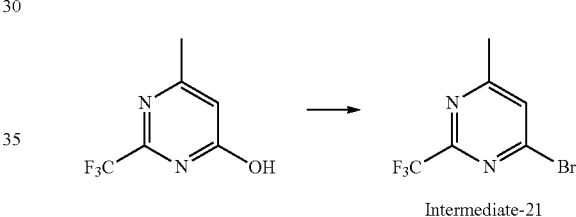

Intermediate-21

A suspension of 6-methyl-2-(trifluoromethyl)pyrimidin-4-ol (0.4 g, 2.3 mmol) and phosphorous oxybromide (3.9 g, 0.013.8 mmol) in acetonitrile (20 mL) was stirred at 90° C. for 2 h. The volatiles were concentrated under reduced pressure to get the residue. The residue was neutralized with 10% sodium bicarbonate solution and extracted with ethyl acetate. The organic layer was washed with water, brine, dried over anhydrous sodium sulphate and evaporated under reduced pressure to get 4-bromo-6-methyl-2-(trifluoromethyl)pyrimidine (0.38 g, 70%). $^1$H NMR (300 MHz, CDCl$_3$): δ 7.59 (s, 1H), 2.62 (s, 3H).

Intermediate-22: Synthesis of 3-bromo-6-ethylpyridazine

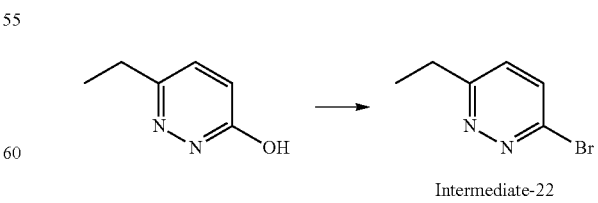

Intermediate-22

A suspension of 6-ethylpyridazin-3-ol (6.0 g, 48.3 mmol) and phosphorous oxybromide (28 g, 9.7 mmol) in acetonitrile (60 mL) was stirred at 90° C. for 2 h. The volatiles were evaporated under reduced pressure to get the residue. The residue was neutralized with 10% sodium bicarbonate solution and extracted with ethyl acetate. The organic layer was washed with water, brine, dried over anhydrous sodium sulphate and concentrated under reduced pressure to get the crude product. The crude product was purified by column chromatography (230-400 mesh silica gel and 0-15% EtOAc in hexane) to obtain 3-bromo-6-ethylpyridazine (3.8 g, 42%). LC-MS: 186.8 [M+H]+.

Intermediate-23: Synthesis of 8-chloro-3-cyclopropylimidazo[1,2-a]pyrazine

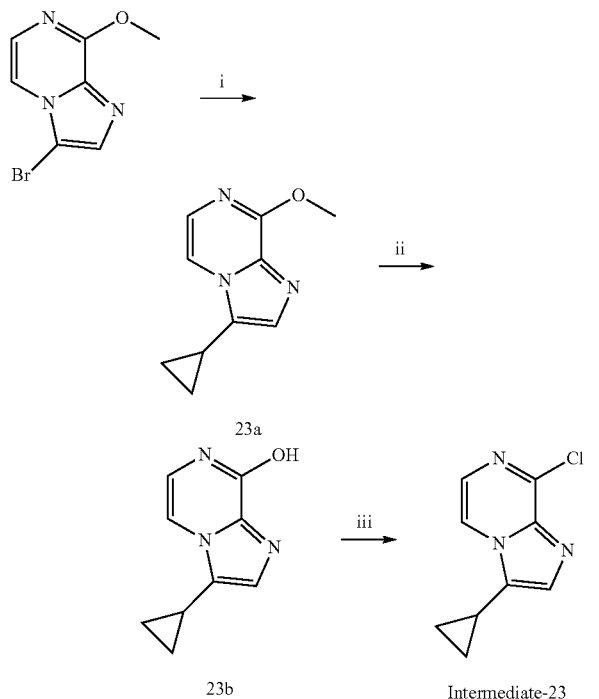

Step-i: Synthesis of 3-cyclopropyl-8-methoxyimidazo[1,2-a]pyrazine

To a degassed mixture of 3-bromo-8-methoxyimidazo[1,2a]pyrazine (1.4 g, 6.2 mmol), cyclopropylboronic acid (0.8 g, 9.3 mmol) potassium phosphate (4.6 g, 21.5 mmol) in water (5 ml) and toluene (30 ml), was added Palladium(ii) acetate and tricyclohexyl phosphine. The resulting reaction mixture was stirred at 90° C. for 12 h. The reaction mixture was cooled and partitioned between ethyl acetate and water. The organic layer was washed with brine, dried over anhydrous sodium sulfate and concentrated under reduced pressure to get the crude product. The crude product was purified by column chromatography (230-400 mesh silica gel and 10-30% EtOAc in hexane) to obtain 3-cyclopropyl-8-methoxyimidazo[1,2-a]pyrazine (1.0 g, 91%). $^1$H NMR (300 MHz, CDCl$_3$): δ 7.79 (d, J=4.8 Hz, 1H), 7.41 (d, J=4.8 Hz, 1H), 7.33 (s, 1H), 4.13 (s, 3H), 1.84-1.83 (m, 1H), 1.07-1.02 (m, 2H) 0.77-0.73 (m, 2H); LC-MS: 190.3 [M+H]+.

Step-ii: Synthesis of Step-ii: Synthesis of 3-cyclopropylimidazo[1,2-a]pyrazin-8-ol 3-cyclopropyl-8-methoxyimidazo[1,2-a]pyrazine (1.2 g, 6.0 mmol) was dissolved in 48% HBr in water (10 mL) and stirred at 60° C. for 2 h. The volatiles were evaporated under reduced pressure to get the residue. The residue was azeotroped with toluene to get 3-cyclopropylimidazo[1,2-a]pyrazin-8-ol (1.0 g, 91%). $^1$H NMR (300 MHz, DMSO-d$_6$): δ 12.25 (br s, 1H), 7.85 (s, 1H), 7.76 (d, J=4.2 Hz, 1H), 7.36 (t, J=5.7 Hz, 1H), 2.10-2.05 (m, 1H), 1.08-1.02 (m, 2H) 0.82-0.77 (m, 2H); LC-MS: 176.3 [M+H]+.

Step-iii: Synthesis of 8-chloro-3-cyclopropylimidazo[1,2-a]pyrazine

The mixture of 3-cyclopropylimidazo[1,2-a]pyrazin-8-ol (1.0 g, 5.7 mmol) and phosphorous oxychloride (15 mL) and N,N-dimethylaniline (0.1 mL) was stirred at 130° C. for 2 h. The volatiles were evaporated under reduced pressure to get the residue. The residue was neutralized with 10% sodium bicarbonate solution and extracted with ethyl acetate. The organic layer was washed with water, brine, dried over anhydrous sodium sulphate and evaporated under reduced pressure to get 8-chloro-3-cyclopropylimidazo[1,2-a]pyrazine (0.42 g, 38%). LC-MS: 194.3 [M+H]+.

Intermediate-24: Synthesis of 4-bromo-2-methyl-6-(trifluoromethyl)pyrimidine

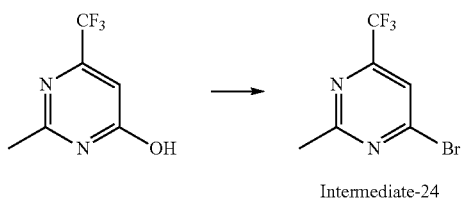

Intermediate-24

A suspension of 6-methyl-2-(trifluoromethyl)pyrimidin-4-ol (3.0 g, 16.8 mmol) and phosphorous oxybromide (19.3 g, 67.3 mmol) in acetonitrile (30 mL) was stirred at 80° C. for 6 h. The volatiles were concentrated under reduced pressure to get the residue. The residue was neutralized with 10% sodium bicarbonate solution and extracted ethyl acetate. Then the organic portion was washed with water, brine and dried over anhydrous sodium sulphate and evaporated under reduced pressure to get 4-bromo-2-methyl-6-(trifluoromethyl)pyrimidine (2.5 g, 62.5%). LC-MS: 243.2 [M+H]+.

Intermediate-25: Synthesis of 8-bromo-2-(trifluoromethyl)imidazo[1,2-a]pyrazine

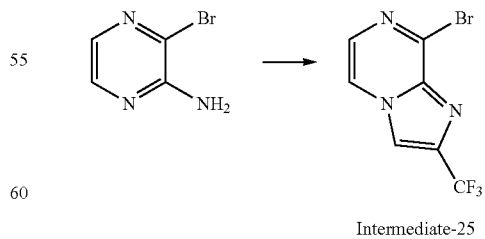

Intermediate-25

A suspension of 2-amino-3-bromopyrazine (2.5 g, 19.3 mmol) in DME (20 mL) was added 3-bromo-1, 1,1-trifluoroacetone (13.7 g, 72.0 mmol) and 4 Å molecular sieves (1.0 g). The reaction mixture was then stirred at 90° C. for 4 h and quenched by the addition of water (25 mL). This mixture was extracted with ethyl acetate. The combined organic layers were washed with brine (10 mL), dried over anhydrous sodium sulphate and concentrated under reduced pressure to give 8-chloro-2-trifluoromethyl-imidazo [1,2-a] pyrazine (0.8 g, 25%). $^1$H NMR (400 MHz, CDCl$_3$): δ 8.13-8.10 (m, 2H), 7.84-7.82 (m, 1H); LC-MS: 268.3.0 [M+2H]$^+$.

Intermediate-26: Synthesis of 2-bromo-5-isopropylpyrazine

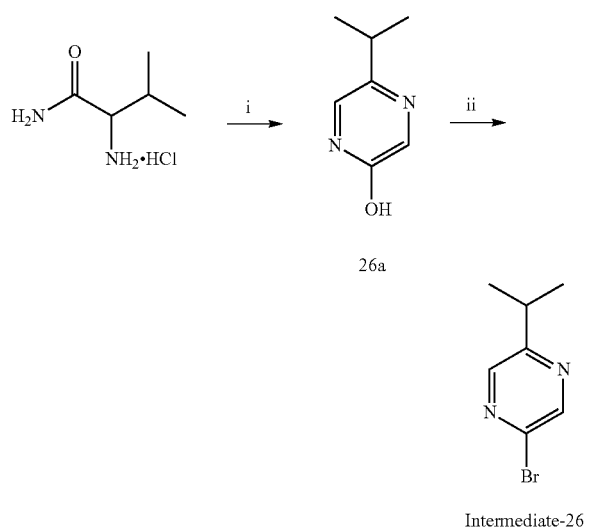

26a

Intermediate-26

Step-i: Synthesis of 5-isopropylpyrazin-2-ol

A solution of 2-amino-3-methylbutanamide hydrochloride (14.5 g, 95.3 mmol) in 140 mL of methanol and 140 mL of water at −40° C. was added 15 mL of aqueous glyoxal (40% by wt) dropwise. The mixture was stirred at −40° C. for 5 min, and then 14.5 mL of 50% aqueous sodium hydroxide was added. The resultant mixture was allowed to stir at room temperature for 18 h. The solution was cooled to 0° C. and 17.5 mL of concentrated hydrochloric acid was added, followed by 21.8 g of sodium bicarbonate. The mixture was stirred at room temperature for 5 min, and then an additional 21.8 g of sodium bicarbonate was added. After stirring for 20 min, the mixture was filtered. The filtrate was extracted with ethyl acetate. The organic layer was washed with water, brine, dried over anhydrous sodium sulphate and evaporated under reduced pressure to get 5-isopropylpyrazin-2-ol (4.5 g, 34%) LC-MS: 139.0 [M+H]$^+$.

Step-ii: Synthesis of 2-bromo-5-isopropylpyrazine

A suspension of 5-isopropylpyrazin-2-ol (4.5 g, 32.0 mmol) and phosphorous oxybromide (27 g, 94.0 mmol) in acetonitrile (45 mL) was stirred at 90° C. for 3 h. The volatiles were evaporated under reduced pressure to get the residue. The residue was neutralized with 10% sodium bicarbonate solution and extracted with ethyl acetate. The organic layer was washed with water, brine, dried over anhydrous sodium sulphate and evaporated under reduced pressure to get 2-bromo-5-isopropylpyrazine (4.2 g, 64%). LC-MS: 200.9 [M+H]$^+$.

Intermediate-27: Synthesis of 3-bromo-6-isopropylpyridazine

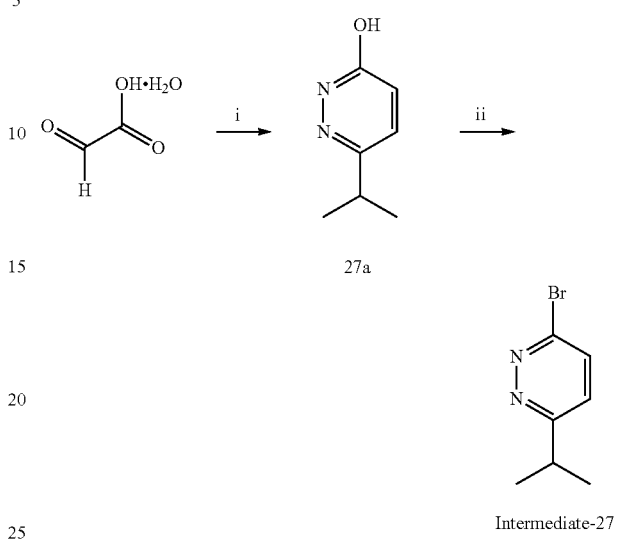

27a

Intermediate-27

Step-i: Synthesis of 6-isopropylpyridazin-3-ol

A mixture of glyoxalic acid monohydrate (15.0 g, 163.0 mmol), and methyl isopropyl ketone (52 ml), was heated to 120° C. for 2 h. The reaction mixture was cooled to 40° C. and 60 ml of water and 100 ml of aqueous ammonia were added. The mixture was extracted with DCM. The aqueous phase was added with hydrazine hydrate (8.2 g, 0.163.0 mmol), refluxed for 18 h and then cooled to room temperature. The reaction mass was extracted into DCM, the organic layer was washed with brine, dried over anhydrous sodium sulphate and evaporated under reduced pressure to get the crude product (6.5 g, 30%). LC-MS: 139.2 [M+H]$^+$.

Step-ii: Synthesis of 3-bromo-6-isopropylpyridazine

A suspension of 6-isopropylpyridazin-3-ol (6.5 g, 47.0 mmol) and phosphorous oxybromide (25 g, 87.0 mmol) in acetonitrile (15 mL) was stirred at 130° C. for 2 h. Poured into ice cold water and extracted ethyl acetate. The organic layer was washed with water, brine, dried over anhydrous sodium sulphate and evaporated under reduced pressure to get 3-bromo-6-isopropylpyridazine (2.5 g, 26.5%), LC-MS: 203.1 [M+2H]$^+$.

Intermediate-28: Synthesis of 4,6-dimethylcyclohexane-1,3-dione

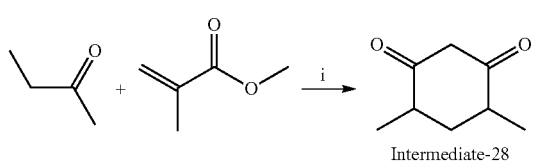

Intermediate-28

A solution of potassium tert-butoxide (15.45 g, 13.8 mmol) in dry THF (500 mL) was cooled to 0° C. and was added butan-2-one (10.0 g, 13.8 mmol), methyl methacrylate (11.6 g, 13.8 mmol) in dry THF over a period of 30 min. Then the reaction mixture was gradually warmed to RT and stirred for 2 h. The reaction was quenched with ice water and adjusted the pH– to 4 using 2N HCl. This mixture was extracted with ethyl acetate and the combined organic portion was dried over anhydrous sodium sulphate, filtered and concentrated to get the compound (8 g). LC-MS: 141.1 [M]+

Intermediate-29: Synthesis of
2-chloro-7,8-dihydroquinolin-5(6H)-one

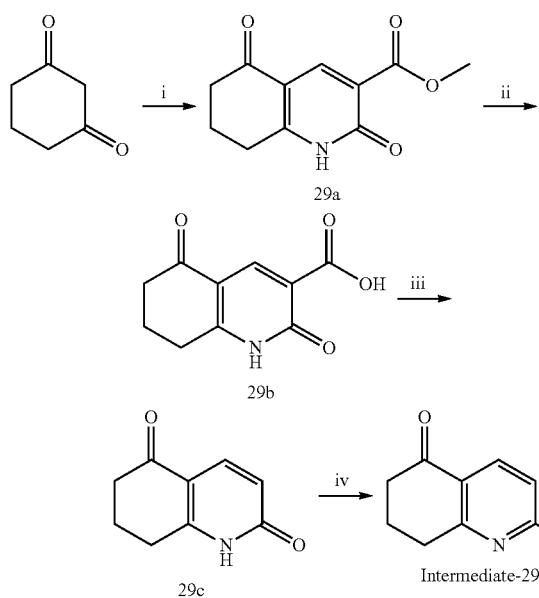

Step-i: Synthesis of methyl 2,5-dioxo-1,2,5,6,7,8-hexahydroquinoline-3-carboxylate A solution of cyclohexane-1,3-dione (200 g, 1785 mmol), DMF-DMA (201.8 g, 1785 mmol) in DCM (2 L) was stirred at room temperature for an hour. The reaction mixture was cooled to room temperature and the volatiles were evaporated under reduced pressure to get yellow solid. This was dissolved in methanol, added methyl 2-cyanoacetate (130 g, 1149 mmol) and refluxed for 12 h. The reaction mixture was cooled to room temperature and the solid formed was filtered and washed with cold methanol to get the title compound (160 g, 54%). LC-MS: 222.0 [M+H]$^+$.

Step-ii: Synthesis of 2,5-dioxo-1,2,5,6,7,8-hexahydroquinoline-3-carboxylic acid To a mixture of methyl 2,5-dioxo-1,2,5,6,7,8-hexahydroquinoline-3-carboxylate (10 g, 45.2 mmol) in 200 ml of MeOH/THF (1:1) was added a solution of lithium hydroxide (9.4 g, 226 mmol) in water (100 mL). The reaction mixture was then heated to 80° C. for 2 h to get clear solution. The reaction mixture was cooled to room temperature and solvents were evaporated under reduced pressure. The aqueous portion was acidified with dil. HCl to pH 4. The solid formed was filtered, washed with water and dried to get the title compound (8.5 g, 91.3%). LC-MS: 208.2 [M+H]$^+$.

Step-iii: Synthesis of
7,8-dihydroquinoline-2,5(1H,6H)-dione 2,5-dioxo-1,2,5,6,7,8-hexahydroquinoline-3-carboxylic acid (8.5 g, 41 mmol) was taken in an RB fitted with a condenser was heated on a heating mantle till it melts. Then the molten reaction mixture was cooled to room temperature, dissolved in 10% methanol in DCM. This solution was filtered and the filtrate was concentrated to get the title compound (5 g, 74.7%). LC-MS: 164.0 [M+H]$^+$.

Step-iv: Synthesis of
2-chloro-7,8-dihydroquinolin-5(6H)-one

To a solution of 7,8-dihydroquinoline-2,5(1H,6H)-dione (5 g, 27.6 mmol) in acetonitrile (50 mL) was added POCl$_3$ (12.6 g, 82.5 mmol) dropwise at 0° C. The cooling bath was removed and the reaction mixture was refluxed for 2 h. The reaction mixture was cooled to room temperature and the volatiles were evaporated under reduced pressure to get the residue, which was neutralized with ammonium hydroxide and extracted with ethyl acetate. The organic layer was dried over sodium sulfate, filtered and concentrated to get the title compound (5 g, 90.9%). LC-MS: 181.9 [M+H]$^+$.

The below Intermediates were prepared according to the protocol described in the synthesis of Intermediate-29 with appropriate variations in reactants, quantities of reagents, solvents and reaction conditions.

| Intermediate No. | Structure | Characterization data |
|---|---|---|
| 30 | 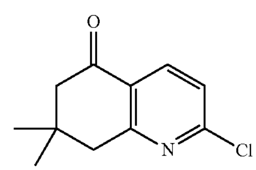 | LC-MS: 210.2 [M + H]$^+$. |
| 31 | 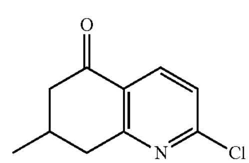 | LC-MS: 196.1 [M + H]$^+$. |
| 32 | 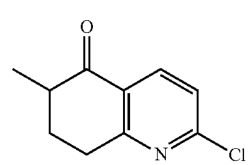 | — |
| 33 | 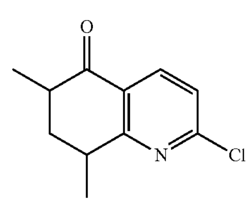 | LC-MS: 210.0 [M]+ |

Intermediate-34: Synthesis of 3-chloro-6,7-dihydroisoquinolin-8(5H)-one

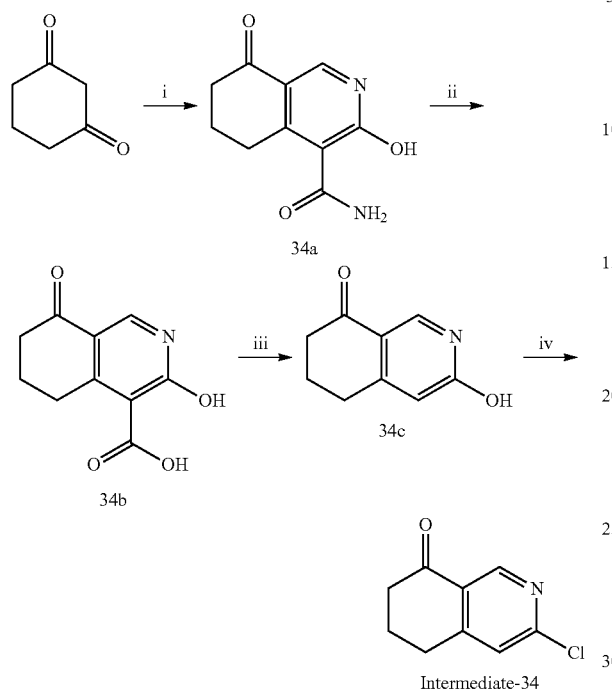

Step-i: Synthesis of 3-hydroxy-8-oxo-5,6,7,8-tetrahydroisoquinoline-4-carboxamide A solution of cyclohexane-1,3-dione (3 g, 26 mmol), DMF-DMA (3.35 g, 28.1 mmol) in DCM (30 mL) was stirred at room temperature for an hour. The reaction mixture was cooled to room temperature and the volatiles were evaporated to get yellow solid. This solid was dissolved in ethanol (78 mL), then added 2-cyanoacetamide (2.18 g, 84.08 mmol), piperidine (1.3 mL), DMF (26 mL) and refluxed for 16 h. The reaction mixture was cooled to room temperature and the solid formed was filtered and washed with cold ethanol to get the title compound (2.06 g, 37.3%). LC-MS: 207.1 [M+H]$^+$.

Step-ii: Synthesis of 3-hydroxy-8-oxo-5,6,7,8-tetrahydroisoquinoline-4-carboxylic acid A mixture of methyl 3-hydroxy-8-oxo-5,6,7,8-tetrahydroisoquinoline-4-carboxamide (2.06 g, 1.0 mmol) in Conc.HCl (10 mL) was heated to 100° C. for 6 h to get a clear solution. The reaction mixture was cooled to room temperature and the solid formed was filtered, washed with water, ethanol and dried to get the title compound (1.2 g, 58%). LC-MS: 207.8 [M+H]$^+$.

Step-iii: Synthesis of 3-hydroxy-6,7-dihydroisoquinolin-8(5H)-one 3-hydroxy-8-oxo-5,6,7,8-tetrahydroisoquinoline-4-carboxylic acid (8.5 g, 41 mmol) was taken in an RB fitted with a condenser was heated on a heating mantle till it melts. Then the molten reaction mixture was cooled to room temperature, and powdered to get the title compound (0.7 g, quantitative). LC-MS: 164.3 [M+H]$^+$.

Step-iv: Synthesis of 3-chloro-6,7-dihydroisoquinolin-8(5H)-one

A solution of 3-hydroxy-6,7-dihydroisoquinolin-8(5H)-one (1 g, 5.5 mmol) in acetonitrile (15 mL) was added POCl$_3$ (2 mL) at RT. The reaction mixture was refluxed for 2 h. The reaction mixture was cooled to room temperature and the volatiles were evaporated under reduced pressure to get residue, which was neutralized with ammonium hydroxide and diluted with ethyl acetate. The organic portion was then dried over sodium sulfate, filtered and concentrated to get the titled compound (0.7 g, 64%). LC-MS: 182.2 [M+H]$^+$.

Intermediate-35: Synthesis of 2-methoxy-6-methyl-7,8-dihydroquinolin-5(6H)-one

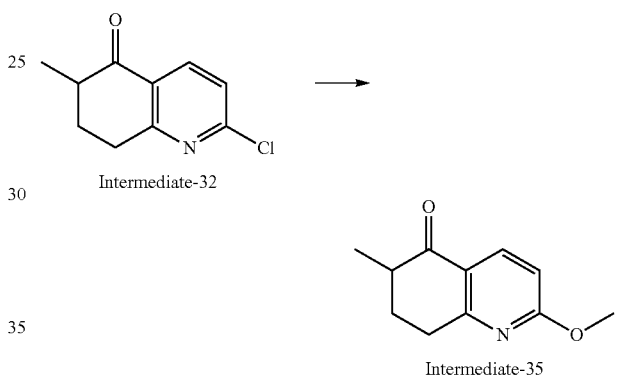

To a solution of 2-chloro-6-methyl-7,8-dihydroquinolin-5(6H)-one (1.5 g, 7.7 mmol) in methanol (25 mL) was added sodium methoxide (8.4 mmol) and stirred at room temperature for 12 h. The volatiles were evaporated under reduced pressure to get the residue. The residue was dissolved in ethyl acetate and washed with water. The organic layer was separated, washed with brine, dried over anhydrous sodium sulfate and concentrated under reduced pressure to get 2-methoxy-6-methyl-7,8-dihydroquinolin-5(6H)-one (1.2 g, 86%). $^1$H NMR (400 MHz, CDCl$_3$): δ 8.17 (d, J=8.4 Hz, 1H), 6.65 (d, J=8.8 Hz, 1H), 3.98 (s, 3H), 3.03-3.06 (m, 2H), 2.53-2.59 (m, 1H), 2.19-2.24 (m, 1H), 1.88-1.91 (m, 1H), 2.27 (d, J=6.8 Hz, 3H); LC-MS: 192.0 [M+H]$^+$.

Intermediate-36: Synthesis of 2-chloro-6-(4-methoxyphenyl)-4,6-dimethyl-7,8-dihydroquinolin-5(6H)-one

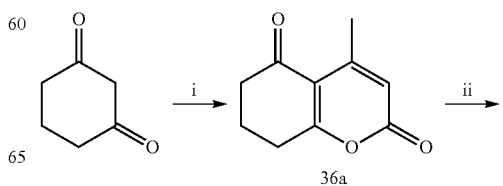

Intermediate-38: 2-chloro-6-(6-methoxypyridin-3-yl)-6-methyl-7,8-dihydroquinolin-5(6H)-one

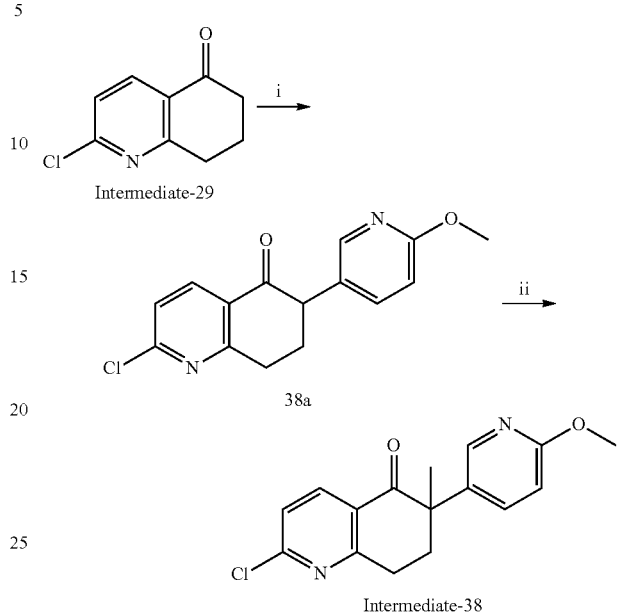

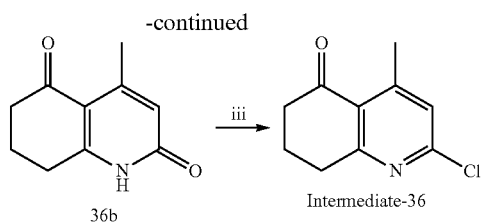

Step-i: Synthesis of 4-methyl-7,8-dihydro-2H-chromene-2,5(6H)-dione

A mixture of cyclohexane-1,3-dione (5 g, 44 mmol), ethylaceto acetate (6.9 g, 53 mmol), DMAP (1.09 g, 89 mmol) was heated to 120° C. for 10 h. The reaction mixture was cooled to room temperature and the volatiles evaporated under reduced pressure to get a residue. The residue was dissolved in ethyl acetate, washed with water followed by brine. The separated organic layer was dried over sodium sulphate, filtered and concentrated to get residue which was purified by silica gel column (230-400 mesh) using 5-10% ethyl acetate in hexanes as eluent to afford the title compound (3.2 g, 40.2%). LC-MS: 179.2 [M+H]$^+$.

Step-ii: Synthesis of 4-methyl-7,8-dihydroquinoline-2,5(1H, 6H)-dione

A mixture of 4-methyl-7,8-dihydro-2H-chromene-2,5(6H)-dione (3.1 g, 17.4 mmol) and methanolic ammonia (50 mL) was taken in a steel bomb and heated to 180° C. for 12 h. The reaction mixture was cooled and the volatiles were evaporated under reduced pressure to get the product (3 g, 97%). LC-MS: 178.3 [M+H]$^+$.

Step-iii: Synthesis of 2-chloro-4-methyl-7,8-dihydroquinolin-5(6H)-one

To a solution of 4-methyl-7,8-dihydroquinoline-2,5(1H, 6H)-dione (3 g, 0.0169 mmol) in acetonitrile (30 mL) was added phosphorous oxychloride (12.9 g, 84 mmol) and heated to 75° C. for 2 h. The reaction mixture was cooled to room temperature and the volatiles were evaporated under reduced pressure to get residue which was purified on 100-200 mesh silica gel column using 5% ethyl acetate in hexanes to obtain the title compound (4.8 g, 66.6%). $^1$H NMR (300 MHz, CDCl$_3$): δ 7.11 (s, 1H), 3.11-3.13 (m, 2H), 2.64-2.68 (m, 4H), 2.08-2.16 (m, 2H). LC-MS: 196.2 [M+H]$^+$.

Intermediate 37: Synthesis of 2-chloro-3-methyl-7,8-dihydroquinolin-5(6H)-one

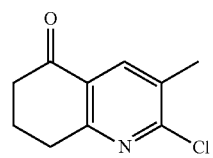

This intermediate was prepared according to the protocol described in the synthesis of Intermediate-36 with appropriate variations in reactants, quantities of reagents, solvents and reaction conditions.

Step-i: Synthesis of 2-chloro-6-(6-methoxypyridin-3-yl)-7,8-dihydroquinolin-5(6H)-one A mixture of 2-chloro-7,8-dihydroquinolin-5(6H)-one (0.4 g, 2.2 mmol), 5-bromo-2-methoxypyridine (0.45 g, 2.4 mmol) and sodium tert-butoxide (0.42 g, 4.4 mmol) in toluene (20 mL) was taken in a sealed tube, was degassed with nitrogen gas and added Pd(amphos)Cl$_2$ (0.0155 g, 0.02 mmol) at room temperature. Later, the reaction mixture was heated to 70° C. for 2 h, cooled it to room temperature, quenched with water and extracted with ethyl acetate. The organic portion was washed with water followed by brine. The separated organic layer was dried over sodium sulphate, filtered and concentrated to get residue which was purified by column chromatography (Silica: 230-400 mesh) using 10% ethyl acetate in hexanes as eluent to afford the title compound (0.2 g, 33%).

Step-ii: Synthesis of 2-chloro-6-(6-methoxypyridin-3-yl)-6-methyl-7,8-dihydroquinolin-5(6H)-one To a solution of 2-chloro-6-(6-methoxypyridin-3-yl)-7,8-dihydroquinolin-5(6H)-one (0.2 g, 0.69 mmol) in DMF (10 mL) was added sodium hydride (0.17 g, 0.76 mmol) at 0° C., stirred for 10 min. Methyl iodide (0.12 g, 0.83 mmol) was then added and stirred for 30 min. The reaction mixture was quenched with ice-water, extracted into ethyl acetate. The organic layer was washed with brine, dried over sodium sulphate, filtered and concentrated to get residue which on purification by column chromatography (Silica: 230-400 mesh) using 5% ethyl acetate in hexanes as eluents yielded the title compound (0.165 g, 79%). $^1$H NMR (300 MHz, CDCl$_3$): δ 8.30-8.33 (m, 1H), 7.9 (m, 1H), 7.47-7.43-7.47 (m, 1H), 7.31 (m, 1H), 6.69-6.72 (m, 1H), 3.87 (s, 3H), 2.97-3.11 (m, 3H), 2.62-2.67 (m, 2H), 2.32 (m, 1H), 1.51 (s, 3H). LC-MS: 303.0 [M+H]$^+$.

The below intermediates were prepared according to the protocol described in the synthesis of intermediate-38 or 38a with appropriate variations in reactants, quantities of reagents, solvents and reaction conditions.

| Intermediate No. | Structure | Characterization Data |
|---|---|---|
| 39 | 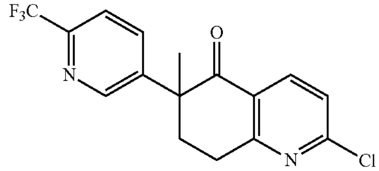 [SMILES: CC1(c2ccc(C(F)(F)F)nc2)CCc2nc(Cl)ccc2C1=O] | LC-MS: 341.3 [M + H]+. |
| 40 | 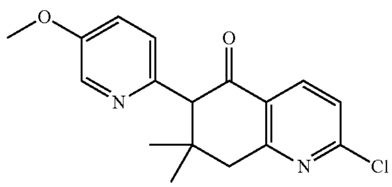 [SMILES: COc1ccc(C2C(=O)c3ccc(Cl)nc3CC2(C)C)nc1] | LC-MS: 317.1 [M + H]+. |
| 41 | 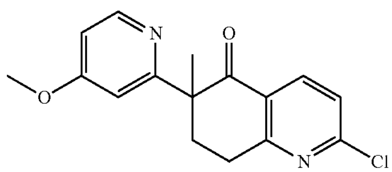 [SMILES: COc1ccnc(C2(C)CCc3nc(Cl)ccc3C2=O)c1] | LC-MS: 303.3 [M + H]+. |
| 42 | 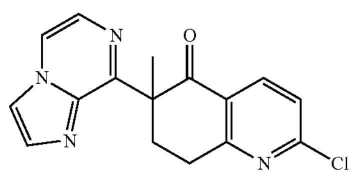 [SMILES: CC1(c2nccn3ccnc23)CCc2nc(Cl)ccc2C1=O] | LC-MS: 313.2 [M + H]+. |
| 43 | 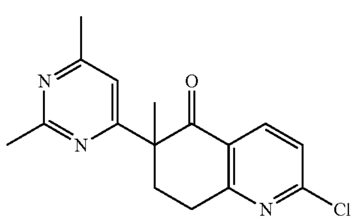 [SMILES: Cc1cc(C2(C)CCc3nc(Cl)ccc3C2=O)nc(C)n1] | LC-MS: 301.9 [M + H]+. |
| 44 | 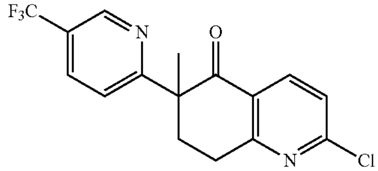 [SMILES: CC1(c2ccc(C(F)(F)F)cn2)CCc2nc(Cl)ccc2C1=O] | LC-MS: 341.0 [M + H]+. |
| 45 | 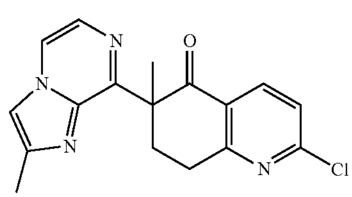 [SMILES: Cc1cn2ccnc(C3(C)CCc4nc(Cl)ccc4C3=O)c2n1] | LC-MS: 326.9 [M + H]+. |

| Intermediate No. | Structure | Characterization Data |
|---|---|---|
| 46 | 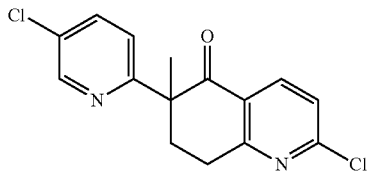 [SMILES: CC1(c2ccc(Cl)cn2)CCc2nc(Cl)ccc2C1=O] | LC-MS: 307.0 [M + H]$^+$. |
| 47 | 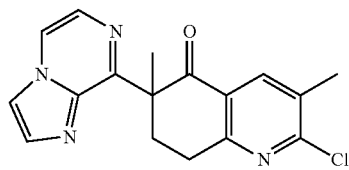 [SMILES: Cc1cc2c(nc1Cl)CCC(C)(c1nccn3ccnc13)C2=O] | LC-MS: 327.0 [M + H]$^+$. |
| 48 | 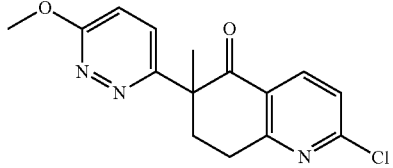 [SMILES: COc1ccc(C2(C)CCc3nc(Cl)ccc3C2=O)nn1] | LC-MS: 303.9 [M + H]$^+$. |
| 49 | 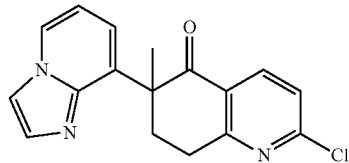 [SMILES: CC1(c2cccn3ccnc23)CCc2nc(Cl)ccc2C1=O] | LC-MS: 312.2 [M + H]$^+$. |
| 50 | 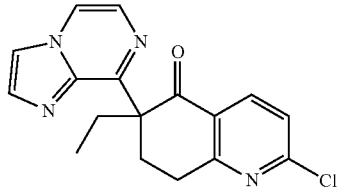 [SMILES: CCC1(c2nccn3ccnc23)CCc2nc(Cl)ccc2C1=O] | LC-MS: 326.9 [M + H]$^+$. |
| 51 | 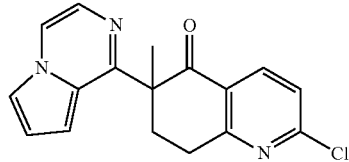 | LC-MS: 312.2 [M + H]$^+$. |
| 52 | 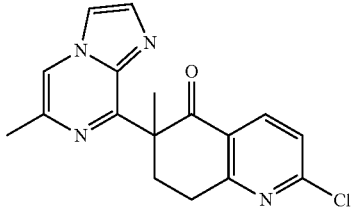 [SMILES: Cc1cn2ccnc2c(C2(C)CCc3nc(Cl)ccc3C2=O)n1] | LC-MS: 327.4 [M + H]$^+$. |

-continued

| Intermediate No. | Structure | Characterization Data |
|---|---|---|
| 53 | 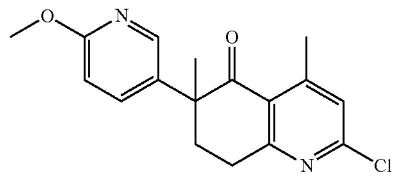 [SMILES: COc1ccc(C2(C)CCc3nc(Cl)cc(C)c3C2=O)cn1] | LC-MS: 317.3 [M + H]+. |
| 54 | 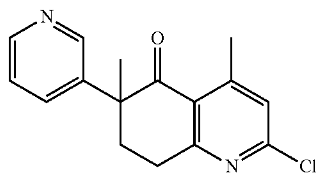 [SMILES: Cc1cc(Cl)nc2c1C(=O)C(C)(c1cccnc1)CC2] | LC-MS: 287.1 [M + H]+. |
| 55 | 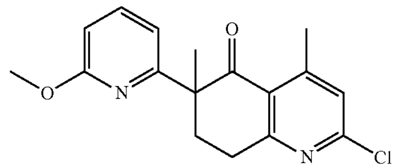 [SMILES: COc1cccc(C2(C)CCc3nc(Cl)cc(C)c3C2=O)n1] | LC-MS: 317.1 [M + H]+. |
| 56 | 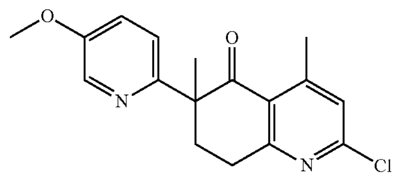 [SMILES: COc1ccc(C2(C)CCc3nc(Cl)cc(C)c3C2=O)nc1] | LC-MS: 316.9 [M + H]+. |
| 57 | 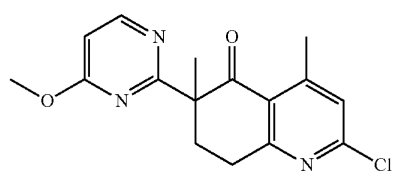 [SMILES: COc1ccnc(C2(C)CCc3nc(Cl)cc(C)c3C2=O)n1] | LC-MS: 318.1 [M + H]+. |
| 58 | 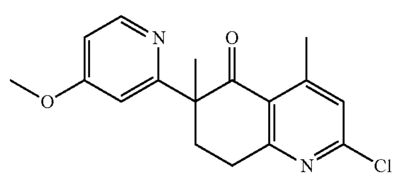 [SMILES: COc1ccnc(C2(C)CCc3nc(Cl)cc(C)c3C2=O)c1] | LC-MS: 317.1 [M + H]+. |
| 59 | 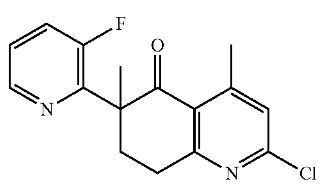 [SMILES: Cc1cc(Cl)nc2c1C(=O)C(C)(c1ncccc1F)CC2] | LC-MS: 305.1 [M + H]+. |
| 60 | 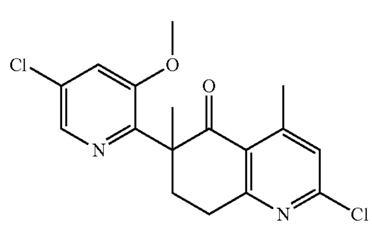 [SMILES: COc1cc(Cl)cnc1C1(C)CCc2nc(Cl)cc(C)c2C1=O] | No ionization |

-continued
| Intermediate No. | Structure | Characterization Data |
|---|---|---|
| 61 | 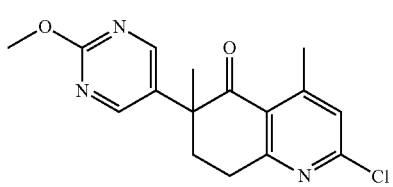 | LC-MS: 381.2 [M + H]+. |
| 62 | 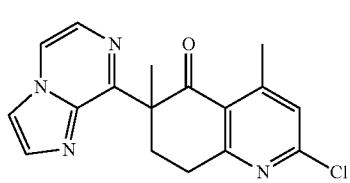 [SMILES: Cc1cc(Cl)nc2c1C(=O)C(C)(c1nccn3ccnc13)CC2] | LC-MS: 327.3 [M + H]+. |
| 63 | 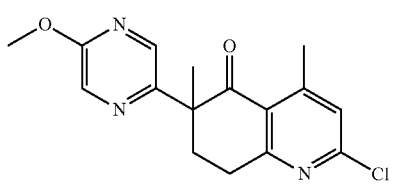 [SMILES: COc1cnc(C2(C)CCc3nc(Cl)cc(C)c3C2=O)cn1] | — |
| 64 | 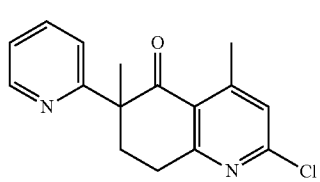 [SMILES: Cc1cc(Cl)nc2c1C(=O)C(C)(c1ccccn1)CC2] | LC-MS: 286.8 [M + H]+. |
| 65 | 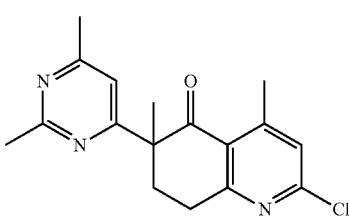 [SMILES: Cc1cc(C2(C)CCc3nc(Cl)cc(C)c3C2=O)nc(C)n1] | LC-MS: 316.3 [M + H]+. |
| 66 | 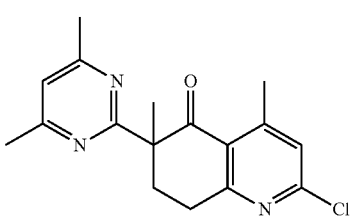 [SMILES: Cc1cc(C)nc(C2(C)CCc3nc(Cl)cc(C)c3C2=O)n1] | LC-MS: 316.3 [M + H]+. |
| 67 | 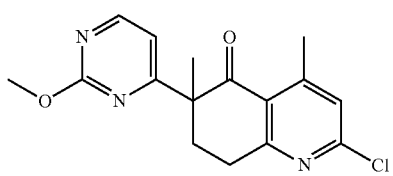 [SMILES: COc1nccc(C2(C)CCc3nc(Cl)cc(C)c3C2=O)n1] | LC-MS: 317.9 [M + H]+. |

-continued

| Intermediate No. | Structure | Characterization Data |
|---|---|---|
| 68 | 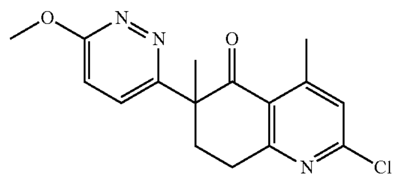 [SMILES: COc1ccc(C2(C)CCc3nc(Cl)cc(C)c3C2=O)nn1] | LC-MS: 318.3 [M + H]+. |
| 69 | 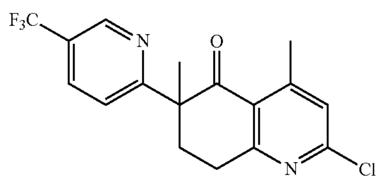 [SMILES: Cc1cc(Cl)nc2c1C(=O)C(C)(c1ccc(C(F)(F)F)cn1)CC2] | LC-MS: 355.1 [M + H]+. |
| 70 | 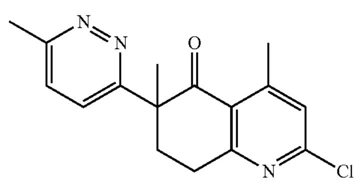 [SMILES: Cc1ccc(C2(C)CCc3nc(Cl)cc(C)c3C2=O)nn1] | LC-MS: 302.0 [M + H]+. |
| 71 | 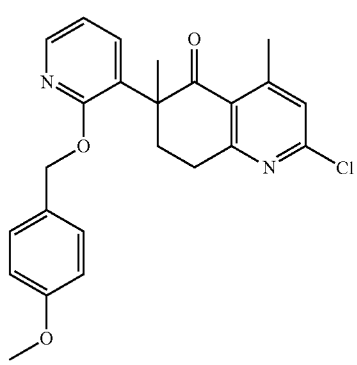 [SMILES: COc1ccc(COc2ncccc2C2(C)CCc3nc(Cl)cc(C)c3C2=O)cc1] | LC-MS: 423.3 [M + H]+. |
| 72 | 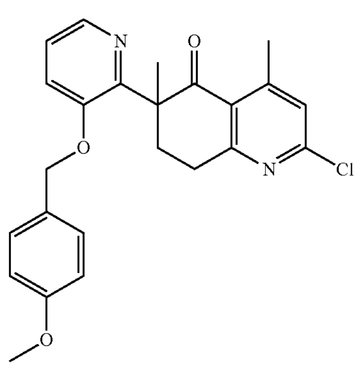 [SMILES: COc1ccc(COc2cccnc2C2(C)CCc3nc(Cl)cc(C)c3C2=O)cc1] | LC-MS: 423.2 [M + H]+. |

-continued

| Intermediate No. | Structure | Characterization Data |
|---|---|---|
| 73 | 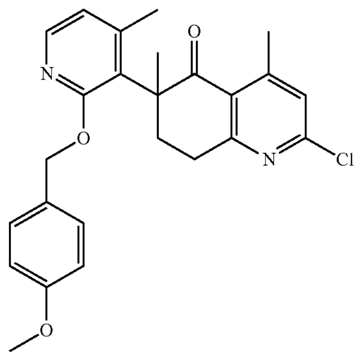 [SMILES: COc1ccc(COc2nccc(C)c2C2(C)CCc3nc(Cl)cc(C)c3C2=O)cc1] | LC-MS: 437.3 [M + H]+. |
| 74 | 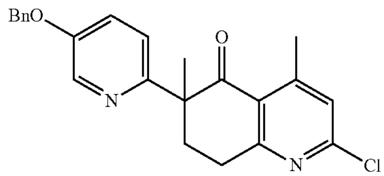 [SMILES: Cc1cc(Cl)nc2c1C(=O)C(C)(c1ccc(OCc3ccccc3)cn1)CC2] | LC-MS: 393.3 [M + H]+. |
| 75 | 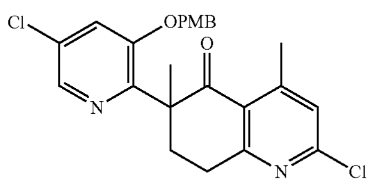 | LC-MS: 456.9 [M + H]+. |
| 76 | 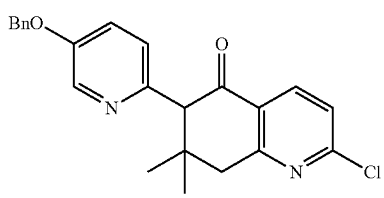 [SMILES: CC1(C)Cc2nc(Cl)ccc2C(=O)C1c1ccc(OCc2ccccc2)cn1] | LC-MS: 393.2 [M + H]+. |
| 77 | 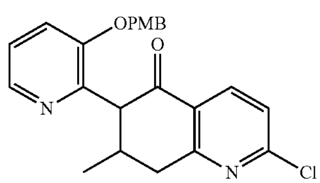 | LC-MS: 409.3 [M + H]+. |
| 78 | 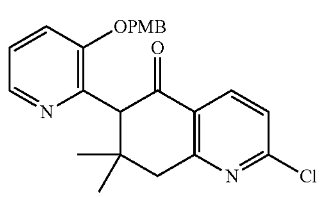 | LC-MS: 423.3 [M + H]+. |
| 79 | 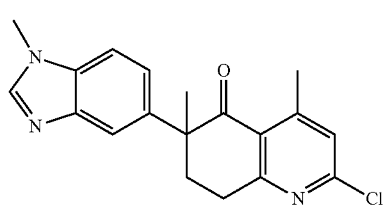 [SMILES: Cc1cc(Cl)nc2c1C(=O)C(C)(c1ccc3c(c1)ncn3C)CC2] | LC-MS: 340.3 [M + H]+. |

| Intermediate No. | Structure | Characterization Data |
|---|---|---|
| 80 | 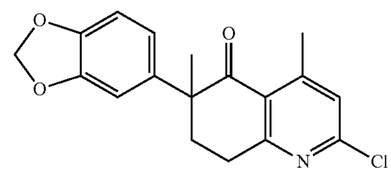 [SMILES: Cc1cc(Cl)nc2c1C(=O)C(C)(c1ccc3c(c1)OCO3)CC2] | LC-MS: 329.8 [M + H]+. |
| 81 | 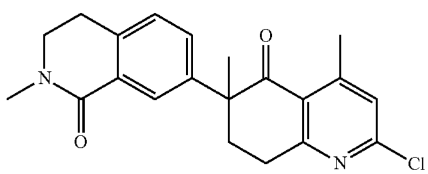 [SMILES: Cc1cc(Cl)nc2c1C(=O)C(C)(c1ccc3c(c1)C(=O)N(C)CC3)CC2] | LC-MS: 369.0 [M + H]+. |
| 82 | 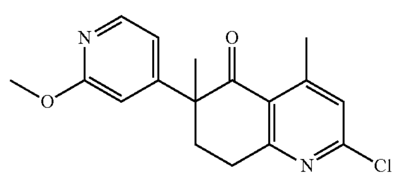 [SMILES: COc1cc(C2(C)CCc3nc(Cl)cc(C)c3C2=O)ccn1] | LC-MS: 316.3 [M + H]+. |
| 83 | 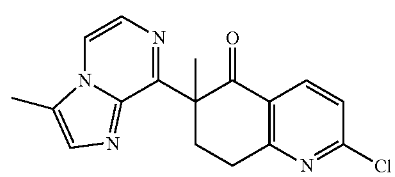 [SMILES: Cc1cnc2c(C3(C)CCc4nc(Cl)ccc4C3=O)nccn12] | LC-MS: 327.2 [M + H]+. |
| 84 | 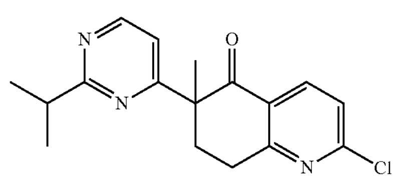 [SMILES: CC(C)c1nccc(C2(C)CCc3nc(Cl)ccc3C2=O)n1] | LC-MS: 315.7 [M + H]+. |
| 85 | 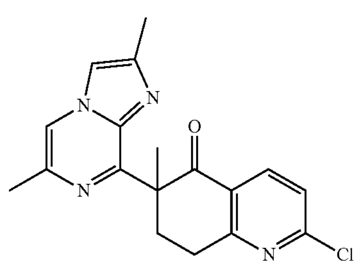 [SMILES: Cc1cn2cc(C)nc2c(C2(C)CCc3nc(Cl)ccc3C2=O)n1] | LC-MS: 340.9 [M + H]+. |
| 86 | 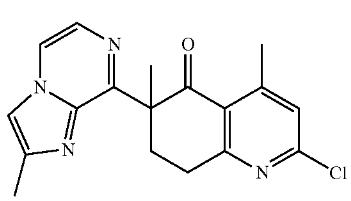 [SMILES: Cc1cn2ccnc(C3(C)CCc4nc(Cl)cc(C)c4C3=O)c2n1] | LCMS: 341.0 [M + H]+. |

-continued

| Intermediate No. | Structure | Characterization Data |
|---|---|---|
| 87 | 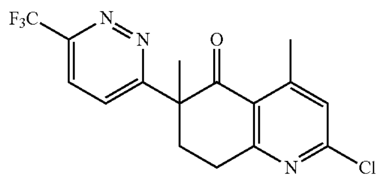 [SMILES: Cc1cc(Cl)nc2c1C(=O)C(C)(c1ccc(C(F)(F)F)nn1)CC2] | LCMS: 356.0 [M + H]+. |
| 88 | 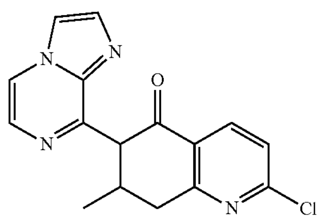 [SMILES: CC1Cc2nc(Cl)ccc2C(=O)C1c1nccn2ccnc12] | — |
| 89 | 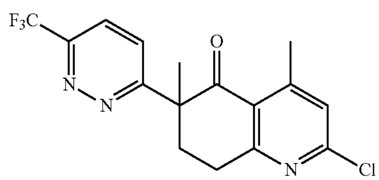 | LCMS: 342.3 [M + H]+ |
| 90 | 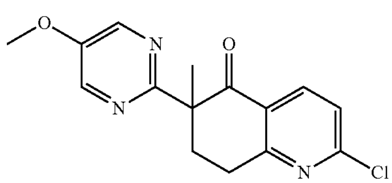 [SMILES: COc1cnc(C2(C)CCc3nc(Cl)ccc3C2=O)nc1] | LC-MS: 303.6 [M + H]+. |
| 91 | 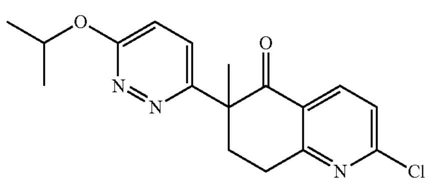 [SMILES: CC(C)Oc1ccc(C2(C)CCc3nc(Cl)ccc3C2=O)nn1] | LC-MS: 332.0 [M + H]+. |
| 92 | 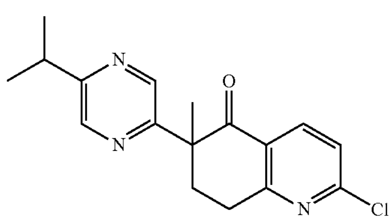 [SMILES: CC(C)c1cnc(C2(C)CCc3nc(Cl)ccc3C2=O)cn1] | LC-MS: 317.0 [M + 2H]+. |
| 93 | 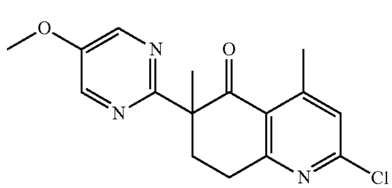 [SMILES: COc1cnc(C2(C)CCc3nc(Cl)cc(C)c3C2=O)nc1] | LC-MS: 318.0 [M + H]+. |

-continued

| Intermediate No. | Structure | Characterization Data |
|---|---|---|
| 94 | 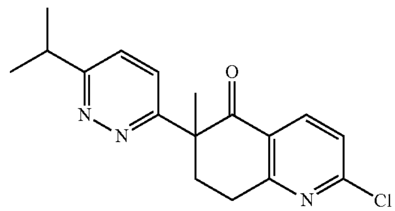 [SMILES: CC(C)c1ccc(C2(C)CCc3nc(Cl)ccc3C2=O)nn1] | LC-MS: 316.2 [M + H]⁺. |
| 95 | 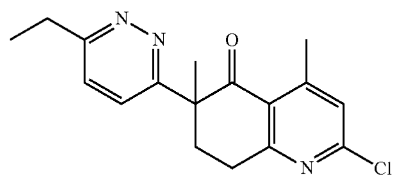 [SMILES: CCc1ccc(C2(C)CCc3nc(Cl)cc(C)c3C2=O)nn1] | LC-MS: 316.3 [M + H]⁺. |
| 96 | 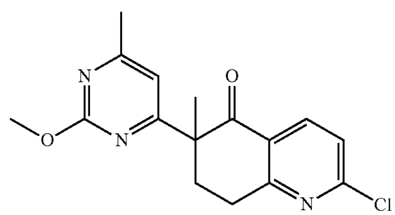 [SMILES: COc1nc(C)cc(C2(C)CCc3nc(Cl)ccc3C2=O)n1] | LC-MS: 317.9 [M + H]⁺ |
| 97 | 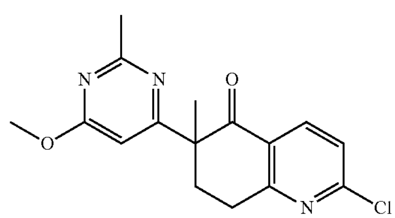 [SMILES: COc1cc(C2(C)CCc3nc(Cl)ccc3C2=O)nc(C)n1] | LC-MS: 318.2 [M + H]⁺. |
| 98 | 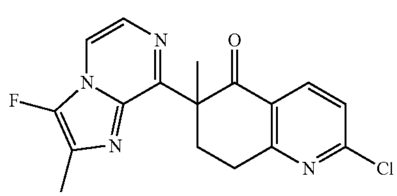 [SMILES: Cc1nc2c(C3(C)CCc4nc(Cl)ccc4C3=O)nccn2c1F] | LC-MS: 345.2 [M + H]⁺. |
| 99 | 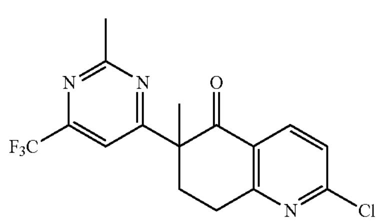 [SMILES: Cc1nc(C(F)(F)F)cc(C2(C)CCc3nc(Cl)ccc3C2=O)n1] | LC-MS: 356.2 [M + H]⁺. |
| 100 | 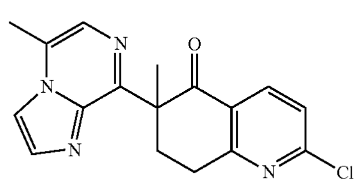 [SMILES: Cc1cnc(C2(C)CCc3nc(Cl)ccc3C2=O)c2nccn12] | LC-MS: 327.0 [M + H]⁺. |

| Intermediate No. | Structure | Characterization Data |
|---|---|---|
| 101 | 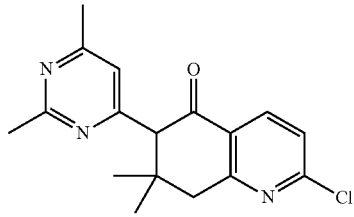 [SMILES: Cc1cc(C2C(=O)c3ccc(Cl)nc3CC2(C)C)nc(C)n1] | LC-MS: 316.4 [M + H]+. |
| 102 | 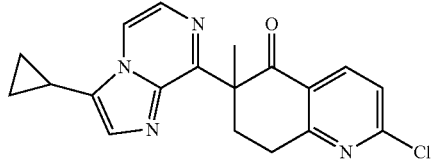 [SMILES: CC1(c2nccn3c(C4CC4)cnc23)CCc2nc(Cl)ccc2C1=O] | LC-MS: 353.2 [M + H]+. |
| 103 | 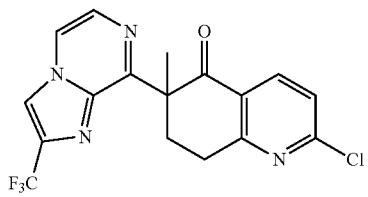 [SMILES: CC1(c2nccn3cc(C(F)(F)F)nc23)CCc2nc(Cl)ccc2C1=O] | LC-MS: 381.3 [M + H]+. |
| 104 | 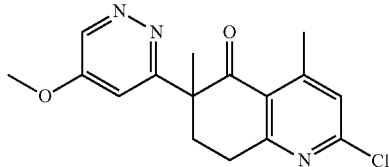 [SMILES: COc1cnnc(C2(C)CCc3nc(Cl)cc(C)c3C2=O)c1] | LC-MS: 318.2 [M + H]+. |
| 105 | 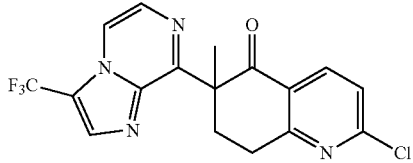 [SMILES: CC1(c2nccn3c(C(F)(F)F)cnc23)CCc2nc(Cl)ccc2C1=O] | LC-MS: 381.3 [M + H]+. |
| 106 | 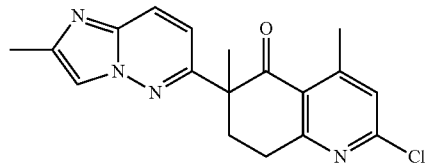 [SMILES: Cc1cn2nc(C3(C)CCc4nc(Cl)cc(C)c4C3=O)ccc2n1] | LC-MS: 341.3 [M + H]+. |
| 107 | 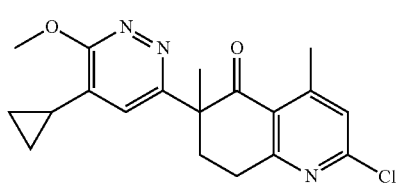 [SMILES: COc1nnc(C2(C)CCc3nc(Cl)cc(C)c3C2=O)cc1C1CC1] | LC-MS: 358.4 [M + H]+. |

| Intermediate No. | Structure | Characterization Data |
|---|---|---|
| 108 | 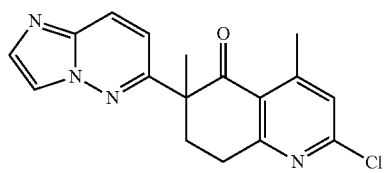 [SMILES: Cc1cc(Cl)nc2c1C(=O)C(C)(c1ccc3nccn3n1)CC2] | LC-MS: 327.1 [M + H]+ |
| 109 | 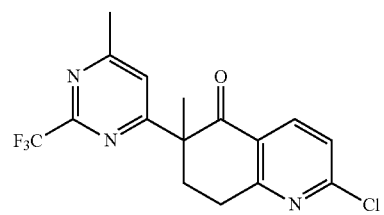 [SMILES: Cc1cc(C2(C)CCc3nc(Cl)ccc3C2=O)nc(C(F)(F)F)n1] | LC-MS: 356.3 [M + H]+. |
| 110 | 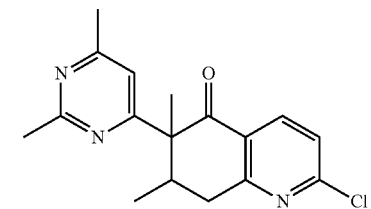 [SMILES: Cc1cc(C2(C)C(=O)c3ccc(Cl)nc3CC2C)nc(C)n1] | LC-MS: 316.3 [M + H]+ |
| 111 | 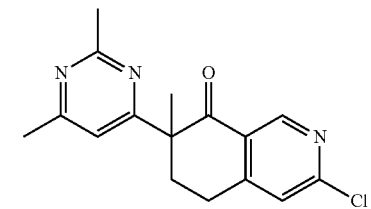 [SMILES: Cc1cc(C2(C)CCc3cc(Cl)ncc3C2=O)nc(C)n1] | LC-MS: 302.2 [M + H]+ |
| 112 | 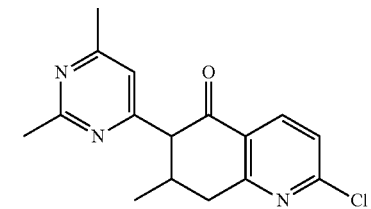 [SMILES: Cc1cc(C2C(=O)c3ccc(Cl)nc3CC2C)nc(C)n1] | LC-MS: 302.3 [M + H]+ |

Intermediate-113: Synthesis of 2-chloro-6-methyl-6-(5-methylthiophen-2-yl)-7,8-dihydroquinolin-5(6H)-one

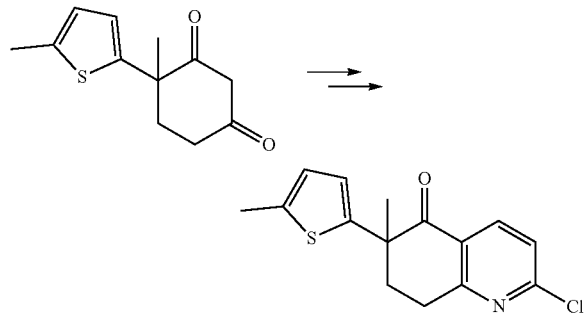

Intermediate 2-chloro-4,6-dimethyl-6-(5-methylthiophen-2-yl)-7,8-dihydroquinolin-5(6H)-one (Intermediate-113) was synthesized using the same procedure as described in Step-i to Step-iv of Intermediate-29. LC-MS: 292.3 [M+H]$^+$.

Intermediate-114: Synthesis of 2-chloro-6-(3,5-dimethyl-1H-pyrazol-1-yl)-6-methyl-7,8-dihydroquinolin-5(6H)-one

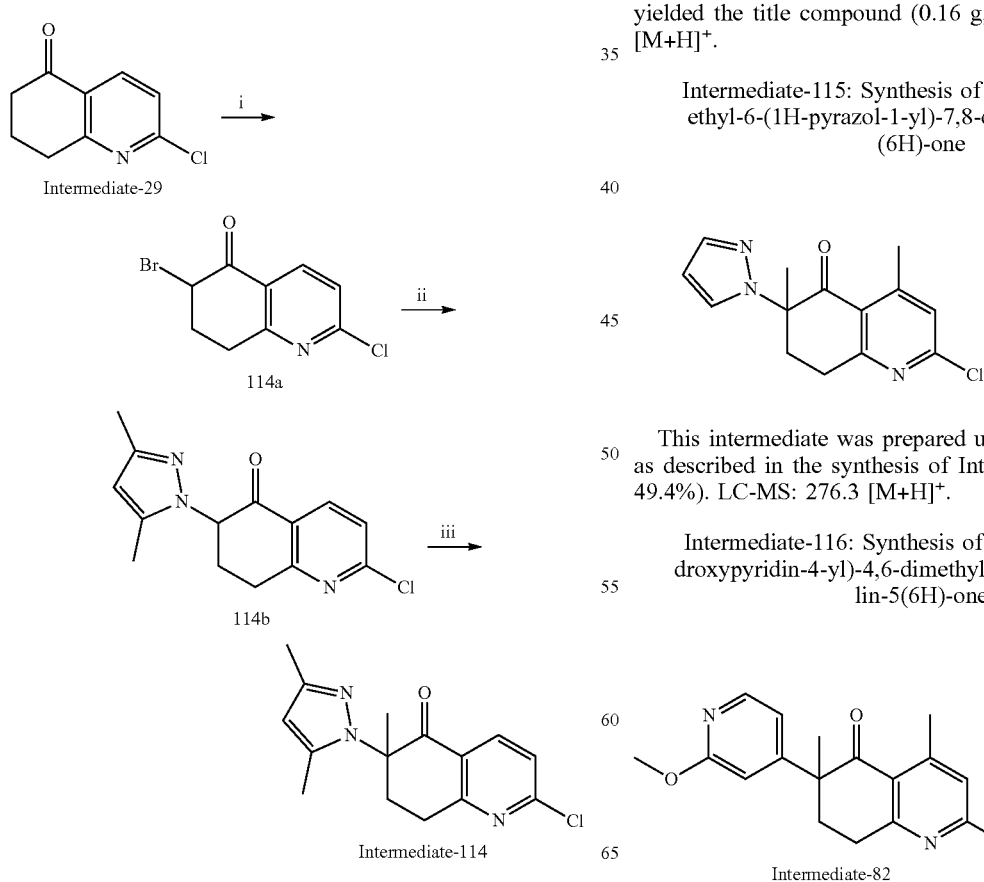

Step-i: 6-bromo-2-chloro-7,8-dihydroquinolin-5(6H)-one

To a solution of 2-chloro-7,8-dihydroquinolin-5(6H)-one (2 g, 11.2 mmol) in HBr (20 mL) was added Br$_2$ (1.79 g, 11.2 mmol) in DCM (20 mL) at RT and stirred for 2 h at the same temperature. The reaction was quenched with ice-water, extracted with ethyl acetate. The organic portion was dried over anhydrous sodium sulphate, filtered and concentrated to get the title compound (1.8 g, 64%). LC-MS: 260.1 [M]$^+$, 262.1 [M+2H]$^+$.

Step-ii: 2-chloro-6-(3,5-dimethyl-1H-pyrazol-1-yl)-7,8-dihydroquinolin-5(6H)-one To a solution of 6-bromo-2-chloro-7,8-dihydroquinolin-5(6H)-one (0.6 g, 2.32 mmol) in DMF (15 mL) was added 3,5-dimethyl-1H-pyrazole (1.13 g, 11.6 mmol) at RT and the reaction mixture was heated to 60° C. for 6 h. The reaction was quenched with ice-water, extracted with ethyl acetate. The organic layer was dried over anhydrous sodium sulphate, filtered and concentrated to get residue, which on purification by column chromatography using 30% ethyl acetate in hexane as eluent yielded the titled compound (0.24 g, 37.1%). LC-MS: 276.2 [M+H]$^+$.

Step-iii: 2-chloro-6-(3,5-dimethyl-1H-pyrazol-1-yl)-6-methyl-7,8-dihydroquinolin-5(6H)-one Alkylation of 2-chloro-6-(3,5-dimethyl-1H-pyrazol-1-yl)-7,8-dihydroquinolin-5(6H)-one by using the similar protocol as described in the step-ii of Intermediate-38, this yielded the title compound (0.16 g, 60%). LC-MS: 290.1 [M+H]$^+$.

Intermediate-115: Synthesis of 2-chloro-4,6-dimethyl-6-(1H-pyrazol-1-yl)-7,8-dihydroquinolin-5(6H)-one

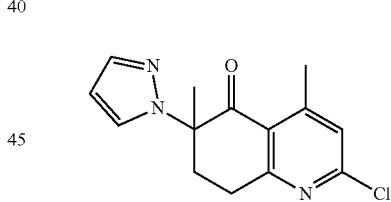

This intermediate was prepared using the same protocol as described in the synthesis of Intermediate-114 (0.13 g, 49.4%). LC-MS: 276.3 [M+H]$^+$.

Intermediate-116: Synthesis of 2-chloro-6-(2-hydroxypyridin-4-yl)-4,6-dimethyl-7,8-dihydroquinolin-5(6H)-one

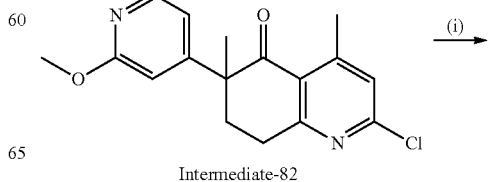

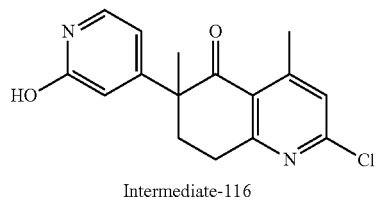

Intermediate-116

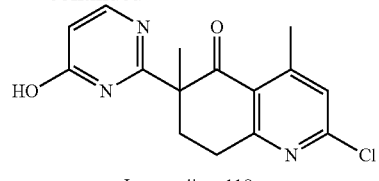

Intermediate-118

A mixture of 2-chloro-6-(2-methoxypyridin-4-yl)-4,6-dimethyl-7,8-dihydroquinolin-5(6H)-one (Intermediate-82, 0.2 g, 0.63 mmol) and 48% aqueous HBr (1 mL) in acetic acid (2 mL) was heated to 90° C. for 12 h. The reaction mixture was cooled to room temperature, neutralized with ammonium hydroxide, and extracted with ethyl acetate. The organic portion was dried over sodium sulphate, filtered and concentrated to get the title compound (0.11 g, 57.9%). LC-MS: 303.2 [M+H]$^+$.

Intermediate-117: Synthesis of 2-chloro-6-(6-hydroxypyridin-3-yl)-4,6-dimethyl-7,8-dihydroquinolin-5(6H)-one A mixture of 2-chloro-6-(4-methoxypyrimidin-2-yl)-4,6-dimethyl-7,8-dihydroquinolin-5(6H)-one (Intermediate-57, 0.45 g, 1.46 mmol), sodium iodide (0.32 g, 2.12 mmol) and trimethylsilyl chloride (0.23 g, 2.12 mmol) in acetonitrile (10 mL) was heated to 70° C. for 12 h. The reaction mixture was cooled to room temperature and filtered. The filtrate was acidified with citric acid and extracted with ethyl acetate. Then the organic phase was washed with water followed by brine. The separated organic layer was dried over sodium sulfate, filtered and concentrated to get the title compound (0.15 g, 35%). LC-MS: 304.3 [M+H]$^+$.

Intermediate-119: Synthesis of 2-chloro-6-(6-hydroxypyridin-2-yl)-4,6-dimethyl-7,8-dihydroquinolin-5(6H)-one

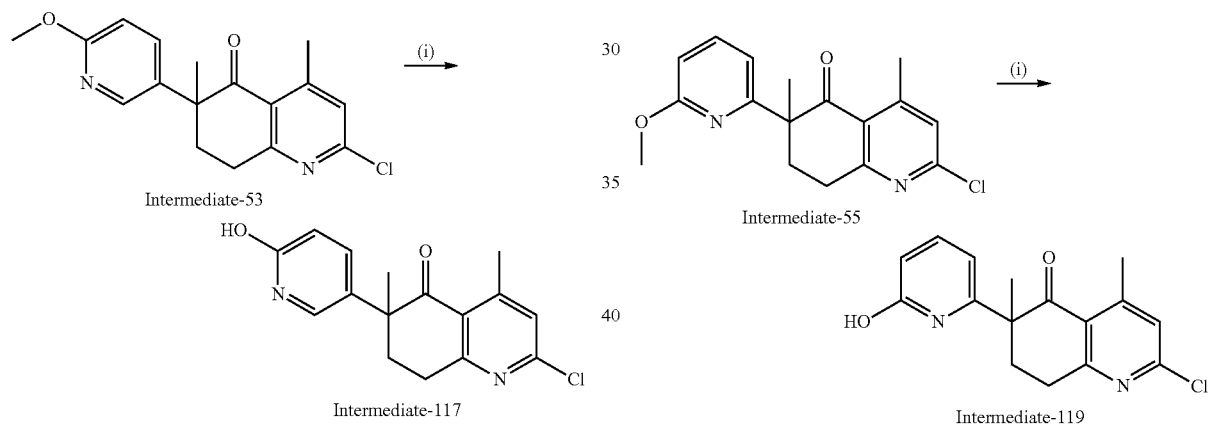

2-chloro-6-(6-hydroxypyridin-3-yl)-4,6-dimethyl-7,8-dihydroquinolin-5(6H)-one was prepared using the protocol as described in the synthesis of Intermediate-116 with appropriate variations in reactants, quantities of reagents, solvents and reaction conditions. LC-MS: 303.2 [M+H]$^+$.

Intermediate-118: Synthesis of 2-chloro-6-(4-hydroxypyrimidin-2-yl)-4,6-dimethyl-7,8-dihydroquinolin-5(6H)-one 2-chloro-6-(6-hydroxypyridin-2-yl)-4,6-dimethyl-7,8-dihydroquinolin-5(6H)-one was prepared using the protocol as described in the synthesis of Intermediate-118 with appropriate variations in reactants, quantities of reagents, solvents and reaction conditions. LC-MS: 303.2 [M+H]$^+$.

Intermediate-120: Synthesis of 2-chloro-6-(5-chloro-3-hydroxypyridin-2-yl)-4,6-dimethyl-7,8-dihydroquinolin-5(6H)-one

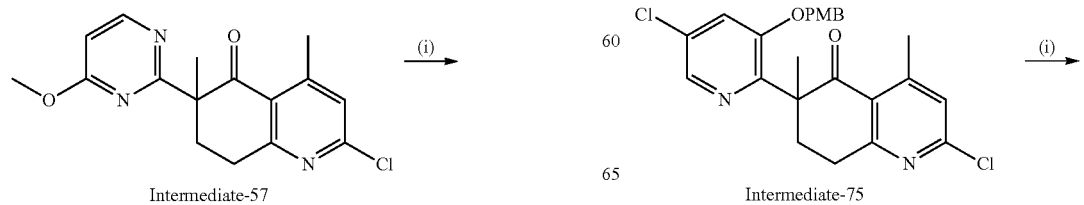

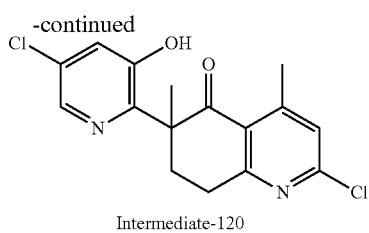

Intermediate-120

A mixture of 2-chloro-6-(5-chloro-3-((4-methoxybenzyl)oxy)pyridin-2-yl)-4,6-dimethyl-7,8-dihydroquinolin-5(6H)-one (0.35 g, 0.76 mmol) in TFA was heated to 100° C. for 30 min. The reaction mixture was concentrated to dryness and the crude was purified by flash chromatography using 20% ethyl acetate in hexanes to afford the titled compound (0.3 g, 85.6%). LC-MS: 337.2 [M+H]$^+$.

Intermediate-121: Synthesis of 2-chloro-6-(6-ethylpyridazin-3-yl)-6-methyl-7,8-dihydroquinolin-5(6H)-one

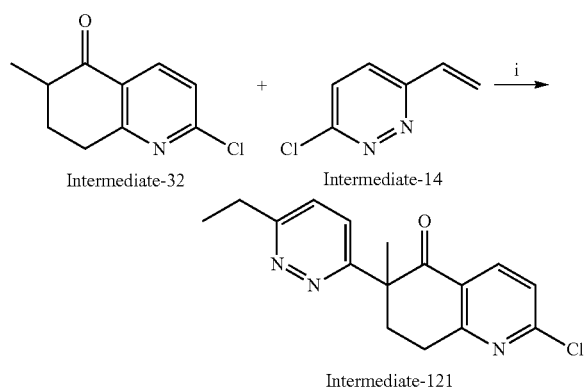

Intermediate-121

2-chloro-6-methyl-7,8-dihydroquinolin-5(6H)-one (0.2 g, 1.1 mmol) was coupled with 3-chloro-6-vinylpyridazine (0.185 g, 1.32 mmol) using the same procedure as described in the step-i of Intermediate-38. The residue after coupling was dissolved in methanol, added 10% Pd—C carefully under nitrogen atmosphere and stirred under the positive pressure of hydrogen using a bladder for 30 min. The reaction mixture was filtered through celite and filtrate was concentrated to get the titled compound as crude (0.4 g). LC-MS: 302.0.1 [M+H]$^+$.

Intermediate-122: Synthesis of 2-chloro-6-(6-hydroxypyridin-3-yl)-6-methyl-7,8-dihydroquinolin-5(6H)-one

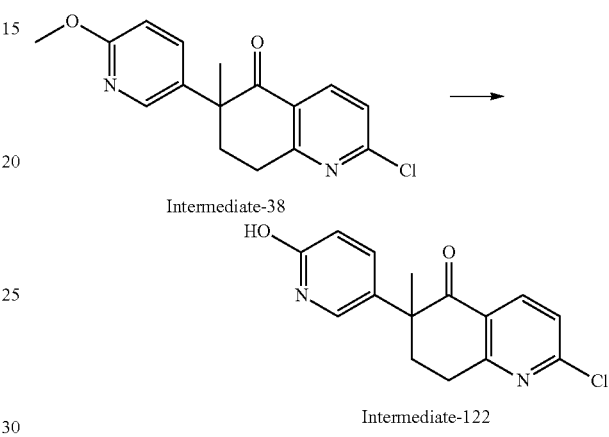

2-chloro-6-(6-hydroxypyridin-3-yl)-6-methyl-7,8-dihydroquinolin-5(6H)-one was prepared using the protocol as described in the synthesis of Intermediate-116 with appropriate variations in reactants, quantities of reagents, solvents and reaction conditions.

Intermediate-123 (Mixture): Synthesis of 2-chloro-6-(6-methoxy-4-methylpyridazin-3-yl)-4,6-dimethyl-7,8-dihydroquinolin-5(6H)-one and 2-chloro-6-(6-methoxy-5-methylpyridazin-3-yl)-4,6-dimethyl-7,8-dihydroquinolin-5(6H)-one

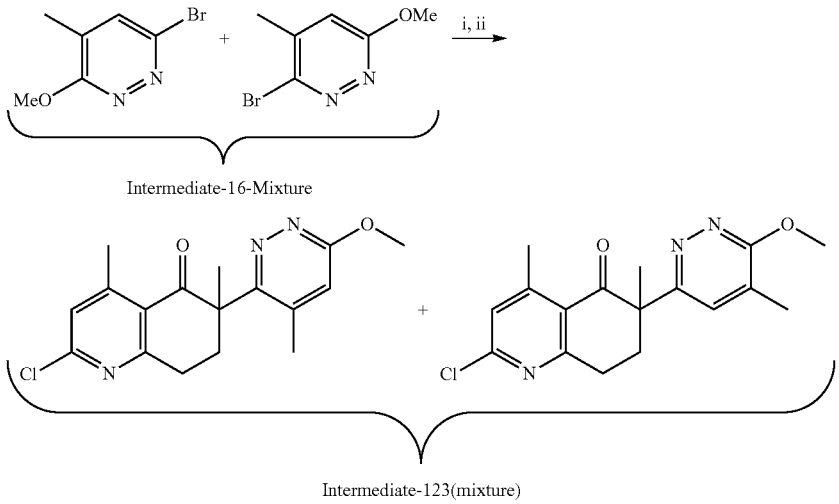

Intermediate 2-chloro-6-(6-methoxy-4-methylpyridazin-3-yl)-4,6-dimethyl-7,8-dihydroquinolin-5(6H)-one and 2-chloro-6-(6-methoxy-5-methylpyridazin-3-yl)-4,6-dimethyl-7,8-dihydroquinolin-5(6H)-one (mixture) was prepared using the same protocol explained in the synthesis of Intermediate-38 and isolated as a mixture of positional isomers. LC-MS: 332.2 [M+H]+.

Intermediate-124: Synthesis of N-(4,6-dimethyl-6-(1-methyl-6-oxo-1,6-dihydropyridazin-3-yl)-5-oxo-5,6,7,8-tetrahydroquinolin-2-yl)-2-(4-(ethylsulfonyl)phenyl)acetamide

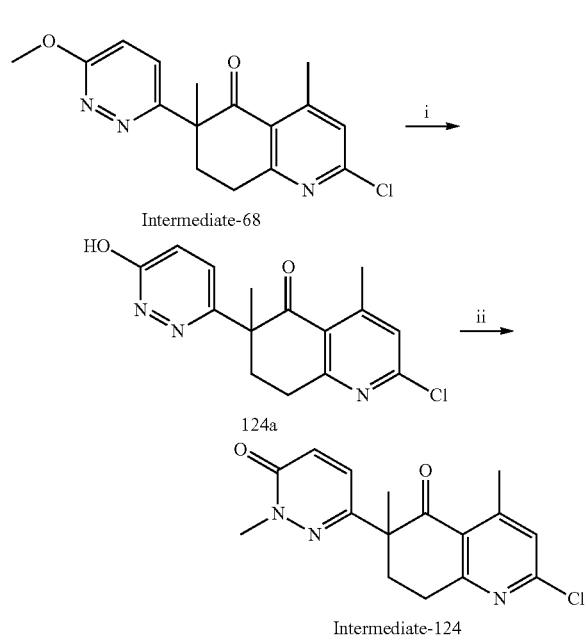

Step-i: Synthesis of 2-chloro-6-(6-hydroxypyridazin-3-yl)-4,6-dimethyl-7,8-dihydro quinolin-5(6H)-one A mixture of 2-chloro-6-(6-methoxypyridazin-3-yl)-4,6-dimethyl-7,8-dihydroquinolin-5(6H)-one (0.4 g, 1.2 mmol) and 48 wt. % hydrobromic acid in water (4 mL) was stirred at 50° C. for 3 h. The reaction mixture was neutralized with 10% aqueous sodium bicarbonate solution, extracted with ethyl acetate. The organic layer was separated, washed with, brine, dried over anhydrous sodium sulfate and concentrated under reduced pressure to get 2-chloro-6-(6-hydroxypyridazin-3-yl)-4,6-dimethyl-7,8-dihydroquinolin-5(6H)-one (0.3 g, 79%). LC-MS: 304.3 [M+H]+.

Step-ii: Synthesis of 2-chloro-4,6-dimethyl-6-(1-methyl-6-oxo-1,6-dihydropyridazin-3-yl)-7,8-dihydroquinolin-5(6H)-one To a solution of 2-chloro-6-(6-hydroxypyridazin-3-yl)-4,6-dimethyl-7,8-dihydroquinolin-5(6H)-one (0.3 g, 0.9 mmol) in DMF (5 mL), was added 60% sodium hydride in mineral oil (0.045 g, 0.18 mmol) and then the reaction mixture was heated to 60° C. At this moment, was added methyl iodide (0.7 g, 4.5 mmol) and the reaction mixture was stirred at 60° C. for 1 h. The reaction mass was quenched with ice cold water and extracted with ethyl acetate. The combined organic layers were washed with water, brine, dried over anhydrous sodium sulfate and concentrated to get 2-chloro-4,6-dimethyl-6-(1-methyl-6-oxo-1,6-dihydro pyridazin-3-yl)-7,8-dihydroquinolin-5(6H)-one (0.26 g, 83%). LC-MS: 317.9 [M+H]+.

Intermediate-125: Synthesis of 2-chloro-6-(imidazo[1,2-a]pyrazin-8-yl)-6,8-dimethyl-7,8-dihydroquinolin-5(6H)-one

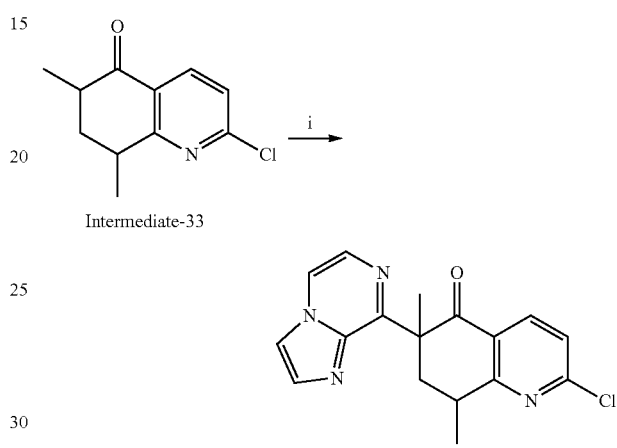

2-chloro-6-methyl-7,8-dihydroquinolin-5(6H)-one, (0.2 g, 1.1 mmol) was coupled with 3-chloro-6-vinylpyridazine (0.185 g, 1.32 mmol) using the same procedure as described in the step-i of Intermediate-38. LC-MS: 327.0 [M+H]+.

Intermediate-126: Synthesis of 2-chloro-6-(6-ethyl-2-methylpyrimidin-4-yl)-6-methyl-7,8-dihydroquinolin-5(6H)-one

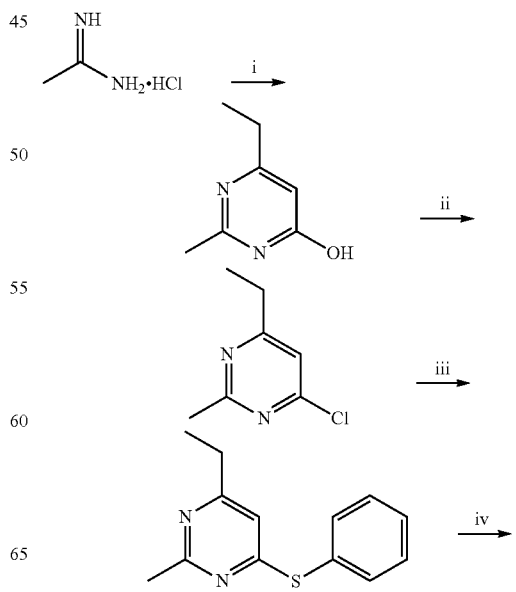

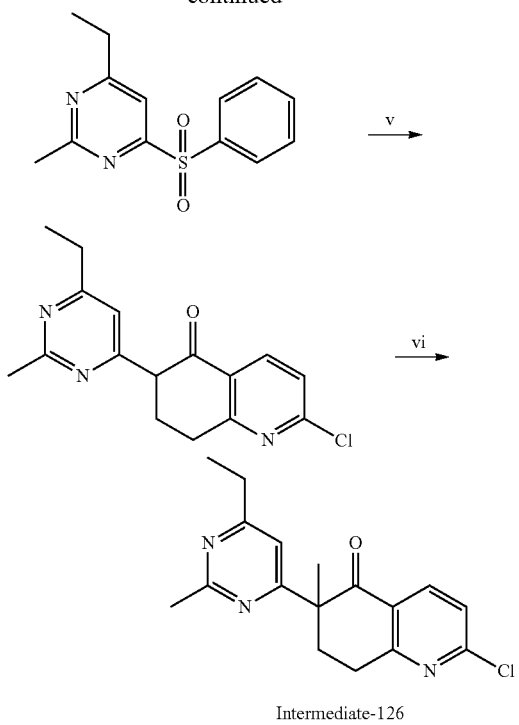

Intermediate-126

Step-i: Synthesis of 6-ethyl-2-methylpyrimidin-4-ol

A 250 mL round bottom flask was added dry methanol (100 mL) followed by careful addition of sodium metal (1.77 g, 76.84 mmol) and stirred at room temperature until all metal had dissolved. To the generated sodium methoxide in methanol, was added acetamidine hydrochloride (10.0 g, 76.84 mmol) and methyl 3-oxo-pentanoate (7.27 g, 76.84 mmol). The resulting reaction mixture was stirred at room temperature for 12 h. The volatiles were evaporated under reduced pressure to get the residue. The residue was extracted with hot chloroform. The organic layer was evaporated under reduced pressure to obtain 6-ethyl-2-methylpyrimidin-4-ol (7.0 g, 66%). 1H NMR (300 MHz, CDCl$_3$): δ 8.93 (br s, 1H), 6.16 (s, 1H), 2.51-2.59 (m, 2H), 2.45 (s, 3H), 1.24 (t, J=7.5 Hz, 3H); LC-MS: 139.3 [M+H]$^+$.

Step-ii: Synthesis of 4-chloro-6-ethyl-2-methylpyrimidine

A suspension of 6-ethyl-2-methylpyrimidin-4-ol (7.0 g, 50.7 mmol) in acetonitrile (14 mL) in a 50 mL round bottomed flask was added phosphorous oxychloride (14 mL) and stirred at 80° C. for 3 h. The reaction mixture was cooled to room temperature, added slowly into ice-cold water and basified to pH 7-8 with aqueous ammonia, keeping the temperature below 0° C. The aqueous layer was extracted with diethyl ether. The combined organic layer was washed with water, brine, dried over anhydrous sodium sulfate and evaporated under reduced pressure to get 4-chloro-6-ethyl-2-methylpyrimidine (6.1 g, 77%). 1H NMR (300 MHz, CDCl$_3$): δ 7.03 (s, 1H), 2.70-2.78 (m, 2H), 2.68 (s, 3H), 1.24 (t, J=7.5 Hz, 3H); LC-MS: 157.0 [M+H]$^+$.

Step-iii: Synthesis of 4-ethyl-2-methyl-6-(phenylthio)pyrimidine

A 250 mL round bottom flask, was added ethanol (50 mL), then carefully added sodium metal (0.97 g, 42.1 mmol) and stirred at room temperature until all metal had dissolved. To the generated sodium ethoxide in ethanol, was added thiophenol (4.64 g, 42.1 mmol) and refluxed for 30 min. To the reaction mixture, was added 4-chloro-6-ethyl-2-methylpyrimidine (6.6 g, 42.1 mmol) and refluxed for 2 h. To the reaction mixture, was added water (2 mL) and the volatiles were evaporated under reduced pressure to get the residue. The residue was dissolved in aqueous 20% HCl and washed with diethyl ether. The aqueous layer was basified to pH 7-8 with solid potassium carbonate and extracted with chloroform. The combined organic layer was washed with water, brine, dried over anhydrous sodium sulfate and evaporated under vacuum to get 4-ethyl-2-methyl-6-(phenylthio)pyrimidine (6.1 g, 63%). LC-MS: 231.0 [M+H]$^+$.

Step-iv: Synthesis of 4-ethyl-2-methyl-6-(phenyl sulfonyl)pyrimidine

To a 100 mL round bottom flask, was added 4-ethyl-2-methyl-6-(phenylsulfonyl)pyrimidine (6.0 g, 26.1 mmol) and dichloromethane (100 mL). The reaction mixture was cooled to 0-5° C., and portion wise added 77% mCPBA (11.7 g, 52.2 mmol) and stirred at room temperature for 12 h. The reaction mixture was cooled to 0-5° C., and portion wise added 77% mCPBA (2.33 g, 10.4 mmol) and stirred at room temperature for 2 h. The reaction mixture was filtered through a pad of celite. The pad was washed with DCM. The combined filtrate was washed with 30% aqueous potassium carbonate solution. The combined organic layer was washed with water, brine, dried over anhydrous sodium sulfate and evaporated under vacuum to get the crude product. The crude product was purified by column chromatography (60-120 mesh silica gel, 5-15% EtOAc in hexane) to get 4-ethyl-2-methyl-6-(phenylsulfonyl)pyrimidine (4.1 g, 60%). LC-MS: 263.0 [M+H]+.

Step-v: Synthesis of 2-chloro-6-(6-ethyl-2-methylpyrimidin-4-yl)-7,8-dihydroquinolin-5(6H)-one To a 50 mL round bottom flask, was added tetrahydrofuran (15 ml). To the same flask, was added 60% sodium hydride in mineral oil (0.88 g, 22.0 mmol), 2-chloro-7,8-dihydroquinolin-5(6H)-one (1.0 g, 5.5 mmol) and 4-ethyl-2-methyl-6-(phenylsulfonyl)pyrimidine (2.89 g, 11.0 mmol) under nitrogen atmosphere. The reaction mixture was refluxed for 30 min. The reaction mixture was quenched with ice cold water and extracted with dichloromethane. The combined organic layer was washed with brine, dried over anhydrous sodium sulfate and evaporated under reduced pressure to get 2-chloro-6-(6-ethyl-2-methylpyrimidin-4-yl)-7,8-dihydroquinolin-5(6H)-one (1.65 g, crude product). The obtained crude product was used in the next step without further purification. LC-MS: 302.2 [M+H]+.

Step-vi: Synthesis of 2-chloro-6-(6-ethyl-2-methylpyrimidin-4-yl)-6-methyl-7,8-dihydroquinolin-5(6H)-one This step was done using the same protocol explained in step-ii of Intermediate-38. LC-MS: 316.3 [M+H]+.

The below intermediates (127-128) were prepared by a procedure similar to the one described in Intermediate-126 with appropriate variations in reactants, quantities of reagents, solvents and reaction conditions.

| Intermediate No | Structure | Characterization data |
|---|---|---|
| 127 | 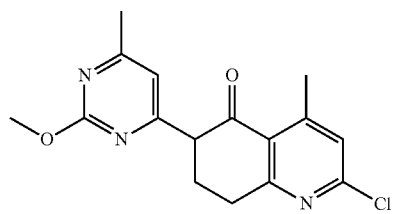 | LC-MS: 316.3 [M + H]+. |
| 128 | 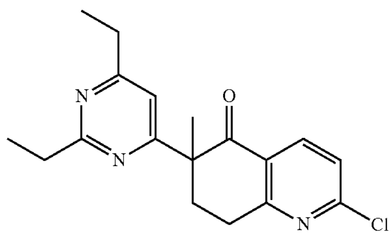 [SMILES: CCc1cc(C2(C)CCc3nc(Cl)ccc3C2=O)nc(CC)n1] | LC-MS: 330.3 [M + H]+. |

Intermediate-129: Synthesis of 2-chloro-6-(2-methoxy-6-methylpyrimidin-4-yl)-4-methyl-7,8-dihydroquinolin-5(6H)-one This intermediate was prepared using the same protocol explained in the synthesis of intermediate-38. LC-MS: 318.2 [M+H]+.

EXAMPLES

The present invention is further exemplified, but not limited, by the following examples that illustrate the preparation of compounds according to the invention.

Example-1: Synthesis of N-(4,6-dimethyl-5-oxo-6-(pyridin-2-yl)-5,6,7,8-tetrahydroquinolin-2-yl)-2-(4-(ethylsulfonyl)phenyl)acetamide (Compound-1)

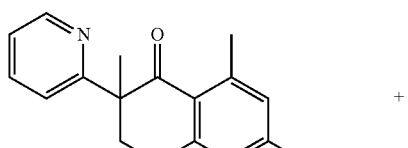

Intermediate-64

+

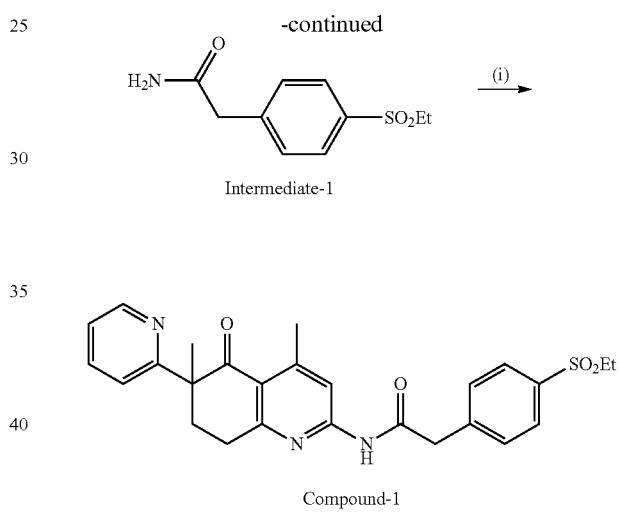

A stirred mixture of 2-chloro-4,6-dimethyl-6-(pyridin-2-yl)-7,8-dihydroquinolin-5(6H)-one (0.25 g, 0.83 mmol) and 2-(4-(ethylsulfonyl)phenyl)acetamide (0.245 g, 1.07 mmol) in 1,4-dioxane (20 mL) and K$_2$CO$_3$ (0.344 g, 2.49 mmol) taken in a screw cap sealed tube was degassed using argon. To this mixture was added palladium(II)acetate (0.093 g, 0.041 mmol), xantphos (0.048 g, 0.08 mmol) and heated to 110° C. for 12 h. The RM was cooled to RT, diluted with ethyl acetate, washed with water, brine solutions, dried over sodium sulfate and concentrated to get residue. The residue was purified by preparative TLC using 50% ethyl acetate in hexanes to get the title compound (0.127 g, 32.22%). $^1$H NMR (300 MHz, CDCl$_3$) δ 8.48 (d, J=3.63 Hz, 1H), 7.84-7.96 (m, 4H), 7.48-7.60 (m, 3H), 7.06-7.14 (m, 2H), 3.79 (s, 2H), 3.11 (q, J=7.58 Hz, 2H), 2.81-2.95 (m, 3H), 2.71 (s, 3H), 2.08-2.28 (m, 1H), 1.51 (s, 3H), 1.28 (t, J=7.42 Hz, 3H). LC-MS: 478.3 [M+H]+.

The below compounds (2-83) were prepared by a procedure similar to the one described in Example-1 with appropriate variations in reactants, quantities of reagents, solvents and reaction conditions.

| Compound No. | Structure | Characterization Data |
|---|---|---|
| 2 | 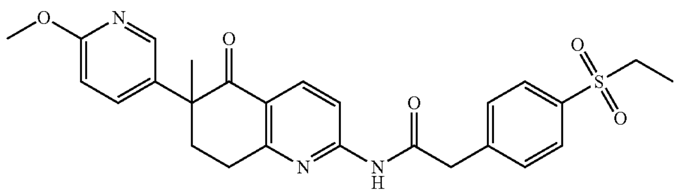 [SMILES: CCS(=O)(=O)c1ccc(CC(=O)Nc2ccc3c(n2)CCC(C)(c2ccc(OC)nc2)C3=O)cc1] | $^1$H NMR (400 MHz, CDCl$_3$): δ 8.40 (d, J = 8.9 Hz, 1H), 8.14 (d, J = 8.6 Hz, 1H), 7.88-8.00 (m, 4H), 7.53 (d, J = 8.1 Hz, 2H), 7.45 (dd, J = 8.7, 2.6 Hz, 1H), 6.69 (d, J = 8.6 Hz, 1H), 3.88 (s, 3H), 3.83 (s, 2H), 3.07-3.17 (m, 2H), 2.77-2.93 (m, 2H), 2.54-2.66 (m, 1H), 2.18-2.32 (m, 1H), 1.49-1.53 (m, 3H), 1.26-1.32 (m, 3H); LC-MS: 494.3 [M + H]$^+$. |
| 3 | 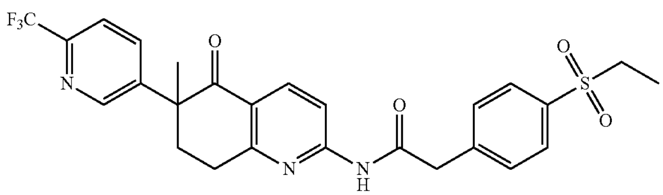 [SMILES: CCS(=O)(=O)c1ccc(CC(=O)Nc2ccc3c(n2)CCC(C)(c2ccc(C(F)(F)F)nc2)C3=O)cc1] | $^1$H NMR (400 MHz, CDCl$_3$): δ 8.64 (br s, 1H), 8.41 (d, J = 8.6 Hz, 1H), 8.18 (d, J = 8.6 Hz, 1H), 7.88-7.99 (m, 3H), 7.69 (br s, 1H), 7.61 (d, J = 8.3 z, 1H), 7.54 (d, J = 7.8 Hz, 2H), 3.85 (s, 2H), 3.12 (q, J = 7.3 Hz, 2H), 2.95 (br s, 1H), 2.75-2.87 (m, 1H), 2.69 (d, J = 14.2 Hz, 1H), 2.34 (d, J = 10.2 Hz, 1H), 1.57 (br s, 3H), 1.26-1.32 (m, 3H); LC-MS: 532.3 [M + H]$^+$. |
| 4 | 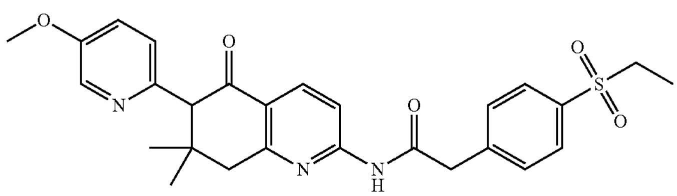 [SMILES: CCS(=O)(=O)c1ccc(CC(=O)Nc2ccc3c(n2)CC(C)(C)C(c2ccc(OC)cn2)C3=O)cc1] | $^1$H NMR (300 MHz, CDCl$_3$): δ 8.32 (d, J = 8.6 Hz, 1H), 8.04-8.22 (m, 3H), 7.93 (d, J = 8.2 Hz, 2H), 7.56 (d, J = 8.2 Hz, 2H), 7.06-7.19 (m, 2H), 3.86 (s, 2H), 3.81 (s, 3H), 3.68 (s, 1H), 3.28 (d, J = 17.1 Hz, 1H), 3.13 (q, J = 7.3 Hz, 2H), 2.75 (d, J = 17.1 Hz, 1H), 1.30 (s, 3H), 1.08 (s, 3H), 0.95 (s, 3H); LC-MS: 508.3 [M + H]$^+$. |
| 5 | 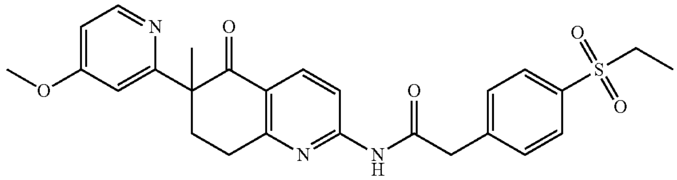 [SMILES: CCS(=O)(=O)c1ccc(CC(=O)Nc2ccc3c(n2)CCC(C)(c2cc(OC)ccn2)C3=O)cc1] | $^1$H NMR (400 MHz, CDCl$_3$): δ 8.40 (d, J = 8.6 Hz, 1H), 8.33 (d, J = 6.2 Hz, 1H), 8.12 (d, J = 8.9 Hz, 1H) 7.92-7.90 (m, 3H), 7.53 (d, J = 8.1 Hz, 2H), 6.61-6.68 (m, 2H), 3.82 (s, 2H), 3.77 (s, 3H), 3.12 (q, J = 7.5 Hz, 2H), 2.74-3.01 (m, 3H), 2.10-2.28 (m, 1H), 1.55 (s, 3H), 1.29 (s, 3H); LC-MS: 494.3 [M + H]$^+$. |
| 6 | 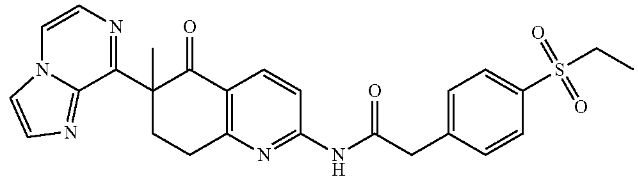 [SMILES: CCS(=O)(=O)c1ccc(CC(=O)Nc2ccc3c(n2)CCC(C)(c2nccn4ccnc24)C3=O)cc1] | $^1$H NMR (300 MHz, CDCl$_3$): δ 8.46 (d, J = 8.6 Hz, 1H), 8.17 (d, J = 8.8 Hz, 1H), 8.05 (s, 1H), 7.95-7.99 (m, 1H), 7.90-7.94 (m, 2H), 7.68-7.72 (m, 2H), 7.63 (s, 1H), 7.55 (d, J = 8.2 Hz, 2H), 3.84 (s, 2H), 3.59-3.71 (m, 1H), 3.12 (d, J = 7.5 Hz, 2H), 2.96-3.07 (m, 1H), 2.69-2.81 (m, 1H), 2.12-2.21 (m, 1H), 1.30 (t, J = 7.4 Hz, 3H); LC-MS: 504.3 [M + H]$^+$. |
| 7 | 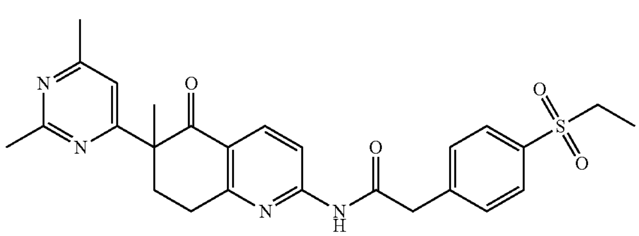 [SMILES: CCS(=O)(=O)c1ccc(CC(=O)Nc2ccc3c(n2)CCC(C)(c2cc(C)nc(C)n2)C3=O)cc1] | $^1$H NMR (300 MHz, CDCl$_3$): δ 8.38 (d, J = 8.78 Hz, 1H), 8.14 (d, J = 8.78 Hz, 1H), 7.89-7.98 (m, 3H), 7.53 (d, J = 8.23 Hz, 2H), 6.77 (s, 1H), 3.83 (s, 2H), 3.12 (q, J = 7.32 Hz, 2H), 2.96 (d, J = 4.39 Hz, 1H), 2.85-2.93 (m, 2H), 2.61 (s, 3H), 2.39 (s, 3H), 2.08-2.19 (m, 1H), 1.52 (s, 3H), 1.29 (s, 3H); LC-MS: 492.9 [M + H]$^+$. |
| 8 | 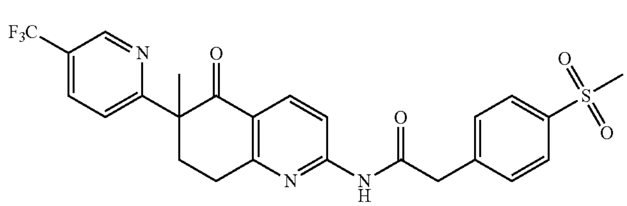 [SMILES: CC1(c2ccc(C(F)(F)F)cn2)CCc2nc(NC(=O)Cc3ccc(S(C)(=O)=O)cc3)ccc2C1=O] | $^1$H NMR (400 MHz, CDCl$_3$): δ 8.75 (s, 1H), 8.38 (d, J = 8.77 Hz, 1H), 8.12 (d, J = 8.77 Hz, 1H), 7.94 (d, J = 8.33 Hz, 3H), 7.77-7.84 (m, 1H), 7.52 (d, J = 8.33 Hz, 2H), 7.31 (d, J = 8.33 Hz, 1H), 3.81 (s, 2H), 3.46 (d, J = 7.02 Hz, 1H), 3.04 (s, 3H), 2.78-2.96 (m, 3H), 2.15-2.27 (m, 1H), 1.15-1.35 (m, 2H); LC-MS: 518 [M + H]$^+$. |

-continued

| Compound No. | Structure | Characterization Data |
|---|---|---|
| 9 | 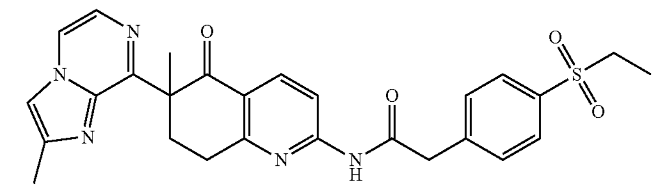 [SMILES: CCS(=O)(=O)c1ccc(CC(=O)Nc2ccc3c(n2)CCC(C)(c2nccn4cc(C)nc24)C3=O)cc1] | $^1$H NMR (400 MHz, DMSO-d$^6$): δ 11.23 (s, 1H), 8.42 (d, J = 4.57 Hz, 1H), 8.26 (d, J = 8.60 Hz, 1H), 8.08 (d, J = 8.60 Hz, 1H), 7.84 (d, J = 3.76 Hz, 3H), 7.58-7.64 (m, 3H), 3.90 (s, 2H), 3.49-3.61 (m, 1H), 3.37 (br s, 1H), 3.27 (d, J = 7.52 Hz, 2H), 2.96-3.06 (m, 1H), 2.59 (m, 1H), 2.36 (s, 3H), 2.06-2.14 (m, 1H), 1.71 (s, 3H), 1.09 (t, J = 7.25 Hz, 3H); LC-MS: 517.8 [M + H]$^+$. |
| 10 | 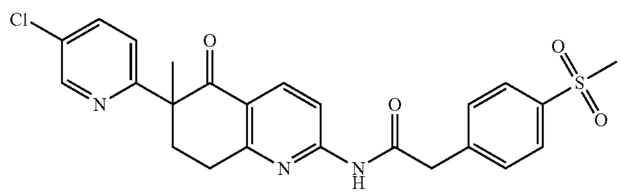 [SMILES: CC1(c2ccc(Cl)cn2)CCc2nc(NC(=O)Cc3ccc(S(C)(=O)=O)cc3)ccc2C1=O] | $^1$H NMR (400 MHz, CDCl$_3$): δ 8.45 (d, J = 2.45 Hz, 1H), 8.13 (d, J = 8.80 Hz, 1H), 7.96 (d, J = 8.07 Hz, 3H), 7.51-7.58 (m, 3H), 7.14 (d, J = 8.56 Hz, 1H), 3.83 (s, 2H), 3.48 (q, J = 7.09 Hz, 2H), 3.06 (s, 3H), 2.84-2.88 (m, 2H), 1.55 (s, 3H); LC-MS: 484.1 [M + H]$^+$. |
| 11 | 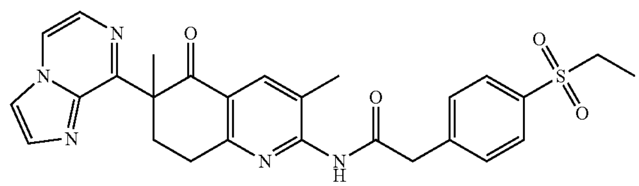 [SMILES: CCS(=O)(=O)c1ccc(CC(=O)Nc2nc3c(cc2C)C(=O)C(C)(c2nccn4ccnc24)CC3)cc1] | $^1$H NMR (300 MHz, CDCl$_3$): δ 8.24 (s, 1H), 7.98 (d, J = 4.57 Hz, 1H), 7.78-7.88 (m, 3H), 7.67-7.73 (m, 2H), 7.63 (s, 1H), 7.52 (d, J = 8.05 Hz, 2H), 4.16 (br s, 2H), 3.56-3.69 (m, 1H), 2.99-3.16 (m, 3H), 2.81 (d, J= 5.12 Hz, 1H), 2.25 (s, 3H), 2.15 (dd, J = 4.76, 8.14, 13.45 Hz, 1H), 1.83 (s, 3H), 1.27 (s, 3H); LC-MS: 518.2 [M + H]$^+$. |
| 12 | 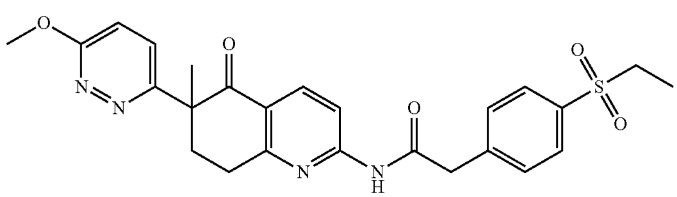 [SMILES: CCS(=O)(=O)c1ccc(CC(=O)Nc2ccc3c(n2)CCC(C)(c2ccc(OC)nn2)C3=O)cc1] | $^1$H NMR (300 MHz, CDCl$_3$): δ 8.37 (d, J= 8.60 Hz, 1H), 8.01-8.18 (m, 2H), 7.91 (d, J = 8.23 Hz, 2H), 7.54 (d, J = 8.23 Hz, 2H), 7.36 (d, J = 9.15 Hz, 1H), 6.92 (d, J = 9.33 Hz, 1H), 4.08 (s, 3H), 3.83 (s, 2H), 2.81-3.22 (m, 5H), 2.20-2.38 (m, 1H), 1.57 (s, 3H), 1.29 (t, J = 7.41 Hz, 3H); LC-MS: 494.9 [M + H]$^+$. |
| 13 | 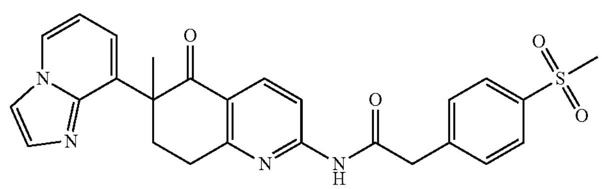 [SMILES: CC1(c2cccn3ccnc23)CCc2nc(NC(=O)Cc3ccc(S(C)(=O)=O)cc3)ccc2C1=O] | $^1$H NMR (300 MHz, CDCl$_3$): δ 8.44 (d, J = 8.60 Hz, 1H), 8.11-8.22 (m, 2H), 8.05 (d, J = 6.77 Hz, 1H), 7.96 (d, J = 8.23 Hz, 2H), 7.55 (d, J = 7.14 Hz, 4H), 6.87 (d, J = 6.95 Hz, 1H), 6.63-6.72 (m, 1H), 3.83 (s, 2H), 3.79 (s, 1H), 3.06 (s, 3H), 2.95-3.04 (m, 1H), 2.69-2.86 (m, 1H), 1.90-2.08 (m, 1H), 1.76 (s, 3H); LC-MS: 488.7 [M + H]$^+$. |
| 14 | 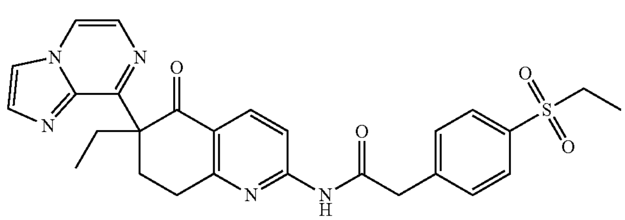 [SMILES: CCC1(c2nccn3ccnc23)CCc2nc(NC(=O)Cc3ccc(S(=O)(=O)CC)cc3)ccc2C1=O] | $^1$H NMR (300 MHz, DMSO-d$^6$): δ 10.98 (s, 1H), 8.53 (d, J = 4.39 Hz, 1H), 8.13 (s, 1H), 7.97 (d, J = 8.42 Hz, 1H), 7.81-7.90 (m, 3H), 7.69-7.75 (m, 2H), 7.62 (d, J = 8.23 Hz, 2H), 3.87 (s, 2H), 3.70 (q, J = 6.95 Hz, 2H), 3.21-3.28 (m, 2H), 2.82-3.01 (m, 4H), 1.08 (t, J = 7.32 Hz, 3H), 0.98 (t, J = 6.95 Hz, 3H); LC-MS: 518 [M + H]$^+$. |
| 15 | 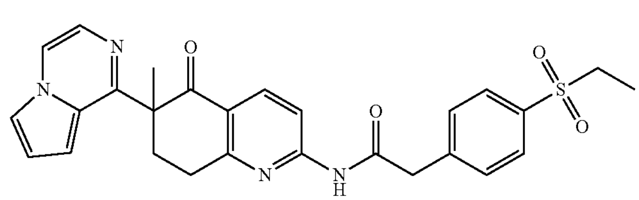 [SMILES: CCS(=O)(=O)c1ccc(CC(=O)Nc2ccc3c(n2)CCC(C)(c2nccn4cccc24)C3=O)cc1] | $^1$H NMR (400 MHz, CDCl$_3$): δ 8.37 (d, J = 8.60 Hz, 1H), 8.11 (d, J = 8.60 Hz, 1H), 8.00 (s, 1H), 7.90 (d, J = 8.06 Hz, 2H), 7.67 (d, J = 4.57 Hz, 1H), 7.52 (d, J = 8.33 Hz, 2H), 7.31-7.37 (m, 2H), 6.72-6.81 (m, 2H), 3.81 (s, 2H), 3.11 (q, J = 7.43 Hz, 3H), 2.96-3.06 (m, 1H), 2.90 (s, 1H), 2.12-2.26 (m, 1H), 1.28 (s, 3H); LC-MS: 503.1 [M + H]$^+$. |

| Compound No. | Structure | Characterization Data |
|---|---|---|
| 16 | 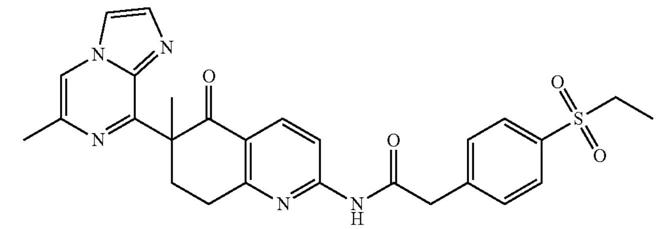 [SMILES: CCS(=O)(=O)c1ccc(CC(=O)Nc2ccc3c(n2)CCC(C)(c2nc(C)cn4ccnc24)C3=O)cc1] | ¹H NMR (400 MHz, CDCl₃): δ 8.43 (d, J = 8.60 Hz, 1H), 8.15 (d, J = 8.60 Hz, 1H), 8.04 (s, 1H), 7.92 (d, J = 8.06 Hz, 2H), 7.77 (s, 1H), 7.64 (s, 1H), 7.48-7.57 (m, 3H), 3.83 (s, 2H), 3.56-3.67 (m, 1H), 3.12 (q, J = 7.52 Hz, 2H), 2.96-3.05 (m, 1H), 2.72-2.82 (m, 1H), 2.34 (s, 3H), 2.13 (dd, J = 5.10, 8.06, 13.43 Hz, 1H), 1.82 (s, 3H), 1.29 (s, 3H); LC-MS: 518 [M + H]⁺. |
| 17 | 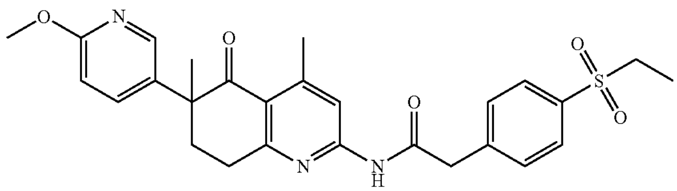 [SMILES: CCS(=O)(=O)c1ccc(CC(=O)Nc2cc(C)c3c(n2)CCC(C)(c2ccc(OC)nc2)C3=O)cc1] | ¹H NMR (400 MHz, CDCl₃): δ 7.99 (s, 1H), 7.85-7.93 (m, 3H), 7.53 (d, J = 8.06 Hz, 2H), 7.43 (dd, J = 2.55, 8.73 Hz, 1H), 6.70 (d, J = 8.87 Hz, 1H), 3.87 (s, 3H), 3.82 (s, 2H), 3.07-3.15 (m, 2H), 2.78-2.98 (m, 2H), 2.72 (s, 3H), 2.52-2.62 (m, 1H), 2.18 (s, 1H), 1.46 (s, 3H), 1.29 (t, J = 7.52 Hz, 3H); LC-MS: 508.3 [M + H]⁺. |
| 18 | 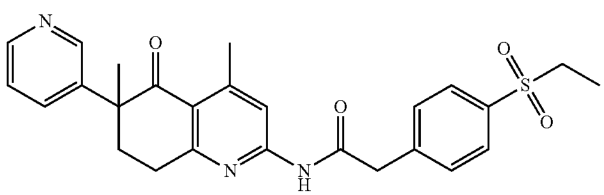 [SMILES: CCS(=O)(=O)c1ccc(CC(=O)Nc2cc(C)c3c(n2)CCC(C)(c2cccnc2)C3=O)cc1] | ¹H NMR (400 MHz, CDCl₃): δ 8.41-8.50 (m, 2H), 7.87-7.99 (m, 3H), 7.45-7.56 (m, 3H), 7.22 (dd, J = 4.84, 7.52 Hz, 1H), 3.81 (s, 2H), 3.12 (q, J = 7.25 Hz, 2H), 2.90 (br s, 1H), 2.79 (br s, 1H), 2.72 (s, 3H), 2.64 (d, J = 14.24 Hz, 1H), 2.22-2.32 (m, 1H), 1.51 (s, 3H), 1.28 (s, 3H); LC-MS: 477.9 [M + H]⁺. |
| 19 | 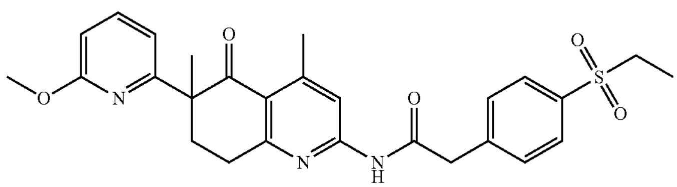 [SMILES: CCS(=O)(=O)c1ccc(CC(=O)Nc2cc(C)c3c(n2)CCC(C)(c2cccc(OC)n2)C3=O)cc1] | ¹H NMR (400 MHz, CDCl₃): δ 7.82-7.96 (m, 4H), 7.52 (d, J = 8.06 Hz, 2H), 7.45 (t, J = 7.79 Hz, 1H), 6.69 (d, J = 7.52 Hz, 1H), 6.53 (d, J = 8.06 Hz, 1H), 3.80 (s, 2H), 3.72 (s, 3H), 3.11 (d, J = 7.25 Hz, 2H), 2.86 (d, J = 5.37 Hz, 2H), 2.74-2.81 (m, 1H), 2.71 (s, 3H), 2.11-2.22 (m, 1H), 1.29 (t, J = 7.52 Hz, 3H). LC-MS: 508.4 [M + H]⁺. |
| 20 | 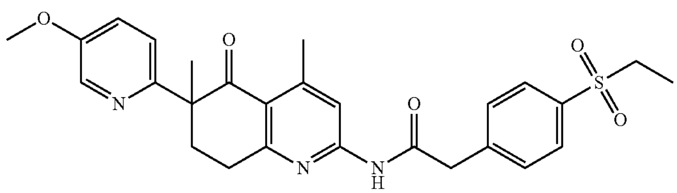 [SMILES: CCS(=O)(=O)c1ccc(CC(=O)Nc2cc(C)c3c(n2)CCC(C)(c2ccc(OC)cn2)C3=O)cc1] | ¹H NMR (400 MHz, CDCl₃): δ 8.17 (br s,, 1H), 7.83-7.96 (m, 4H), 7.51 (d, J = 6.72 Hz, 2H), 6.94-7.16 (m, 2H), 3.79 (br s, 6H), 3.11 (d, J = 6.72 Hz, 2H), 2.78-2.96 (m, 3H), 2.70 (br s, 3H), 2.15 (br s, 1H), 1.48 (s, 3H), 1.26-1.30 (m, 3H); LC-MS: 508.3 [M + H]⁺. |
| 21 | 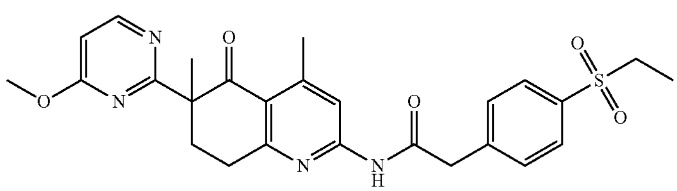 [SMILES: CCS(=O)(=O)c1ccc(CC(=O)Nc2cc(C)c3c(n2)CCC(C)(c2nccc(OC)n2)C3=O)cc1] | ¹H NMR (400 MHz, CDCl₃): δ 8.31 (d, J = 5.64 Hz, 1H), 7.85-7.97 (m, 4H), 7.53 (d, J = 8.06 Hz, 2H), 6.50 (d, J = 5.37 Hz, 1H), 3.80 (s, 2H), 3.77 (s, 3H), 3.12 (q, J = 7.43 Hz, 2H), 2.86 (br s, 3H), 2.70 (s, 3H), 2.08-2.22 (m, 1H), 1.56 (s, 3H), 1.27-1.31 (m, 3H); LC-MS: 509.3 [M + H]⁺. |
| 22 | 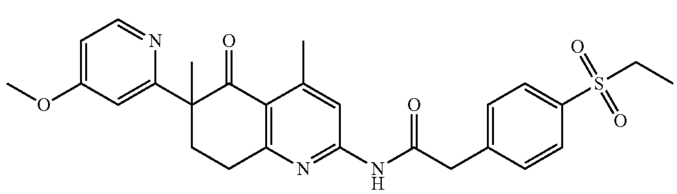 [SMILES: CCS(=O)(=O)c1ccc(CC(=O)Nc2cc(C)c3c(n2)CCC(C)(c2cc(OC)ccn2)C3=O)cc1] | ¹H NMR (400 MHz, CDCl₃): δ 8.32 (d, J = 5.64 Hz, 1H), 7.91 (d, J = 8.33 Hz, 4H), 7.53 (d, J = 8.33 Hz, 2H), 6.58-6.66 (m, 2H), 3.81 (s, 2H), 3.77 (s, 3H), 3.12 (q, J = 7.34 Hz, 2H), 2.81-2.99 (m, 3H), 2.72 (s, 3H), 2.11-2.22 (m, 1H), 1.51 (s, 3H), 1.29 (t, J = 7.52 Hz, 3H); LC-MS: 509.4 [M + H]⁺. |

| Compound No. | Structure | Characterization Data |
|---|---|---|
| 23 | 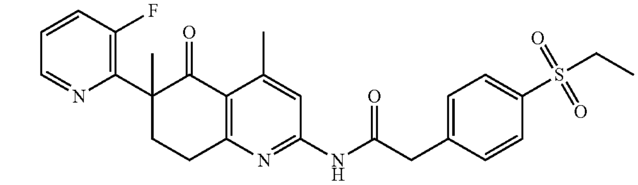 [SMILES: CCS(=O)(=O)c1ccc(CC(=O)Nc2cc(C)c3c(n2)CCC(C)(c2ncccc2F)C3=O)cc1] | $^1$H NMR (400 MHz, CDCl$_3$): δ 8.30 (d, J = 4.57 Hz, 1H), 7.88-7.98 (m, 3H), 7.54 (d, J = 8.06 Hz, 2H), 7.28-7.35 (m, 1H), 7.17 (td, J = 4.26, 8.40 Hz, 1H), 3.81 (s, 2H), 3.12 (q, J = 7.52 Hz, 2H), 2.83-3.02 (m, 3H), 2.68 (s, 3H), 2.03-2.21 (m, 1H), 1.59 (s, 3H), 1.29 (t, J = 7.39 Hz, 3H); LC-MS: 496.3 [M + H]$^+$. |
| 24 | 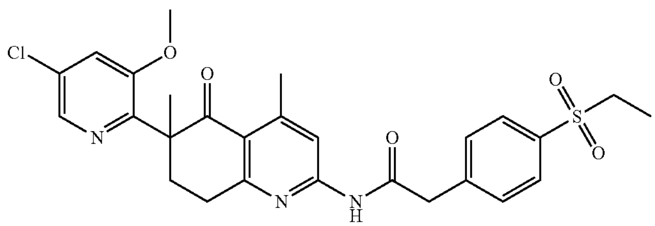 [SMILES: CCS(=O)(=O)c1ccc(CC(=O)Nc2cc(C)c3c(n2)CCC(C)(c2ncc(Cl)cc2OC)C3=O)cc1] | $^1$H NMR (400 MHz, CDCl$_3$): δ 8.07-8.14 (m, 1H), 8.04 (d, J= 1.88 Hz, 1H), 7.89 (d, J = 8.06 Hz, 2H), 7.55 (d, J = 8.33 Hz, 2H), 7.08 (d, J = 1.88 Hz, 1H), 3.85 (s, 2H), 3.71 (s, 3H), 2.90-3.15 (m, 5H), 2.68 (s, 3H), 1.51 (s, 3H), 1.26-1.30 (m, 4H); LC-MS: 542.3 [M + H]$^+$. |
| 25 | 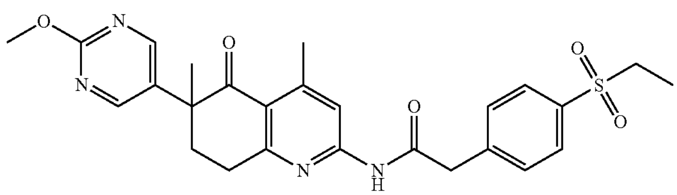 [SMILES: CCS(=O)(=O)c1ccc(CC(=O)Nc2cc(C)c3c(n2)CCC(C)(c2cnc(OC)nc2)C3=O)cc1] | $^1$H NMR (400 MHz, CDCl$_3$): δ 8.35 (s, 2H), 7.98 (s, 1H), 7.92 (d, J = 8.06 Hz, 2H), 7.88 (s, 1H), 7.53 (d, J = 8.06 Hz, 2H), 3.97 (s, 3H), 3.83 (s, 2H), 3.12 (q, J = 7.34 Hz, 2H), 2.94-3.04 (m, 1H), 2.70 (s, 3H), 2.58 (td, J = 4.84, 14.24 Hz, 1H), 2.18-2.31 (m, 1H), 1.53 (s, 3H), 1.29 (t, J = 7.39 Hz, 3H); LC-MS: 509.3 [M + H]$^+$. |
| 26 | 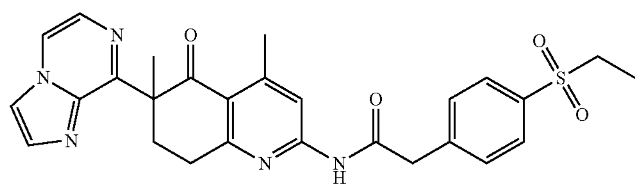 [SMILES: CCS(=O)(=O)c1ccc(CC(=O)Nc2cc(C)c3c(n2)CCC(C)(c2nccn4ccnc24)C3=O)cc1] | $^1$H NMR (400 MHz, CDCl$_3$): δ 7.90 (d, J = 8.06 Hz, 4H), 7.84 (br s, 1H), 7.67-7.72 (m, 2H), 7.59 (s, 1H), 7.52 (d, J = 8.06 Hz, 2H), 3.79 (s, 2H), 3.44-3.55 (m, 1H), 3.11 (d, J = 7.52 Hz, 2H), 2.85-3.03 (m, 2H), 2.72 (s, 3H), 2.15 (dd, J = 5.64, 8.87, 13.97 Hz, 1H), 1.75 (s, 3H), 1.28 (t, J = 7.52 Hz, 3H); LC-MS: 518.1 [M + H]$^+$. |
| 27 | 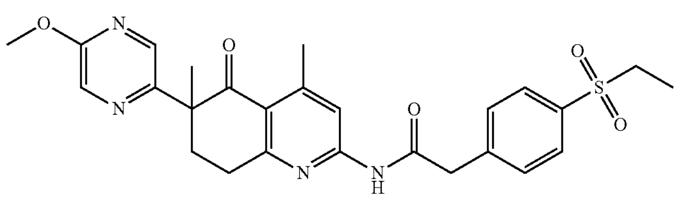 [SMILES: CCS(=O)(=O)c1ccc(CC(=O)Nc2cc(C)c3c(n2)CCC(C)(c2cnc(OC)cn2)C3=O)cc1] | $^1$H NMR (400 MHz, CDCl$_3$): δ 8.13 (d, J = 1.07 Hz, 1H), 7.83-7.97 (m, 5H), 7.53 (d, J = 8.06 Hz, 2H), 3.90 (s, 3H), 3.81 (s, 2H), 3.12 (q, J = 7.52 Hz, 2H), 2.78-2.95 (m, 3H), 2.70 (s, 3H), 2.10-2.23 (m, 1H), 1.52 (s, 3H), 1.29 (t, J = 7.52 Hz, 3H); LC-MS: 509.3 [M + H]$^+$. |
| 28 | 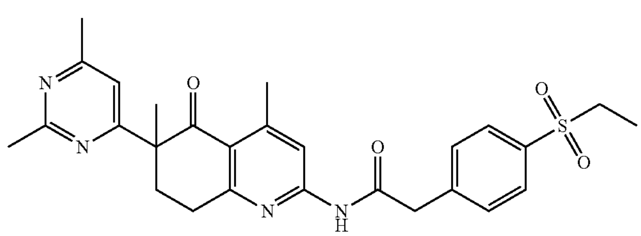 [SMILES: CCS(=O)(=O)c1ccc(CC(=O)Nc2cc(C)c3c(n2)CCC(C)(c2cc(C)nc(C)n2)C3=O)cc1] | $^1$H NMR (400 MHz, DMSOd$^6$): δ 11.05 (s, 1H), 7.77-7.88 (m, 3H), 7.58 (d, J = 8.06 Hz, 2H), 7.17 (s, 1H), 3.86 (s, 2H), 3.18-3.30 (m, 3H), 2.94 (d, J = 18.27 Hz, 1H), 2.74 (dd, J = 4.70, 14.10 Hz, 2H), 2.57 (s, 3H), 2.39 (d, J = 18.00 Hz, 6H), 2.09-2.19 (m, 1H), 1.38 (s, 3H), 1.08 (t, J = 7.25 Hz, 3H); LC-MS: 506.8 [M + H]$^+$. |
| 29 | 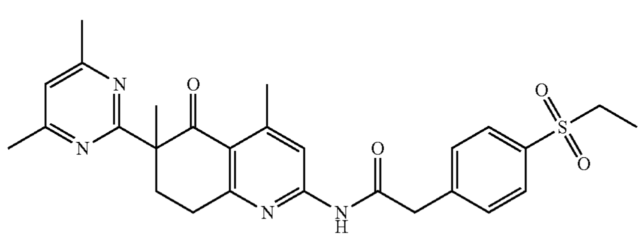 [SMILES: CCS(=O)(=O)c1ccc(CC(=O)Nc2cc(C)c3c(n2)CCC(C)(c2nc(C)cc(C)n2)C3=O)cc1] | $^1$H NMR (300 MHz, CDCl$_3$): δ 7.89 (d, J = 8.23 Hz, 3H), 7.82 (s, 1H), 7.52 (d, J = 8.23 Hz, 2H), 6.76 (s, 1H), 3.78 (s, 2H), 3.40-3.54 (m, 1H), 3.11 (q, J = 7.38 Hz, 2H), 2.78-2.98 (m, 3H), 2.69 (s, 3H), 2.31 (s, 6H), 2.03-2.19 (m, 1H), 1.51 (s, 3H), 1.28 (t, J = 7.41 Hz, 3H); LC-MS: 507.3 [M + H]$^+$. |

| Compound No. | Structure | Characterization Data |
|---|---|---|
| 30 | 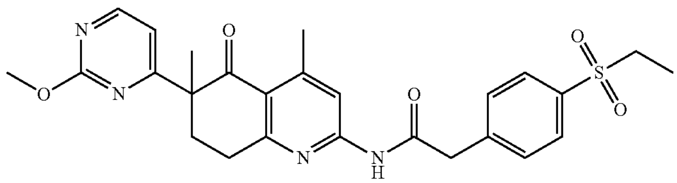 [SMILES: CCS(=O)(=O)c1ccc(CC(=O)Nc2cc(C)c3c(n2)CCC(C)(c2ccnc(OC)n2)C3=O)cc1] | ¹H NMR (300 MHz, CDCl₃): δ 8.39 (d, J = 5.12 Hz, 1H), 7.86-8.00 (m, 4H), 7.53 (d, J = 8.23 Hz, 2H), 6.75 (d, J = 5.12 Hz, 1H), 3.89 (s, 3H), 3.82 (s, 2H), 3.12 (q, J = 7.50 Hz, 2H), 2.79-2.96 (m, 3H), 2.69 (s, 3H), 2.04-2.23 (m, 1H), 1.52 (s, 3H), 1.29 (t, J = 7.41 Hz, 3H); LC-MS: 509.3 [M + H]⁺. |
| 31 | 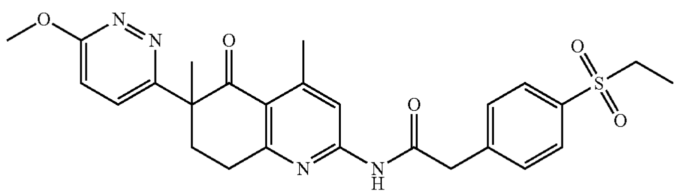 [SMILES: CCS(=O)(=O)c1ccc(CC(=O)Nc2cc(C)c3c(n2)CCC(C)(c2ccc(OC)nn2)C3=O)cc1] | ¹H NMR (300 MHz, CDCl₃): δ 7.83-8.03 (m, 4H), 7.52 (d, J = 8.05 Hz, 2H), 7.28-7.32 (m, 1H), 6.91 (d, J = 9.15 Hz, 1H), 4.07 (s, 3H), 3.81 (s, 2H), 3.11 (q, J = 7.44 Hz, 3H), 2.84-3.01 (m, 2H), 2.68 (s, 3H), 2.13-2.31 (m, 1H), 1.55 (s, 3H), 1.28 (s, 3H); LC-MS: 509.3 [M + H]⁺. |
| 32 | 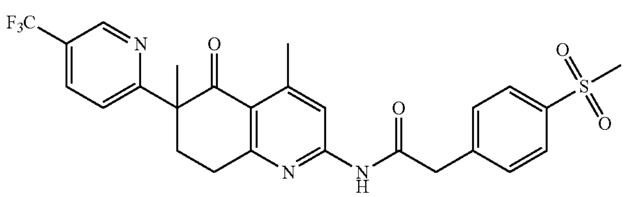 [SMILES: Cc1cc(NC(=O)Cc2ccc(S(C)(=O)=O)cc2)nc2c1C(=O)C(C)(c1ccc(C(F)(F)F)cn1)CC2] | ¹H NMR (400 MHz, CDCl₃): δ 8.73 (s, 1H), 7.93 (d, J = 8.33 Hz, 3H), 7.74-7.84 (m, 2H), 7.50 (d, J = 7.89 Hz, 2H), 7.27 (s, 1H), 3.79 (s, 2H), 3.03 (s, 3H), 2.83-2.92 (m, 3H), 2.69 (s, 3H), 2.11-2.26 (m, 1H), 1.53 (s, 3H); LC-MS: 531.9 [M + H]⁺. |
| 33 | 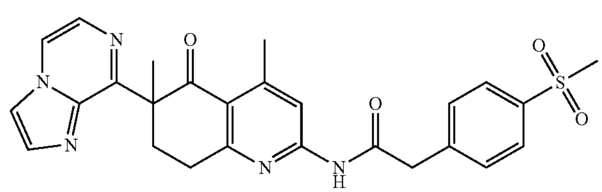 [SMILES: Cc1cc(NC(=O)Cc2ccc(S(C)(=O)=O)cc2)nc2c1C(=O)C(C)(c1nccn3ccnc13)CC2] | ¹H NMR (300 MHz, CDCl₃): δ 7.97-8.06 (m, 1H), 7.90-7.95 (m, 4H), 7.66-7.72 (m, 2H), 7.59 (s, 1H), 7.51 (d, J = 8.05 Hz, 2H), 3.79 (s, 2H), 3.44-3.53 (m, 2H), 3.05 (s, 3H), 2.89-2.98 (m, 2H), 2.71 (s, 3H), 2.15 (dd, J = 5.85, 8.69, 14.00 Hz, 1H), 1.75 (s, 3H); LC-MS: 504.7 [M + H]⁺. |
| 34 | 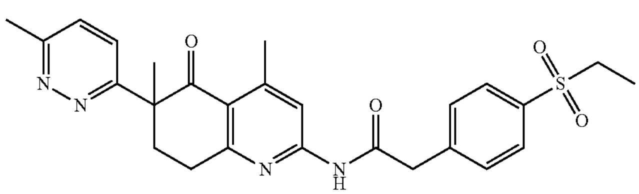 [SMILES: CCS(=O)(=O)c1ccc(CC(=O)Nc2cc(C)c3c(n2)CCC(C)(c2ccc(C)nn2)C3=O)cc1] | ¹H NMR (300 MHz, DMSO-d⁶): δ 11.03 (s, 1H), 7.78-7.84 (m, 3H), 7.69 (d, J = 8.78 Hz, 1H), 7.53-7.58 (m, 3H), 3.84 (s, 2H), 3.13-3.29 (m, 3H), 2.71 (br s, 1H), 2.55 (s, 5H), 2.25 (s, 1H), 1.42 (s, 3H), 1.22 (br s, 1H), 1.06 (t, J = 7.41 Hz, 4H); LC-MS: 493.19 [M + H]⁺. |
| 35 | 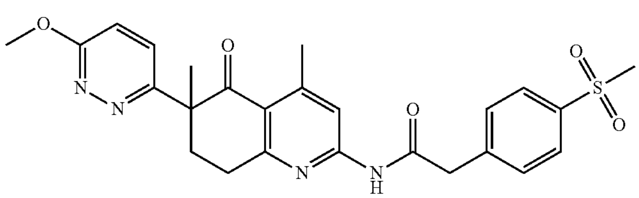 | ¹H NMR (400 MHz, CDCl₃): δ 7.97 (d, J = 8.33 Hz, 4H), 7.55 (d, J = 8.06 Hz, 2H), 7.32 (d, J = 9.13 Hz, 1H), 6.93 (d, J = 9.13 Hz, 1H), 4.10 (s, 3H), 3.83 (s, 2H), 3.51 (s, 1H), 3.07 (s, 4H), 2.89-3.00 (m, 2H), 2.70 (s, 3H), 1.58 (s, 3H); LC-MS: 494.1 [M + H]⁺. |
| 36 | 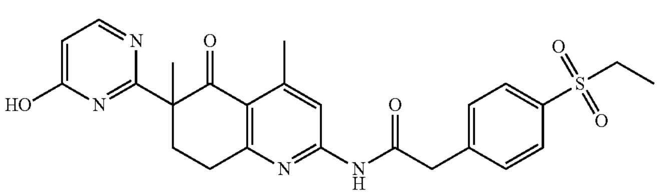 [SMILES: CCS(=O)(=O)c1ccc(CC(=O)Nc2cc(C)c3c(n2)CCC(C)(c2nccc(O)n2)C3=O)cc1] | ¹H NMR (400 MHz, DMSO-d⁶): δ 11.11 (s, 1H), 7.80-7.93 (m, 3H), 7.60 (d, J = 8.33 Hz, 2H), 3.89 (s, 2H), 3.28 (q, J = 7.34 Hz, 3H), 3.00 (d, J = 18.00 Hz, 1H), 2.69-2.85 (m, 2H), 2.56 (s, 3H), 2.01-2.16 (m, 1H), 1.48 (s, 3H), 1.09 (t, J = 7.39 Hz, 3H); LC-MS: 495.1 [M + H]⁺. |

| Compound No. | Structure | Characterization Data |
|---|---|---|
| 37 | 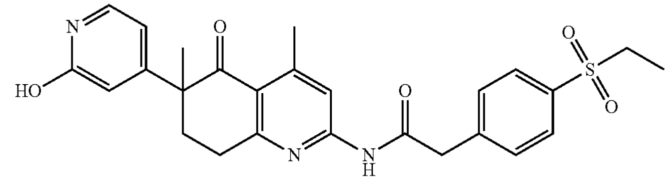 [SMILES: CCS(=O)(=O)c1ccc(CC(=O)Nc2cc(C)c3c(n2)CCC(C)(c2ccnc(O)c2)C3=O)cc1] | $^1$H NMR (400 MHz, CDCl$_3$): δ 8.79 (s, 1H), 7.98 (s, 1H), 7.88 (d, J = 8.06 Hz, 2H), 7.53 (d, J = 8.33 Hz, 2H), 7.21 (d, J = 6.72 Hz, 1H), 6.29 (s, 1H), 6.10 (d, J = 6.98 Hz, 1H), 4.13 (d, J = 6.99 Hz, 1H), 3.85 (d, J = 2.69 Hz, 1H), 3.13 (q, J = 7.34 Hz, 2H), 2.89-2.93 (m, 2H), 2.68 (s, 3H), 2.45-2.55 (m, 1H), 2.18 (s, 1H), 2.05 (s, 1H), 1.46 (s, 3H), 1.27 (d, J = 7.52 Hz, 4H); LC-MS: 494.3 [M + H]$^+$. |
| 38 | 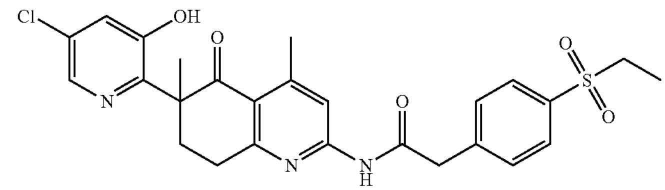 [SMILES: CCS(=O)(=O)c1ccc(CC(=O)Nc2cc(C)c3c(n2)CCC(C)(c2ncc(Cl)cc2O)C3=O)cc1] | $^1$H NMR (400 MHz, CDCl$_3$): δ 8.35 (s, 1H), 7.97 (d, J = 1.88 Hz, 1H), 7.86 (d, J = 8.33 Hz, 2H), 7.59 (d, J = 8.06 Hz, 2H), 7.11 (d, J = 1.61 Hz, 1H), 3.95 (s, 2H), 3.05-3.31 (m, 6H), 2.77 (s, 3H), 1.96-2.22 (m, 1H), 1.24-1.30 (m, 5H); LC-MS: 528.3 [M + H]$^+$. |
| 39 | 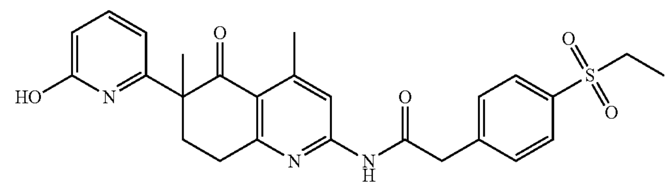 [SMILES: CCS(=O)(=O)c1ccc(CC(=O)Nc2cc(C)c3c(n2)CCC(C)(c2cccc(O)n2)C3=O)cc1] | $^1$H NMR (400 MHz, DMSO-d$^6$): δ 11.1 (br s, 1H), 7.88-7.82 (m, 3H), 7.56-7.58 (m, 2H), 7.20 (br s, 1H), 5.55-5.7 (m, 1H), 3.88 (s, 2H), 3.24-3.26 (m, 3H), 2.96-3.08 (m, 2H), 2.70-2.80 (m, 2H) 2.67 (s, 3H), 1.99-2.08 (m, 2H), 1.06-1.10 (m, 3H); LC-MS: 494.3 [M + H]$^+$. |
| 40 | 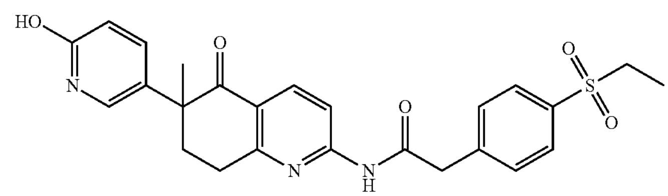 [SMILES: CCS(=O)(=O)c1ccc(CC(=O)Nc2ccc3c(n2)CCC(C)(c2ccc(O)nc2)C3=O)cc1] | $^1$H NMR (400 MHz, CDCl$_3$): δ 9.24 (br s, 1H), 8.35 (d, J = 8.87 Hz, 1H), 8.19 (d, J = 8.60 Hz, 1H), 7.86 (d, J = 8.33 Hz, 2H), 7.55 (d, J = 8.06 Hz, 2H), 7.46 (dd, J = 2.42, 9.67 Hz, 1H), 7.07 (s, 1H), 6.59 (d, J = 9.40 Hz, 1H), 3.89 (s, 2H), 3.48 (q, J = 6.98 Hz, 1H), 3.12 (q, J = 7.43 Hz, 2H), 2.80-3.03 (m, 2H), 2.51 (d, J = 14.51 Hz, 1H, 2.19-2.33 (m, 1H), 1.48 (s, 3H), 1.27-1.30 (m, 3H); LC-MS: 480.3 [M + H]$^+$. |
| 41 | 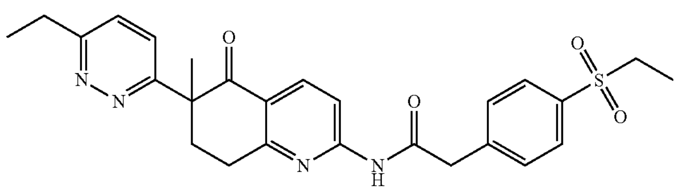 [SMILES: CCc1ccc(C2(C)CCc3nc(NC(=O)Cc4ccc(S(=O)(=O)CC)cc4)ccc3C2=O)nn1] | $^1$H NMR (400 MHz, CD$_3$OD): δ 9.02 (br s, 1H), 8.13 (d, J = 8.60 Hz, 1H), 7.98 (d, J = 8.87 Hz, 1H), 7.72-7.83 (m, 4H), 7.54 (d, J = 8.06 Hz, 2H), 3.82 (s, 2H), 3.11 (q, J = 7.25 Hz, 1H), 2.99-3.05 (m, 2H), 2.94 (t, J = 8.33 Hz, 2H), 1.87-2.24 (m, 4H), 1.19 (s, 3H), 1.12 (s, 3H); LC-MS: 493.3 [M + H]$^+$. |
| 42 | 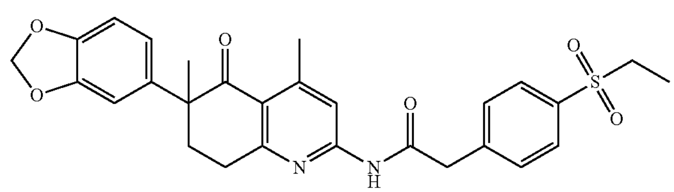 [SMILES: CCS(=O)(=O)c1ccc(CC(=O)Nc2cc(C)c3c(n2)CCC(C)(c2ccc4c(c2)OCO4)C3=O)cc1] | $^1$H NMR (400 MHz, CDCl$_3$): δ 7.90 (d, J = 8.06 Hz, 3H), 7.52 (d, J = 8.33 Hz, 2H), 6.63-6.70 (m, 2H), 6.53 (dd, J = 1.48, 8.19 Hz, 1H), 5.90 (d, J = 2.96 Hz, 2H), 3.80 (s, 2H), 3.11 (q, J = 7.34 Hz, 2H), 2.79-2.97 (m, 2H), 2.71 (s, 3H), 2.50-2.58 (m, 1H), 2.14-2.26 (m, 1H), 1.43 (s, 3H), 1.28 (t, J = 7.52 Hz, 3H); LC-MS: 521.3 [M + H]$^+$. |
| 43 | 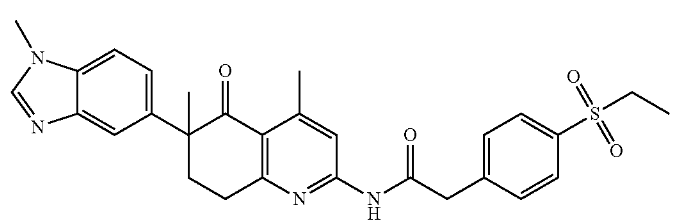 [SMILES: CCS(=O)(=O)c1ccc(CC(=O)Nc2cc(C)c3c(n2)CCC(C)(c2ccc4c(c2)ncn4C)C3=O)cc1] | $^1$H NMR (400 MHz, CDCl$_3$): δ 7.97 (s, 1H), 7.91 (s, 1H), 7.88 (d, J = 8.06 Hz, 2H), 7.83 (s, 1H), 7.60 (s, 1H), 7.49 (d, J = 8.33 Hz, 2H), 7.30 (d, J = 8.33 Hz, 1H), 7.10 (dd, J = 1.48, 8.46 Hz, 1H), 3.79 (s, 3H), 3.77 (s, 2H), 3.10 (q, J = 7.43 Hz, 2H), 2.80-2.99 (m, 2H), 2.74 (s, 3H), 2.70 (d, J = 2.69 Hz, 1H), 2.28 (dd, J = 5.64, 11.82, 14.24 Hz, 1H), 1.51 (s, 3H), 1.27 (t, J = 7.39 Hz, 3H) LC-MS: 531.4 [M + H]$^+$. |

-continued

| Compound No. | Structure | Characterization Data |
|---|---|---|
| 44 | 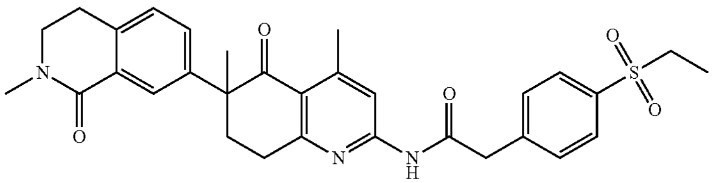 [SMILES: CCS(=O)(=O)c1ccc(CC(=O)Nc2cc(C)c3c(n2)CCC(C)(c2ccc4c(c2)C(=O)N(C)CC4)C3=O)cc1] | $^1$H NMR (400 MHz, CDCl$_3$): δ 8.00 (d, J = 5.10 Hz, 2H), 7.87-7.94 (m, 3H), 7.52 (d, J = 8.06 Hz, 2H), 7.01-7.10 (m, 2H), 3.80 (s, 2H), 3.52 (t, J = 6.72 Hz, 2H), 3.14 (s, 2H), 3.11 (d, J = 7.52 Hz, 2H), 2.93 (dt, J = 2.82, 6.51 Hz, 2H), 2.83 (dd, J = 4.03, 8.33 Hz, 2H), 2.72 (s, 3H), 2.68 (br s, 1H), 2.16-2.26 (m, 1H), 1.46 (s, 3H), 1.28 (t, J = 7.39 Hz, 3H) LC-MS: 560.3 [M + H]$^+$. |
| 45 | 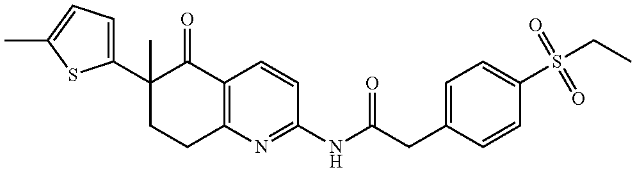 [SMILES: CCS(=O)(=O)c1ccc(CC(=O)Nc2ccc3c(n2)CCC(C)(c2ccc(C)s2)C3=O)cc1] | $^1$H-NMR (400 MHz, DMSO-d$^6$): δ 8.40 (d, J = 8.0 Hz, 1H), 8.14 (d, J = 8.0 Hz, 1H), 8.00 (s, 1H), 7.92 (d, J = 8.0 Hz, 2H), 7.54 (d, J = 8.0 Hz, 2H), 6.48 (s, 1H), 6.42 (d, J = 3.6 Hz, 1H), 3.14-3.06 (m, 3H), 2.89-2.80 (m, 1H), 2.51-2.05 (m, 4H), 1.30-1.25 (m, 4H). LC-MS: 483.1 [M + H]$^+$. |
| 46 | 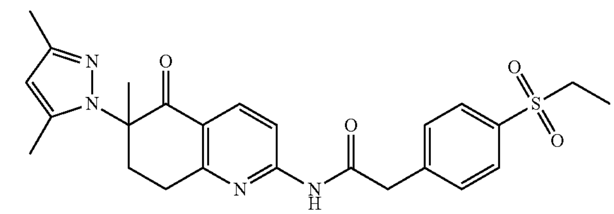 [SMILES: CCS(=O)(=O)c1ccc(CC(=O)Nc2ccc3c(n2)CCC(C)(n2nc(C)cc2C)C3=O)cc1] | $^1$H NMR (400 MHz, CD$_3$OD): δ 8.00 (d, J = 8.33 Hz, 1H), 7.91 (d, J = 8.06 Hz, 2H), 7.82 (d, J = 8.33 Hz, 1H), 7.67 (d, J = 8.33 Hz, 2H), 6.01 (s, 1H), 3.92 (s, 2H), 3.37 (s, 3H), 3.23 (q, J = 7.25 Hz, 2H), 3.11 (t, J = 8.19 Hz, 2H), 2.73-2.81 (m, 2H), 2.24 (d, J = 12.09 Hz, 6H), 1.24 (t, J = 7.39 Hz, 3H); LC-MS: 481.2 [M + H]$^+$. |
| 47 | 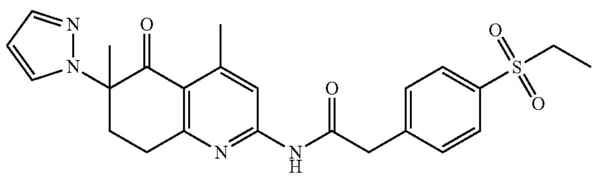 [SMILES: CCS(=O)(=O)c1ccc(CC(=O)Nc2cc(C)c3c(n2)CCC(C)(n2cccn2)C3=O)cc1] | $^1$H NMR (400 MHz, DMSO-d$^6$): δ 7.80-7.90 (m, 4H), 7.59 (d, J = 8.33 Hz, 2H), 7.40 (d, J = 1.34 Hz, 1H), 6.29 (s, 1H), 3.88 (s, 2H), 3.62 (br s, 3H), 3.18-3.43 (m, 2H), 2.80-3.10 (m, 3H), 2.27-2.37 (m, 1H), 1.64 (s, 3H), 1.08 (t, J = 7.25 Hz, 3H); LC-MS: 467.3 [M + H]$^+$. |
| 48 | 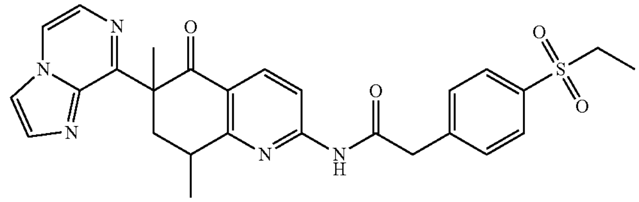 [SMILES: CCS(=O)(=O)c1ccc(CC(=O)Nc2ccc3c(n2)C(C)CC(C)(c2nccn4ccnc24)C3=O)cc1] | $^1$H NMR (400 MHz, CDCl3): δ 8.46 (d, J = 8.8 Hz, 1H), 8.13 (d, J = 8.8 Hz, 1H), 8.01 (s, 1H), 7.92-7.90 (m, 3H), 7.79 (s, 1H), 7.60 (s, 1H), 7.56-7.54 (m, 3H), 3.84 (s, 2H), 3.78-3.74 (m, 1H), 3.15-3.09 (m, 2H), 2.54-2.53 (m, 1H), 2.02-1.99 (m, 1H), 1.87 (s, 3H), 1.31-1.27 (m, 6H). LC-MS: 518.0 [M + H]$^+$. |
| 49 | 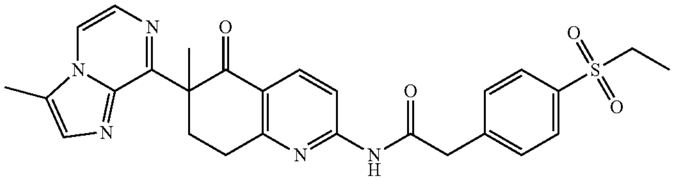 [SMILES: CCS(=O)(=O)c1ccc(CC(=O)Nc2ccc3c(n2)CCC(C)(c2nccn4c(C)cnc24)C3=O)cc1] | $^1$H NMR (400 MHz, CDCl$_3$): δ 8.45 (d, J = 8.8 Hz, 1H), 8.16 (d, J = 8.8 Hz, 1H), 8.01 (s, 1H), 7.92 (d, J = 8.0 Hz, 2H), 7.72 (s, 2H), 7.55 (d, J = 8.4 Hz, 2H), 7.49 (s, 1H), 3.83 (s, 1H), 3.69-3.62 (m, 1H), 3.15-3.09 (m, 2H) 3.19-2.96 (m, 1H), 2.77-2.70 (m, 1H), 2.47 (s, 3H), 2.19-2.12 (m, 1H), 1.84 (s, 3H), 1.31 (t, J = 7.2 Hz, 3H); LC-MS: 518.1 [M + H]$^+$. |
| 50 | 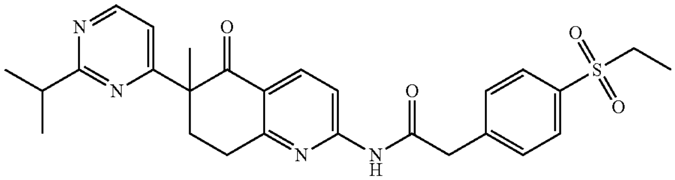 [SMILES: CCS(=O)(=O)c1ccc(CC(=O)Nc2ccc3c(n2)CCC(C)(c2ccnc(C(C)C)n2)C3=O)cc1] | $^1$H NMR (300 MHz, CDCl$_3$): δ 8.53 (d, J= 5.1 Hz, 1H), 8.39 (d, J = 8.7 Hz, 1H), 8.04-8.15 (m, 2H), 7.92 (d, J = 8.1 Hz, 2H), 7.54 (d, J = 8.1 Hz, 2H), 6.98 (d, J = 5.4 Hz, 1H), 3.83 (s, 2H), 3.07-3.16 (m, 3H), 2.87-2.93 (m, 3H), 2.15-2.21 (m, 1H), 1.55 (s, 3H), 1.21-1.31 (m, 9H); LC-MS: 507.3 [M + H]$^+$. |

-continued

| Compound No. | Structure | Characterization Data |
|---|---|---|
| 51 | 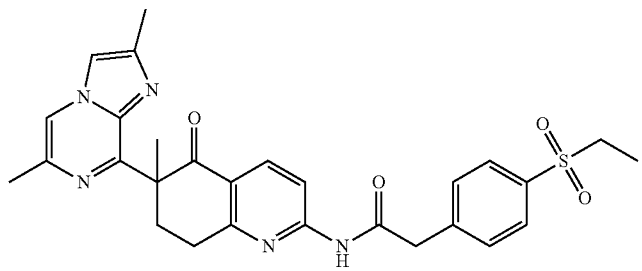 [SMILES: CCS(=O)(=O)c1ccc(CC(=O)Nc2ccc3c(n2)CCC(C)(c2nc(C)cn4cc(C)nc24)C3=O)cc1] | $^1$H NMR (400 MHz, CDCl3): δ 8.44 (d, J = 8.8 Hz, 1H), 8.17-8.13 (m, 2H), 7.93 (d, J = 8.4 Hz, 2H), 7.67 (s, 1H), 7.57 (d, J = 8.4 Hz, 2H), 3.83 (s, 2H), 3.70-3.64 (m, 1H), 3.16-3.10 (m, 2H), 2.99-2.94 (m, 1H), 2.73-2.65 (m, 1H), 2.42 (s, 3H), 2.27 (s, 3H), 2.21-2.10 (m, 1H), 1.83 (s, 3H), 1.32-1.27 (m, 3H). LC-MS: 532.0 [M + H]$^+$. |
| 52 | 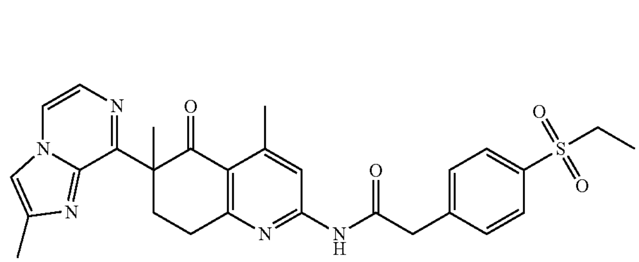 [SMILES: CCS(=O)(=O)c1ccc(CC(=O)Nc2cc(C)c3c(n2)CCC(C)(c2nccn4cc(C)nc24)C3=O)cc1] | $^1$H NMR (400 MHz, DMSO-d$^6$): δ 11.0 (br s, 1H), 8.39 (d, J = 4.4 Hz, 1H), 7.83-7.80 (m, 4H), 7.68 (d, J = 4.4 Hz, 1H), 7.59 (d, J = 8.4 Hz, 2H), 3.84 (s, 2H), 3.34-3.23 (m, 3H), 3.00-2.96 (m, 2H), 2.75-2.68 (m, 1H), 2.67 (s, 3H), 2.38 (s, 3H), 2.10-2.05 (m, 1H), 1.59 (s, 3H), 1.10 (t, J = 7.6 Hz, 3H); LC-MS: 531.9 [M + H]$^+$. |
| 53 | 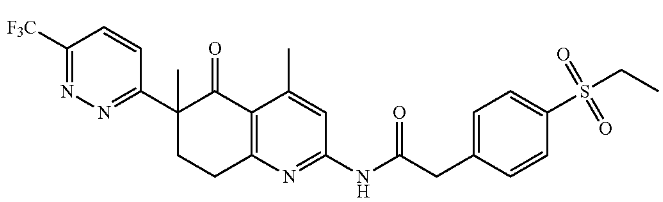 [SMILES: CCS(=O)(=O)c1ccc(CC(=O)Nc2cc(C)c3c(n2)CCC(C)(c2ccc(C(F)(F)F)nn2)C3=O)cc1] | 1H NMR (300 MHz, CDCl3): δ 7.97-7.90 (m, 4H), 7.75 (d, J = 9 Hz, 1H), 7.63 (d, J = 8.4 Hz, 1H), 7.53 (d, J = 9 Hz, 2H), 3.88 (s, 2H), 3.16-3.08 (m, 3H), 3.03-2.99 (m, 2H), 2.69 (s, 3H), 1.58 (s, 6H), 1.31-1.21 (m, 5H); LC-MS: 547 [M + H]+. |
| 54 | 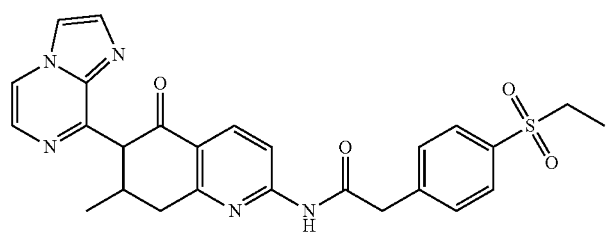 [SMILES: CCS(=O)(=O)c1ccc(CC(=O)Nc2ccc3c(n2)CC(C)C(c2nccn4ccnc24)C3=O)cc1] | 1H NMR (300 MHz, CDCl3): δ 8.34 (d, J = 8.99 Hz, 1H), 8.18 (t, J = 8.99 Hz, 2H), 8.05 (d, J = 4.49 Hz, 1H), 7.96 (d, J = 8.4 Hz, 2H), 7.87 (d, J = 4.5 Hz, 1H), 7.75-7.70 (m, 2H), 7.59 (d, J = 8.4 Hz, 2H), 4.51 (d, J = 11.7 Hz, 1H), 3.88 (s, 2H), 3.38-3.22 (m, 1H), 3.18-3.10 (m, 3H), 3.01-2.98 (m, 1H), 1.33 (t, J = 15 Hz, 3H), 1.04 (d, J = 6.6 Hz, 3H); LC-MS: 504.0 [M + H]+. |
| 55 | 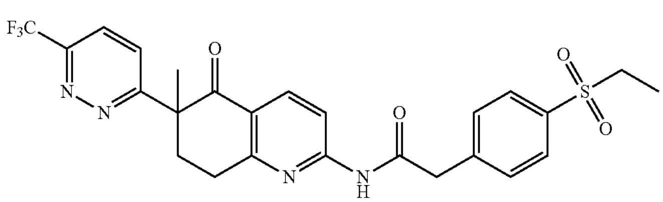 [SMILES: CCS(=O)(=O)c1ccc(CC(=O)Nc2ccc3c(n2)CCC(C)(c2ccc(C(F)(F)F)nn2)C3=O)cc1] | 1H NMR (300 MHz, CDCl3): δ 8.6 (br, 1H), 8.40 (d, J = 9 Hz, 1H), 8.20 (d, J = 8.7 Hz, 1H), 7.91 (d, J = 9 Hz, 2H), 7.76 (d, J = 9 Hz, 1H), 7.68 (d, 3.88, J = 9.3 Hz, 1H), 7.54 (d, J = 8.1 Hz, 2H), 3.86 (s, 2H), 3.49 (s, 1H), 3.16-3.05 (m, 6H), 2.41-2.42 (m, 1H), 1.31-1.21 (m, 5H); LC-MS: 532 [M + H]+. |
| 56 | 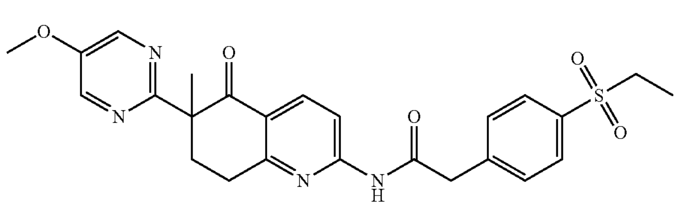 [SMILES: CCS(=O)(=O)c1ccc(CC(=O)Nc2ccc3c(n2)CCC(C)(c2ncc(OC)cn2)C3=O)cc1] | 1H NMR (300 MHz, CDCl3): δ 8.45 (d, J = 8.7 Hz, 1H), 8.28 (s, 2H), 8.16 (d, J = 8.7 Hz, 1H), 7.92 (d, J = 6.6 Hz, 2H), 7.55 (d, J = 8.4 Hz, 2H), 3.85 (s, 3H), 3.83 (s, 2H), 3.08-3.15 (m, 2H), 2.70-2.88 (m, 3H), 2.15-2.25 (m, 1H), 1.61 (s, 3H), 1.31 (t, J = 7.5 Hz, 3H); LC-MS: 495.0 [M + H]+. |

-continued

| Compound No. | Structure | Characterization Data |
|---|---|---|
| 57 | 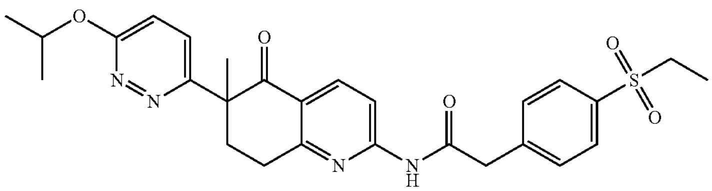 [SMILES: CCS(=O)(=O)c1ccc(CC(=O)Nc2ccc3c(n2)CCC(C)(c2ccc(OC(C)C)nn2)C3=O)cc1] | $^1$H NMR (400 MHz, DMSO-d$^6$): δ 11.0 (br s, 1H), 8.39 (d, J = 4.4 Hz, 1H), 8.09 (d, J = 8.8 Hz, 1H), 7.81 (d, J= 8.4 Hz, 2H), 7.74 (d, J = 9.2 Hz, 1H), 7.57 (d, J = 8.0 Hz, 2H), 7.12 (d, J = 9.2 Hz, 2H), 5.29-5.26 (m, 1H), 3.85 (s, 2H), 3.26-3.20 (m, 3H), 2.90-2.86 (m, 1H), 2.66-2.59 (m, 2H), 1.45 (s, 3H), 1.26 (d, J = 6.0 Hz, 6H), 1.10 (t, J = 7.6 Hz, 3H); LC-MS: 522.8 [M + H]$^+$. |
| 58 | 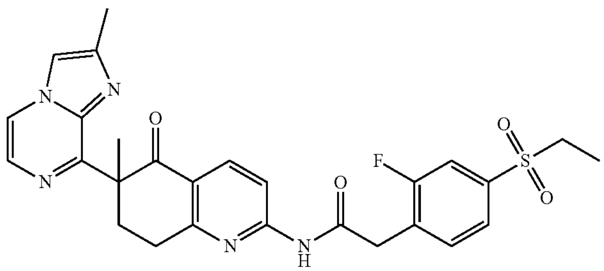 [SMILES: CCS(=O)(=O)c1ccc(CC(=O)Nc2ccc3c(n2)CCC(C)(c2nccn4cc(C)nc24)C3=O)c(F)c1] | 1H NMR (300 MHz, CDCl3): δ 8.44 (d, J = 8.70 Hz, 1H), 8.25 (s, 1H), 8.13 (d, J = 8.70 Hz, 1H), 7.85 (d, J = 4.50 Hz, 1H), 7.72-7.57 (m, 4H), 7.37 (s, 1H), 3.83 (s, 2H), 374-3.66 (m, 1H), 3.49-3.48 (m, 1H), 3.16-3.09 (m, 2H), 2.97-2.91 (m, 1H), 2.73-2.62 (m, 1H), 2.45 (s, 3H), 2.20-2.11 (m, 1H), 1.84 (s, 3H), 1.32 (t, J = 15 Hz, 3H); LC-MS: 535.9 [M + H]+. |
| 59 | 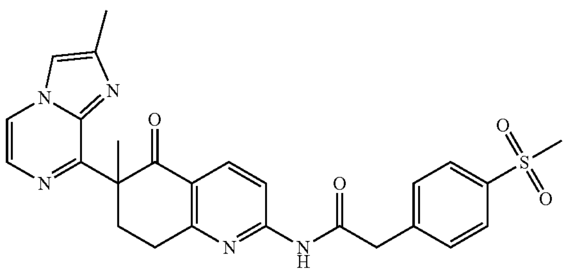 [SMILES: Cc1cn2ccnc(C3(C)CCc4nc(NC(=O)Cc5ccc(S(C)(=O)=O)cc5)ccc4C3=O)c2n1] | $^1$H NMR (400 MHz, DMSO-d$^6$): δ 11.21 (br s, 1H), 8.42 (d, J = 8.4.8 Hz, 1H), 8.26 (d, J = 8.8 Hz, 1H), 8.08 (d, J = 8.8 Hz, 1H), 7.89-7.83 (m, 3H), 7.62-7.59 (m, 3H), 3.88 (s, 2H), 3.56-3.53 (m, 1H), 3.19 (s, 3H), 2.98-2.96 (m, 1H), 2.50-2.49 (m, 2H), 2.35 (s, 3H), 2.10-2.05 (m, 1H), 1.70 (s, 3H); LC-MS: 503.6 [M + H]$^+$. |
| 60 | 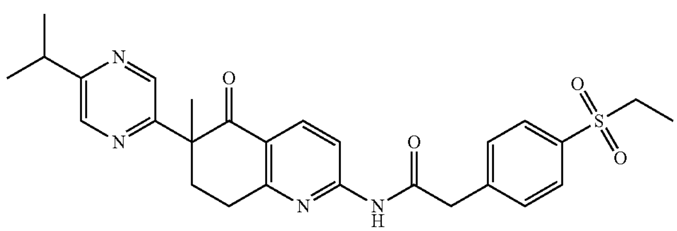 [SMILES: CCS(=O)(=O)c1ccc(CC(=O)Nc2ccc3c(n2)CCC(C)(c2cnc(C(C)C)cn2)C3=O)cc1] | $^1$H NMR (400 MHz, CDCl$_3$): δ 8.43-8.38 (m, 2H) 8.29 (d, J = 2.4 Hz, 1H), ) 8.19 (d, J = 8.8 Hz, 1H), 8.01 (s, 1H), 7.93 (d, J = 8.4 Hz, 2H), 7.56 (d, J = 8.4 Hz, 2H), 3.85 (s, 2H), 3.14-3.09 (m, 4H), 2.99-2.92 (m, 1H), 2.78-2.73 (m, 1H), 2.62-2.58 (m, 1H), 2.10-2.04 (m, 1H), 1.68 (s, 3H), 1.30 (t, J = 7.6 Hz, 3H), 1.14-1.12 (m, 6H), LC-MS: 506.9 [M + H]$^+$. |
| 61 | 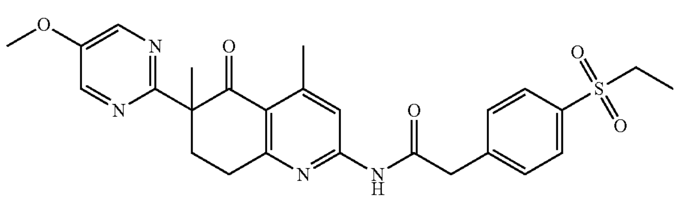 [SMILES: CCS(=O)(=O)c1ccc(CC(=O)Nc2cc(C)c3c(n2)CCC(C)(c2ncc(OC)cn2)C3=O)cc1] | $^1$H NMR (300 MHz, CDCl$_3$): δ 8.26 (s, 2H), 7.99 (br s, 1H), 7.88-7.91 (m, 3H), 7.53 (d, J = 8.1 Hz, 2H), 3.84 (s, 3H), 3.79 (s, 2H), 3.07-3.15 (m, 2H), 2.80-2.88 (m, 3H), 2.70 (s, 3H), 2.13-2.17 (m, 1H), 1.54 (s, 3H), 1.30 (t, J = 7.5 Hz, 3H); LC-MS: 509.2 [M + H]$^+$. |
| 62 | 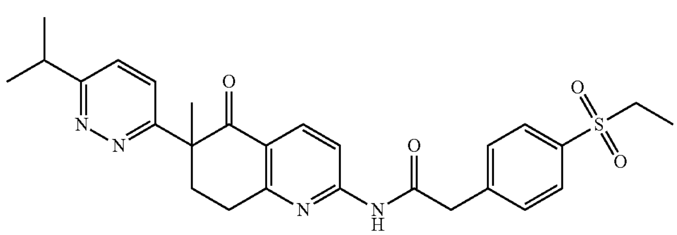 [SMILES: CCS(=O)(=O)c1ccc(CC(=O)Nc2ccc3c(n2)CCC(C)(c2ccc(C(C)C)nn2)C3=O)cc1] | $^1$H NMR (400 MHz, CDCl$_3$): δ 7.90-7.83 (m, 4H), 7.54 (d, J = 8.4 Hz, 2H), 7.37 (d, J = 9.2 Hz, 1H), 7.20 (d, J = 8.4 Hz, 1H), 7.15 (d, J = 8.8 Hz, 1H), 3.78 (s, 2H), 3.21-3.18 (m, 1H) 3.12-2.96 (m, 4H), 2.55 (t, J = 8.4 Hz, 2H), 1.80 (s, 3H), 1.33-1.24 (m, 9H), LC-MS: 507.6 [M + H]$^+$. |

| Compound No. | Structure | Characterization Data |
|---|---|---|
| 63 | 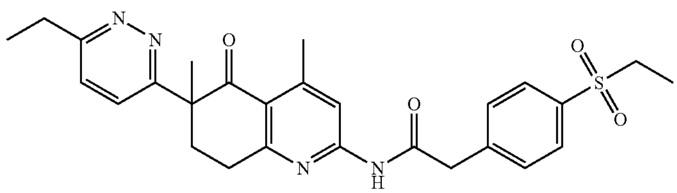 [SMILES: CCc1ccc(C2(C)CCc3nc(NC(=O)Cc4ccc(S(=O)(=O)CC)cc4)cc(C)c3C2=O)nn1] | ¹H NMR (400 MHz, CDCl₃): δ 7.92-7.89 (m, 4H), 7.53 (d, J = 8.0 Hz, 2H), 7.30-7.23 (m, 2H), 3.80 (s, 2H), 3.50 (d, J = 5.6 Hz, 1H), 3.12-3.09 (m, 2H) 3.02-2.92 (m, 4H), 2.69 (s, 3H), 2.41 (s, 3H), 2.30-2.20 (m, 2H), 1.57 (s, 3H), 1.35-1.26 (m, 6H); LC-MS: 507.0 [M + H]⁺. |
| 64 | 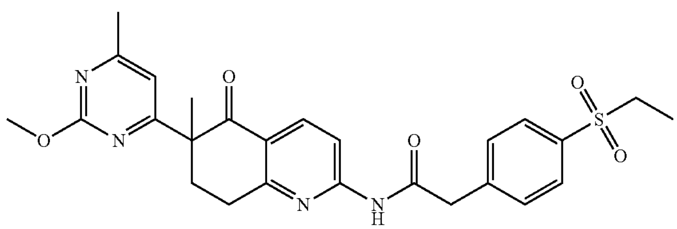 [SMILES: CCS(=O)(=O)c1ccc(CC(=O)Nc2ccc3c(n2)CCC(C)(c2cc(C)nc(OC)n2)C3=O)cc1] | ¹H NMR (300 MHz, CD3OD): δ 8.33 (d, J = 8.4 Hz, 1H), 8.10 (d, J = 8.7 Hz, 1H), 7.89 (d, J = 8.7 Hz, 2H), 7.63 (d, J = 8.4 Hz, 2H), 6.90 (s, 1H), 3.89 (s, 2H), 3.79 (s, 3H), 3.23-3.16 (m, 2H), 3.06-2.98 (m, 1H), 2.93-2.79 (m, 2H), 2.38 (s, 3H), 1.54 (s, 3H), 1.28-1.18 (m, 3H). LC-MS: 509.3 [M + H]⁺. |
| 65 | 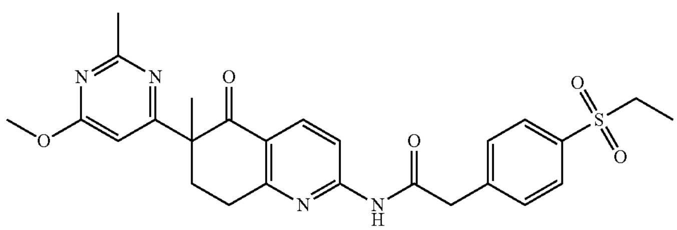 [SMILES: CCS(=O)(=O)c1ccc(CC(=O)Nc2ccc3c(n2)CCC(C)(c2cc(OC)nc(C)n2)C3=O)cc1] | ¹H NMR (300 MHz, CDCl₃): δ 8.38 (d, J = 8.7 Hz, 1H), 8.14 (d, J = 8.7 Hz, 1H), 8.04 (br s, 1H), 7.91 (d, J = 6.3 Hz, 2H), 7.54 (d, J = 8.4 Hz, 2H), 6.22 (s, 1H), 3.87 (s, 3H), 3.82 (s, 2H), 3.08-3.15 (m, 2H), 2.83-2.92 (m, 3H), 2.12-2.16 (m, 1H), 2.51 (s, 3H), 1.50 (s, 3H), 1.30 (t, J = 7.5 Hz, 3H); LC-MS: 509.3 [M + H]⁺. |
| 66 | 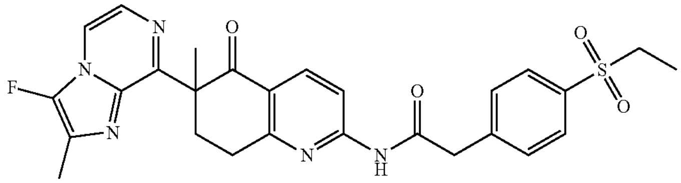 [SMILES: CCS(=O)(=O)c1ccc(CC(=O)Nc2ccc3c(n2)CCC(C)(c2nccn4c(F)c(C)nc24)C3=O)cc1] | ¹H NMR (300 MHz, CDCl₃): δ 8.44 (d, J = 8.7 Hz, 1H), 8.17 (d, J = 8.7 Hz, 1H), 8.08 (br s, 1H), 7.91 (d, J = 8.1 Hz, 2H), 7.52-7.67 (m, 2H), 7.55 (d, J = 8.1 Hz, 2H), 3.82 (s, 2H), 3.57-3.65 (m, 1H), 3.07-3.15 (m, 2H), 2.90-2.98 (m, 1H), 2.67-2.73 (m, 1H), 2.39 (s, 3H), 2.11-2.18 (m, 1H), 1.82 (s, 3H), 1.31 (t, J = 7.5 Hz, 3H); LC-MS: 535.9 [M + H]⁺. |
| 67 | 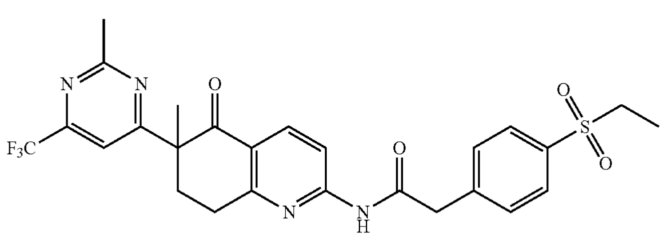 [SMILES: CCS(=O)(=O)c1ccc(CC(=O)Nc2ccc3c(n2)CCC(C)(c2cc(C(F)(F)F)nc(C)n2)C3=O)cc1] | ¹H NMR (400 MHz, CDCl₃): δ 7.91 (d, J = 8.4 Hz, 3H), 7.55 (d, J = 8.4 Hz, 2H), 7.20 (d, J = 8.4 Hz, 1H), 7.00 (s, 1H), 3.81 (s, 2H), 3.14-3.09 (m, 2H), 3.02 (t, J = 8.0 Hz, 2H) 2.60 (s, 2H), 2.59 (t, J = 8.4 Hz, 2H), 1.75 (s, 3H), 1.31 (t, J = 7.6 Hz, 3H); LC-MS: 547.3 [M + H]⁺. |
| 68 | 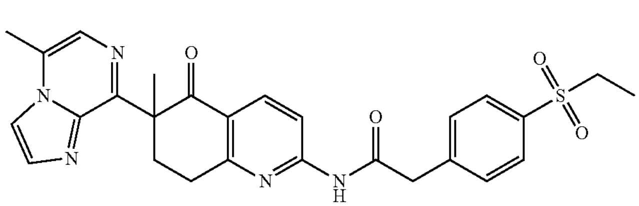 [SMILES: CCS(=O)(=O)c1ccc(CC(=O)Nc2ccc3c(n2)CCC(C)(c2ncc(C)n4ccnc24)C3=O)cc1] | ¹H NMR (400 MHz, CD3OD): δ 8.38 (d, J = 8.8 Hz, 2H), 8.306 (d, J = 4.4 Hz, 2H), 8.09 (d, J = 8.8 Hz, 1H), 7.92 (d, J = 8 Hz, 2H) 7.76 (s, 1H), 7.68 (d, J = 7.6 Hz, 2H), 7.62 (d, J = 4.4 Hz, 1H) 4.86 (s, 2H), 3.70-3.33 (m, 2H), 3.30-3.24 (m, 2H), 3.15-3.05 (m, 1H), 2.75-2.68 (m, 1H), 2.45 (s, 3H), 2.20-2.16 (m, 2H), 1.80 (s, 1H), 1.29-1.22 (m, 3H); LC-MS: 518.4 [M + H]⁺. |

-continued

| Compound No. | Structure | Characterization Data |
|---|---|---|
| 69 | 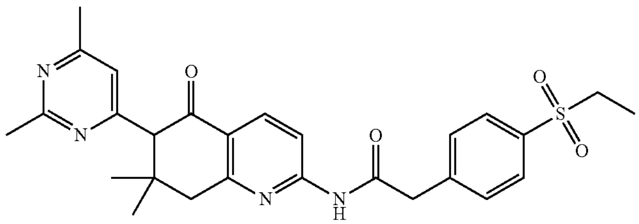 [SMILES: CCS(=O)(=O)c1ccc(CC(=O)Nc2ccc3c(n2)CC(C)(C)C(c2cc(C)nc(C)n2)C3=O)cc1] | ¹H NMR (400 MHz, CDCl3): δ 8.31 (d, J = 8.4 Hz, 1H), 8.18 (d, J = 8.4 Hz, 1H), 8.08 (s, 1H), 7.95 (d, J = 8.4 Hz, 2H), 7.58 (d, J = 8.0 Hz, 2H), 6.85 (s, 1H), 3.87 (s, 2H), 3.67 (s, 1H), 3.33-3.29 (m, 1H), 3.16-3.11 (m, 2H), 2.83-2.79 (m, 1H), 2.53 (s, 3H), 2.47 (s, 3H), 1.32-1.25 (m, 3H), 1.08 (s, 3H), 0.99 (s, 3H). LC-MS: 506.9 [M + H]⁺. |
| 70 | 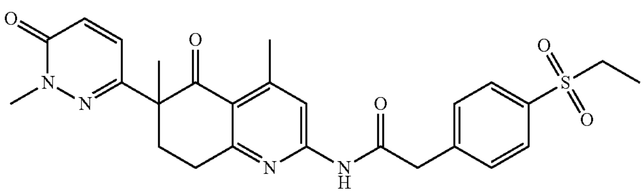 [SMILES: CCS(=O)(=O)c1ccc(CC(=O)Nc2cc(C)c3c(n2)CCC(C)(c2ccc(=O)n(C)n2)C3=O)cc1] | ¹H NMR (300 MHz, CDCl₃): δ 7.90-7.96 (m, 4H), 7.55 (d, J = 8.4 Hz, 2H), 7.23 (d, J = 9.6 Hz, 1H), 6.90 (d, J = 9.6 Hz, 1H), 3.82 (s, 2H), 3.64 (s, 3H), 3.09-3.13 (m, 2H), 2.98-3.00 (m, 2H), 2.65 (s, 3H), 2.59-2.64 (m, 1H), 2.12-2.15 (m, 1H), 1.48 (s, 3H), 1.31 (t, J = 7.5 Hz, 3H). LC-MS: 509.3 [M + H]⁺. |
| 71 | 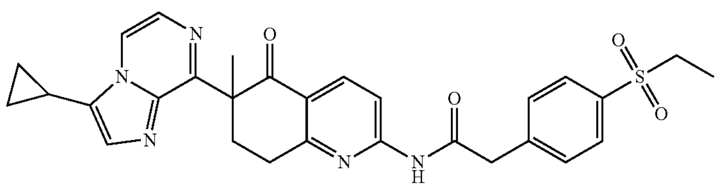 [SMILES: CCS(=O)(=O)c1ccc(CC(=O)Nc2ccc3c(n2)CCC(C)(c2nccn4c(C5CC5)cnc24)C3=O)cc1] | ¹H NMR (400 MHz, CDCl₃): δ 8.44 (d, J = 8.4 Hz, 1H), 8.16 (d, J = 8.0 Hz, 1H), 8.07 (s, 1H), 8.01 (d, J = 4.4 Hz, 1H), 7.91 (d, J = 7.6 Hz, 2H), 7.73 (d, J = 4.4 Hz, 1H) 7.54 (d, J= 8.0 Hz, 2H), 7.39 (s, 1H), 3.82 (s, 2H), 3.63-3.60 (m, 1H), 3.14-3.08 (m, 2H) 3.08-2.98 (m, 1H), 2.73-2.65 (m, 1H), 2.23-2.13 (m, 1H), 1.82 (s, 3H), 1.30 (t, J = 7.2 Hz, 3H), 1.22-1.18 (m, 1H), 1.07-1.05 (m, 2H), 0.73-0.80 (m, 2H); LC-MS: 544.6 [M + H]⁺. |
| 72 | 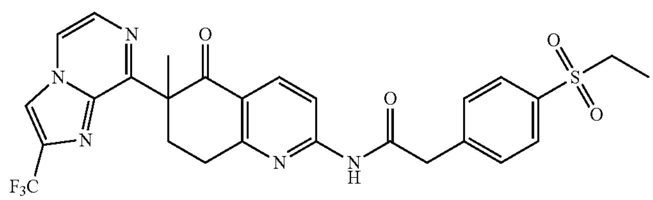 [SMILES: CCS(=O)(=O)c1ccc(CC(=O)Nc2ccc3c(n2)CCC(C)(c2nccn4cc(C(F)(F)F)nc24)C3=O)cc1] | ¹H NMR (400 MHz, CDCl₃): δ 8.46 (d, J = 8.8 Hz, 1H), 8.20 (d, J = 8.4 Hz, 1H), 8.03 (s, 1H), 7.99-7.92 (m, 3H), 7.97 (d, J = 8.0 Hz, 1H) 7.57 (d, J = 8.0 Hz, 2H), 3.86 (s, 2H), 3.69-3.62 (m, 1H), 3.17-3.11 (m, 2H) 3.02-2.98 (m, 1H), 2.73-2.65 (m, 1H), 2.23-2.2.16 (m, 1H), 1.87 (s, 3H), 1.33 (t, J = 7.2 Hz, 3H); LC-MS: 572.1 [M + H]⁺. |
| 73 | 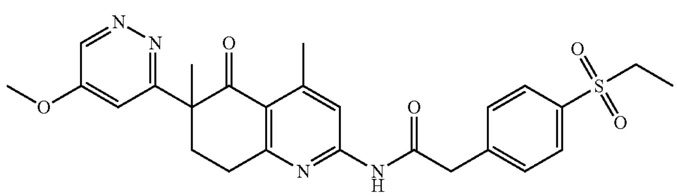 [SMILES: CCS(=O)(=O)c1ccc(CC(=O)Nc2cc(C)c3c(n2)CCC(C)(c2cc(OC)cnn2)C3=O)cc1] | ¹H NMR (400 MHz, CDCl3): δ 8.79 (d, J = 2.8 Hz, 1H) 8.24 (s, 1H), 7.92 (s, 1H), 7.90 (d, J = 8.0 Hz, 2H), 7.54 (d, J = 8.0 Hz, 2H) 6.76 (d, J = 2.8 Hz, 1H), 3.85 (s, 2H), 3.82 (s, 2H), 3.14-3.01 (m, 4H), 2.92-2.90 (m, 1H), 2.68 (s, 3H), 2.23-2.01 (m, 1H), 1.61-1.59 (m, 3H), 1.30-1.26 (m, 3H). LC-MS: 509.5 [M + H]⁺. |
| 74 | 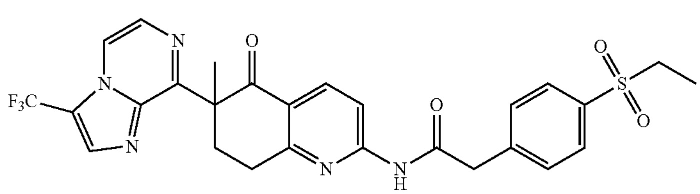 [SMILES: CCS(=O)(=O)c1ccc(CC(=O)Nc2ccc3c(n2)CCC(C)(c2nccn4c(C(F)(F)F)cnc24)C3=O)cc1] | ¹H NMR (400 MHz, CDCl₃): δ 8.43 (d, J = 8.4 Hz, 1H), 8.19 (d, J = 8.8 Hz, 1H), 8.06 (d, J= 4.4 Hz, 1H), 7.99 (s, 1H), 7.94-7.91 (m, 4H), 7.55 (d, J = 8.0 Hz, 2H) 3.84 (s, 1H), 3.55-3.48 (m, 1H), 3.15-3.09 (m, 2H) 3.09-3.04 (m, 1H), 2.82-2.77 (m, 1H), 2.16-2.09 (m, 1H), 1.83 (s, 3H), 1.31 (t, J = 7.6 Hz, 3H); LC-MS: 572.4 [M + H]⁺. |
| 75 | 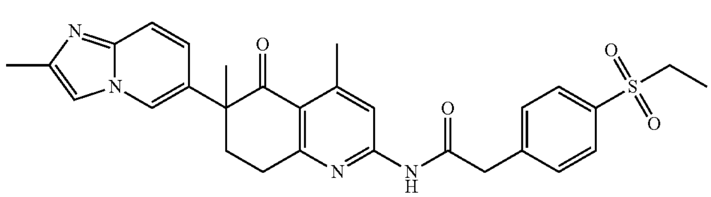 [SMILES: CCS(=O)(=O)c1ccc(CC(=O)Nc2cc(C)c3c(n2)CCC(C)(c2ccc4nc(C)cn4c2)C3=O)cc1] | ¹H NMR (400 MHz, CDCl3): δ 8.13 (s, 1H), 7.96 (s, 1H), 7.90 (d, J = 8.0 Hz, 2H), 7.76 (d, J = 9.6 Hz, 1H), 7.57 (d, J = 8.4 Hz, 2H), 6.92 (d, J = 8.8 Hz, 1H), 3.80 (s, 2H), 3.13-3.09 (m, 2H), 2.99-2.96 (m, 2H), 2.80-2.76 (m, 2H), 2.69 (s, 3H), 2.44 (s, 3H), 2.24-2.13 (m, 2H), 1.60-1.57 (m, 3H) 1.33-1.28 (m, 4H), 0.88-0.81 (m, 2H). LC-MS: 532.4 [M + H]⁺. |

| Compound No. | Structure | Characterization Data |
|---|---|---|
| 76 | 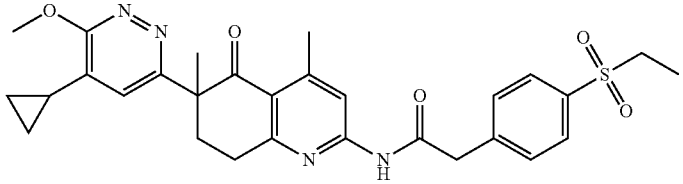 [SMILES: CCS(=O)(=O)c1ccc(CC(=O)Nc2cc(C)c3c(n2)CCC(C)(c2cc(C4CC4)c(OC)nn2)C3=O)cc1] | ¹H NMR (400 MHz, CDCl3): δ 7.94-7.89 (m, 4H), 7.53 (d, J = 8.0 Hz, 2H), 6.67 (s, 1H), 4.11 (s, 3H), 3.80 (s, 2H), 3.14-3.05 (m, 3H), 2.95-2.86 (m, 2H), 2.65 (s, 3H), 2.20-2.03 (m, 2H), 1.50 (s, 3H), 1.30-1.26 (m, 6H), 1.08-1.02 (m, 2H), 0.90-0.86 (m, 2H), 0.76-0.72 (m, 1H), 0.66-0.63 (m, 1H). LC-MS: 549.3 [M + H]⁺. |
| 77 | 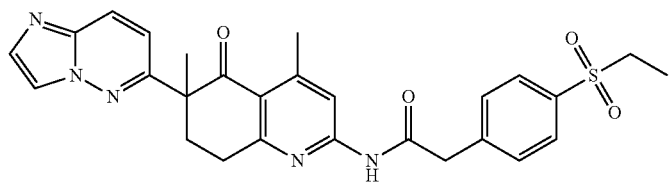 [SMILES: CCS(=O)(=O)c1ccc(CC(=O)Nc2cc(C)c3c(n2)CCC(C)(c2ccc4nccn4n2)C3=O)cc1] | ¹H NMR (400 MHz, CDCl3): δ 7.96-7.87 (m, 5H), 7.81 (s, 1H), 7.70 (s, 1H), 7.53 (d, J = 8.0 Hz, 2H), 7.00 (d, J = 9.60 Hz, 1H) 3.81 (s, 2H), 3.14-3.10 (m, 2H), 3.01-3.00 (m, 2H), 2.70 (s, 3H), 2.25-2.40 (m, 1H), 1.59 (s, 3H), 1.30-1.26 (m, 4H). LC-MS: 518.4 [M + H]⁺. |
| 78 | 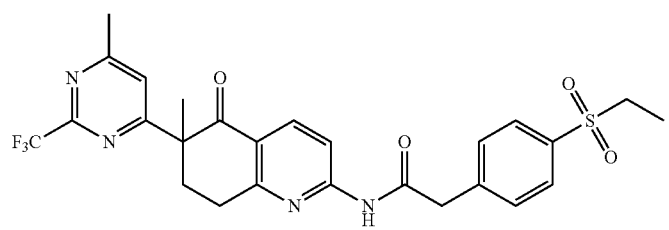 [SMILES: CCS(=O)(=O)c1ccc(CC(=O)Nc2ccc3c(n2)CCC(C)(c2cc(C)nc(C(F)(F)F)n2)C3=O)cc1] | ¹H NMR (400 MHz, CDCl₃): δ 8.38 (d, J = 8.4 Hz, 1H), 8.17 (d, J = 8.4 Hz, 1H), 8.07 (s, 1H), 7.92 (d, J = 7.2 Hz, 2H), 7.54 (d, J = 7.2 Hz, 2H), 7.18 (s, 1H), 3.84 (s, 1H), 3.13-3.11 (m, 2H), 3.03-2.95 (m, 2H), 2.55 (s, 3H), 2.27-2.20 (m, 2H), 1.58 (s, 3H), 1.3 (t, J = 6.4 Hz, 3H); LC-MS: 547.2 [M + H]⁺. |
| 79 | 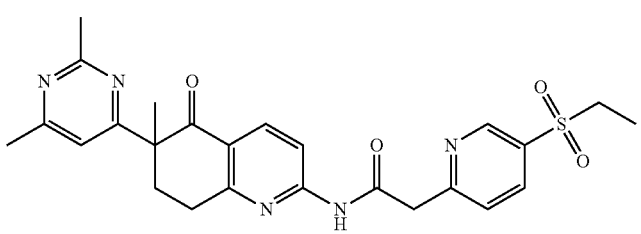 [SMILES: CCS(=O)(=O)c1ccc(CC(=O)Nc2ccc3c(n2)CCC(C)(c2cc(C)nc(C)n2)C3=O)nc1] | ¹H NMR (400 MHz, CDCl₃): δ 9.64 (br s, 1H) 9.13 (d, J = 2.4 Hz, 1H), 8.38 (d, J = 8.4 Hz, 1H), 8.20-8.11 (m, 2H), 7.54 (d, J = 8.4 Hz, 1H), 6.77 (s, 1H), 4.02 (s, 2H), 3.19-3.14 (m, 2H), 2.97-2.93 (m, 3H), 2.61 (s, 3H), 2.38 (s, 3H), 2.16-2.11 (m, 1H), 1.52 (s, 3H), 1.34 (t, J = 4.8 Hz, 3H); LC-MS: 494.6 [M + H]⁺. |
| 80 | 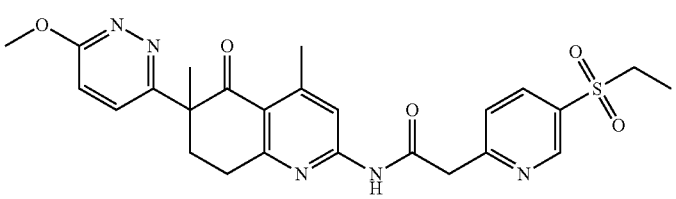 [SMILES: CCS(=O)(=O)c1ccc(CC(=O)Nc2cc(C)c3c(n2)CCC(C)(c2ccc(OC)nn2)C3=O)nc1] | ¹H NMR (300 MHz, CDCl₃): δ 9.40 (br s, 1H), 9.12 (d, J = 2.4 Hz, 1H), 8.19-8.22 (m, 1H), 7.91 (br s, 1H) 7.54 (d, J = 8.1 Hz, 1H), 7.31 (d, J = 9.3 Hz, 1H), 6.91 (d, J = 9.3 Hz, 1H), 4.07 (s, 3H), 4.00 (s, 2H), 3.13-3.12 (m, 2H), 2.89-3.14 (m, 3H), 2.68 (s, 3H), 2.18-2.20 (m, 1H), 1.59 (s, 3H), 1.35 (t, J = 7.5 Hz, 3H); LC-MS: 510.3 [M + H]⁺. |
| 81 | 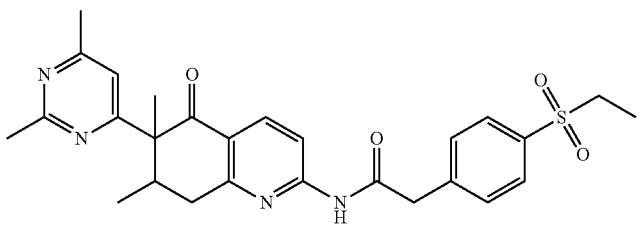 [SMILES: CCS(=O)(=O)c1ccc(CC(=O)Nc2ccc3c(n2)CC(C)C(C)(c2cc(C)nc(C)n2)C3=O)cc1] | ¹H NMR (400 MHz, CDCl3): δ 8.34 (d, J = 8.8 Hz, 1H), 8.17 (d, J = 8.8 Hz, 1H), 8.06 (s, 1H), 7.57 (d, J = 8.4 Hz, 2H), 6.88 (s, 1H), 3.86 (s, 2H), 3.15-3.03 (m, 3H), 2.83-2.77 (m, 1H), 2.44-2.39 (m, 6H), 1.64 (s, 3H), 1.31-1.27 (m, 3H), 1.13-1.10 (m, 3H). LC-MS: 507.7 [M + H]⁺. |

| Compound No. | Structure | Characterization Data |
|---|---|---|
| 82 | 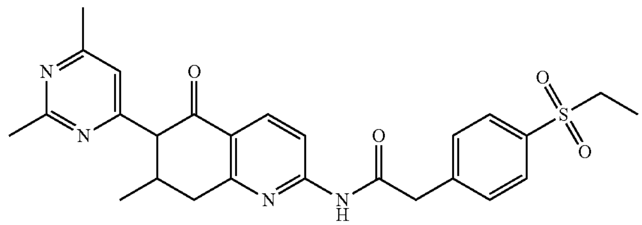 [SMILES: CCS(=O)(=O)c1ccc(CC(=O)Nc2ccc3c(n2)CC(C)C(c2cc(C)nc(C)n2)C3=O)cc1] | 1H NMR (400 MHz, CDCl3): δ 8.30 (d, J = 8.8 Hz, 1H), 8.17 (d, J = 8.8 Hz, 1H), 8.08 (s, 1H), 7.94 (d, J= 6.4 Hz, 2H), 7.57-7.55 (m, 2H), 6.84 (s, 1H), 3.87 (s, 2H), 3.49 (d, J = 10.8 Hz, 1H), 3.16-3.10 (m, 3H), 2.87-2.83 (m, 2H), 2.65 (s, 3H), 2.49 (s, 3H), 1.31-1.28 (m, 3H), 0.99-0.98 (m, 2H). LC-MS: 493.1 [M + H]+. |
| 83 | 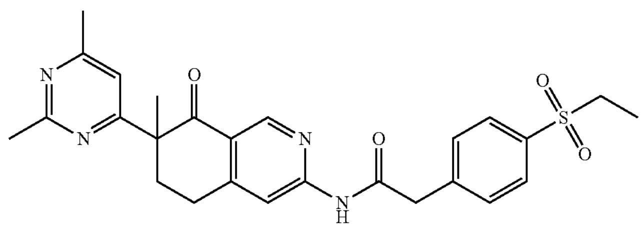 [SMILES: CCS(=O)(=O)c1ccc(CC(=O)Nc2cc3c(cn2)C(=O)C(C)(c2cc(C)nc(C)n2)CC3)cc1] | $^1$H NMR (300 MHz, DMSO-d$^6$): δ 11.1 (s, 1H), 8.26 (d, J = 8.7 Hz, 1H), 8.06 (d, J = 8.7 Hz, 1H), 7.85 (d, J = 8.4 Hz, 2H), 7.61 (d, J = 8.1 Hz, 2H), 7.13 (s, 1H), 3.89 (s, 2H), 3.25 (s, 3H), 2.76-2.72 (m, 2H), 2.43 (s, 3H), 2.36 (s, 3H), 1.45 (s, 3H), 1.1-105 (m, 3H). LC-MS: 493.3 [M + H]+. |

Example-2: Synthesis of 2-(4-(ethylsulfonyl)phenyl)-N-(6-(2-hydroxypyridin-3-yl)-4,6-dimethyl-5-oxo-5,6,7,8-tetrahydroquinolin-2-yl)acetamide (Compound-84)

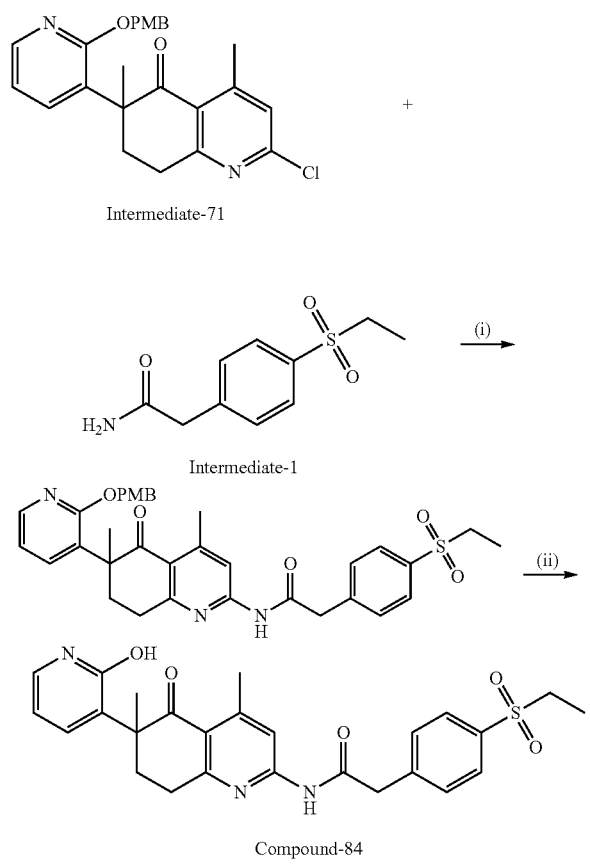

Step-i: Synthesis of 2-(4-(ethylsulfonyl)phenyl)-N-(6-(2-((4-methoxybenzyl)oxy)pyridin-3-yl)-4,6-dimethyl-5-oxo-5,6,7,8-tetrahydroquinolin-2-yl)acetamide 2-(4-(ethylsulfonyl)phenyl)-N-(6-(2-((4-methoxybenzyl)oxy)pyridin-3-yl)-4,6-dimethyl-5-oxo-5,6,7,8-tetrahydroquinolin-2-yl)acetamide was prepared by procedure similar to the one described in Example-1 with appropriate variations in reactants, quantities of reagents, solvents and reaction conditions. LC-MS: 614.4 [M+H]+.

Step-ii: Synthesis of 2-(4-(ethylsulfonyl)phenyl)-N-(6-(2-hydroxypyridin-3-yl)-4,6-dimethyl-5-oxo-5,6,7,8-tetrahydroquinolin-2-yl)acetamide To a stirred solution of 2-(4-(ethylsulfonyl)phenyl)-N-(6-(2-((4-methoxybenzyl)oxy)pyridin-3-yl)-4,6-dimethyl-5-oxo-5,6,7,8-tetrahydroquinolin-2-yl)acetamide (0.08 g, 0.13 mmol) in methanol/ethyl acetate (3 mL/3 mL) was added 10% palladium on carbon (0.015 g) under nitrogen atmosphere and the reaction mixture was stirred under the positive pressure of hydrogen using a bladder for 12 h. The Pd—C was filtered off and filtrate concentrated to get crude, which on purification by preparative HPLC afforded the titled compound (0.01 g, 15.6%). $^1$H NMR (400 MHz, CDCl$_3$): δ 11.58-11.71 (m, 1H), 9.34 (br s, 1H), 7.74-7.89 (m, 3H), 7.44 (d, J=8.02 Hz, 3H), 7.15 (d, J=6.06 Hz, 1H), 6.29 (t, J=6.75 Hz, 1H), 3.60-3.82 (m, 2H), 3.00-3.15 (m, 3H), 2.82-2.97 (m, 2H), 2.58 (s, 3H), 1.70-1.81 (m, 1H), 1.51 (s, 3H), 1.24-1.27 (m, 3H). LC-MS: 494.6 [M+H]+.

The below compounds (85-91) were prepared by a procedure similar to the one described in Example-2 with appropriate variations in reactants, quantities of reagents, solvents and reaction conditions.

| Compound No. | Characterization Data |
|---|---|
| 85 | $^1$H NMR (400 MHz, CDCl$_3$): δ 8.37 (br s, 1H), 8.02-8.14 (m, 2H), 7.85-7.96 (m, 3H), 7.51 (d, J = 8.06 Hz, 2H), 7.03-7.13 (m, 2H), 3.81 (s, 2H), 3.32-3.47 (m, 1H), 3.04-3.17 (m, 3H), 2.88-2.99 (m, 1H), 2.62 (s, 3H), 2.03-2.15 (m, 1H), 1.60 (s, 3H), 1.28 (t, J = 7.39 Hz, 3H); LC-MS: 494.3 [M + H]$^+$. |
| 86 | $^1$H NMR (400 MHz, DMSO-d$^6$): δ 11.55 (br s, 1H), 11.00 (s, 1H), 7.75-7.92 (m, 3H), 7.61 (d, J = 8.33 Hz, 2H), 7.37 (d, J = 6.98 Hz, 1H), 6.00 (d, J = 6.98 Hz, 1H), 3.97 (br s, 1H), 3.88 (s, 2H), 3.28 (q, J = 7.25 Hz, 2H), 2.97-3.07 (m, 1H), 2.78-2.88 (m, 1H), 2.61-2.70 (m, 1H), 2.11 (s, 3H), 1.63-1.76 (m, 1H), 1.33 (s, 3H), 1.09 (t, J = 7.25 Hz, 3H); LC-MS: 508.3 [M + H]$^+$. |
| 87 | $^1$H NMR (400 MHz, DMSO-d$^6$): δ 11.24 (s, 1H), 10.07 (br s, 1H), 8.12-8.18 (m, 1H), 8.06 (d, J = 8.60 Hz, 1H), 7.83-7.88 (m, 2H), 7.63 (d, J = 8.06 Hz, 2H), 7.22 (d, J = 6.98 Hz, 1H), 7.09 (br s, 1H), 4.16 (br s, 1H), 3.93 (s, 2H), 3.24-3.30 (m, 2H), 3.17 (s, 1H), 2.69 (d, J = 15.85 Hz, 1H), 2.09 (s, 1H), 1.08 (d, J = 11.82 Hz, 5H), 0.92 (br s, 3H); LC-MS: 494.2 [M + H]$^+$. |
| 88 | $^1$H NMR (300 MHz, DMSO-d$^6$): δ 11.03 (s, 1H), 9.81 (s, 1H), 7.95 (s, 1H), 7.79-7.87 (m, 3H), 7.58 (d, J = 8.24 Hz, 2H), 7.08 (d, J = 1.32 Hz, 2H), 4.03 (q, J = 7.25 Hz, 1H), 3.85 (s, 2H), 3.26 (d, J = 7.58 Hz, 1H), 2.72 (br s, 2H), 2.56 (s, 3H), 2.03-2.20 (m, 1H), 1.99 (s, 1H), 1.34 (s, 3H), 1.08 (t, J = 7.25 Hz, 3H); LC-MS: 494.4 [M + H]$^+$. |
| 89 | $^1$H NMR (300 MHz, CDCl$_3$): δ 8.36 (br s, 1H), 8.11 (d, J = 2.20 Hz, 2H), 7.90-7.99 (m, 3H), 7.53 (d, J = 8.23 Hz, 2H), 7.05-7.15 (m, 2H), 3.83 (s, 2H), 3.51 (br s, 1H), 3.33-3.47 (m, 1H), 3.12 (d, J = 5.12 Hz, 1H), 3.07 (s, 3H), 2.90-3.01 (m, 1H), 2.64 (s, 3H), 2.06-2.16 (m, 1H), 1.67 (br s, 2H); LC-MS: 480.3 [M + H]$^+$. |
| 90 | $^1$H NMR (300 MHz, CDCl$_3$): δ 8.26-8.33 (m, 2H), 8.14 (d, J = 8.57 Hz, 1H), 7.90 (d, J = 8.57 Hz, 3H), 7.52 (d, J = 8.24 Hz, 2H), 6.99 (s, 2H), 3.84 (s, 2H), 3.64 (s, 1H), 3.25 (d, J = 17.48 Hz, 1H), 3.13 (q, J = 7.25 Hz, 2H), 2.70 (d, J = 17.15 Hz, 1H), 1.29 (t, J = 7.42 Hz, 3H), 1.06 (s, 3H), 0.91 (s, 3H); LC-MS: 494.3 [M + H]$^+$. |
| 91 | $^1$H NMR (300 MHz, CDCl$_3$): δ 8.26-8.33 (m, 2H), 8.14 (d, J = 8.57 Hz, 1H), 7.90 (d, J = 8.57 Hz, 3H), 7.52 (d, J = 8.24 Hz, 2H), 6.99 (s, 2H), 3.84 (s, 2H), 3.64 (s, 1H), 3.25 (d, J = 17.48 Hz, 1H), 3.13 (q, J = 7.25 Hz, 2H), 2.70 (d, J = 17.15 Hz, 1H), 1.29 (t, J = 7.42 Hz, 3H), 1.06 (s, 3H), 0.91 (s, 3H); LC-MS: 479.8 [M + H]$^+$. |

Example-3: Synthesis of N-(6-(5-chloroimidazo[1,2-a]pyrazin-8-yl)-6-methyl-5-oxo-5,6,7,8-tetrahydroquinolin-2-yl)-2-(4-(ethyl sulfonyl)phenyl)acetamide (Compound-92)

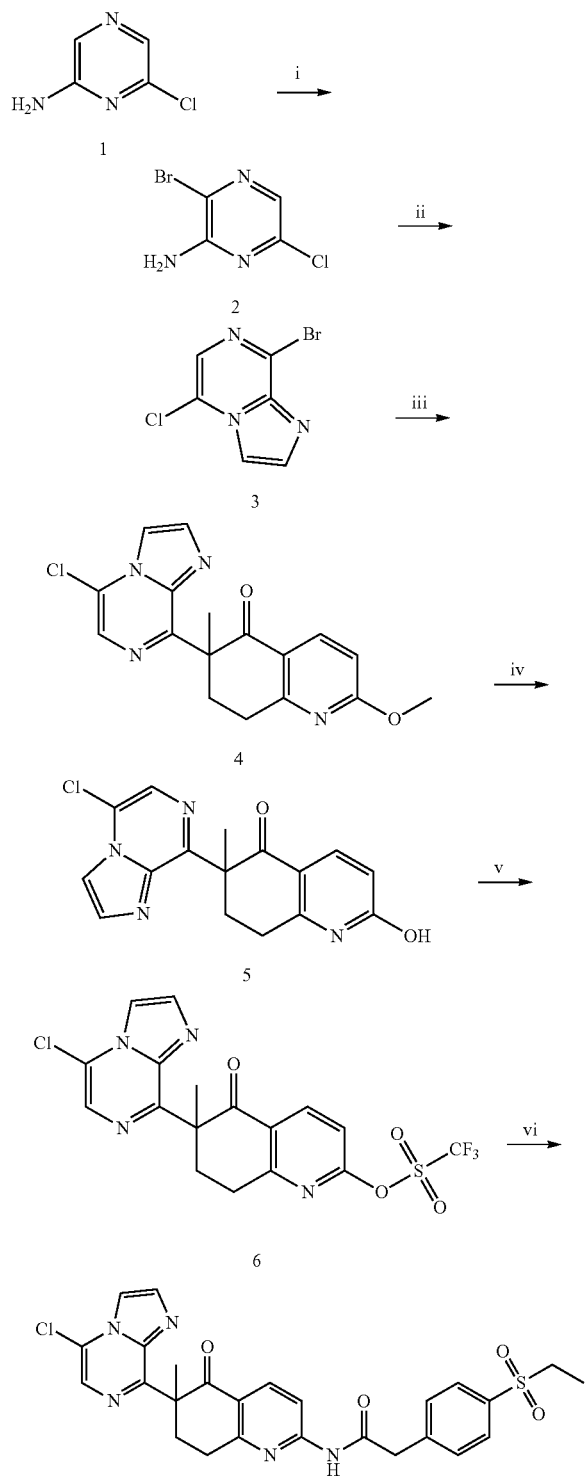

Step-i: Synthesis 3-bromo-6-chloropyrazin-2-amine

To a solution of 6-chloropyrazin-2-amine (15.0 g, 115 mmol) in DCM (150 mL), N-bromo succinimide (20.6 g, 115 mmol) was slowly added in portions at −10° C. and stirred for 4 h. The reaction mixture was washed with water and the organic layer was separated. The organic layer was dried over $Na_2SO_4$, and concentrated under reduced pressure to afford the crude product. The crude product was purified by column chromatography over silica gel (100-200 mesh) eluting with DCM to afford 3-bromo-6-chloropyrazin-2-amine (7.5 g, 31%).

Step-ii: Synthesis of 8-bromo-5-chloroimidazo[1,2-a]pyrazine

A mixture of 3-bromo-6-chloropyrazin-2-amine (5 g, 24.0 mmol) and bromoacetaldehyde diethyl acetal (5.2 g, 26.0 mmol) in DMF (20 mL) was stirred at 50° C. for 12 h. The volatiles were evaporated under high vacuum to get a residue. The residue was dissolved in ethanol (20 mL) and refluxed for 12 h. The volatiles were evaporated under reduced pressure to get the crude product. The crude product was purified by column chromatography over silica gel (100-200 mesh) eluting with DCM to afford 8-bromo-5-chloroimidazo[1,2-a]pyrazine (0.35 g, 6%).

Step-iii: Synthesis of 6-(5-chloroimidazo[1,2-a]pyrazin-8-yl)-2-methoxy-6-methyl-7,8-dihydroquinolin-5(6H)-one This step was done using the same protocol explained in the preparation of Intermediate-38

Step-iv: Synthesis of 6-(5-chloroimidazo[1,2-a]pyrazin-8-yl)-2-hydroxy-6-methyl-7,8-dihydroquinolin-5(6H)-one A mixture of 6-(5-chloroimidazo[1,2-a]pyrazin-8-yl)-2-methoxy-6-methyl-7,8-dihydroquinolin-5(6H)-one (0.12 g, 0.35 mmol), trimethylsilyl chloride (0.041 g, 0.38 mmol) and sodium iodide (0.06 g, 0.38 mmol) in acetonitrile (10 mL) was stirred at 60° C. for 1 h. The reaction mixture was diluted with ethyl acetate and washed with water. The organic layer was separated, washed with brine, dried over anhydrous sodium sulfate and evaporated under reduced pressure to get 6-(5-chloroimidazo[1,2-a]pyrazin-8-yl)-2-hydroxy-6-methyl-7,8-dihydroquinolin-5(6H)-one (0.08 g, 70%).

Step-v: Synthesis of 6-(5-chloroimidazo[1,2-a]pyrazin-8-yl)-6-methyl-5-oxo-5,6,7,8-tetrahydro quinolin-2-yl trifluoromethanesulfonate To a solution of 6-(5-chloroimidazo[1,2-a]pyrazin-8-yl)-2-hydroxy-6-methyl-7,8-dihydroquinolin-5(6H)-one (0.08 g, 0.24 mmol) in pyridine (10 mL) at 0° C., was added triflic anhydride (0.14 g, 0.48 mmol) and stirred at room temperature for 0.5 h. The volatiles were evaporated from the reaction mixture to get a residue. The residue was dissolved in ethyl acetate and washed with water. The organic layer was separated, washed with brine, dried over anhydrous sodium sulfate and evaporated under reduced pressure to get 6-(5-chloroimidazo[1,2-a]pyrazin-8-yl)-6-methyl-5-oxo-5,6,7,8-tetrahydroquinolin-2-yl trifluoromethanesulfonate (0.07 g, 63%).

Step-vi: Synthesis of N-(6-(5-chloroimidazo[1,2-a]pyrazin-8-yl)-6-methyl-5-oxo-5,6,7,8-tetrahydroquinolin-2-yl)-2-(4-(ethyl sulfonyl)phenyl)acetamide 6-(5-chloroimidazo[1,2-a]pyrazin-8-yl)-6-methyl-5-oxo-5,6,7,8-tetrahydroquinolin-2-yl trifluoromethanesulfonate was coupled using the same protocol as explained in Example-1.

¹HNMR (400 MHz, CDCl₃): δ 8.44 (d, J=8.4 Hz, 1H), 8.18 (d, J=8.8 Hz, 1H), 8.11 (s, 1H), 7.92 (d, J=8.4 Hz, 2H), 7.80-7.77 (m, 3H), 7.55 (d, J=8.4 Hz, 2H), 3.84 (s, 1H), 3.62-3.56 (m, 1H), 3.14-3.09 (m, 2H) 3.05-2.99 (m, 1H), 2.80-2.73 (m, 1H), 2.17-2.12 (m, 1H), 1.88 (s, 3H), 1.31 (t, J=7.6 Hz, 3H); LC-MS: 538.1 [M+H]⁺.

Compound-93: Synthesis of N-(6-(6-chloropyridazin-3-yl)-6-methyl-5-oxo-5,6,7,8-tetrahydroquinolin-2-yl)-2-(4-(ethyl sulfonyl)phenyl)acetamide

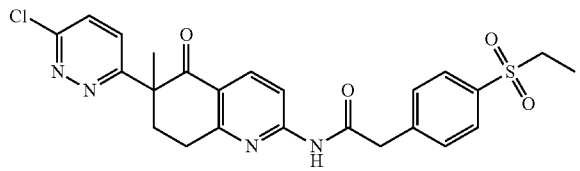 [SMILES: CCS(=O)(=O)c1ccc(CC(=O)Nc2ccc3c(n2)CCC(C)(c2ccc(Cl)nn2)C3=O)cc1]

This compound was prepared by procedure similar to the one described in Example-3 with appropriate variations in reactants, quantities of reagents, solvents and reaction conditions.

¹HNMR (400 MHz, CDCl₃): δ 8.34 (d, J=8.8 Hz, 1H), 8.13 (d, J=8.8 Hz, 1H), 8.05 (s, 1H) 7.90 (d, J=8.0 Hz, 2H), 7.53 (d, J=8.0 Hz, 2H), 7.42 (s, 2H), 3.82 (s, 2H), 3.13-2.92 (m, 5H) 2.32-2.25 (m, 1H), 1.61 (s, 3H), 1.29 (t, J=7.6 Hz, 3H) LC-MS: 499.1 [M+H]⁺.

Example-4: Synthesis of 3-(2-(2-(4-(ethylsulfonyl)phenyl)acetamido)-4,6-dimethyl-5-oxo-5,6,7,8-tetrahydroquinolin-6-yl)-6-methoxypyridazine 1-oxide (Compound-94)

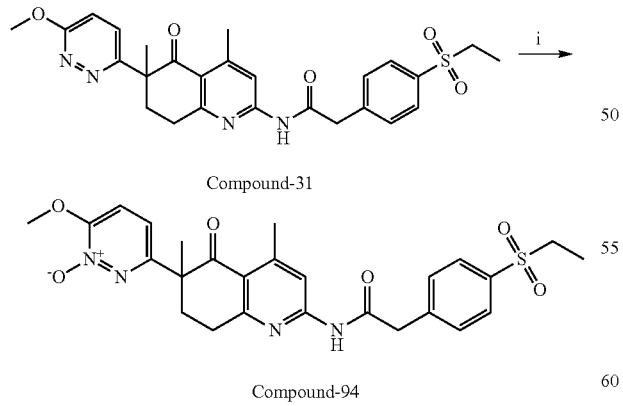

A mixture of 2-(4-(ethylsulfonyl)phenyl)-N-(6-(6-methoxypyridazin-3-yl)-4,6-dimethyl-5-oxo-5,6,7,8-tetrahydroquinolin-2-yl)acetamide (0.1 g, 0.196 mmol) in Dichloromethane (5 mL) was added mCPBA (0.34 g, 0.196 mmol) at 0° C. and was warmed to RT and stirred at room temperature for 4 h. The reaction mixture was then quenched with ice water and diluted with dichloromethane and washed with water. The organic layer was dried over sodium sulphate, filtered and concentrated under reduced pressure to get residue. The residue was purified by flash chromatography using 80% ethyl acetate in hexanes to get pure title compound (0.03 g, 29%).

1H NMR (400 MHz, CDCl₃): δ 10.39 (s, 1H), 8.22 (s, 1H) 7.94 (d, J=8.0 Hz, 2H), 7.57 (d, J=8.4 Hz, 2H), 7.30 (s, 1H), 6.95 (d, J=9.2 Hz 1H), 4.07 (s, 3H), 3.93 (S, 2H), 3.39-3.34 (m, 1H), 3.15-3.10 (m, 2H), 2.97-2.93 (m, 2H), 2.72 (s, 3H), 2.28-2.19 (m, 1H), 1.55 (s, H), 1.31-1.27 (m, 3H); LC-MS: 525.3 [M+H]⁺.

Example-5: Synthesis of 2-(4-(ethylsulfonyl)phenyl)-N-(6-(6-methoxy-4-methylpyridazin-3-yl)-4,6-dimethyl-5-oxo-5,6,7,8-tetrahydroquinolin-2-yl)acetamide (Compound-95) and 2-(4-(ethylsulfonyl)phenyl)-N-(6-(6-methoxy-5-methylpyridazin-3-yl)-4,6-dimethyl-5-oxo-5,6,7,8-tetrahydroquinolin-2-yl)acetamide (Compound-96)

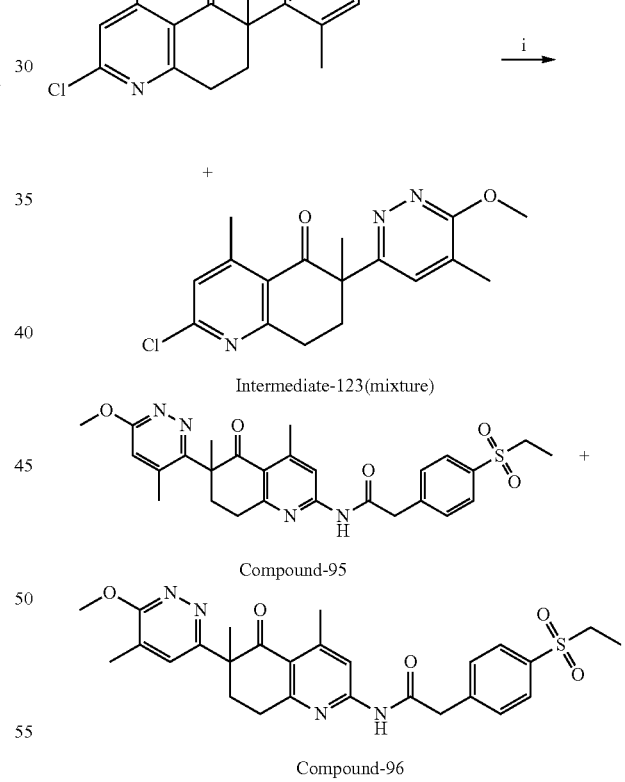

A mixture of 2-chloro-6-(6-methoxy-4-methylpyridazin-3-yl)-4,6-dimethyl-7,8-dihydroquinolin-5(6H)-one and 2-chloro-6-(6-methoxy-5-methylpyridazin-3-yl)-4,6-dimethyl-7,8-dihydroquinolin-5(6H)-one was coupled using the same protocol explained in example-1.

Purification and separation of regio-isomers: The crude product was subjected to column chromatography (60-120 mesh silica gel, 30-70% hexane in ethyl acetate) followed by preparative HPLC [Column: Kinetex EVO C18 100A axia (21.2 mm×150 mm, 5µ); Mobile phase: water and 1:1 mixture of acetonitrile and methanol] to obtain the fast moving isomer 2-(4-(ethylsulfonyl)phenyl)-N-(6-(6-methoxy-4-methylpyridazin-3-yl)-4,6-dimethyl-5-oxo-5,6,7,8-tetrahydroquinolin-2-yl)acetamide (0.042 g, 13%) and the slow moving isomer 2-(4-(ethylsulfonyl)phenyl)-N-(6-(6-methoxy-5-methylpyridazin-3-yl)-4,6-dimethyl-5-oxo-5,6,7,8-tetrahydroquinolin-2-yl)acetamide (0.03 g, 10%). The spectral data are depicted below respectively.

Compound-95:

$^1$H NMR (300 MHz, CDCl3): δ 7.89-7.95 (m, 4H), 7.54 (d, J=8.1 Hz, 1H), 6.66 (s, 1H), 4.07 (s, 3H), 3.81 (s, 2H), 2.89-3.15 (m, 5H), 2.67 (s, 3H), 2.05-2.12 (m, 1H), 2.14 (s, 3H), 1.65 (s, 3H), 1.3 (t, J=7.5 Hz, 3H); LC-MS: 523.3 [M+H]+.

Compound-96:

$^1$H NMR (300 MHz, CDCl3): δ 7.89-7.92 (m, 4H), 7.54 (d, J=8.1 Hz, 1H), 7.08 (d, J=0.9 Hz, 1H), 4.08 (s, 3H), 3.80 (s, 2H), 3.08-3.15 (m, 2H), 2.91-2.96 (m, 3H), 2.69 (s, 3H), 2.05-2.14 (m, 1H), 2.16 (s, 3H), 1.53 (s, 3H), 1.3 (t, J=7.5 Hz, 3H); LC-MS: 523.2 [M+H]+.

Example-6: Synthesis of 2-(4-(ethylsulfonyl)phenyl)-N-(6-(3-fluoroimidazo[1,2-a]pyrazin-8-yl)-6-methyl-5-oxo-5,6,7,8-tetrahydroquinolin-2-yl)acetamide (Compound-97)

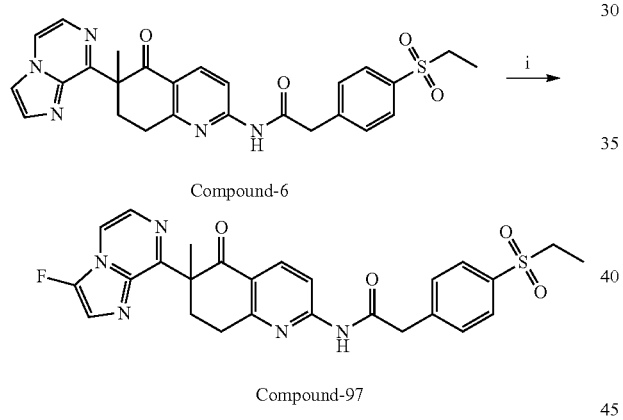

To a solution of 2-(4-(ethylsulfonyl)phenyl)-N-(6-(imidazo[1,2-a]pyrazin-8-yl)-6-methyl-5-oxo-5,6,7,8-tetrahydroquinolin-2-yl)acetamide (Compound-6) (0.4 g, 0.8 mmol) in acetonitrile (15 mL) at 0° C., was added a solution of Selectfluor® (0.28 g, 0.145 mmol) in THF:Water (1:1, 15 mL) for 20 min. The reaction mixture was allowed to warm to room temperature and stirred at room temperature for 48 h. The reaction mixture was evaporated under reduced pressure to get the residue. The residue was partitioned between ethyl acetate and water. The organic layer was washed with brine, dried over anhydrous sodium sulfate and evaporated under reduced pressure to get the crude product. The crude product was purified by preparative HPLC (Column: Gemini NX C18: 1.2 mm*150 mm; mobile phase: acetonitrile and water) to get 2-(4-(ethylsulfonyl)phenyl)-N-(6-(3-fluoroimidazo[1,2-a]pyrazin-8-yl)-6-methyl-5-oxo-5,6,7,8-tetrahydroquinolin-2-yl)acetamide (0.03 g, 7%).

$^1$H NMR (300 MHz, CDCl$_3$): δ 8.46 (d, J=8.7 Hz, 1H), 8.19 (d, J=8.7 Hz, 1H), 7.93 (d, J=6.6 Hz, 2H), 7.72-7.78 (m, 2H), 7.56 (d, J=8.1 Hz, 2H), 7.27-7.29 (m, 1H), 3.84 (s, 2H), 3.54-3.59 (m, 1H), 3.08-3.15 (m, 2H), 2.96-3.08 (m, 1H), 2.79-2.81 (m, 1H), 2.11-2.17 (m, 1H), 1.82 (s, 3H), 1.31 (t, J=7.5 Hz, 3H); LC-MS: 522.4 [M+H]+.

Example-7: Synthesis of N-(6-(6-(dimethylamino)pyridazin-3-yl)-4,6-dimethyl-5-oxo-5,6,7,8-tetrahydroquinolin-2-yl)-2-(4-(ethylsulfonyl)phenyl)acetamide (Compound-98)

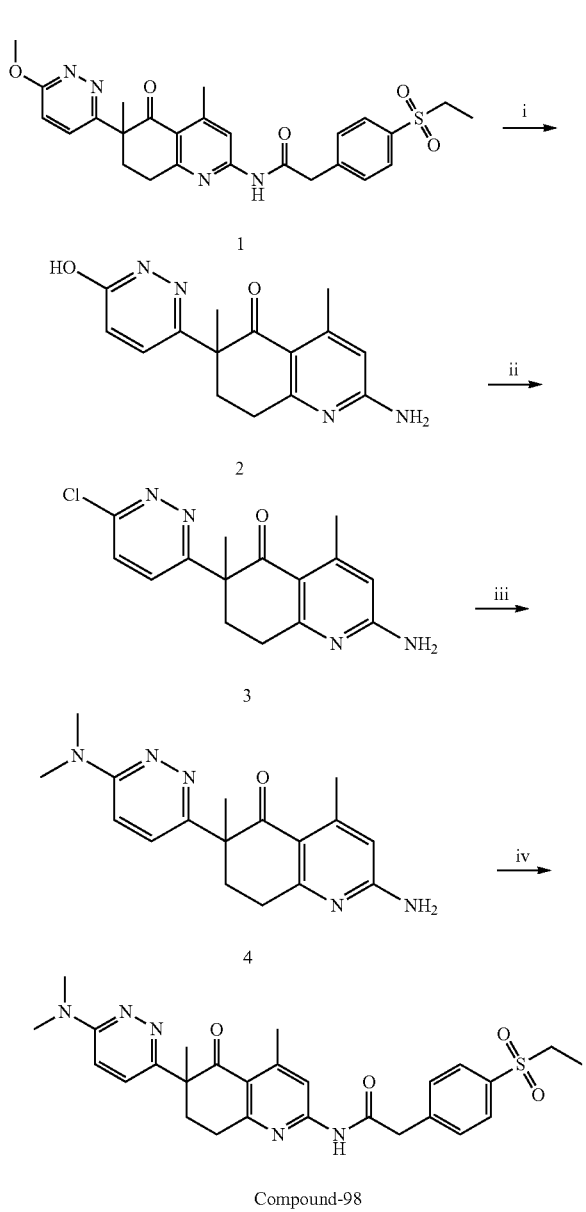

Step-i: Synthesis of 2-amino-6-(6-hydroxypyridazin-3-yl)-4,6-dimethyl-7,8-dihydroquinolin-5(6H)-one A mixture of 2-(4-(ethylsulfonyl)phenyl)-N-(6-(6-methoxypyridazin-3-yl)-4,6-dimethyl-5-oxo-5,6,7,8-tetrahydroquinolin-2-yl)acetamide (Compound-31) (0.5 g, 0.098 mmol) and 48% HBr in water (10 ml) was stirred at 60° C. for 3 h. The volatiles were evaporated under reduced pressure to get the residue. The residue was neutralized with 10% sodium bicarbonate solution and extracted with ethyl acetate. The organic was washed with water, brine, dried over anhydrous sodium sulphate and evaporated under reduced pressure to give 2-amino-6-(6-hydroxypyridazin-3-yl)-4,6-dimethyl-7,8-dihydroquinolin-5(6H)-one (0.25 g, 89%), $^1$H NMR (300 MHz, DMSO-$d_6$): δ 12.79 (br s, 1H), 7.45 (d, J=9.9 Hz, 1H), 6.83-6.77 (m, 3H), 6.10 (s, 1H), 2.41 (s, 3H), 1.96-1.93 (m, 2H), 1.33 (s, 3H) 1.21-1.06 (m, 2H); LC-MS: 285.1 [M+H]$^+$.

Step-ii: Synthesis of 2-amino-6-(6-chloropyridazin-3-yl)-4,6-dimethyl-7,8-dihydro quinolin-5(6H)-one The mixture of 2-amino-6-(6-hydroxypyridazin-3-yl)-4,6-dimethyl-7,8-dihydroquinolin-5(6H)-one (0.24 g, 0.000.84 mmol) and phosphorous oxychloride (15 mL) was stirred at 130° C. for 3 h. The volatiles were evaporated under reduced pressure to get the residue. The residue was neutralized with 10% sodium bicarbonate solution and extracted ethyl acetate. The organic was washed with water, brine, dried over anhydrous sodium sulphate and evaporated under reduced pressure to give 2-amino-6-(6-chloro-pyridazin-3-yl)-4,6-dimethyl-7,8-dihydroquinolin-5(6H)-one (0.18 g, 72%), LC-MS: 303.3.0 [M+H]$^+$.

Step-iii: Synthesis of 2-amino-6-(6-(dimethylamino) pyridazin-3-yl)-4,6-dimethyl-7,8-dihydroquinolin-5 (6H)-one A mixture 2-amino-6-(6-chloropyridazin-3-yl)-4,6-dimethyl-7,8-dihydroquinolin-5(6H)-one (0.17 g, 0.56 mmol) and 40% dimethylamine in water (5.0 ml) was stirred at 100° C. in seal tube for 12 h and then cooled to get the solids. The solids collected by filtration to obtain 2-amino-6-(6-(dimethylamino)pyridazin-3-yl)-4,6-dimethyl-7,8-dihydroquinolin-5(6H)-one (0.1 g, 58%). LC-MS: 312.2 [M+H]$^+$.

Step-iv: N-(6-(6-(dimethylamino)pyridazin-3-yl)-4,6-dimethyl-5-oxo-5,6,7,8-tetrahydroquinolin-2-yl)-2-(4-(ethylsulfonyl)phenyl)acetamide To a solution of 2-amino-6-(6-(dimethylamino)pyridazin-3-yl)-4,6-dimethyl-7,8-dihydroquinolin-5(6H)-one (0.08 g, 0.26 mmol), 2-(4-(ethylsulfonyl)phenyl)acetic acid (0.07 g, 0.31 mmol) and triethyl amine (0.052 g, 0.5 mmol) in dichloromethane (20 mL) was added 50 wt. % propylphosphonic anhydride solution in ethyl acetate (0.245 mL, 0.52 mmol) and stirred at room temperature for 2 h. The reaction mixture was washed with water. The organic layer was washed with brine, dried over anhydrous sodium sulfate and evaporated under reduced pressure to get the crude product. The crude product was purified by flash column chromatography (50-100% ethyl acetate in hexane) to get N-(6-(6-(dimethylamino)pyridazin-3-yl)-4,6-dimethyl-5-oxo-5,6,7,8-tetrahydroquinolin-2-yl)-2-(4-(ethyl sulfonyl)phenyl) acetamide (0.04 g, 30%).

$^1$H NMR (400 MHz, CDCl$_3$): δ 8.20 (br s, 1H) 7.90-7.88 (m, 3H), 7.533 (s, 1H), 7.51 (s, 1H), 7.08 (d, J=9.6 Hz, 1H), 6.7 (d, J=9.6 Hz, 1H), 3.80 (s, 2H), 3.12-3.08 (m, 5H), 2.99-2.92 (m, 2H), 2.67 (s, 3H), 2.18-2.16 (m, 2H), 1.51 (s, 3H), 1.298-1.261 (t, J=7.2 Hz, 3H); LC-MS: 522.3 [M+H]$^+$.

Example-8: Synthesis of 6-(2,6-dimethylpyrimidin-4-yl)-N-(4-(ethylsulfonyl)benzyl)-6-methyl-5-oxo-5,6,7,8-tetrahydroquinoline-2-carboxamide (Compound-99)

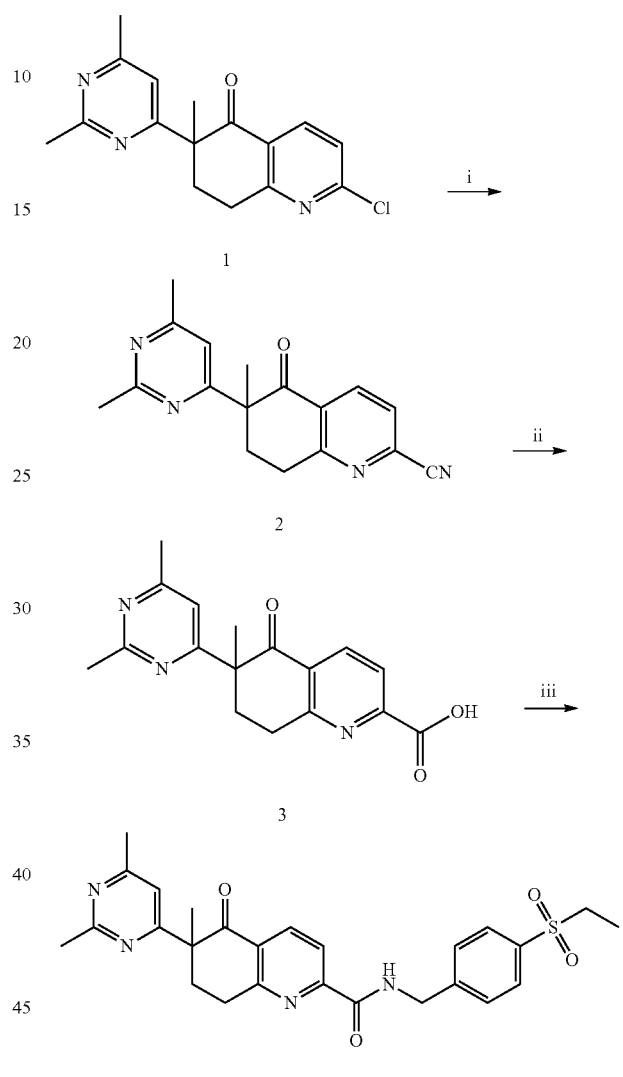

Compound-99

Step-i: 6-(2,6-dimethylpyrimidin-4-yl)-6-methyl-5-oxo-5,6,7,8-tetrahydroquinoline-2-carbonitrile A mixture of 2-chloro-6-(2,6-dimethylpyrimidin-4-yl)-6-methyl-7,8-dihydroquinolin-5(6H)-one (2.5 g, 8.3 mmol) in dimethyl acetamide (25 mL) was added zinc cyanide (1.9 g, 17.7 mmol) and tetrakis(triphenylphosphine)palladium(0) (0.38 g, 0.33 mmol). The resulting reaction mixture was stirred at 120° C. for 2 h. The reaction mixture was cooled to room temperature and filtered through a pad of celite. The filtrate was diluted with ethyl acetate and washed with water. The organic layer was washed with brine, dried over anhydrous sodium sulfate and evaporated under reduced pressure to get the crude product. The crude product was purified by flash column chromatography (30-50% ethyl acetate in hexane) to get 6-(2,6-dimethyl pyrimidin-4-yl)-6-methyl-5-oxo-5,6,7,8-tetrahydroquinoline-2-carbonitrile (1.5 g, 63%). LC-MS: 293.3 [M+H]+.

Step-ii: 6-(2,6-dimethylpyrimidin-4-yl)-6-methyl-5-oxo-5,6,7,8-tetrahydroquinoline-2-carboxylic acid A mixture of 6-(2,6-dimethylpyrimidin-4-yl)-6-methyl-5-oxo-5,6,7,8-tetrahydroquinoline-2-carbonitrile (0.5 g, 1.7 mmol) in concentrated hydrochloric acid (4.0 mL) and water (6.0 mL) was stirred at 100° C. for 6 h. The volatiles were evaporated under reduced pressure to get the residue. The residue was basified with triethyl amine and extracted with dichloromethane. The organic layer was evaporated under reduced pressure to get the crude product. The crude product was purified by flash column chromatography (0-10% methanol in chloroform) to get 6-(2,6-dimethylpyrimidin-4-yl)-6-methyl-5-oxo-5,6,7,8-tetrahydroquinoline-2-carboxylic acid (0.4 g, 75%). LC-MS: 312.3 [M+H]+.

Step-iii: 6-(2,6-dimethylpyrimidin-4-yl)-N-(4-(ethylsulfonyl)benzyl)-6-methyl-5-oxo-5,6,7,8-tetrahydroquinoline-2-carboxamide To a solution of 6-(2,6-dimethylpyrimidin-4-yl)-6-methyl-5-oxo-5,6,7,8-tetrahydro quinoline-2-carboxylic acid (0.22 g, 0.7 mmol), (4-(ethylsulfonyl)phenyl)methanamine (0.141 g, 0.7 mmol) and DIPEA (0.182 g, 1.4 mmol) in DMF (10 mL) was added HATU (0.4 g, 1.0 mmol) and stirred at room temperature for 12 h. The reaction mixture was partitioned between ethyl acetate and water. The organic layer was washed with brine, dried over anhydrous sodium sulfate and evaporated under reduced pressure to get the crude product. The crude product was purified by flash column chromatography (0-2% methanol in chloroform) to get 6-(2,6-dimethylpyrimidin-4-yl)-N-(4-(ethylsulfonyl)benzyl)-6-methyl-5-oxo-5,6,7,8-tetrahydroquinoline-2-carboxamide (0.11 g, 32%).
$^1$H NMR (400 MHz, CDCl$_3$): δ 8.54 (d, J=7.6 Hz, 1H), 8.49 (br s, 1H), 8.20 (d, J=8.0 Hz, 1H), 7.87 (d, J=8.0 Hz, 2H), 7.54 (d, J=8.0 Hz, 2H), 6.80 (s, 1H), 4.76 (d, J=6.0 Hz, 2H), 3.12-3.07 (m, 2H), 3.07-3.04 (m, 2H) 2.97-2.94 (m, 1H), 2.58 (s, 3H), 2.41 (s, 3H), 2.27-2.17 (m, 1H), 1.57 (s, 3H), 1.28 (t, J=5.1 Hz, 3H); LC-MS: 493.4 [M+H]+.

Example-9: Synthesis of N-(6-(2,6-dimethylpyrimidin-4-yl)-6-methyl-5-oxo-5,6,7,8-tetrahydronaphthalen-2-yl)-2-(4-(ethylsulfonyl)phenyl)acetamide (Compound-100)

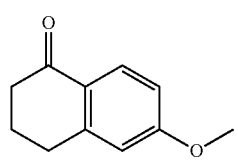

1

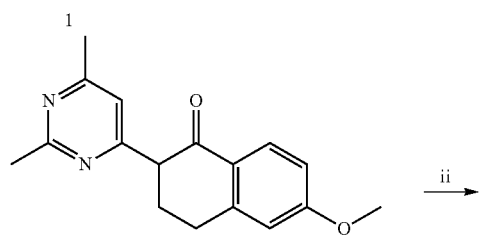

2

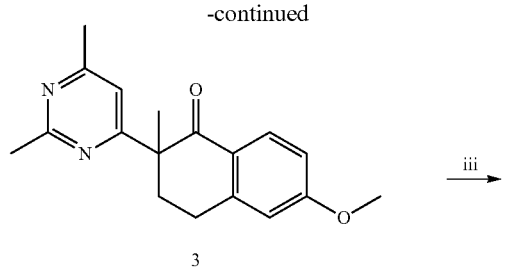

3

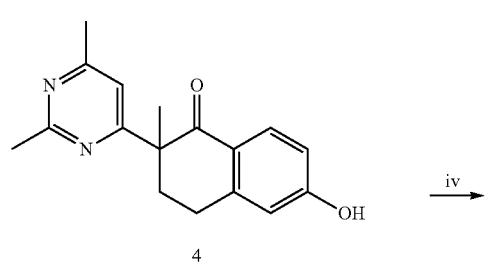

4

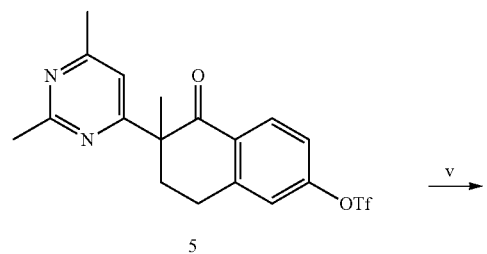

5

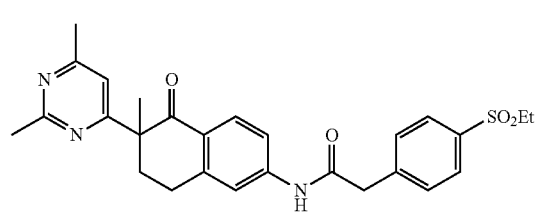

Compound-100

Step-i: Synthesis of 2-(2,6-dimethylpyrimidin-4-yl)-6-methoxy-3,4-dihydronaphthalen-1(2H)-one The compound was prepared according to the protocol as described in the synthesis of Intermediate-38a. LC-MS: 283.0 [M]+.

Step-ii: Synthesis of 2-(2,6-dimethylpyrimidin-4-yl)-6-methoxy-2-methyl-3,4-dihydronaphthalen-1 (2H)-one The compound was prepared according to the protocol as described in the synthesis of Intermediate-38. LC-MS: 297.02 [M]+.

Step-iii: Synthesis of 2-(2,6-dimethylpyrimidin-4-yl)-6-hydroxy-2-methyl-3,4-dihydronaphthalen-1(2H)-one A suspension of 2-(2,6-dimethylpyrimidin-4-yl)-6-methoxy-2-methyl-3,4-dihydronaphthalen-1(2H)-one (1.0 g, 0.35 mmol) in 30% aq HBr in acetic acid (10 mL) was heated to 100° C. for 12 h. The reaction was quenched with NH$_4$OH solution, extracted with ethyl acetate. The organic layer was dried over anhydrous sodium sulphate, filtered and concentrated to get the pure compound (0.45 g). LC-MS: 283.4 [M]$^+$.

Step-iv: Synthesis of 6-(2,6-dimethylpyrimidin-4-yl)-6-methyl-5-oxo-5,6,7,8-tetrahydronaphthalen-2-yl trifluoromethanesulfonate To a solution of 2-(2,6-dimethylpyrimidin-4-yl)-6-hydroxy-2-methyl-3,4-dihydronaphthalen-1(2H)-one (0.35 g, 0.12 mmol) in DCM (10 mL) was added Et$_3$N (0.52 mL, 0.377 mmol), triflic anhydride (0.42 g, 0.14 mmol) at 0° C. The reaction mixture was stirred at RT for 2 h. The reaction was quenched with ice water, extracted with DCM. The organic layer was dried over anhydrous sodium sulphate, filtered and concentrated to get the pure compound (0.40 g). LC-MS: 415.3 [M]$^+$.

Step-v: Synthesis of N-(6-(2,6-dimethylpyrimidin-4-yl)-6-methyl-5-oxo-5,6,7,8-tetrahydronaphthalen-2-yl)-2-(4-(ethyl sulfonyl)phenyl)acetamide To a solution of 6-(2,6-dimethylpyrimidin-4-yl)-6-methyl-5-oxo-5,6,7,8-tetrahydronaphthalen-2-yl trifluoromethanesulfonate (0.4 g, 0.96 mmol) in 1,4-dioxane (10 mL) was added 2-(4-(ethylsulfonyl)phenyl)acetamide (0.2 g, 0.96 mmol), Cs$_2$CO$_3$ (0.62 g, 1.92 mmol), Pd2(dba)3 (0.0.088 g, 0.096 mmol), XantPhos (0.055 g, 0.096 mmol) under nitrogen atmosphere. The reaction mixture was purged with nitrogen for 15 min and then heated to 100° C. for 12 h. The reaction was quenched with ice water, extracted with ethyl acetate. The organic portion was dried over anhydrous sodium sulphate, filtered and concentrated to get the title compound (0.06 g, 12.6%).
$^1$H NMR (400 MHz, CDCl3): δ 8.07 (d, J=8.4 Hz, 1H), 7.89 (d, J=8.40 Hz, 2H), 7.54-7.51 (M, 3H), 7.43 (s, 1H), 7.26-7.21 (m, 1H), 6.76 (s, 1H), 3.81 (s, 2H), 3.14-3.09 (m, 2H), 2.91-2.82 (m, 3H), 2.62 (s, 3H), 2.37 (s, 3H), 2.12-2.10 (m, 1H), 1.51 (s, 3H), 1.30-1.26 (m, 2H). LC-MS: 492.4 [M+H]$^+$.

Example-10: 2-(4-(ethylsulfonyl)phenyl)-N-(6-(3-hydroxypyridin-2-yl)-4,6-dimethyl-5-oxo-5,6,7,8-tetrahydroquinolin-2-yl)acetamide (Compound-101 and 102)

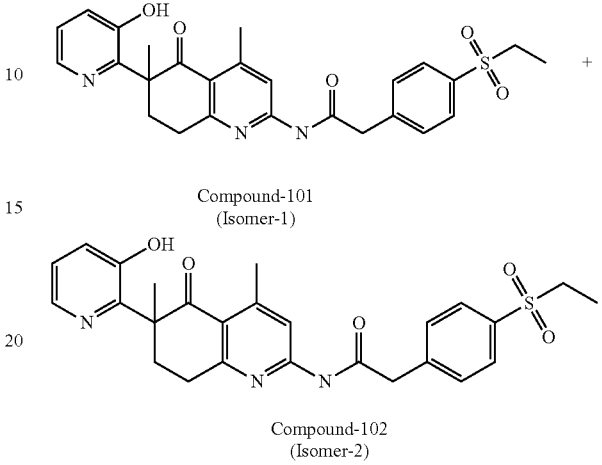

Compound-101
(Isomer-1)

Compound-102
(Isomer-2)

Enantiomeric mixture of 2-(4-(ethylsulfonyl)phenyl)-N-(6-(3-hydroxypyridin-2-yl)-4,6-dimethyl-5-oxo-5,6,7,8-tetrahydroquinolin-2-yl)acetamide was separated by chiral preparative HPLC to obtain two separated enantiomers (Isomer-1, Compound-101 & Isomer-2, Compound-102). Method: Column: Chiralpak IA (250 mm×10.00 mm), 5.0μ; Hexane: 0.1% DEA in EtOH:Ethanol: (40:60); Flow Rate: 7 mL/min.
Characterization data of Isomer-1: $^1$H NMR (400 MHz, CDCl$_3$): δ 8.11 (d, J=2.96 Hz, 1H), 7.89-7.97 (m, 3H), 7.53 (d, J=8.33 Hz, 2H), 7.07-7.16 (m, 2H), 3.82 (s, 2H), 3.44-3.55 (m, 1H), 3.08-3.17 (m, 3H), 2.95 (td, J=4.57, 18.00 Hz, 1H), 2.66 (s, 3H), 2.05-2.18 (m, 1H), 1.26-1.32 (m, 6H). LC-MS: 493.9 [M+H]$^+$.
Characterization data of Isomer-2: $^1$H NMR (400 MHz, CDCl$_3$): δ 8.28 (br s, 1H), 8.07-8.11 (m, 1H), 7.87-7.94 (m, 3H), 7.52 (d, J=8.33 Hz, 2H), 7.04-7.15 (m, 2H), 3.81 (s, 2H), 3.34-3.47 (m, 1H), 3.12 (q, J=7.43 Hz, 3H), 2.94 (td, J=4.84, 18.00 Hz, 1H), 2.63 (s, 3H), 2.01-2.17 (m, 1H), 1.61 (s, 3H), 1.29 (t, J=7.39 Hz, 3H). LC-MS: 494.3 [M+H]$^+$.

The below compounds (103-128) were separated by a procedure similar to the one described in Example-10 with appropriate variation in separation methods as shown in the table.

| Compound No | Structure/Method of separation | Characterization Data |
| --- | --- | --- |
| 103 | Isomer-1 of Compound-7<br>Column: Chiral Pak IA<br>(250 mm × 10 mm, 5 micron); Mobile Phase: n-Hexane (A), IPA (B); Flow Rate: 6 mL/min; Isocratic: 60:40 (A:B). | $^1$H NMR (400 MHz, DMSO-d6): δ 11.22 (br s, 1H), 8.25(d, J = 8.8 Hz, 2H), 8.05 (d, J = 9.2 Hz, 1H), 7.83 (d, J = 8.4 Hz, 2H), 7.60 (d, J = 8.4 Hz, 1H), 7.11 (s, 1H), 3.88 (s, 2H), 3.28-3.23 (m, 2H), 2.90-2.75 (m, 1H), 2.73-2.72 (m, 2H), 2.43 (s, 3H), 2.35(s, 3H), 2.18-2.16 (m, 1H), 1.44 (s, 3H), 1.09-1.05 (m, 3H); LC-MS: 493.05 [M + H]$^+$. |

| Compound No | Structure/Method of separation | Characterization Data |
|---|---|---|
| 104 | 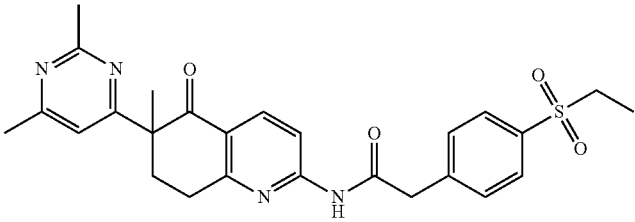<br>Isomer-2 of Compound-7<br>Column: Chiral Pak IA (250 mm × 10 mm, 5 micron); Mobile Phase: n-Hexane (A), IPA (B); Flow Rate: 6 mL/min; Isocratic: 60:40 (A:B). | $^1$H NMR (400 MHz, DMSO-d6): δ 11.22 (s, 1H), 8.25(d, J = 8.8 Hz, 2H), 8.05 (d, J = 9.2 Hz, 1H), 7.83 (d, J = 8.4 Hz, 2H), 7.60 (d, J = 8.4 Hz, 1H), 7.11 (s, 1H), 3.88 (s, 2H), 3.28-3.23 (m, 2H), 2.90-2.75 (m, 1H), 2.73-2.72 (m, 2H), 2.43 (s, 3H), 2.35 (s, 3H), 2.18-2.16 (m, 1H), 1.44 (s, 3H), 1.09-1.05 (m, 3H); LC-MS: 493.05 [M + H]$^+$. |
| 105 | 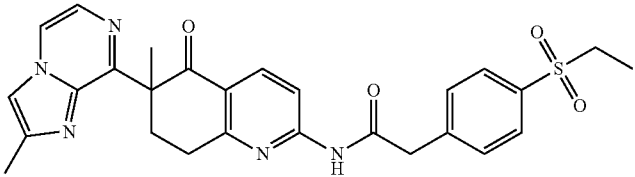<br>Isomer-1 of Compound-9<br>Column: CHIRALPAK IC(50 * 250), Mobile phase: ACN/MeOH (90/10); Flowrate: 8 mL/min; U.V: 300 nM | $^1$H NMR (400 MHz, DMSO-d6): δ 8.42 (d, J = 8.8 Hz, 1H), 8.13 (d, J = 8.4 Hz, 1H), 8.03 (s, 1H), 7.89 (d, J = 8.4 Hz, 2H), 7.82 (d, J = 4.0 Hz, 1H), 7.56-7.50 (m, 3H), 7.34 (s, 1H), 3.84 (s, 2H), 3.70-3.64 (m, 2H), 3.12-3.06 (m, 2H), 2.93-2.89 (m, 2H), 2.69-2.63 (m, 2H), 2.61 (s, 3H), 2.42-2.12 (m, J = 7.25 Hz, 2H), 1.82 (s, 3H), 1.28-1.25 (m, 3H); LC-MS: 518.2 [M + H]+. |
| 106 | 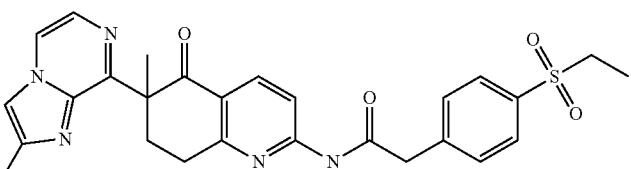<br>Isomer-2 of Compound-9<br>Column: CHIRALPAK IC (50 * 250), Mobile phase: ACN/MeOH (90/10); Flowrate: 8 mL/min; U.V: 300 nM | $^1$H NMR (400 MHz, DMSO-d6): δ 8.42 (d, J = 8.8 Hz, 1H), 8.13 (d, J = 8.4 Hz, 1H), 8.03 (s, 1H), 7.89 (d, J = 8.4 Hz, 2H), 7.82 (d, J = 4.0 Hz, 1H), 7.56-7.50 (m, 3H), 7.34 (s, 1H), 3.84 (s, 2H), 3.70-3.64 (m, 2H), 3.12-3.06 (m, 2H), 2.93-2.89 (m, 2H), 2.69-2.63 (m, 2H), 2.61 (s, 3H), 2.42-2.12 (m, 2H), 1.82 (s, 3H), 1.28-1.25 (m, 3H); LC-MS: 518.2 [M + H]+. |
| 107 | 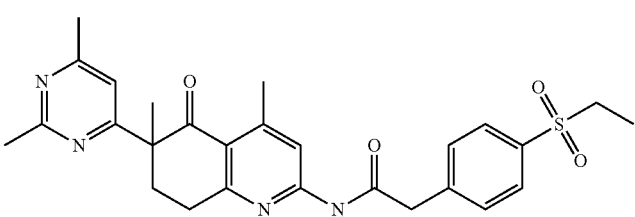<br>Isomer-1 of Compound-28<br>Column: Chiral Pak IA (20 mm × 250 mm, 5 micron); mobile phase: n-Hexane: DCM (90:10)(A); IPA (B), Flowrate: 14 mL/min; Isocratic: 82:18 (A:B) | $^1$H NMR (400 MHz, DMSO-d6): δ 11.03 (s, 1H), 7.83(d, J = 3.6 Hz, 2H), 7.80 (s, 1H), 7.58 (d, J = 8.0 Hz, 2H), 7.15 (s, 1H), 3.84 (s, 2H), 3.28-3.22, (m, 2H), 2.95-2.90 (m, 1H), 2.79-2.65 (m, 2H), 2.55 (s, 3H), 2.40 (s, 3H), 2.35 (s, 3H), 2.16-2.09 (m, 1H), 1.37 (s, 3H), 1.08-1.05 (m, 3H); LC-MS: 507.3 [M + H]+. |

| Compound No | Structure/Method of separation | Characterization Data |
|---|---|---|
| 108 | 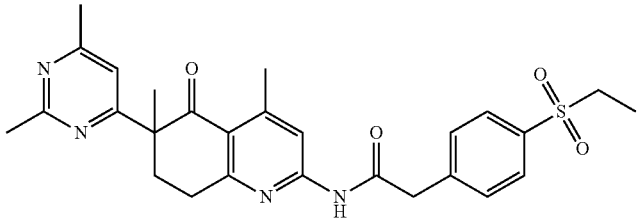<br>Isomer-2 of Compound-28<br>Column: Chiral Pak IA (20 mm × 250 mm, 5 micron); mobile phase: n-Hexane: DCM (90:10) (A); IPA (B), Flowrate: 14 mL/min; Isocratic: 82:18 (A:B) | $^1$H NMR (400 MHz, DMSO-d6): δ 11.03 (br s, 1H), 7.83 (d, J = 3.6 Hz, 2H), 7.80 (s, 1H), 7.58 (d, J = 8.0 Hz, 2H), 7.15 (s, 1H), 3.84 (s, 2H), 3.28-3.22 (m, 2H), 2.95-2.90 (m, 1H), 2.79-2.65 (m, 2H), 2.55 (s, 3H), 2.48 (s, 3H), 2.40 (s, 3H), 2.16-2.09 (m, 1H), 1.37 (s, 3H), 1.08-1.05 (m, 3H); LC-MS: 507.3 [M + H]+. |
| 109 | 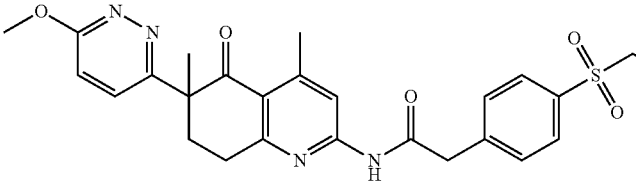<br>Isomer-1 of Compound-31<br>Column: Chiral Pak IC (30 mm × 250 mm); Mobile phase: acetonitrile; UV: 300 nM | $^1$H NMR (400 MHz, CDCl3): δ 7.92-7.89 (m, 4H), 7.53 (d, J = 8.4 Hz, 2H), 7.31 (d, J = 8.8 Hz, 1H), 6.92 (d, J = 8.8 Hz, 1H), 4.08 (s, 3H), 3.81 (s, 2H), 3.12-3.10 (m, 2H) 2.94-2.92 (m, 2H), 2.30-2.20 (m, 2H), 1.57 (s, 3H), 1.30 (t, J = 7.2 Hz, 3H). LC-MS: 508.6 [M + H]$^+$. |
| 110 | 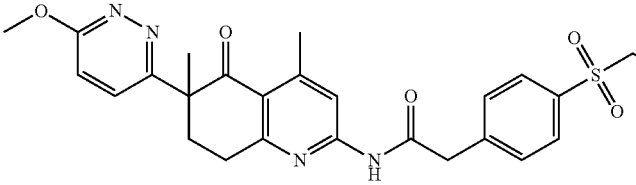<br>Isomer-2 of Compound-31<br>Column: Chiral Pak IC (30 mm × 250 mm); Mobile phase: acetonitrile | $^1$H NMR (400 MHz, CDCl3): δ 7.97 (s, 1H), 7.92-7.89 (m, 4H), 7.53 (d, J = 8.4 Hz, 2H), 7.31 (d, J = 8.8 Hz, 1H), 6.92 (d, J = 8.8 Hz, 1H), 4.08 (s, 3H), 3.81 (s, 2H), 3.12-3.10 (m, 2H) 2.94-2.92 (m, 2II), 2.30-2.20 (m, 2II), 1.57 (s, 3H), 1.30 (t, J = 7.2 Hz, 3H), LC-MS: 508.6 [M + H]$^+$. |
| 111 | 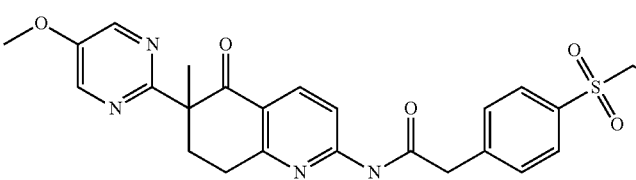<br>Isomer-1 of Compound-56<br>Column: Chiral Pak IA (20 mm × 250 mm, 5 micron; Mobile phase: n-Hexane (A): Ethanol (B)-isocratic (45:55-A:B) | $^1$H NMR (300 MHz, CDCl3): δ 8.43 (d, J = 8.7 Hz, 1H), 8.27 (s, 2H), 8.14 (d, J = 8.7 Hz, 1H), 7.96 (br s, 1H), 7.92 (d, J = 6.6 Hz, 2H), 7.54 (d, J = 8.4 Hz, 2H), 3.84 (s, 3H), 3.82 (s, 2H), 3.07-3.15 (m, 2H), 2.70-2.89 (m, 3H), 2.16-2.24 (m, 1H), 1.60 (s, 3H), 1.31 (t, J = 7.5 Hz, 3H); LC-MS: 495.0 [M + H]$^+$. |
| 112 | 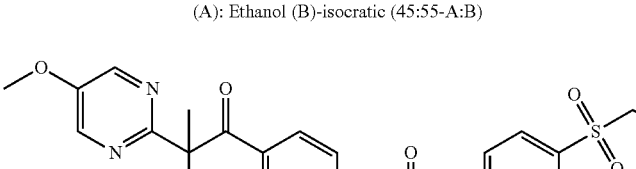<br>Isomer-2 of Compound-56<br>Column: Chiral Pak IA (20 mm × 250 mm, 5 micron; Mobile phase: n-Hexane (A): Ethanol (B)- isocratic (45:55-A:B) | $^1$H NMR (300 MHz, CDCl3): δ 8.45 (d, J = 8.7 Hz, 1H), 8.28 (s, 2H), 8.14 (d, J = 8.7 Hz, 1H), 7.96 (br s, 1H), 7.91 (d, J = 6.6 Hz, 2H), 7.54 (d, J = 8.4 Hz, 2H), 3.84 (s, 3H), 3.82 s, 2H), 3.07-3.15 (m, 2H), 2.70-2.89 (m, 3H), 2.15-2.25 (m, 1H), 1.60 (s, 3H), 1.31 (t, J = 7.5 Hz, 3H); LC-MS: 495.0 [M + H]$^+$. |

| Compound No | Structure/Method of separation | Characterization Data |
|---|---|---|
| 113 | 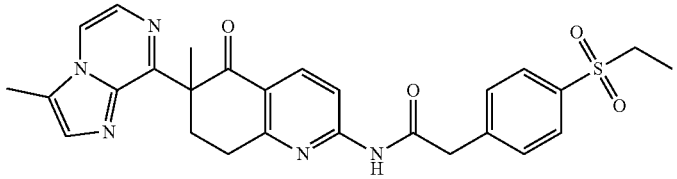<br>Isomer-1 of Compound-49<br>Column: Chiral Pak IA (10 mm × 250 mm, 5 micron); Mobile Phase: ACN (A), EtOH (B); Flow: 8 mL/min; Isocratic: 90:10 (A:B) | $^1$H NMR (400 MHz, CDCl3): δ 8.45 (d, J = 8.8 Hz, 1H), 8.16 (d, J = 8.8 Hz, 1H), 8.08 (s, 1H), 7.92 (d, J = 8.0 Hz, 2H), 7.72 (s, 2H), 7.55 (d, J = 8.4 Hz, 2H), 7.49 (s, 1H), 3.83 (s, 1H), 3.69-3.62 (m, 1H), 3.15-3.09 (m, 2H) 3.19-2.96 (m, 1H), 2.77-2.70 (m, 1H), 2.47 (s, 3H), 2.19-2.12 (m, 1H), 1.84 (s, 3H), 1.31 (t, J = 7.2 Hz, 3H); LC-MS: 518.1 [M + H]$^+$. |
| 114 | 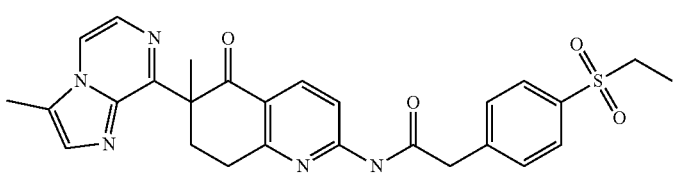<br>Isomer-2 of Compound-49<br>Column: Chiral Pak IA (10 mm × 250 mm, 5 micron); Mobile Phase: ACN (A), EtOH (B); Flow: 8 mL/min; Isocratic: 90:10 (A:B) | $^1$H NMR (400 MHz, CDCl3): δ 8.45 (d, J = 8.8 Hz, 1H), 8.16 (d, J = 8.8 Hz, 1H), 8.08 (s, 1H), 7.92 (d, J = 8.0 Hz, 2H), 7.72 (s ,2H), 7.55 (d, J = 8.4 Hz, 2H), 7.49 (s, 1H), 3.83 (s, 1H), 3.69-3.62 (m, 1H), 3.15-3.09 (m, 2H) 3.19-2.96 (m, 1H), 2.77-2.70 (m, 1H), 2.47 (s, 3H), 2.19-2.12 (m, 1H), 1.84 (s, 3H), 1.31 (t, J = 7.2 Hz, 3H); LC-MS: 518.1 [M + H]$^+$. |
| 115 | 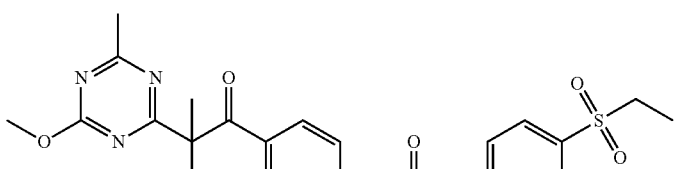<br>Isomer-1 of Compound-65<br>Column: Chiral Pak IA (10 mm × 250 mm, 5 micron); Mobile phase: n-Hexane: IPA (70:30) | $^1$H NMR (300 MHz, CDCl3): δ 8.38 (d, J = 8.7 Hz, 1H), 8.14 (d, J = 8.7 Hz, 1H), 7.99 (br s, 1H), 7.91 (d, J = 6.3 Hz, 2H), 7.54 (d, J = 8.4 Hz, 2H), 6.27 (s, 1H), 3.87 (s, 3H), 3.82 (s, 2H), 3.08-3.15 (m, 2H), 2.83-2.92 (m, 3H), 2.51 (s, 3H), 2.12-2.16 (m, 1H), 1.50 (s, 3H), 1.30 (t, J = 7.5 Hz, 3H); LC-MS: 509.6 [M + H]$^+$. |
| 116 | 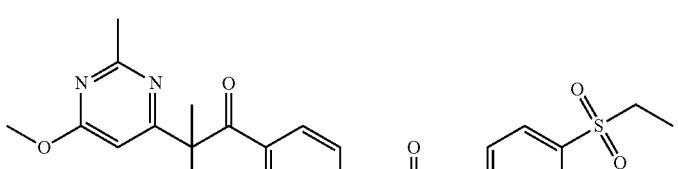<br>Isomer-2 of Compound-65<br>Column: Chiral Pak IA (10 mm × 250 mm, 5 micron); Mobile phase: n-Hexane: IPA (70:30) | $^1$H NMR (300 MHz, CDCl3): δ 8.38 (d, J = 8.7 Hz, 1H), 8.14 (d, J = 8.7 Hz, 1H), 7.99 (br s, 1H), 7.92 (d, J = 6.3 Hz, 2H), 7.54 (d, J = 8.4 Hz, 2H), 6.27 (s, 1H), 3.87 (s, 3H), 3.82 (s, 2H), 3.08-3.15 (m, 2H), 2.83-2.91 (m, 3H), 2.51 (s, 3H), 2.12-2.16 (m, 1H), 1.49 (s, 3H), 1.31 (t, J = 7.5 Hz, 3H); LC-MS: 509.6 [M + H]$^+$. |

| Compound No | Structure/Method of separation | Characterization Data |
|---|---|---|
| 117 | 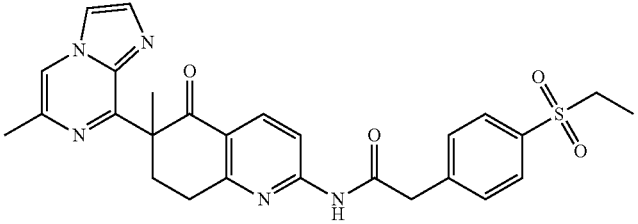<br>Isomer-1 of Compound-16<br>Column: Chiral Pak IC<br>(10 mm × 250 mm, 5 micron); Mobile Phase: ACN (A); Flow: 9 mL/min; Isocratic: 100 (A) | $^1$H NMR (400 MHz, CD3OD): δ 8.38 (d, J = 8.8 Hz, 2H), 8.30 (d, J = 4.4 Hz, 2H), 8.09 (d, J = 8.8 Hz, 1H), 7.92 (d, J = 8 Hz, 2H) 7.76 (s, 1H), 7.68 (d, J = 7.6 Hz, 2H), 7.62 (d, J = 4.4 Hz , 1H), 4.86 (s, 2H), 3.70-3.33 (m, 2H), 3.30-3.24 (m, 2H), 3.15-3.05 (m, 1H), 2.75-2.68 (m, 1H), 2.45 (s, 3H), 2.20-2.16 (m, 2H), 1.80 (s, 3H), 1.29-1.22 (m, 3H); LCMS: 518.3 [M + H]$^+$. |
| 118 | 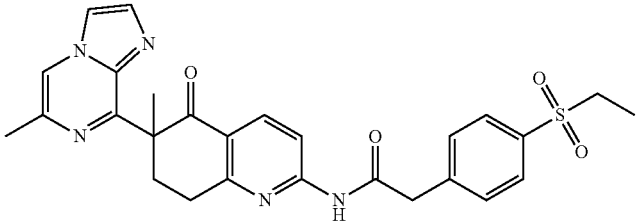<br>Isomer-2 of Compound-16<br>Column: Chiral Pak IC<br>(10 mm × 250 mm, 5 micron); Mobile Phase: ACN (A); Flow: 9 mL/min; Isocratic: 100(A) | $^1$H NMR (400 MHz, CD3OD): δ 8.38 (d, J = 8.8 Hz, 2H), 8.30 (d, J = 4.4 Hz, 2H), 8.09 (d, J = 8.8 Hz 1H), 7.92 (d, J = 8 Hz, 2H) 7.76 (s, 1H), 7.68 (d, J = 7.6 Hz, 2H), 7.62 (d, J = 4.4 Hz, 1H), 4.86 (s, 2H), 3.70-3.33 (m, 2H), 3.30-3.24 (m, 2H), 3.15-3.05 (m, 1H), 2.75-2.68 (m, 1H), 2.45 (s, 3H), 2.20-2.16 (m, 2H), 1.80 (s, 3H), 1.29-1.22 (m, 3H); LCMS: 518.3 [M + H]$^+$. |
| 119 | 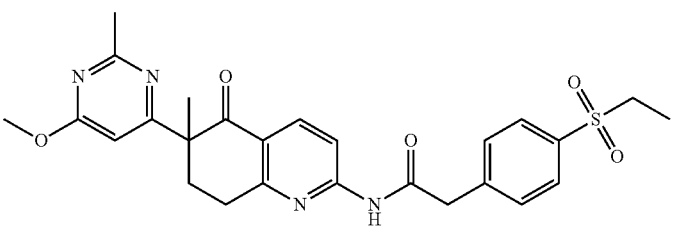<br>Isomer-1 of Compound-64<br>Column: Chiral Pak IA (10 mm × 250 mm, 5 micron); Mobile phase: n-Hexane (A), IPA (B) (70:30); Isocratic (65:35-A:B) | $^1$H NMR (400 MHz, CDCl3): δ 8.39-8.37 (d, J = 8.8 Hz, 1H), 8.19-8.18 (m, 1H), 8.06 (s, 1H), 7.92 (d, J = 8.4 Hz, 2H), 7.55 (d, J = 8.4 Hz, 2H), 6.59 (s, 1H), 3.89 (s, 3H), 3.84 (s, 2H), 3.13-3.11 (m, 2H), 2.98-2.90 (m, 2H), 2.36 (s, 3H), 2.21-2.1 (m, 1H), 1.53 (s, 3H), 1.31-1.27 (m, 3H). LC-MS: 509.4 [M + H]$^+$. |
| 120 | 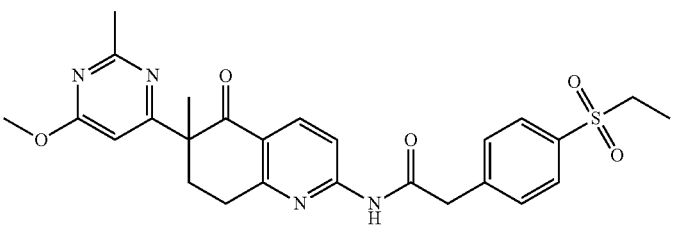<br>Isomer-2 of Compound-64<br>Column: Chiral Pak IA (10 mm × 250 mm, 5 micron); Mobile phase: n-Hexane (A), IPA (B) (70:30); Isocratic (65:35-A:B) | $^1$H NMR (400 MHz, CDCl3): δ 8.37-8.35 (d, J = 8.0 Hz, 1H), 8.13-8.09 (m, 2H), 7.9-7.88 (d, J = 8.0 Hz, 2H), 7.53-7.51 (d, J = 8.0 Hz, 2H), 6.57 (s, 1H), 3.86 (s, 3H), 3.81(s, 2H), 3.12-3.07 (m, 2H), 2.90-2.83(m, 3H), 2.34 (s, 3H), 2.15-2.12 (m, 1H), 1.51 (s, 3H), 1.28-1.23 (m, 3H). LC-MS: 509.4 [M + H]$^+$. |

| Compound No | Structure/Method of separation | Characterization Data |
|---|---|---|
| 121 | 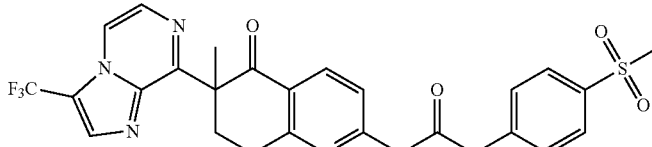<br>Isomer-1 of Compound-74<br>Column: Chiral Pak IA (10 mm × 250 mm, 5 micron); Mobile Phase: n-Hexane (A) EtOH: MeOH, 1:1 (B); Flow rate: 8 mL/min; Isocratic: 40:60 (A:B) | $^1$H NMR (400 MHz, CDCl3): δ 8.43 (d, J = 8.4 Hz, 1H), 8.19 (d, J = 8.8 Hz, 1H), 8.06 (d, J = 4.4 Hz, 1H), 7.99 (s, 1H), 7.94-7.91 (m, 4H), 7.55 (d, J = 8.0 Hz, 2H) 3.84 (s, 1H), 3.55-3.48 (m, 1H), 3.15-3.09 (m, 2H) 3.09-3.04 (m, 1H), 2.82-2.77 (m, 1H), 2.16-2.09 (m, 1H), 1.83 (s, 3H), 1.31 (t, J = 7.6 Hz, 3H); LC-MS: 572.1 [M+H]$^+$. |
| 122 | 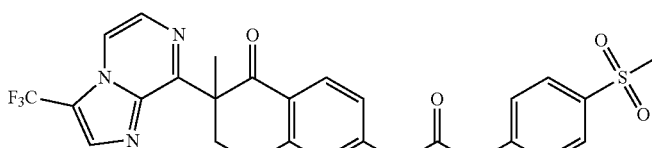<br>Isomer-2 of Compound-74<br>Column: Chiral Pak IA (10 mm × 250 mm, 5 micron); Mobile Phase: n-Hexane (A), EtOH:MeOH, 1:1 (B); Flow rate: 8 mL/min; Isocratic: 40:60 (A:B) | $^1$H NMR (400 MHz, CDCl3): δ 8.43 (d, J = 8.4 Hz, 1H), 8.19 (d, J = 8.8 Hz, 1H), 8.06 (d, J = 4.4 Hz, 1H), 7.99 (s, 1H), 7.94-7.91 (m, 4H), 7.55 (d, J = 8.0 Hz, 2H) 3.84 (s, 1H), 3.55-3.48 (m, 1H), 3.15-3.09 (m, 2H) 3.09-3.04 (m, 1H), 2.82-2.77 (m, 1H), 2.16-2.09 (m, 1H), 1.83 (s, 3H), 1.31 (t, J = 7.6 Hz, 3H); LC-MS: 572.0 [M + H]$^+$. |
| 123 | 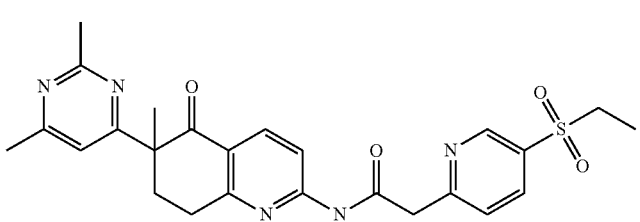<br>Isomer-1 of Compound-79<br>Column: Chiral Pak IA (10 mm × 250 mm, 5 micron); Mobile Phase: ACN (A); EtOH (B); Flow: 9 mL/min; Isocratic: 95:05 (A:B). | $^1$H NMR (400 MHz, CDCl3): δ 9.64 (br s, 1H) 9.13 (d, J = 2.4 Hz, 1H), 8.38 (d, J = 8.4 Hz, 1H), 8.20-8.11 (m, 2H), 7.54 (d, J = 8.4 Hz, 1H), 6.77 (s, 1H), 4.02 (s, 2H), 3.19-3.14 (m, 2H), 2.97-2.93 (m, 3H), 2.61 (s, 3H), 2.38 (s, 3H), 2.16-2.11 (m, 1H), 1.52 (s, 3H), 1.34 (t, J = 4.8 Hz, 3H); LC-MS: 494.6 [M + H]$^+$. |
| 124 | 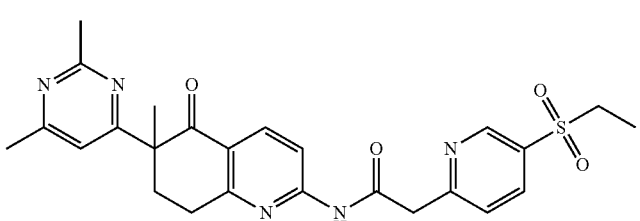<br>Isomer-2 of Compound-79<br>Column: Chiral Pak IA (10mm × 250 mm, 5 micron); Mobile Phase ACN (A), EtOH (B); Flow: 9 mL/min; Isocratic: 95:05 (A:B) | $^1$H NMR (400 MHz, CDCl3): δ9.64(br s, 1H), 9.13 (d, J = 2.4 Hz, 1H), 8.38 (d, J = 8.4 Hz, 1H), 8.20-8.11 (m, 2H), 7.54 (d, J = 8.4 Hz, 1H), 6.77 (s, 1H), 4.02 (s, 2H), 3.19-3.14 (m, 2H), 2.97-2.93 (m, 3H), 2.61 (s, 3H), 2.38 (s, 3H), 2.16-2.11 (m, 1H), 1.52 (s, 3H), 1.34 (t, J = 4.8 Hz, 3H); LC-MS: 494.6 [M +H]$^+$. |

| Compound No | Structure/Method of separation | Characterization Data |
|---|---|---|
| 125 | Isomer-1 of Compound-99<br>Column: Chirapak-IA (20 mm × 250 mm, 5 micron); mobile phase: n-hexane(A); IPA:MeOH (9:1) (B); Flow: 20 mL/min; Isocratic: 75:25 (A:B) | $^1$H NMR (400 MHz, CDCl3): δ 8.54 (d, J = 7.6 Hz, 1H), 8.49 (br s, 1H), 8.20 (d, J = 8.0 Hz, 1H), 7.87 (d, J = 8.0 Hz, 2H), 7.54 (d, J = 8.0 Hz, 2H), 6.80 (s, 1H), 4.76 (d, J = 6.0 Hz, 2H), 3.12-3.07 (m, 2H), 3.07-3.04 (m, 2H) 2.97-2.94 (m, 1H), 2.58 (s, 3H), 2.41 (s, 3H), 2.27-2.17 (m, 1H), 1.57 (s, 3H), 1.28 (t, J = 5.1 Hz, 3H); LC-MS: 493.4 [M+H]$^+$. |
| 126 | Isomer-2 of Compound-99<br>Column: Chirapak-IA (20 mm × 250 mm, 5 micron); mobile phase: n-hexane (A); IPA:MeOH (9:1) (B); Flow: 20 mL/min; Isocratic: 75:25 (A:B) | $^1$H NMR (400 MHz, CDCl3): δ 8.54 (d, J = 7.6 Hz, 1H), 8.49 (br s, 1H), 8.20 (d, J = 8.0 Hz, 1H), 7.87 (d, J = 8.0 Hz, 2H), 7.54 (d, J = 8.0 Hz, 2H), 6.80 (s, 1H), 4.76 (d, J = 6.0 Hz, 2H), 3.12-3.07 (m, 2H), 3.07-3.04 (m, 2H) 2.97-2.94 (m, 1H), 2.58 (s, 3H), 2.41 (s, 3H), 2.27-2.17 (m, 1H), 1.57 (s, 3H), 1.28 (t, J = 5.1 Hz, 3H); LC-MS: 493.4 [M + H]$^+$. |
| 127 | Isomer-1 of Compound-83<br>Column: Chiral Pak IA (10 mm × 250 mm, 5 micron) Mobile Phase: Hexane (A), Isopropanol (B); Flow: 8 mL/min; Isocratic: 80:20 (A:B) | $^1$H NMR (400 MHz, DMSO-d$^6$): δ 11.2(s, 1H), 8.25-8.13 (d, J = 8.4 Hz, 1H), 8.06-8.04 (d, J = 8.4 Hz, 1H), 7.84-7.82 (d, J = 8.4 Hz, 2H), 7.60-7.58 (d, J = 8.4 Hz, 2H), 7.12 (s, 1H), 3.89 (s, 2H), 3.2 (m, 2H), 3.0-2.6 (m, 4H), 2.4 (s, 3H), 2.36 (s, 3H), 1.44 (s, 3H), 1.10-1.05 (t, J = 7.2 Hz, 3H; LC-MS: 493.3 [M + H]$^+$. |
| 128 | Isomer-2 of Compound-83<br>Column: Chiral Pak IA(10 mm × 250 mm, 5 micron)<br>Mobile Phase: Hexane (A), Isopropanol (B); Flow: 8 mL/min; Isocratic: 80:20 (A:B) | $^1$H NMR (400 MHz, DMSO-d$^6$): δ 8.39-8.37 (d, J = 8.8 Hz, 1H), 7.97 (s, 1H), 8.148-8.126 (d, J = 8.8 Hz, 1H), 7.922-7.902 (d, J = 8.0 Hz, 2H), 7.54-7.52 (d, J = 8.4 Hz, 2H), 6.77 (s, 1H), 3.83 (s, 2H), 3.14-3.09 (m, 2H), 2.94-2.86 (m, 3H), 2.6 (s, 3H), 2.38 (s, 3H), 2.4-2.1 (m, 1H), 1.52 (s, 3H), 1.30-1.26 (t, J = 7.2Hz, 3H); LC-MS: 493.3 [M + H]$^+$. |

Example-11: Synthesis of 2-(4-(ethylsulfonyl)phenyl)-N-(6-(3-fluoro-2-methylimidazo[1,2-a]pyrazin-8-yl)-6-methyl-5-oxo-5,6,7,8-tetrahydroquinolin-2-yl)acetamide (Compound-129)

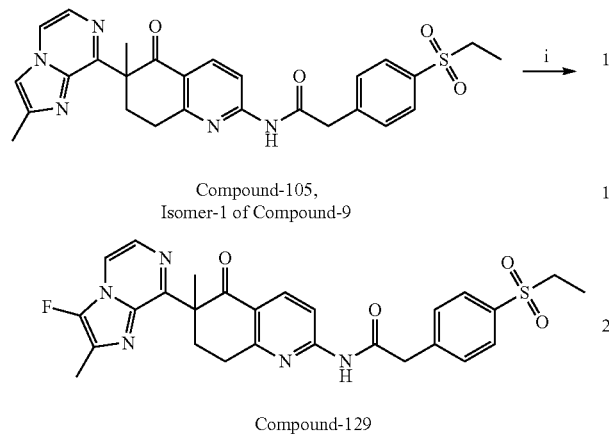

Compound-105,
Isomer-1 of Compound-9

Compound-129

To a solution of 2-(4-(ethylsulfonyl)phenyl)-N-(6-methyl-6-(2-methylimidazo[1,2-a]pyrazin-8-yl)-5-oxo-5,6,7,8-tetrahydroquinolin-2-yl)acetamide (Compound-105) (0.075 g, 0.145 mol) in acetonitrile (5 mL) at 0° C., was added a solution of Selectfluor (0.05 g, 0.145 mol.) in THF:Water (1:1, 5 mL) for 20 min. The reaction mixture was allowed to warm to room temperature and stirred at room temperature for 48 h. The reaction mixture was evaporated under reduced pressure to get the residue. The residue was partitioned between ethyl acetate and water. The organic layer was washed with brine, dried over anhydrous sodium sulfate and evaporated under reduced pressure to get the crude product. The crude product was purified by preparative thin layer chromatography (70:30 ethyl acetate:hexane) to get 2-(4-(ethylsulfonyl)phenyl)-N-(6-(3-fluoro-2-methylimidazo[1,2-a]pyrazin-8-yl)-6-methyl-5-oxo-5,6,7,8-tetrahydroquinolin-2-yl)acetamide (0.025 g, 32%).

$^1$H NMR (300 MHz, CDCl$_3$): δ 8.44 (d, J=8.7 Hz, 1H), 8.17 (d, J=8.7 Hz, 1H), 8.07 (br s, 1H), 7.92 (d, J=8.1 Hz, 2H), 7.63-7.68 (m, 2H), 7.55 (d, J=8.1 Hz, 2H), 3.82 (s, 2H), 3.59-3.64 (m, 1H), 3.08-3.15 (m, 2H), 2.90-2.97 (m, 1H), 2.69-2.77 (m, 1H), 2.39 (s, 3H), 2.11-2.17 (m, 1H), 1.82 (s, 3H), 1.31 (t, J=7.5 Hz, 3H); LC-MS: 536.5 [M+H]$^+$.

Compound-130: Synthesis of 2-(4-(ethylsulfonyl)phenyl)-N-(6-(3-fluoro-2-methylimidazo[1,2-a]pyrazin-8-yl)-6-methyl-5-oxo-5,6,7,8-tetrahydroquinolin-2-yl)acetamide

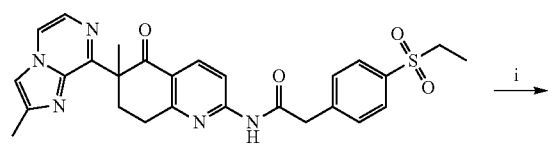

Compound-106, Isomer-2 of Compound-9

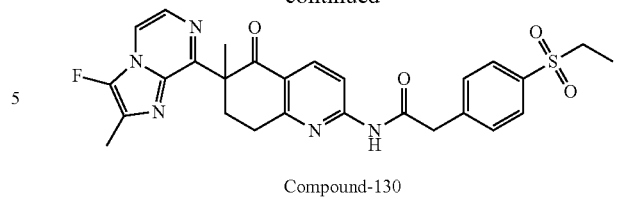

Compound-130

2-(4-(ethylsulfonyl)phenyl)-N-(6-(3-fluoro-2-methylimidazo[1,2-a]pyrazin-8-yl)-6-methyl-5-oxo-5,6,7,8-tetrahydroquinolin-2-yl)acetamide was prepared using the same protocol used for the synthesis of compound-126 of Example-9. Yield (0.025 g, 32%).

$^1$H NMR (300 MHz, CDCl$_3$): δ 8.44 (d, J=8.7 Hz, 1H), 8.17 (d, J=8.7 Hz, 1H), 8.06 (br s, 1H), 7.92 (d, J=8.1 Hz, 2H), 7.63-7.68 (m, 2H), 7.55 (d, J=8.1 Hz, 2H), 3.82 (s, 2H), 3.59-3.64 (m, 1H), 3.08-3.15 (m, 2H), 2.90-2.97 (m, 1H), 2.69-2.77 (m, 1H), 2.39 (s, 3H), 2.11-2.17 (m, 1H), 1.82 (s, 3H), 1.31 (t, J=7.5 Hz, 3H); LC-MS: 536.4 [M+H]$^+$.

Compound-131: Synthesis of 2-(4-(ethylsulfonyl)phenyl)-N-(6-(3-fluoro-2-methylimidazo[1,2-a]pyrazin-8-yl)-6-methyl-5-oxo-5,6,7,8-tetrahydroquinolin-2-yl)acetamide

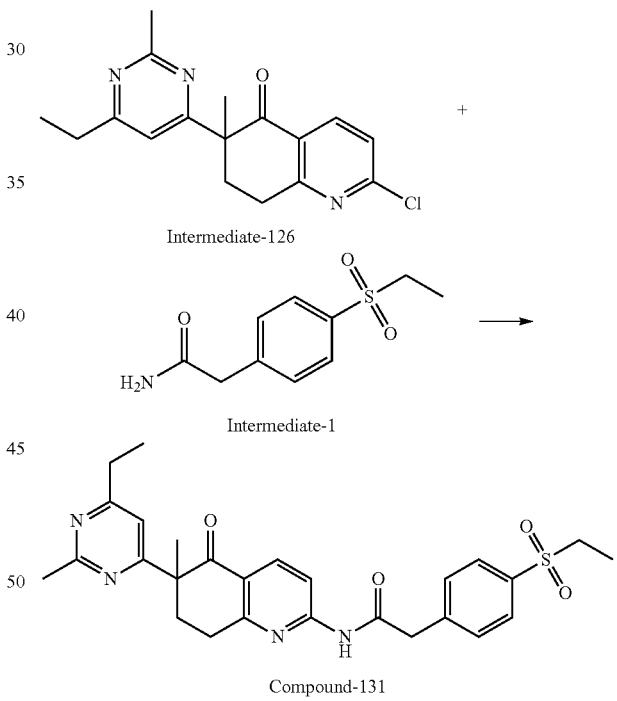

This compound was prepared using the same protocol explained in step-v of Example-9.

$^1$HNMR (300 MHz, CDCl$_3$): δ 8.39 (d, J=8.7 Hz, 1H), 8.14 (d, J=9.0 Hz, 1H), 8.02 (br s, 1H), 7.92 (d, J=6.6 Hz, 2H), 7.54 (d, J=8.4 Hz, 2H), 6.77 (s, 1H), 3.83 (s, 2H), 3.15 (m, 2H), 2.85-3.15 (m, 3H), 2.60-2.67 (m, 5H), 2.12-2.16 (m, 1H), 1.52 (m, 3H), 1.30 (t, J=7.5 Hz, 3H), 1.22 (d, J=7.5 Hz, 3H); LC-MS: 507.3 [M+H]$^+$.

The below compounds (132-133) were prepared by a procedure similar to the one described above (for compound-131) with appropriate variations in reactants, quantities of reagents, solvents and reaction conditions.

| Compound No. | Structure | Characterization Data |
|---|---|---|
| 132 | 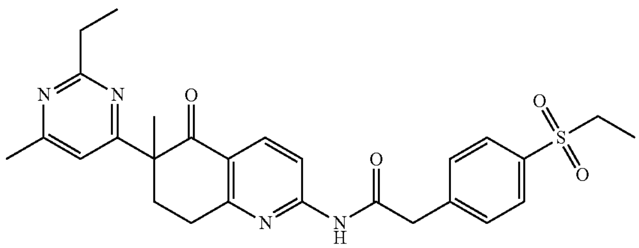 [SMILES: CCc1nc(C)cc(C2(C)CCc3nc(NC(=O)Cc4ccc(S(=O)(=O)CC)cc4)ccc3C2=O)n1] | $^1$H NMR (300 MHz, CDCl$_3$): δ 8.39 (d, J = 8.7 Hz, 1H), 8.14 (d, J = 9.0 Hz, 1H), 8.05 (br s, 1H), 7.92 (d, J = 6.6 Hz, 2H), 7.54 (d, J = 8.4 Hz, 2H), 6.78 (s, 1H), 3.82 (s, 2H), 3.07-3.15 (m, 2H), 2.81-2.95 (m, 5H), 2.39 (s, 3H), 2.11-2.18 (m, 1H), 1.52 (s, 3H), 1.20-1.30 (m, 6H); LC-MS: 507.0 [M + H]$^+$. |
| 133 | 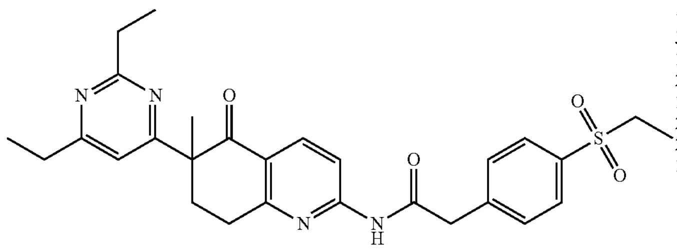 [SMILES: CCc1cc(C2(C)CCc3nc(NC(=O)Cc4ccc(S(=O)(=O)CC)cc4)ccc3C2=O)nc(CC)n1] | $^1$H NMR (300 MHz, CDCl$_3$): δ 8.39 (d, J = 8.7 Hz, 1H), 8.14 (d, J = 8.7 Hz, 1H), 8.03 (br s, 1H), 7.91 (d, J = 8.1 Hz, 2H), 7.54 (d, J = 7.8 Hz, 2H), 6.78 (s, 1H), 3.82 (s, 2H), 3.10-3.15 (m, 2H), 2.81-2.96 (m, 5H), 2.61-2.68 (m, 2H), 2.10-2.18 (m, 1H), 1.53 (s, 3H), 1.17-1.30 (m, 9H); LC-MS: 521.4 [M + H]$^+$. |

Compound-134: Synthesis of 7-(2,6-dimethylpyrimidin-4-yl)-N-(4-(ethylsulfonyl)benzyl)-7-methyl-8-oxo-5,6,7,8-tetrahydroisoquinoline-3-carboxamide

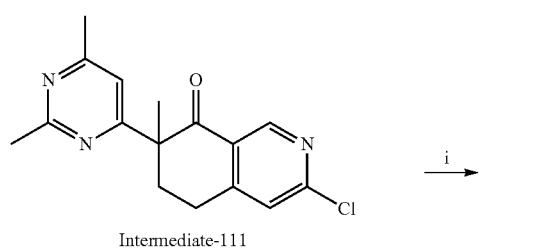

Intermediate-111

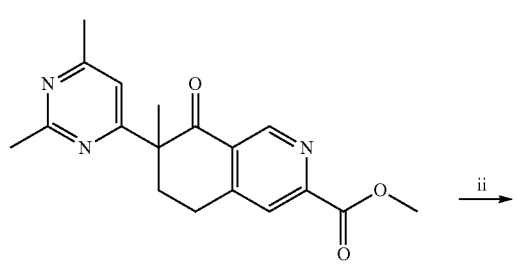

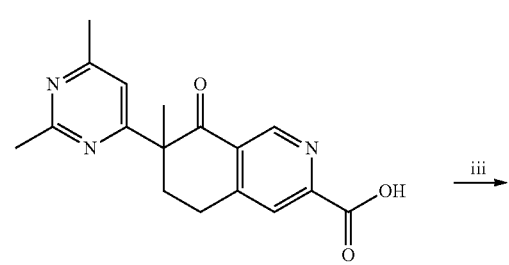

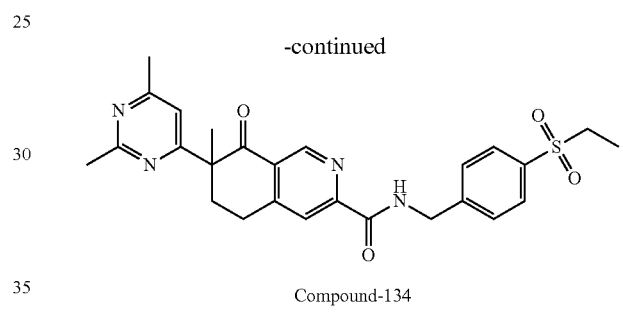

Compound-134

Step-i: Synthesis of methyl 7-(2,6-dimethylpyrimidin-4-yl)-7-methyl-8-oxo-5,6,7,8-tetrahydroisoquinoline-3-carboxylate A solution of 3-chloro-7-(2,6-dimethylpyrimidin-4-yl)-7-methyl-6,7-dihydroisoquinolin-8(5H)-one (0.1 g, 0.54 mmol) in dry MeOH (4 mL) was added Et3N (0.016 g, 0.10 mmol), Pd(dppf)Cl2 (0.045 g, 0.054 mmol). The reaction mixture was purged with nitrogen for 15 min and reaction mixture was stirred at 60° C. under positive pressure of carbon monoxide using a bladder stirred at same temperature for 12 h. The reaction was quenched with ice water extracted with ethyl acetate. The organic layer was dried over anhydrous sodium sulphate, filtered and concentrated to get the crude compound was purified by combiflash chromatography to obtained the title compound LC-MS: 326.3 [M+H]$^+$

Step-ii: Synthesis of 7-(2,6-dimethylpyrimidin-4-yl)-7-methyl-8-oxo-5,6,7,8-tetrahydroisoquinoline-3-carboxylic acid A solution of methyl 7-(2,6-dimethylpyrimidin-4-yl)-7-methyl-8-oxo-5,6,7,8-tetrahydroisoquinoline-3-carboxylate (0.1 g, 0.54 mmol) in THF:Ethanol:water (3:1:1) was added lithium hydroxide (0.063 g, 1.53 mmol) at RT and the reaction mixture was stirred for 3 h. Reaction mixture concentrated to residue, pH was adjusted to pH-4 using citric acid. This portion was extracted using 5% methanol in chloroform. The organic layer was dried over anhydrous sodium sulphate, filtered and concentrated to get the titled compound LC-MS: 312.3 [M+H]$^+$

Step-iii: Synthesis of 7-(2,6-dimethylpyrimidin-4-yl)-N-(4-(ethylsulfonyl)benzyl)-7-methyl-8-oxo-5,6,7,8-tetrahydroisoquinoline-3-carboxamide A solution of 7-(2,6-dimethylpyrimidin-4-yl)-7-methyl-8-oxo-5,6,7,8-tetrahydroisoquinoline-3-carboxylic acid (0.1 g, 0.32 mmol) in DMF (5 mL) was added DIPEA (0.2 g, 1.60 mmol), HATU (0.24 g, 0.64 mmol), (4-(ethylsulfonyl)phenyl)methanamine (0.077 g, 0.38 mmol) at 0° C. The reaction mixture was stirred at RT for 12 h. This was then quenched with ice water and extracted with ethyl acetate. The organic portion was dried over anhydrous sodium sulphate, filtered and concentrated to get the crude compound. Crude compound was purified by combiflash chromatography to obtain the titled compound. $^1$H NMR (400 MHz, CDCl3): δ 8.54 (d, J=8.0 Hz, 1H), 8.48 (m, 1H), 8.18 (d, J=8.0 Hz, 1H), 7.87 (d, J=8.4 Hz, 2H), 7.54 (d, J=8.0 Hz, 2H), 6.80 (s, 1H), 4.75 (d, J=6.4 Hz, 2H), 3.10-2.84 (m, 5H), 2.58 (s, 3H), 2.41 (s, 3H), 2.24-2.19 (m, 1H), 1.56 (s, 3H), 1.28-1.24 (m, 3H). LC-MS: 493.3 [M+H]$^+$.

Compound-135: Synthesis of 2-(4-(ethylsulfonyl)phenyl)-N-(6-(2-methoxy-6-methylpyrimidin-4-yl)-4,6-dimethyl-5-oxo-5,6,7,8-tetrahydroquinolin-2-yl)acetamide

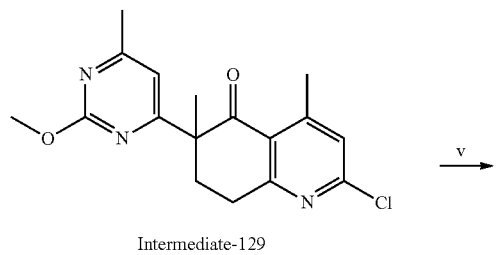

Intermediate-129 v →

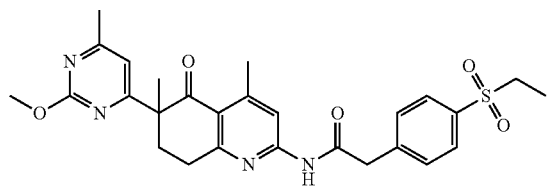

Compound-135

This compound was prepared using the same protocol explained in Example-1.

$^1$H NMR (400 MHz, CDCl3): δ 7.94-7.89 (m, 3H), 7.53 (d, J=8.4 Hz, 1H), 6.58 (s, 1H), 3.85 (s, 3H), 3.81 (s, 2H), 3.14-3.08 (m, 2H), 2.90-2.80 (m, 2H), 2.79 (s, 3H), 2.36 (s, 3H), 2.15-2.14 (m, 1H), 1.49 (s, 3H), 1.30-1.24 (m, 3H). LC-MS: 523.3 [M+H]$^+$.

Although the present invention has been illustrated by certain preceding examples, it is not to be construed as being limited thereby; but rather, the present invention encompasses the generic area as hereinbefore disclosed. Various modifications and embodiments can be made without departing from the spirit and scope thereof. For example, the following compounds which can be prepared by following similar procedures as described above with suitable modifications known to the one ordinary skilled in the art are also included in the scope of the present invention.

| Compound No. | Structure |
|---|---|
| 136 | 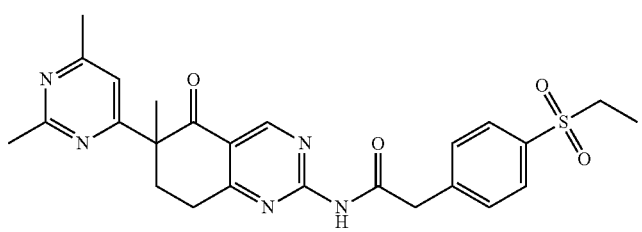 |
| 137 | 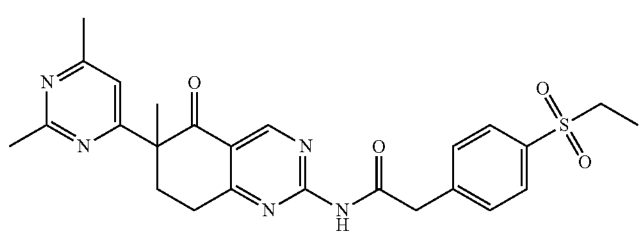 [SMILES: CCS(=O)(=O)c1ccc(CC(=O)Nc2ncc3c(n2)CCC(C)(c2cc(C)nc(C)n2)C3=O)cc1] |

-continued
| Compound No. | Structure |
|---|---|
| 138 | 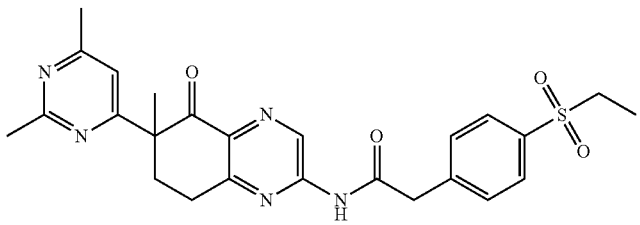 [SMILES: CCS(=O)(=O)c1ccc(CC(=O)Nc2cnc3c(n2)CCC(C)(c2cc(C)nc(C)n2)C3=O)cc1] |
| 139 | 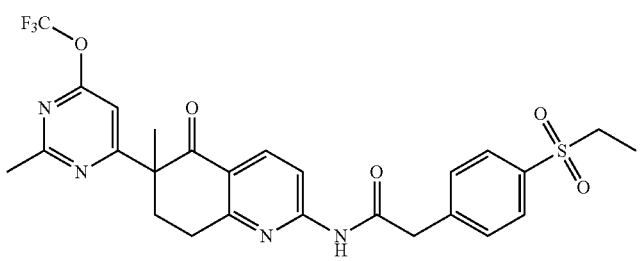 [SMILES: CCS(=O)(=O)c1ccc(CC(=O)Nc2ccc3c(n2)CCC(C)(c2cc(OC(F)(F)F)nc(C)n2)C3=O)cc1] |
| 140 | 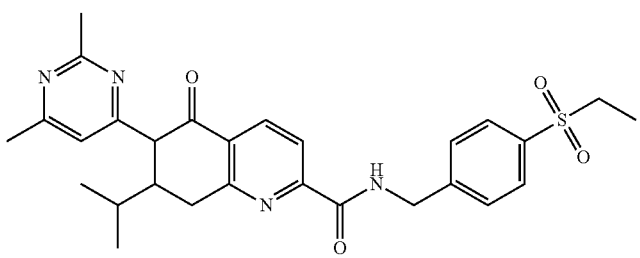 [SMILES: CCS(=O)(=O)c1ccc(CNC(=O)c2ccc3c(n2)CC(C(C)C)C(c2cc(C)nc(C)n2)C3=O)cc1] |
| 141 | 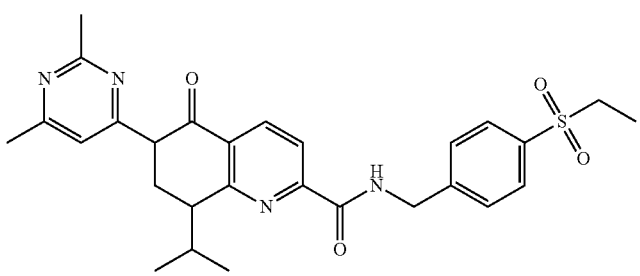 [SMILES: CCS(=O)(=O)c1ccc(CNC(=O)c2ccc3c(n2)C(C(C)C)CC(c2cc(C)nc(C)n2)C3=O)cc1] |
| 142 | 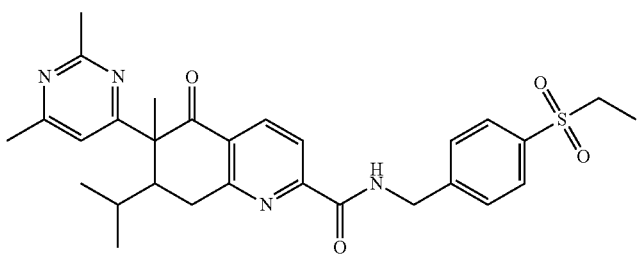 [SMILES: CCS(=O)(=O)c1ccc(CNC(=O)c2ccc3c(n2)CC(C(C)C)C(C)(c2cc(C)nc(C)n2)C3=O)cc1] |

Expression and Purification of RORγ

Gene corresponding to the ligand binding domain of RORγ (247-497 amino acids) was sub-cloned into pGEX4T1 vector. Transformants of *E. coli* BL21 (DE3) containing pGEX4T1-RORγ (247-497) were grown to an OD of 0.8 at 37° C. and induced with 0.5 mM isopropyl-β-D-thiogalactopyranoside (IPTG) for 18 hours at 18° C. Cells were harvested and resuspended in 20 mM Tris-HCl (pH 8.5), 0.3 M NaCl, 10% Glycerol, 2 mM β-Me (β-Mercaptoethanol), 2 mM CHAPS, protease inhibitors, 0.6 mM PMSF and Lysozyme. Supernatant of lysate was passed through glutathione sepharose 4B affinity beads (GE health care) pre-equilibrated with 20 mM Tris-HCl (pH 8.5), 0.3 M NaCl, 10% Glycerol, 2 mM β-Me. RORγ was eluted using a gradient of reduced glutathione (3-20 mM). Fractions containing RORγ protein were pooled, concentrated and passed through Superdex 75 gel filtration (GE health care) column equilibrated with 20 mM Na-phosphate pH 8.0, 0.2 M NaCl, 10% glycerol. The peak fractions from gel filtration column were pooled and stored at −80° C. for Binding assay.

In-Vitro Biochemical Data

ROR Gamma Radio-Ligand Binding Assay:

ROR gamma radioligand binding was performed using $^3$H 25-Hydroxycholesterol in a competitive displacement assay using dextran charcoal method. Using 5 nM $^3$H 25-Hydroxycholesterol with 300 ng RORγ LBD (in house expressed in *E. coli*) along with the compound were incubated in the binding buffer (50 mM HEPES, pH 7.5, 150 mM NaCl, 0.01% BSA and 5 mM $MgCl_2$) for 30 min at room temperature. Then dextran-charcoal mixture (0.5% charcoal: 0.05% dextran) was used for separation and the supernatant was read on the Perkin Elmer Trilux Microbeta counter. Dose response curves were generated for 10 compound concentrations using GraphPad Prism software Version 5 (San Diego, Calif., USA) using non-linear regression curve fit for sigmoidal dose response (variable slope).

ROR Gamma Luciferase Reporter Assay:

The Ligand Binding Domain (LBD) of ROR gamma was cloned into pFN26A (BIND) hRluc-neo Flexi vector (Promega) which expresses a fusion protein comprised of a DNA binding domain of the yeast GAL4 gene, a linker segment and ROR gamma ligand binding domain. For the reporter assay 0.02×10$^6$ HEK293 cells were seeded per well in a 96 well plate in complete media and incubated overnight in an incubator with 5% CO2 at 37° C. before transfection. Cells were then co-transfected with pFN26A hRluc-neo Flexi vector containing the LBD of ROR gamma and pGL4.35 [luc2P/9XGAL4 UAS/Hygro] Vector (Promega) in low serum media. Post transfection and recovery, cells were treated with the test compounds for 48 hours. The assay was terminated using the Bright-Glo Luciferase assay system from Promega and the Luminescence was measured using a luminescence reader. The luminescence values were used to calculate the potency of the compounds.

The selected compounds were screened at 1 μM/10 μM concentration followed by $IC_{50}$ measurement and the results are summarized in the Table-1 below along with $IC_{50}$ (nM) details for selected compounds. The $IC_{50}$ values of the selected compounds (in range) are set forth in below table wherein "A" refers to an $IC_{50}$ value of less than 150 nM, "B" refers to an $IC_{50}$ value in a range of 150-300 nM and C refers to an $IC_{50}$ value of greater than 300 nM.

TABLE-1

RORγ ligand binding assay data

| Compound No. | RORγ ligand binding assay: % inhibition @1 μM | RORγ ligand binding assay: % inhibition @ 10 μM | RORγ ligand binding assay: $IC_{50}$ (nM) |
| --- | --- | --- | --- |
| 2 | 84 | 89 | A |
| 6 | 72 | 96 | B |
| 7 | 91 | 100 | A |
| 9 | 90 | 100 | A |
| 11 | 25 | 71 | — |
| 12 | — | — | A |
| 14 | 0 | 26 | — |
| 15 | 95 | 92 | A |
| 16 | 86 | 93 | B |
| 17 | 92 | 96 | — |
| 19 | 98 | 98 | B |
| 20 | 76 | 95 | — |
| 21 | 94 | 92 | B |
| 22 | 76 | 95 | A |
| 26 | 65 | 99 | C |
| 28 | 77 | 100 | B |
| 29 | 84 | 91 | B |
| 31 | 90 | 88 | A |
| 34 | 74 | 97 | C |
| 35 | 80 | 98 | B |
| 40 | 44 | 88 | — |
| 41 | 47 | 82 | — |
| 42 | 94 | 92 | A |
| 43 | 82 | — | A |
| 45 | 66 | 73 | — |
| 46 | 56 | 92 | C |
| 47 | 82 | 98 | A |
| 49 | 93 | 82 | B |
| 50 | 91 | 90 | A |
| 56 | 96 | 94 | A |
| 61 | 90 | 74 | A |
| 62 | 96 | 91 | A |
| 84 | 82 | 100 | B |
| 85 | 62 | 95 | C |
| 86 | 72 | 100 | A |
| 87 | 82 | 99 | B |
| 88 | 86 | 90 | B |
| 89 | 53 | 79 | C |
| 90 | 57 | 84 | B |
| 91 | 36 | 100 | C |
| 92 | 96 | 80 | A |
| 103 | 26 | 0 | — |
| 104 | 94 | 88 | A |
| 105 | 100 | 97 | A |
| 106 | 70 | 1 | — |
| 107 | 91 | 90 | A |
| 108 | 78 | 28 | C |
| 109 | 91 | 36 | C |
| 110 | 100 | 81 | A |
| 111 | 62 | 19 | C |
| 112 | 100 | 73 | A |
| 127 | 14 | 46 | — |
| 128 | 79 | 110 | A |
| 131 | 51 | 42 | — |
| 132 | 99 | 103 | A |
| 133 | 96 | 109 | A |
| 135 | 90 | 104 | A |

The $IC_{50}$ values of RORγ luciferase reporter assay for selected compounds are set forth in the Table-2 below wherein "A" refers to an $IC_{50}$ value of less than 100 nM, "B" refers to an $IC_{50}$ value in a range of 100-500 nM and C refers to an $IC_{50}$ value of greater than 500 nM.

TABLE-2

RORγ luciferase reporter assay data

| RORγ luciferase Reporter assay: IC$_{50}$ (nM) (in range) | Compound No. |
|---|---|
| A | 15, 16, 17, 21, 29, 31, 45, 51, 52, 56, 64, 65, 66, 72, 74, 81, 105, 110, 113, 115, 118, 120, 125 and 129. |
| B | 2, 6, 7, 9, 12, 20, 22, 26, 28, 35, 49, 50, 58, 60, 68, 71, 75, 76, 77, 78, 83, 92, 96, 98, 104, 107, 112, 124 and 134. |
| C | 11, 14, 34, 40, 41, 48, 53, 57, 59, 62, 67, 70, 73, 82, 88, 89, 90, 91, 93, 94, 95, 97, 103, 106, 108, 109, 111, 114, 116, 117, 123 and 126. |

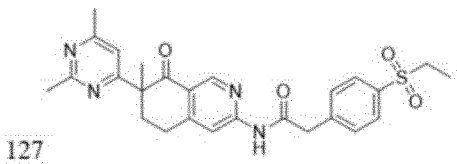

What is claimed is:

1. A compound of formula (I):

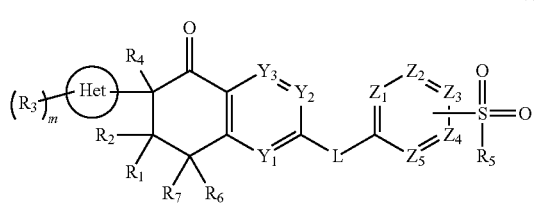

(I)

or a pharmaceutically acceptable salt or a stereoisomer thereof;

wherein, ring Het is heterocyclyl;

each $Y_1$, $Y_2$ and $Y_3$ are independently $CR_a$ or N, wherein 0-2 of $Y_1$, $Y_2$ and $Y_3$ are N;

each $Z_1$, $Z_2$, $Z_3$, $Z_4$ and $Z_5$ are independently $CR_a$ or N, wherein 0-3 of $Z_1$, $Z_2$, $Z_3$, $Z_4$ and $Z_5$ are N;

L is *—NR$_b$—C(O)—(CR$_b$R$_c$)$_n$—, *—C(O)—NR$_b$—(CR$_b$R$_c$)$_n$—, *—NR$_b$—S(O)$_2$—(CR$_b$R$_c$)$_n$— or *—S(O)$_2$—NR$_b$—(CR$_b$R$_c$)$_n$—; wherein the group marked with * is connected to the ring containing $Y_1$, $Y_2$ and $Y_3$;

each $R_1$, $R_2$, $R_6$ and $R_7$ are independently hydrogen, halo, alkyl, hydroxy, hydroxyalkyl, cyano, alkoxy, haloalkyl, haloalkoxy, alkenyl, alkynyl, cycloalkyl, aryl, heteroaryl, —COR$_d$ or —COOR$_d$;

$R_3$ at each occurrence is independently hydroxy, halo, alkyl, alkylamino, alkoxy, haloalkyl, haloalkoxy or cycloalkyl; alternatively, two $R_3$ on the same carbon together form an oxo (=O) group;

$R_4$ is hydrogen, alkyl or alkoxy;

$R_5$ is alkyl, —(CH$_2$)$_n$NR$_b$R$_c$, hydroxyalkyl, cycloalkyl, aryl or heterocyclyl;

$R_a$ is hydrogen, alkyl, alkoxy, halo, cycloalkyl or aryl;

$R_b$ and $R_c$ are each independently hydrogen, alkyl or alkoxyalkyl;

alternatively, $R_b$ and $R_c$ on the same atom together form a ring;

$R_d$ is hydrogen, alkyl, alkoxy or cycloalkyl;

m is 0 to 3; and n is 0 to 3.

2. The compound of claim 1, wherein the compound is of formula (IA):

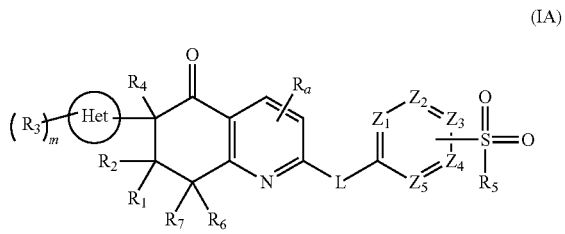

(IA)

or a pharmaceutically acceptable salt or a stereoisomer thereof.

3. The compound of claim 1, wherein the compound is of formula (ID):

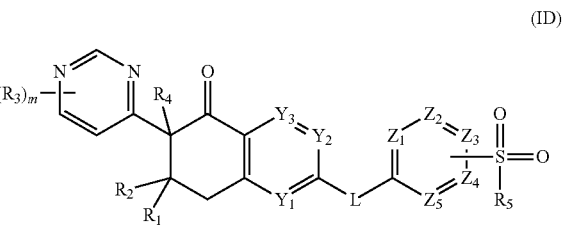

(ID)

or a pharmaceutically acceptable salt or a stereoisomer thereof.

4. The compound of claim 1, wherein the compound is of formula (IE):

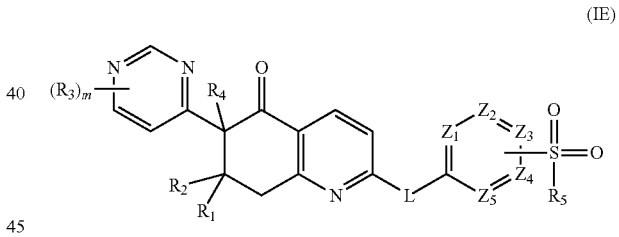

(IE)

or a pharmaceutically acceptable salt or a stereoisomer thereof.

5. The compound of claim 3, wherein L is *—CONHCH$_2$— wherein the group marked with * is connected to the ring containing $Y_1$, $Y_2$ and $Y_3$.

6. The compound of claim 5, wherein $R_1$ and $R_2$ are each hydrogen.

7. The compound of claim 5, wherein $R_4$ is alkyl.

8. The compound of claim 7, wherein $R_4$ is methyl.

9. The compound of claim 5, wherein $R_3$ at each occurrence is alkyl.

10. The compound of claim 5, wherein $R_5$ is alkyl.

11. The compound of claim 10, wherein $R_5$ is ethyl.

12. The compound of claim 5, wherein each $Y_1$, $Y_2$ and $Y_3$ are independently $CR_a$ or N, wherein $R_a$ is hydrogen and 0-2 of $Y_1$, $Y_2$ and $Y_3$ are N.

13. The compound of claim 5, wherein each $Z_1$, $Z_2$, $Z_3$, $Z_4$ and $Z_5$ are independently $CR_a$ or N, wherein $R_a$ is hydrogen and 0-3 of $Z_1$, $Z_2$, $Z_3$, $Z_4$ and $Z_5$ are N.

14. The compound of claim 1, or a pharmaceutically acceptable salt or a stereoisomer thereof; wherein ring Het is pyridyl, pyridazinyl, pyridazinone, pyrimidinyl, pyrazinyl, pyrazolyl, imidazopyrazinyl, imidazopyridyl, pyrrolopyrazinyl, thienyl, benzodioxolyl, benzimidazolyl, imidazolyl, imidazopyridazinyl or tetrahydroisoquinolinonyl.

15. The compound of claim 1, or a pharmaceutically acceptable salt or a stereoisomer thereof wherein,

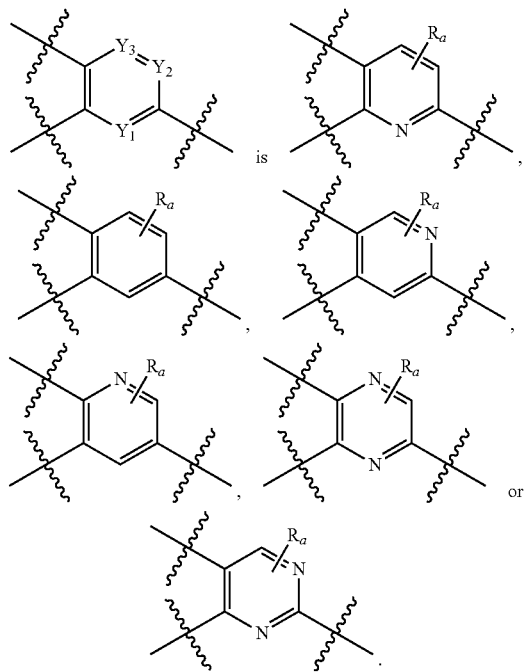

is

16. The compound of claim 1, or a pharmaceutically acceptable salt or a stereoisomer thereof wherein

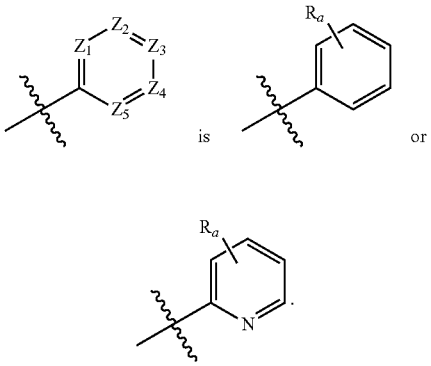

is    or

17. The compound of claim 1, or a pharmaceutically acceptable salt or a stereoisomer thereof wherein L is *—NHCOCH$_2$— or *CONHCH$_2$— wherein the group marked with * is connected to the ring containing Y$_1$, Y$_2$ and Y$_3$.

18. The compound of claim 1, or a pharmaceutically acceptable salt or a stereoisomer thereof wherein each of R$_1$, R$_2$, R$_6$ and R$_7$ are each hydrogen; and R$_4$ is alkyl.

19. The compound of claim 1, or a pharmaceutically acceptable salt or a stereoisomer thereof wherein R$_5$ is alkyl.

20. The compound of claim 1, or a pharmaceutically acceptable salt or a stereoisomer thereof wherein R$_a$ is hydrogen or alkyl.

21. A compound, selected from among:

| Compound No. | IUPAC Name |
| --- | --- |
| 1 | N-(4,6-dimethyl-5-oxo-6-(pyridin-2-yl)-5,6,7,8-tetrahydroquinolin-2-yl)-2-(4-(ethylsulfonyl)phenyl)acetamide; |
| 2 | 2-(4-(ethylsulfonyl)phenyl)-N-(6-(6-methoxypyridin-3-yl)-6-methyl-5-oxo-5,6,7,8-tetrahydroquinolin-2-yl)acetamide; |
| 3 | 2-(4-(ethylsulfonyl)phenyl)-N-(6-methyl-5-oxo-6-(6-(trifluoromethyl)pyridin-3-yl)-5,6,7,8-tetrahydroquinolin-2-yl)acetamide; |
| 4 | 2-(4-(ethylsulfonyl)phenyl)-N-(6-(5-methoxypyridin-2-yl)-7,7-dimethyl-5-oxo-5,6,7,8-tetrahydroquinolin-2-yl)acetamide; |
| 5 | 2-(4-(ethylsulfonyl)phenyl)-N-(6-(4-methoxypyridin-2-yl)-6-methyl-5-oxo-5,6,7,8-tetrahydroquinolin-2-yl)acetamide; |
| 6 | 2-(4-(ethylsulfonyl)phenyl)-N-(6-(imidazo[1,2-a]pyrazin-8-yl)-6-methyl-5-oxo-5,6,7,8-tetrahydroquinolin-2-yl)acetamide; |
| 7 | N-(6-(2,6-dimethylpyrimidin-4-yl)-6-methyl-5-oxo-5,6,7,8-tetrahydroquinolin-2-yl)-2-(4-(ethylsulfonyl)phenyl)acetamide; |
| 8 | N-(6-methyl-5-oxo-6-(5-(trifluoromethyl)pyridin-2-yl)-5,6,7,8-tetrahydroquinolin-2-yl)-2-(4-(methylsulfonyl)phenyl)acetamide; |
| 9 | 2-(4-(ethylsulfonyl)phenyl)-N-(6-methyl-6-(2-methylimidazo[1,2-a]pyrazin-8-yl)-5-oxo-5,6,7,8-tetrahydroquinolin-2-yl)acetamide; |
| 10 | N-(6-(5-chloropyridin-2-yl)-6-methyl-5-oxo-5,6,7,8-tetrahydroquinolin-2-yl)-2-(4-(methylsulfonyl)phenyl)acetamide; |
| 11 | 2-(4-(ethylsulfonyl)phenyl)-N-(6-(imidazo[1,2-a]pyrazin-8-yl)-3,6-dimethyl-5-oxo-5,6,7,8-tetrahydroquinolin-2-yl)acetamide; |
| 12 | 2-(4-(ethylsulfonyl)phenyl)-N-(6-(6-methoxypyridazin-3-yl)-6-methyl-5-oxo-5,6,7,8-tetrahydroquinolin-2-yl)acetamide; |
| 13 | N-(6-(imidazo[1,2-a]pyridin-8-yl)-6-methyl-5-oxo-5,6,7,8-tetrahydroquinolin-2-yl)-2-(4-(methylsulfonyl)phenyl)acetamide; |
| 14 | N-(6-ethyl-6-(imidazo[1,2-a]pyrazin-8-yl)-5-oxo-5,6,7,8-tetrahydroquinolin-2-yl)-2-(4-(ethylsulfonyl)phenyl)acetamide; |
| 15 | 2-(4-(ethylsulfonyl)phenyl)-N-(6-methyl-5-oxo-6-(pyrrolo[1,2-a]pyrazin-1-yl)-5,6,7,8-tetrahydroquinolin-2-yl)acetamide; |
| 16 | 2-(4-(ethylsulfonyl)phenyl)-N-(6-methyl-6-(6-methylimidazo[1,2-a]pyrazin-8-yl)-5-oxo-5,6,7,8-tetrahydroquinolin-2-yl)acetamide; |

| Compound No. | IUPAC Name |
|---|---|
| 17 | 2-(4-(ethylsulfonyl)phenyl)-N-(6-(6-methoxypyridin-3-yl)-4,6-dimethyl-5-oxo-5,6,7,8-tetrahydroquinolin-2-yl)acetamide; |
| 18 | N-(4,6-dimethyl-5-oxo-6-(pyridin-3-yl)-5,6,7,8-tetrahydroquinolin-2-yl)-2-(4-(ethylsulfonyl)phenyl)acetamide; |
| 19 | 2-(4-(ethylsulfonyl)phenyl)-N-(6-(6-methoxypyridin-2-yl)-4,6-dimethyl-5-oxo-5,6,7,8-tetrahydroquinolin-2-yl)acetamide; |
| 20 | 2-(4-(ethylsulfonyl)phenyl)-N-(6-(5-methoxypyridin-2-yl)-4,6-dimethyl-5-oxo-5,6,7,8-tetrahydroquinolin-2-yl)acetamide; |
| 21 | 2-(4-(ethylsulfonyl)phenyl)-N-(6-(4-methoxypyrimidin-2-yl)-4,6-dimethyl-5-oxo-5,6,7,8-tetrahydroquinolin-2-yl)acetamide; |
| 22 | 2-(4-(ethylsulfonyl)phenyl)-N-(6-(4-methoxypyridin-2-yl)-4,6-dimethyl-5-oxo-5,6,7,8-tetrahydroquinolin-2-yl)acetamide; |
| 23 | 2-(4-(ethylsulfonyl)phenyl)-N-(6-(3-fluoropyridin-2-yl)-4,6-dimethyl-5-oxo-5,6,7,8-tetrahydroquinolin-2-yl)acetamide; |
| 24 | N-(6-(5-chloro-3-methoxypyridin-2-yl)-4,6-dimethyl-5-oxo-5,6,7,8-tetrahydroquinolin-2-yl)-2-(4-(ethylsulfonyl)phenyl)acetamide; |
| 25 | 2-(4-(ethylsulfonyl)phenyl)-N-(6-(2-methoxypyrimidin-5-yl)-4,6-dimethyl-5-oxo-5,6,7,8-tetrahydroquinolin-2-yl)acetamide; |
| 26 | 2-(4-(ethylsulfonyl)phenyl)-N-(6-(imidazo[1,2-a]pyrazin-8-yl)-4,6-dimethyl-5-oxo-5,6,7,8-tetrahydroquinolin-2-yl)acetamide; |
| 27 | 2-(4-(ethylsulfonyl)phenyl)-N-(6-(5-methoxypyrazin-2-yl)-4,6-dimethyl-5-oxo-5,6,7,8-tetrahydroquinolin-2-yl)acetamide; |
| 28 | N-(6-(2,6-dimethylpyrimidin-4-yl)-4,6-dimethyl-5-oxo-5,6,7,8-tetrahydroquinolin-2-yl)-2-(4-(ethylsulfonyl)phenyl)acetamide; |
| 29 | N-(6-(4,6-dimethylpyrimidin-2-yl)-4,6-dimethyl-5-oxo-5,6,7,8-tetrahydroquinolin-2-yl)-2-(4-(ethylsulfonyl)phenyl)acetamide; |
| 30 | 2-(4-(ethylsulfonyl)phenyl)-N-(6-(2-methoxypyrimidin-4-yl)-4,6-dimethyl-5-oxo-5,6,7,8-tetrahydroquinolin-2-yl)acetamide; |
| 31 | 2-(4-(ethylsulfonyl)phenyl)-N-(6-(6-methoxypyridazin-3-yl)-4,6-dimethyl-5-oxo-5,6,7,8-tetrahydroquinolin-2-yl)acetamide; |
| 32 | N-(4,6-dimethyl-5-oxo-6-(5-(trifluoromethyl)pyridin-2-yl)-5,6,7,8-tetrahydroquinolin-2-yl)-2-(4-(methylsulfonyl)phenyl)acetamide; |
| 33 | N-(6-(imidazo[1,2-a]pyrazin-8-yl)-4,6-dimethyl-5-oxo-5,6,7,8-tetrahydroquinolin-2-yl)-2-(4-(methylsulfonyl)phenyl)acetamide; |
| 34 | N-(4,6-dimethyl-6-(6-methylpyridazin-3-yl)-5-oxo-5,6,7,8-tetrahydroquinolin-2-yl)-2-(4-(ethylsulfonyl)phenyl)acetamide; |
| 35 | N-(6-(6-methoxypyridazin-3-yl)-4,6-dimethyl-5-oxo-5,6,7,8-tetrahydroquinolin-2-yl)-2-(4-(methylsulfonyl)phenyl)acetamide; |
| 36 | 2-(4-(ethylsulfonyl)phenyl)-N-(6-(4-hydroxypyrimidin-2-yl)-4,6-dimethyl-5-oxo-5,6,7,8-tetrahydroquinolin-2-yl)acetamide; |
| 37 | 2-(4-(ethylsulfonyl)phenyl)-N-(6-(2-hydroxypyridin-4-yl)-4,6-dimethyl-5-oxo-5,6,7,8-tetrahydroquinolin-2-yl)acetamide; |
| 38 | N-(6-(5-chloro-3-hydroxypyridin-2-yl)-4,6-dimethyl-5-oxo-5,6,7,8-tetrahydroquinolin-2-yl)-2-(4-(ethylsulfonyl)phenyl)acetamide; |
| 39 | 2-(4-(ethylsulfonyl)phenyl)-N-(6-(6-hydroxypyridin-2-yl)-4,6-dimethyl-5-oxo-5,6,7,8-tetrahydroquinolin-2-yl)acetamide; |
| 40 | 2-(4-(ethylsulfonyl)phenyl)-N-(6-(6-hydroxypyridin-3-yl)-6-methyl-5-oxo-5,6,7,8-tetrahydroquinolin-2-yl)acetamide; |
| 41 | N-(6-(6-ethylpyridazin-3-yl)-6-methyl-5-oxo-5,6,7,8-tetrahydroquinolin-2-yl)-2-(4-(ethylsulfonyl)phenyl)acetamide; |
| 42 | N-(6-(benzo[d][1,3]dioxol-5-yl)-4,6-dimethyl-5-oxo-5,6,7,8-tetrahydroquinolin-2-yl)-2-(4-(ethylsulfonyl)phenyl)acetamide; |
| 43 | N-(4,6-dimethyl-6-(1-methyl-1H-benzo[d]imidazol-5-yl)-5-oxo-5,6,7,8-tetrahydroquinolin-2-yl)-2-(4-(ethylsulfonyl)phenyl)acetamide; |
| 44 | N-(4,6-dimethyl-6-(2-methyl-1-oxo-1,2,3,4-tetrahydroisoquinolin-7-yl)-5-oxo-5,6,7,8-tetrahydroquinolin-2-yl)-2-(4-(ethylsulfonyl)phenyl)acetamide; |
| 45 | 2-(4-(ethylsulfonyl)phenyl)-N-(6-methyl-6-(5-methylthiophen-2-yl)-5-oxo-5,6,7,8-tetrahydroquinolin-2-yl)acetamide; |
| 46 | N-(6-(3,5-dimethyl-1H-pyrazol-1-yl)-6-methyl-5-oxo-5,6,7,8-tetrahydroquinolin-2-yl)-2-(4-(ethylsulfonyl)phenyl)acetamide; |
| 47 | 2-(4-(ethylsulfonyl)phenyl)-N-(6-methyl-5-oxo-6-(1H-pyrazol-1-yl)-5,6,7,8-tetrahydroquinolin-2-yl)acetamide; |
| 48 | 2-(4-(ethylsulfonyl)phenyl)-N-(6-(imidazo[1,2-a]pyrazin-8-yl)-6,8-dimethyl-5-oxo-5,6,7,8-tetrahydroquinolin-2-yl)acetamide; |
| 49 | 2-(4-(ethylsulfonyl)phenyl)-N-(6-methyl-6-(3-methylimidazo[1,2-a]pyrazin-8-yl)-5-oxo-5,6,7,8-tetrahydroquinolin-2-yl)acetamide; |
| 50 | 2-(4-(ethylsulfonyl)phenyl)-N-(6-(2-isopropylpyrimidin-4-yl)-6-methyl-5-oxo-5,6,7,8-tetrahydroquinolin-2-yl)acetamide; |
| 51 | N-(6-(2,6-dimethylimidazo[1,2-a]pyrazin-8-yl)-6-methyl-5-oxo-5,6,7,8-tetrahydroquinolin-2-yl)-2-(4-(ethylsulfonyl)phenyl)acetamide; |
| 52 | N-(4,6-dimethyl-6-(2-methylimidazo[1,2-a]pyrazin-8-yl)-5-oxo-5,6,7,8-tetrahydroquinolin-2-yl)-2-(4-(ethylsulfonyl)phenyl)acetamide; |
| 53 | N-(4,6-dimethyl-5-oxo-6-(6-(trifluoromethyl)pyridazin-3-yl)-5,6,7,8-tetrahydroquinolin-2-yl)-2-(4-(ethylsulfonyl)phenyl)acetamide; |
| 54 | 2-(4-(ethylsulfonyl)phenyl)-N-(6-(imidazo[1,2-a]pyrazin-8-yl)-7-methyl-5-oxo-5,6,7,8-tetrahydroquinolin-2-yl)acetamide; |

| Compound No. | IUPAC Name |
| --- | --- |
| 55 | 2-(4-(ethylsulfonyl)phenyl)-N-(6-methyl-5-oxo-6-(6-(trifluoromethyl)pyridazin-3-yl)-5,6,7,8-tetrahydroquinolin-2-yl)acetamide; |
| 56 | 2-(4-(ethylsulfonyl)phenyl)-N-(6-(5-methoxypyrimidin-2-yl)-6-methyl-5-oxo-5,6,7,8-tetrahydroquinolin-2-yl)acetamide; |
| 57 | 2-(4-(ethylsulfonyl)phenyl)-N-(6-(6-isopropoxypyridazin-3-yl)-6-methyl-5-oxo-5,6,7,8-tetrahydroquinolin-2-yl)acetamide; |
| 58 | 2-(4-(ethylsulfonyl)-2-fluorophenyl)-N-(6-methyl-6-(2-methylimidazo[1,2-a]pyrazin-8-yl)-5-oxo-5,6,7,8-tetrahydroquinolin-2-yl)acetamide; |
| 59 | N-(6-methyl-6-(2-methylimidazo[1,2-a]pyrazin-8-yl)-5-oxo-5,6,7,8-tetrahydroquinolin-2-yl)-2-(4-(methylsulfonyl)phenyl)acetamide; |
| 60 | 2-(4-(ethylsulfonyl)phenyl)-N-(6-(5-isopropylpyrazin-2-yl)-6-methyl-5-oxo-5,6,7,8-tetrahydroquinolin-2-yl)acetamide; |
| 61 | 2-(4-(ethylsulfonyl)phenyl)-N-(6-(5-methoxypyrimidin-2-yl)-4,6-dimethyl-5-oxo-5,6,7,8-tetrahydroquinolin-2-yl)acetamide; |
| 62 | 2-(4-(ethylsulfonyl)phenyl)-N-(6-(6-isopropylpyridazin-3-yl)-6-methyl-5-oxo-5,6,7,8-tetrahydroquinolin-2-yl)acetamide; |
| 63 | N-(6-(6-ethylpyridazin-3-yl)-4,6-dimethyl-5-oxo-5,6,7,8-tetrahydroquinolin-2-yl)-2-(4-(ethylsulfonyl)phenyl)acetamide; |
| 64 | 2-(4-(ethylsulfonyl)phenyl)-N-(6-(2-methoxy-6-methylpyrimidin-4-yl)-6-methyl-5-oxo-5,6,7,8-tetrahydroquinolin-2-yl)acetamide; |
| 65 | 2-(4-(ethylsulfonyl)phenyl)-N-(6-(6-methoxy-2-methylpyrimidin-4-yl)-6-methyl-5-oxo-5,6,7,8-tetrahydroquinolin-2-yl)acetamide; |
| 66 | 2-(4-(ethylsulfonyl)phenyl)-N-(6-(3-fluoro-2-methylimidazo[1,2-a]pyrazin-8-yl)-6-methyl-5-oxo-5,6,7,8-tetrahydroquinolin-2-yl)acetamide; |
| 67 | 2-(4-(ethylsulfonyl)phenyl)-N-(6-methyl-6-(2-methyl-6-(trifluoromethyl)-pyrimidin-4-yl)-5-oxo-5,6,7,8-tetrahydroquinolin-2-yl)acetamide; |
| 68 | 2-(4-(ethylsulfonyl)phenyl)-N-(6-methyl-6-(5-methylimidazo[1,2-a]pyrazin-8-yl)-5-oxo-5,6,7,8-tetrahydroquinolin-2-yl)acetamide; |
| 69 | N-(6-(2,6-dimethylpyrimidin-4-yl)-7,7-dimethyl-5-oxo-5,6,7,8-tetrahydroquinolin-2-yl)-2-(4-(ethylsulfonyl)phenyl)acetamide; |
| 70 | N-(4,6-dimethyl-6-(1-methyl-6-oxo-1,6-dihydropyridazin-3-yl)-5-oxo-5,6,7,8-tetrahydroquinolin-2-yl)-2-(4-(ethylsulfonyl)phenyl)acetamide; |
| 71 | N-(6-(3-cyclopropylimidazo[1,2-a]pyrazin-8-yl)-6-methyl-5-oxo-5,6,7,8-tetrahydroquinolin-2-yl)-2-(4-(ethylsulfonyl)phenyl)acetamide; |
| 72 | 2-(4-(ethylsulfonyl)phenyl)-N-(6-(methyl-5-oxo-6-(2-(trifluoromethyl)-imidazo[1,2-a]pyrazin-8-yl)-5,6,7,8-tetrahydroquinolin-2-yl)acetamide; |
| 73 | 2-(4-(ethylsulfonyl)phenyl)-N-(6-(5-methoxypyridazin-3-yl)-4,6-dimethyl-5-oxo-5,6,7,8-tetrahydroquinolin-2-yl)acetamide; |
| 74 | 2-(4-(ethylsulfonyl)phenyl)-N-(6-methyl-5-oxo-6-(3-(trifluoromethyl)-imidazo[1,2-a]pyrazin-8-yl)-5,6,7,8-tetrahydroquinolin-2-yl)acetamide; |
| 75 | N-(4,6-dimethyl-6-(2-methylimidazo[1,2-b]pyridazin-6-yl)-5-oxo-5,6,7,8-tetrahydroquinolin-2-yl)-2-(4-(ethylsulfonyl)phenyl)acetamide; |
| 76 | N-(6-(5-cyclopropyl-6-methoxypyridazin-3-yl)-4,6-dimethyl-5-oxo-5,6,7,8-tetrahydroquinolin-2-yl)-2-(4-(ethylsulfonyl)phenyl)acetamide; |
| 77 | 2-(4-(ethylsulfonyl)phenyl)-N-(6-(imidazo[1,2-b]pyridazin-6-yl)-4,6-dimethyl-5-oxo-5,6,7,8-tetrahydroquinolin-2-yl)acetamide; |
| 78 | 2-(4-(ethylsulfonyl)phenyl)-N-(6-methyl-6-(6-methyl-2-(trifluoromethyl)-pyrimidin-4-yl)-5-oxo-5,6,7,8-tetrahydroquinolin-2-yl)acetamide; |
| 79 | N-(6-(2,6-dimethylpyrimidin-4-yl)-6-methyl-5-oxo-5,6,7,8-tetrahydroquinolin-2-yl)-2-(5-(ethylsulfonyl)pyridin-2-yl)acetamide; |
| 80 | 2-(5-(ethylsulfonyl)pyridin-2-yl)-N-(6-(6-methoxypyridazin-3-yl)-4,6-dimethyl-5-oxo-5,6,7,8-tetrahydroquinolin-2-yl)acetamide; |
| 81 | N-(6-(2,6-dimethylpyrimidin-4-yl)-6,7-dimethyl-5-oxo-5,6,7,8-tetrahydroquinolin-2-yl)-2-(4-(ethylsulfonyl)phenyl)acetamide; |
| 82 | N-(6-(2,6-dimethylpyrimidin-4-yl)-7-methyl-5-oxo-5,6,7,8-tetrahydroquinolin-2-yl)-2-(4-(ethylsulfonyl)phenyl)acetamide; |
| 84 | 2-(4-(ethylsulfonyl)phenyl)-N-(6-(2-hydroxypyridin-3-yl)-4,6-dimethyl-5-oxo-5,6,7,8-tetrahydroquinolin-2-yl)acetamide; |
| 85 | 2-(4-(ethylsulfonyl)phenyl)-N-(6-(3-hydroxypyridin-2-yl)-4,6-dimethyl-5-oxo-5,6,7,8-tetrahydroquinolin-2-yl)acetamide; |
| 86 | 2-(4-(ethylsulfonyl)phenyl)-N-(6-(2-hydroxy-4-methylpyridin-3-yl)-4,6-dimethyl-5-oxo-5,6,7,8-tetrahydroquinolin-2-yl)acetamide; |
| 87 | 2-(4-(ethylsulfonyl)phenyl)-N-(6-(3-hydroxypyridin-2-yl)-7,7-dimethyl-5-oxo-5,6,7,8-tetrahydroquinolin-2-yl)acetamide; |
| 88 | 2-(4-(ethylsulfonyl)phenyl)-N-(6-(5-hydroxypyridin-2-yl)-4,6-dimethyl-5-oxo-5,6,7,8-tetrahydroquinolin-2-yl)acetamide; |
| 89 | N-(6-(3-hydroxypyridin-2-yl)-4,6-dimethyl-5-oxo-5,6,7,8-tetrahydroquinolin-2-yl)-2-(4-(methylsulfonyl)phenyl)acetamide; |
| 90 | 2-(4-(ethylsulfonyl)phenyl)-N-(6-(5-hydroxypyridin-2-yl)-7,7-dimethyl-5-oxo-5,6,7,8-tetrahydroquinolin-2-yl)acetamide; |
| 91 | 2-(4-(ethylsulfonyl)phenyl)-N-(6-(3-hydroxypyridin-2-yl)-7-methyl-5-oxo-5,6,7,8-tetrahydroquinolin-2-yl)acetamide; |
| 92 | N-(6-(5-chloroimidazo[1,2-a]pyrazin-8-yl)-6-methyl-5-oxo-5,6,7,8-tetrahydroquinolin-2-yl)-2-(4-(ethylsulfonyl)phenyl)acetamide; |
| 93 | N-(6-(6-chloropyridazin-3-yl)-6-methyl-5-oxo-5,6,7,8-tetrahydroquinolin-2-yl)-2-(4-(ethylsulfonyl)phenyl)acetamide; |

| Compound No. | IUPAC Name |
| --- | --- |
| 94 | 3-(2-(2-(4-(ethylsulfonyl)phenyl)acetamido)-4,6-dimethyl-5-oxo-5,6,7,8-tetrahydroquinolin-6-yl)-6-methoxypyridazine 1-oxide; |
| 95 | 2-(4-(ethylsulfonyl)phenyl)-N-(6-(6-methoxy-4-methylpyridazin-3-yl)-4,6-dimethyl-5-oxo-5,6,7,8-tetrahydroquinolin-2-yl)acetamide; |
| 96 | 2-(4-(ethylsulfonyl)phenyl)-N-(6-(6-methoxy-5-methylpyridazin-3-yl)-4,6-dimethyl-5-oxo-5,6,7,8-tetrahydroquinolin-2-yl)acetamide; |
| 97 | 2-(4-(ethylsulfonyl)phenyl)-N-(6-(3-fluoroimidazo[1,2-a]pyrazin-8-yl)-6-methyl-5-oxo-5,6,7,8-tetrahydroquinolin-2-yl)acetamide; |
| 98 | N-(6-(6-(dimethylamino)pyridazin-3-yl)-4,6-dimethyl-5-oxo-5,6,7,8-tetrahydroquinolin-2-yl)-2-(4-(ethylsulfonyl)phenyl)acetamide; |
| 99 | 6-(2,6-dimethylpyrimidin-4-yl)-N-(4-(ethylsulfonyl)benzyl)-6-methyl-5-oxo-5,6,7,8-tetrahydroquinoline-2-carboxamide; |
| 100 | N-(6-(2,6-dimethylpyrimidin-4-yl)-6-methyl-5-oxo-5,6,7,8-tetrahydronaphthalen-2-yl)-2-(4-(ethylsulfonyl)phenyl)acetamide; |
| 101 | 2-(4-(ethylsulfonyl)phenyl)-N-(6-(3-hydroxypyridin-2-yl)-4,6-dimethyl-5-oxo-5,6,7,8-tetrahydroquinolin-2-yl)acetamide; (Isomer-1 of Compound-85); |
| 102 | 2-(4-(ethylsulfonyl)phenyl)-N-(6-(3-hydroxypyridin-2-yl)-4,6-dimethyl-5-oxo-5,6,7,8-tetrahydroquinolin-2-yl)acetamide; (Isomer-2 of Compound-85); |
| 103 | N-(6-(2,6-dimethylpyrimidin-4-yl)-6-methyl-5-oxo-5,6,7,8-tetrahydroquinolin-2-yl)-2-(4-(ethylsulfonyl)phenyl)acetamide; (Isomer-1 of Compound-7); |
| 104 | N-(6-(2,6-dimethylpyrimidin-4-yl)-6-methyl-5-oxo-5,6,7,8-tetrahydroquinolin-2-yl)-2-(4-(ethylsulfonyl)phenyl)acetamide; (Isomer-2 of Compound-7); |
| 105 | 2-(4-(ethylsulfonyl)phenyl)-N-(6-methyl-6-(2-methylimidazo[1,2-a]pyrazin-8-yl)-5-oxo-5,6,7,8-tetrahydroquinolin-2-yl)acetamide; (Isomer-1 of Compound-9); |
| 106 | 2-(4-(ethylsulfonyl)phenyl)-N-(6-methyl-6-(2-methylimidazo[1,2-a]pyrazin-8-yl)-5-oxo-5,6,7,8-tetrahydroquinolin-2-yl)acetamide; (Isomer-2 of Compound-9); |
| 107 | N-(6-(2,6-dimethylpyrimidin-4-yl)-4,6-dimethyl-5-oxo-5,6,7,8-tetrahydroquinolin-2-yl)-2-(4-(ethylsulfonyl)phenyl)acetamide; (Isomer-1 of Compound-28); |
| 108 | N-(6-(2,6-dimethylpyrimidin-4-yl)-4,6-dimethyl-5-oxo-5,6,7,8-tetrahydroquinolin-2-yl)-2-(4-(ethylsulfonyl)phenyl)acetamide; (Isomer-2 of Compound-28); |
| 109 | 2-(4-(ethylsulfonyl)phenyl)-N-(6-(6-methoxypyridazin-3-yl)-4,6-dimethyl-5-oxo-5,6,7,8-tetrahydroquinolin-2-yl)acetamide; (Isomer-1 of Compound-31); |
| 110 | 2-(4-(ethylsulfonyl)phenyl)-N-(6-(6-methoxypyridazin-3-yl)-4,6-dimethyl-5-oxo-5,6,7,8-tetrahydroquinolin-2-yl)acetamide; (Isomer-2 of Compound-31); |
| 111 | 2-(4-(ethylsulfonyl)phenyl)-N-(6-(5-methoxypyrimidin-2-yl)-6-methyl-5-oxo-5,6,7,8-tetrahydroquinolin-2-yl)acetamide; (Isomer-1 of Compound-56); |
| 112 | 2-(4-(ethylsulfonyl)phenyl)-N-(6-(5-methoxypyrimidin-2-yl)-6-methyl-5-oxo-5,6,7,8-tetrahydroquinolin-2-yl)acetamide; (Isomer-2 of Compound-56); |
| 113 | 2-(4-(ethylsulfonyl)phenyl)-N-(6-methyl-6-(3-methylimidazo[1,2-a]pyrazin-8-yl)-5-oxo-5,6,7,8-tetrahydroquinolin-2-yl)acetamide; (Isomer-1 of Compound-49); |
| 114 | 2-(4-(ethylsulfonyl)phenyl)-N-(6-methyl-6-(3-methylimidazo[1,2-a]pyrazin-8-yl)-5-oxo-5,6,7,8-tetrahydroquinolin-2-yl)acetamide; (Isomer-2 of Compound-49); |
| 115 | 2-(4-(ethylsulfonyl)phenyl)-N-(6-(6-methoxy-2-methylpyrimidin-4-yl)-6-methyl-5-oxo-5,6,7,8-tetrahydroquinolin-2-yl)acetamide; (Isomer-1 of Compound-65); |
| 116 | 2-(4-(ethylsulfonyl)phenyl)-N-(6-(6-methoxy-2-methylpyrimidin-4-yl)-6-methyl-5-oxo-5,6,7,8-tetrahydroquinolin-2-yl)acetamide; (Isomer-2 of Compound-65); |
| 117 | 2-(4-(ethylsulfonyl)phenyl)-N-(6-methyl-6-(6-methylimidazo[1,2-a]pyrazin-8-yl)-5-oxo-5,6,7,8-tetrahydroquinolin-2-yl)acetamide; (Isomer-1 of Compound-16); |
| 118 | 2-(4-(ethylsulfonyl)phenyl)-N-(6-methyl-6-(6-methylimidazo[1,2-a]pyrazin-8-yl)-5-oxo-5,6,7,8-tetrahydroquinolin-2-yl)acetamide; (Isomer-2 of Compound-16); |
| 119 | 2-(4-(ethylsulfonyl)phenyl)-N-(6-(2-methoxy-6-methylpyrimidin-4-yl)-6-methyl-5-oxo-5,6,7,8-tetrahydroquinolin-2-yl)acetamide; (Isomer-1 of Compound-64); |
| 120 | 2-(4-(ethylsulfonyl)phenyl)-N-(6-(2-methoxy-6-methylpyrimidin-4-yl)-6-methyl-5-oxo-5,6,7,8-tetrahydroquinolin-2-yl)acetamide; (Isomer-2 of Compound-64); |
| 121 | 2-(4-(ethylsulfonyl)phenyl)-N-(6-methyl-5-oxo-6-(3-(trifluoromethyl)imidazo[1,2-a]pyrazin-8-yl)-5,6,7,8-tetrahydroquinolin-2-yl)acetamide; (Isomer-1 of Compound-74); |
| 122 | 2-(4-(ethylsulfonyl)phenyl)-N-(6-methyl-5-oxo-6-(3-(trifluoromethyl)imidazo[1,2-a]pyrazin-8-yl)-5,6,7,8-tetrahydroquinolin-2-yl)acetamide; (Isomer-2 of Compound-74); |
| 123 | N-(6-(2,6-dimethylpyrimidin-4-yl)-6-methyl-5-oxo-5,6,7,8-tetrahydroquinolin-2-yl)-2-(5-(ethylsulfonyl)pyridin-2-yl)acetamide; (Isomer-1 of Compound-79); |
| 124 | N-(6-(2,6-dimethylpyrimidin-4-yl)-6-methyl-5-oxo-5,6,7,8-tetrahydroquinolin-2-yl)-2-(5-(ethylsulfonyl)pyridin-2-yl)acetamide; (Isomer-2 of Compound-79); |
| 125 | 6-(2,6-dimethylpyrimidin-4-yl)-N-(4-(ethylsulfonyl)benzyl)-6-methyl-5-oxo-5,6,7,8-tetrahydroquinoline-2-carboxamide; (Isomer-1 of Compound-99); |
| 126 | 6-(2,6-dimethylpyrimidin-4-yl)-N-(4-(ethylsulfonyl)benzyl)-6-methyl-5-oxo-5,6,7,8-tetrahydroquinoline-2-carboxamide; (Isomer-2 of Compound-99); |
| 129 | 2-(4-(ethylsulfonyl)phenyl)-N-(6-(3-fluoro-2-methylimidazo[1,2-a]pyrazin-8-yl)-6-methyl-5-oxo-5,6,7,8-tetrahydroquinolin-2-yl)acetamide; |
| 130 | 2-(4-(ethylsulfonyl)phenyl)-N-(6-(3-fluoro-2-methylimidazo[1,2-a]pyrazin-8-yl)-6-methyl-5-oxo-5,6,7,8-tetrahydroquinolin-2-yl)acetamide; |
| 131 | N-(6-(6-ethyl-2-methylpyrimidin-4-yl)-6-methyl-5-oxo-5,6,7,8-tetrahydroquinolin-2-yl)-2-(4-(ethylsulfonyl)phenyl)acetamide; |

-continued

| Compound No. | IUPAC Name |
|---|---|
| 132 | N-(6-(2-ethyl-6-methylpyrimidin-4-yl)-6-methyl-5-oxo-5,6,7,8-tetrahydroquinolin-2-yl)-2-(4-(ethylsulfonyl)phenyl)acetamide; |
| 133 | N-(6-(2,6-diethylpyrimidin-4-yl)-6-methyl-5-oxo-5,6,7,8-tetrahydroquinolin-2-yl)-2-(4-(ethylsulfonyl)phenyl)acetamide; |
| 135 | 2-(4-(ethylsulfonyl)phenyl)-N-(6-(2-methoxy-6-methylpyrimidin-4-yl)-4,6-dimethyl-5-oxo-5,6,7,8-tetrahydroquinolin-2-yl)acetamide; |
| 136 | N-(7-(2,6-dimethylpyrimidin-4-yl)-7-methyl-8-oxo-5,6,7,8-tetrahydroquinolin-3-yl)-2-(4-(ethylsulfonyl)phenyl)acetamide; |
| 137 | N-(6-(2,6-dimethylpyrimidin-4-yl)-6-methyl-5-oxo-5,6,7,8-tetrahydroquinazolin-2-yl)-2-(4-(ethylsulfonyl)phenyl)acetamide; |
| 138 | N-(6-(2,6-dimethylpyrimidin-4-yl)-6-methyl-5-oxo-5,6,7,8-tetrahydroquinoxalin-2-yl)-2-(4-(ethylsulfonyl)phenyl)acetamide; |
| 139 | 2-(4-(ethylsulfonyl)phenyl)-N-(6-methyl-6-(2-methyl-6-(trifluoromethoxy)-pyrimidin-4-yl)-5-oxo-5,6,7,8-tetrahydroquinolin-2-yl)acetamide; |
| 140 | 6-(2,6-dimethylpyrimidin-4-yl)-N-(4-(ethylsulfonyl)benzyl)-7-isopropyl-5-oxo-5,6,7,8-tetrahydroquinoline-2-carboxamide; |
| 141 | 6-(2,6-dimethylpyrimidin-4-yl)-N-(4-(ethylsulfonyl)benzyl)-8-isopropyl-5-oxo-5,6,7,8-tetrahydroquinoline-2-carboxamide; and |
| 142 | 6-(2,6-dimethylpyrimidin-4-yl)-N-(4-(ethylsulfonyl)benzyl)-7-isopropyl-6-methyl-5-oxo-5,6,7,8-tetrahydroquinoline-2-carboxamide; | or a pharmaceutically acceptable salt or a stereoisomer thereof.

22. A pharmaceutical composition comprising a therapeutically effective amount of a compound of claim 1, or a pharmaceutically acceptable salt or a stereoisomer thereof and a pharmaceutically acceptable carrier or excipient.

23. The compound of claim 21 having the structure:

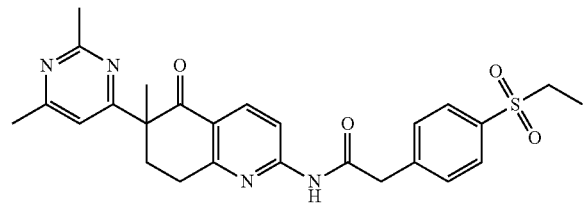

(Compound 7)

or a pharmaceutically acceptable salt thereof or a stereoisomer thereof.

24. The compound of claim 23, which is N-(6-(2,6-dimethylpyrimidin-4-yl)-6-methyl-5-oxo-5,6,7,8-tetrahydroquinolin-2-yl)-2-(4-(ethyl sulfonyl)phenyl)acetamide or an enantiomer thereof.

25. The compound of claim 23, which is N-(6-(2,6-dimethylpyrimidin-4-yl)-6-methyl-5-oxo-5,6,7,8-tetrahydroquinolin-2-yl)-2-(4-(ethyl sulfonyl)phenyl)acetamide or a pharmaceutically acceptable salt thereof.

26. The compound of claim 23, which is the (S)-enantiomer of N-(6-(2,6-dimethylpyrimidin-4-yl)-6-methyl-5-oxo-5,6,7,8-tetrahydroquinolin-2-yl)-2-(4-(ethylsulfonyl)phenyl)acetamide or a pharmaceutically acceptable salt thereof.

27. The compound of claim 23, which is the (R)-enantiomer of N-(6-(2,6-dimethylpyrimidin-4-yl)-6-methyl-5-oxo-5,6,7,8-tetrahydroquinolin-2-yl)-2-(4-(ethylsulfonyl)phenyl)acetamide or a pharmaceutically acceptable salt thereof.

28. A pharmaceutical composition comprising a compound of claim 23, or a pharmaceutically acceptable salt thereof, and a pharmaceutically acceptable carrier or excipient.

29. The compound of claim 25 having the structure:

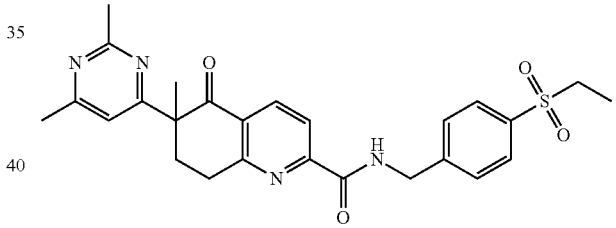

(Compound 99)

or a pharmaceutically acceptable salt or a stereoisomer thereof.

30. The compound of claim 29, which is 6-(2,6-dimethylpyrimidin-4-yl)-N-(4-(ethyl sulfonyl)benzyl)-6-methyl-5-oxo-5,6,7,8-tetrahydroquinoline-2-carboxamide or an enantiomer thereof.

31. The compound of claim 29, which is 6-(2,6-dimethylpyrimidin-4-yl)-N-(4-(ethylsulfonyl)benzyl)-6-methyl-5-oxo-5,6,7,8-tetrahydroquinoline-2-carboxamide or a pharmaceutically acceptable salt thereof.

32. The compound of claim 29, which is the (S)-enantiomer of 6-(2,6-dimethylpyrimidin-4-yl)-N-(4-(ethylsulfonyl)benzyl)-6-methyl-5-oxo-5,6,7,8-tetrahydroquinoline-2-carboxamide or a pharmaceutically acceptable salt thereof.

33. The compound of claim 29, which is the (R)-enantiomer of 6-(2,6-dimethylpyrimidin-4-yl)-N-(4-(ethylsulfonyl)benzyl)-6-methyl-5-oxo-5,6,7,8-tetrahydroquinoline-2-carboxamide or a pharmaceutically acceptable salt thereof.

34. A pharmaceutical composition comprising a compound of claim 29, or a pharmaceutically acceptable salt thereof, and a pharmaceutically acceptable carrier or excipient.

35. A compound, having the structure:

(Compound 99)

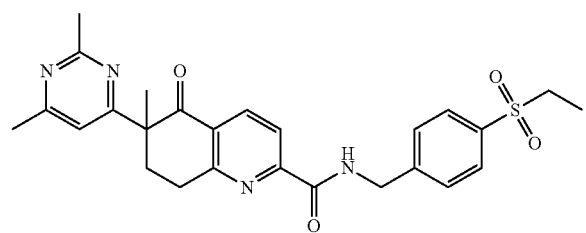

or a pharmaceutically acceptable salt or an enantiomer thereof.

36. A method of treating a disorder or disease mediated by RORγ in a subject in need thereof comprising administering to the subject a compound of claim 1, wherein the disorder or disease mediated by RORγ is an immune disorder or an inflammatory disease.

37. The method according to claim 36, wherein the disease or disorder is rheumatoid arthritis, psoriasis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, asthma, epidermal hyperplasia, scleroderma or ulcerative colitis.

38. The method according to claim 37, wherein the disease or disorder is psoriasis.

39. The method of claim 36, further comprising administering to the subject a second therapeutic agent.

40. A method of reducing an amount of IL-17 in a subject in need thereof, comprising administering to the subject a therapeutically effective amount of the compound of claim 1.

41. The method of claim 36, wherein the subject is a human or other mammal.

* * * * *

UNITED STATES PATENT AND TRADEMARK OFFICE
CERTIFICATE OF CORRECTION

PATENT NO. : 11,229,636 B2
APPLICATION NO. : 16/709692
DATED : January 25, 2022
INVENTOR(S) : Ravi Kotrabasaiah Ujjinamatada et al.

It is certified that error appears in the above-identified patent and that said Letters Patent is hereby corrected as shown below:

In the Specification

Column 41, beginning at Line 4 to Line 12, should read as:
A mixture of 1-((3-chloropyrazin-2-yl)amino)propan-2-one (11g, 59 mmol), TFA (22.5 ml) and triflic anhydride (35 ml) was stirred at rt for 2h. The volatiles were evaporated under reduced pressure to obtain a residue. The residue was extracted with DCM and the DCM extract was washed with water, dried over sodium sulfate, filtered and concentrated under vacuum to obtain 8-chloro-3-methylimidazo[1,2-a]pyrazine (7.9 g, 80%). 1HNMR (400 MHz, DMSO-d6 ): δ 8.46 (d, J= 4.8 Hz, 1H), 7.76 (d, J= 4.4 Hz, 1H), 7.68 (s, 1H), 2.23 (s, 3H), LC-MS: 168.2 [M+H]+.

The Characterization Data for Intermediate No. 61, at Column 59, should read as follows:
LC-MS: 318.2 [M+H]+.

The correct structure at Intermediate 89, Column 67, is:

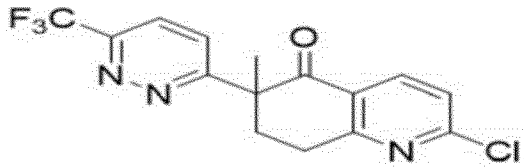

The Characterization Data for Compound 68, at Column 106, should read as:
1H NMR (400 MHz, CD30D): δ 8.38 (d, J = 8.8 Hz, 2H), 8.306 (d, J = 4.4 Hz, 2H), 8.09 (d, J =8.8 Hz 1H), 7.92 (d, J = 8 Hz, 2H) 7.76 (s, 1H), 7.68 (d, J = 7.6 Hz 2H), 7.62 (d, J = 4.4 Hz, 1H) 4.86 (s, 2H), 3.70-3.33 (m, 2H), 3.30-3.24 (m, 2H), 3.15-3.05 (m, 1H), 2.75-2.68 (m, 1H), 2.45(s, 3H), 2.20-2.16 (m, 2H), 1.80 (s, 3H), 1.29-1.22 (m, 3H); LC-MS: 518.4 [M+H]+.

Signed and Sealed this
Nineteenth Day of April, 2022

Katherine Kelly Vidal
*Director of the United States Patent and Trademark Office*

CERTIFICATE OF CORRECTION (continued)
U.S. Pat. No. 11,229,636 B2

Page 2 of 2

The correct Compound 75, at Column 107, is:

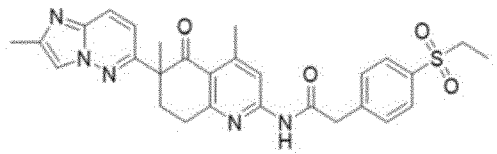

The correct Compounds 101 and 102, at Column 126, are:

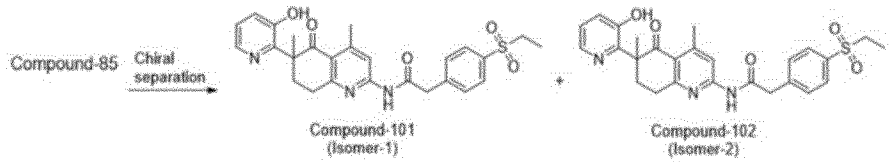

The correct Compound 115, at Column 131, is:

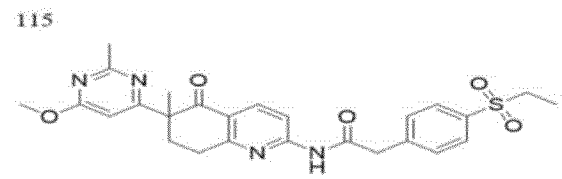

The correct Compound 127, at Column 137, is: